US009790473B2

(12) United States Patent
Towner et al.

(10) Patent No.: US 9,790,473 B2
(45) Date of Patent: Oct. 17, 2017

(54) HUMAN EBOLA VIRUS SPECIES AND COMPOSITIONS AND METHODS THEREOF

(71) Applicant: The United States, as represented by the Secretary, Department of Health and Human Services, Washington, DC (US)

(72) Inventors: Jonathan S. Towner, Decatur, GA (US); Stuart T. Nichol, Atlanta, GA (US); James A. Comer, Decatur, GA (US); Thomas G. Ksiazek, Galveston, TX (US); Pierre E. Rollin, Lilburn, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/694,036

(22) Filed: Apr. 23, 2015

(65) Prior Publication Data

US 2015/0218525 A1    Aug. 6, 2015

Related U.S. Application Data

(62) Division of application No. 13/125,890, filed as application No. PCT/US2009/062079 on Oct. 26, 2009, now abandoned.

(60) Provisional application No. 61/108,175, filed on Oct. 24, 2008.

(51) Int. Cl.
| | |
|---|---|
| C12N 7/00 | (2006.01) |
| A61K 39/12 | (2006.01) |
| C07K 16/10 | (2006.01) |
| G01N 33/569 | (2006.01) |
| C07K 14/005 | (2006.01) |
| C12Q 1/70 | (2006.01) |
| A61K 39/00 | (2006.01) |

(52) U.S. Cl.
CPC ............ *C12N 7/00* (2013.01); *A61K 39/12* (2013.01); *C07K 14/005* (2013.01); *C07K 16/10* (2013.01); *C12Q 1/701* (2013.01); *G01N 33/56983* (2013.01); *A61K 39/00* (2013.01); *A61K 2039/5254* (2013.01); *A61K 2039/5256* (2013.01); *A61K 2039/53* (2013.01); *A61K 2039/542* (2013.01); *A61K 2039/543* (2013.01); *C07K 2317/76* (2013.01); *C12N 2760/14121* (2013.01); *C12N 2760/14134* (2013.01); *C12N 2760/14143* (2013.01); *C12N 2760/14145* (2013.01); *C12N 2810/6072* (2013.01); *G01N 2333/08* (2013.01)

(58) Field of Classification Search
None
See application file for complete search history.

(56) References Cited

U.S. PATENT DOCUMENTS

| | | | |
|---|---|---|---|
| 6,630,144 B1 | 10/2003 | Hart et al. | |
| 6,713,069 B1 * | 3/2004 | Gallaher ............. | C07K 14/005 424/218.1 |
| 6,852,324 B1 | 2/2005 | Nabel et al. | |
| 7,267,823 B2 | 9/2007 | Hart et al. | |
| 2001/0053519 A1 | 12/2001 | Fodor et al. | |
| 2003/0215794 A1 | 11/2003 | Kawaoka et al. | |
| 2008/0069838 A1 | 3/2008 | Peiris et al. | |
| 2012/0251502 A1 | 10/2012 | Towner et al. | |

FOREIGN PATENT DOCUMENTS

| | | |
|---|---|---|
| WO | WO 2005/023837 | 3/2005 |
| WO | WO 2007/044731 | 4/2007 |
| WO | WO 2009/116983 | 9/2009 |
| WO | 2009/128867 A2 | 10/2009 |

OTHER PUBLICATIONS

Nakayama and Saijo, Frontiers in Microbiology, 2013, vol. 4, Article 267, 20 pages.*
Henao-Restrepo et al., The Lancet, 2015, 386(9996):857-866.*
Genbank AF272001.1, Aug. 28, 2002.
Jonathan S. Towner et al; Newly Discovered Ebola Virus Associated with Hemorrhagic Fever Outbreak in Uganda; XP-002669470; PLOS Pathogens; Nov. 2008; vol. 4; Issue 11; pp. 1-6.
Viktor Volchkov et al; Emergence of Subtype Zaire Ebola Virus in Garbon[1]; Virology, 232, pp. 139-144; 1997.
Anthony Sanchez et al.; Complete genome sequence of an Ebola virus (Sudan species) responsible for a 2000 outbreak of human disease in Uganda; Virus Research 113; (2005) pp. 16-25.
Ebihara et al., Journal of Infectious Diseases, 196:S313-22, 2007.
Neumann et al., Journal of Virology, 78:406-410, 2002.
Warfield et al., Journal of Infectious Diseases, 196:S276-283, Nov. 15, 2007.
Towner et al., Virology, 332:20-27, 2005.
Genbank AF086833.2, Feb. 13, 2012.
GenBank FJ217162.1, Nov. 21, 2008.
Le Guenno et al. (Lancet 345:1271-74, 1995).
NCBI Genbank Accession No. AAG40171.1, available at https://www.ncbi.nlm.nih.gov/protein/AAG40171.1, as accessed May 4, 2017.
NCBI Genbank Accession No. AAM76038.1, available at https://www.ncbi.nlm.nih.gov/protein/AAM76038.1, as accessed May 4, 2017.

(Continued)

*Primary Examiner* — Stacy B Chen
(74) *Attorney, Agent, or Firm* — Klarquist Sparkman, LLP

(57) ABSTRACT

Compositions and methods including and related to the Ebola Bundibugyo virus (EboBun) are provided. Compositions are provided that are operable as immunogens to elicit and immune response or protection from EboBun challenge in a subject such as a primate. Inventive methods are directed to detection and treatment of EboBun infection.

15 Claims, 27 Drawing Sheets

(56) References Cited

OTHER PUBLICATIONS

International Search Report and Written Opinion for PCT/US2009/062079, mailed Sep. 27, 2010, by the Korean Intellectual Property Office acting as ISA, 10 pages.

Winget et al. "Randomly amplified polymorphic DNA PCR as a tool for assessment of marine viral richness." *Applied and Environmental Microbiology* 74, No. 9 (2008): 2612-2618.

NCBI Genbank Accession No. X67110.1, available at https://www.ncbi.nlm.nih.gov/nuccore/x67110, as accessed Mar. 14, 2017.

\* cited by examiner

```
                      2910      2920      2930      2940      2950      2960      2970      2980      2990      3000
                      ....|....|....|....|....|....|....|....|....|....|....|....|....|....|....|....|....|....|....|....|
Ebola Bundibugyo '07  CAACCCCTTAGC---CAACTCCACCACAGAAGCACCACCACCCCAAACCA--CAACACTGCATGTAAGTATGTCTCACCCCAAGATGA
Ebola IC '94          CACACCATCCAGAT---CAACCCAAACCCTCAAACACACCACTCCG--CGATCCCAGACCAAACTCCGCCCCAGACAAGCACCCCATCCCAGAAAC
Ebola Zaire '76       AATGCAAATAGGCGTTAAGCCACAGTTATAGCCATAGTGTAACTCAAT-ATTCTAACTAGCGATTTATCTAAATTAAATTACATTATGCTTTATAACT 3010      3020      3030      3040      3050      3060      3070      3080      3090      3100
                      ....|....|....|....|....|....|....|....|....|....|....|....|....|....|....|....|....|....|....|....|
Ebola Bundibugyo '07  TCCCTGGACACCAACAACCCCCTAACCTCCCAAGTTGTCATTAAGAAAAATATATGATGAAGATTAAAACCTTCATCAGAGCTATTTCTTCTACGCTT
Ebola IC '94          CGCACGGCCAGAATCGATCCCCAGCATTCAAATGCCATTCAAAATGCGTTATTAAGAAAAACATATGATGAAGATTAAAACCTTCATCAACATTGCACAGACTTTGATC
Ebola Zaire '76       TACCTACTAGCCTGCCCAACATTTACACGATCGTTTTATAATTAAGAAAAAACTAATGATGAAGATTAAAACCTTCATCATCCTTACGTCAATTGAATTC 3110      3120      3130      3140      3150      3160      3170      3180      3190      3200
                      ....|....|....|....|....|....|....|....|....|....|....|....|....|....|....|....|....|....|....|....|
Ebola Bundibugyo '07  GGTTAGGACCAGTATTCACAAACTATTTTACAATC--------CCTACCCAATATGACCTCTAACAGAGACAAGGGTGACTTACAACCCACCAACAACCA
Ebola IC '94          CTTAGGAGTTTATTCTAGCTATCTACAAAACGGGT-------CCAAAACGGAATGATTTCCACTAGGGCTGCAGCAATCAATGATCCTTCATTACCAATCA
Ebola Zaire '76       TCTAGCACTCGAAGCTTATTGTCTTCAATGTAAAAGAAAAGCTGTCTAACAAGATGCAACAAGTAGAACAAAGGGCAGGGCCATACTGCGGCCACGACTC 3210      3220      3230      3240      3250      3260      3270      3280      3290      3300
                      ....|....|....|....|....|....|....|....|....|....|....|....|....|....|....|....|....|....|....|....|
Ebola Bundibugyo '07  CAGGCACACAGATCGTGTGGGCCGGAACTTTCCGGGGTGATCTCTGAGCAATTGATGACAGGCAAGATTCCGATTACCGATATCTTCAATGAAATTGAAAC
Ebola IC '94          GAAACCAGTGCTACACGTGGCCCCTGACTATCAGGATGGATGATCTCGAACAATTAATGACAGGCAAAATTCCGGTACATGAAATCTTCAACGACACTGAGCC
Ebola Zaire '76       AAAACGACAGAATGCCAGCCCCTGAGCTTCTGGATCTCTGAGCAGTAATGACCGGAAGAATTCCTGTAAGCGACATCTTCTGTGATATTGAGAA 3310      3320      3330      3340      3350      3360      3370      3380      3390      3400
                      ....|....|....|....|....|....|....|....|....|....|....|....|....|....|....|....|....|....|....|....|
Ebola Bundibugyo '07  CTTACCTAGTATAAGTCCCTCGATCCACTCCAAATCAAAACCCAAGTGTCAAACACCCAAACGCAGTGTCCAGACCCAGACTGACCAAACTGTAATCATGAT
Ebola IC '94          CCACATAAGCTCAGGGTCCAGGGTCCAGACTACGCCGATCGCCTTCCGAAGACCCAAAAACACGGCCCCCCGGACTCGCAACACAGACCGATCCGGTTTGCAATCACAAT
Ebola Zaire '76       CAATCCAGGATTATGCTACGACGCCATCCCAAATGCAACAACAAATGGCTTCATTCATACATCACAGGCAAAACAGGCTCTCGAACTTAGAGTCTCGGAACAACGATCTAGAGA 3410      3420      3430      3440      3450      3460      3470      3480      3490      3500
                      ....|....|....|....|....|....|....|....|....|....|....|....|....|....|....|....|....|....|....|....|
Ebola Bundibugyo '07  TTTGCAGAGAGTTGTGAAAATGCTAACATCTCTAACCCTTGTCGTACAAAAACAAACCCTTGCAACTGAACTCACTTCGACTGAACGCATTACTGACCTGGAAG
Ebola IC '94          TTTGAAGACGTTACACAAGCACTAACATCAATTGGCTTCATTGTGCTACTGTTGTCAACAACAAACAATCATTGGCTACTGTTGTGCAACAACAAACAGGCTCTTAACTTAGAGTCTCGAACAACCAGCATCCATCATACGAGTCTTAGA
Ebola Zaire '76       TTTGAGGAGGTAGTACAAACATTGGCTTCATTGGCTACTGTTGTCAACAACAACAAACAGGCTTTATCAAGAATCATTAGAACAACACGCATTACGAGTCTTGAGA 3510      3520      3530      3540      3550      3560      3570      3580      3590      3600
                      ....|....|....|....|....|....|....|....|....|....|....|....|....|....|....|....|....|....|....|....|
Ebola Bundibugyo '07  GTAGCCTGAAACCAGTGCTCTGAGATCACCAAGATTCTTTCTGACTAAATAGATCCTGTGCAGAGATGGCCAAATATGATCTTCTAGTAATGACGAC
Ebola IC '94          ATGGCTTAAAGCCAATGATGATGACATGGCTAAAGTCATTTCTGCATTGAAATAGATCTTGTGCTGAGATGGTAGCAAATGATAAAATATGATCTCCTGGTGATGACAAC
Ebola Zaire '76       ATGGCTCTAAAGCCAGTTTATGATGAATGGCAAAAACAATCCCTCCATTGAACAGGGTTGTGCTGATGGTTGCAAATAATAATGATCTTCGGATGACGAACAAC
```

```
                          5910      5920      5930      5940      5950      5960      5970      5980      5990      6000
                         ....|....|....|....|....|....|....|....|....|....|....|....|....|....|....|....|....|....|....|....|
Ebola Bundibugyo '07     GTAAA-TTGTTATGGTATCAAAATCTTATTAAGAAAAGAACACGATGAAGATTAACGCGACCTAGAGCGCTGCCTTCATCTCATCAATTAACTTGTCAA
Ebola IC '94             ACGCACTTCTTATGCCA-CAGCTTATATTAAGAAAAGAAGAACTTGATGAAGATTAAGGCAACCAGTGGTGCTATCTTCATCTCTTGATTGAGTCTTAAG
Ebola Zaire '76          ATCCAAGTACAGACATTGCCCTTCTAATTAAGAAGAAAATCGGCGATGAGATTAAGCCGACAGTGAGCGTAATCTTCATCTCTTAGATTATTTGTTTT 6010      6020      6030      6040      6050      6060      6070      6080      6090      6100
                         ....|....|....|....|....|....|....|....|....|....|....|....|....|....|....|....|....|....|....|....|
Ebola Bundibugyo '07     TAGAGCAACCTAGTTGTGATTACTCATCT-TCCGTAGTTGACAAACACTTTGCTGGTTAATTGTAAATATACCACAGTCATCATGGTTACATCAGGAAT
Ebola IC '94             TGAATACACAGGTTCTAATACTGTTCTTCTGTCTGCCAGGCCTATAATTCAGCCAGGCGTATAACCAAATAAACTCCACTAGAACAGTAGCTA-ATCACAGTCATCATGGAGCGCTCAGGGAT
Ebola Zaire '76          CCAGAGTAGGGGTCGTCAGGTCCTTTTCAAATCGTGTAACCAAATAAACTCCACTAGAACAGGATATTGTGGGCAACAA-CACAATGGGCGTTACAGGAAT 6110      6120      6130      6140      6150      6160      6170      6180      6190      6200
                         ....|....|....|....|....|....|....|....|....|....|....|....|....|....|....|....|....|....|....|....|
Ebola Bundibugyo '07     TCTACAATTGCCCCGTGAACGCTTCAGAAAAACATCATTTTTTGTTGGTAATAATCCTATTTCACAAAGTTTTCCCTATCCATTGGGCGTAGTTCAC
Ebola IC '94             TCTGCAATTGCCCCGTGAGCGCTTCAGGAAAAACATCTCTTCTTTGTGTGCCGAGACAAACTCTCTTCAACTAGCCAATTGAAGTCAGTCGGGTTGAACTGGAGGGCA
Ebola Zaire '76          ATTGCAGTTACCTCTGATCGATCCAAGAGGACATCAAGGACATCATTCTTCTTTGGTAATTATCCTTTCCAAAGAACATTTTCCATCCACTTGGAGTCATCCAC 6210      6220      6230      6240      6250      6260      6270      6280      6290      6300
                         ....|....|....|....|....|....|....|....|....|....|....|....|....|....|....|....|....|....|....|....|
Ebola Bundibugyo '07     AACAACACTCTCCAGTAAGTAAGTGATATAGATAATAAATTGGTGTGCCGGGATAAACTTTCCTCCACAAGTCAGCTCGGCTTAATCTAGAAGGTA
Ebola IC '94             AACAATACCCTACAAGTGAGTGAATTGACAAGTTTGTGTGCCGAGACAAACTCTCTTCAACTAGCCAATCAATTGAAGTCAGTCGGGTTGAACTGGAGGGCA
Ebola Zaire '76          AATAGCACATTACAGGTTAGTGATGTCGACAAACTAGTTTGTCGTGACAAACTCAATCAATTGAGATCAGTTGGACTGAGATCAGTGAATCGAAGGGA 6310      6320      6330      6340      6350      6360      6370      6380      6390      6400
                         ....|....|....|....|....|....|....|....|....|....|....|....|....|....|....|....|....|....|....|....|
Ebola Bundibugyo '07     ATGGAGTTGCCACAGATGTACCAACAGCAACGGCAACCAACGGCAACCAACATCTGCAATCGCAATCTAAAAGATGGGATTGGGATTCCAGCTGGTGTTCCACCCAAAGTGGTGAACTACGAAGCTGGGAGCTGGGGAGCTGA
Ebola IC '94             ATGGAGTAGCAACTGATGTACCAACGGCAACCAATCGCAATCTGCAATCGCCATCTGCCATTCGCAATCTAAAAGATGGGGTTTTGCAGCCTGGTGTTCCACCAAAGGTGGTGACAGCTGGTAAATTGCCAAGGTGGTGAGAATTGGGCTGA
Ebola Zaire '76          ATGGAGTGCCAACTGACGTGCCATTCGCAACTGCAACTCTGCAATTCAAAAGATGGGGTGCCCGTGCCAGTCCAGTGCCAGGCTTCAGTGCCGTCCAGTGCCAGTGCCAGTGCCGGATTCGGGGGCGCGTGGAATTGAAGCCTGGAGGGGCGAGG 6410      6420      6430      6440      6450      6460      6470      6480      6490      6500
                         ....|....|....|....|....|....|....|....|....|....|....|....|....|....|....|....|....|....|....|....|
Ebola Bundibugyo '07     AAACTGCTACAACCTGGACATCAAGAAAGCAGAATGGTAGCGAATGGTAAGCGAATGCCTACCTGAAGCCCCTGAGGGTGTAAGAGGCTTCCCTGCTGCCGTTATGTGCAC
Ebola IC '94             GAACTGTTATAACCTGGCTATAAGAAGAAGTTGATGGTAGTGATGGTGAGTGCCTACCAGAAGCCCTACCTGAAGCCCTGAGGGAGTGAGGAGTTCGGGGCGATTTTCCCCGTGCCGATGTACAC
Ebola Zaire '76          AAACTGCTACAAATCTTGAAATCAAAAACAAAAAACCTGAGTGACGGGGAGTGAGTGTCTACGACGAGGAGTCCGGATTCGGGGCGGATTCGGGGCGGATTCGGGGCGGATTCGGGGCGGATTCGGGGCGCGGATCGGGGCGCGGTGCGGCGTGCGGATCAAATCATTATCGCAC 6510      6520      6530      6540      6550      6560      6570      6580      6590      6600
                         ....|....|....|....|....|....|....|....|....|....|....|....|....|....|....|....|....|....|....|....|
Ebola Bundibugyo '07     AAGGTTTCTGGAACAGGGCCGTGCCCTGAAGTTACGCTTCCACAAAGAAGGCGCTTTCTTCCTGTATGATCGACTGGCATCAACAATCATCATCGAA
Ebola IC '94             AAAGTCTCAGGAACTGGACCATGCCCAGGAGGACTCGCCTTTCCCTTCCCAGGACTGACTGACTTTGCCTCCTGTATGACCGATCGACGACCGATCAACAATCATTATCGGG
Ebola Zaire '76          AAAGTATCAGGAACGGGACCGTGCCGTGCCAGTCCAGTCCAGCCGACTCCATAAAAGAGGGGGCTGCTTTTCCACAGTTAATCACGAG

```
                                10410     10420     10430     10440     10450     10460     10470     10480     10490     10500
                            ....|....|....|....|....|....|....|....|....|....|....|....|....|....|....|....|....|....|....|....|
Ebola Bundibugyo '07        AACAAGATCGATACTAATATAGGGATTTGTT-TCATACTAGCTCTCTGCAAACACAATGGCTAAGGCAACAGGTAGGTACAACTTGGTTTCACCTAAAAA
Ebola IC '94                AGTGAACAAGCTCATACTATCAAGGCTAATCCTCGGGCCTGCCTGGAGTC--CACAATGGCCAAGGCTACTGGGAGGTACAACCTTATCTCCCCAAAGAA
Ebola Zaire '76             AGACAACAAAATATTGATACT----CCAGACACCAAGCAAGACCTGAGAAAAAACCATGGCTAAAGCTACGGGACGATACAATCTAATATCGCCCAAAAA 10510     10520     10530     10540     10550     10560     10570     10580     10590     10600
                            ....|....|....|....|....|....|....|....|....|....|....|....|....|....|....|....|....|....|....|....|
Ebola Bundibugyo '07        GGACCTCGAGAGGGGGCTTGTTTTGAGTGATTTGTGCACGTTTTTAGTTGATCAGACTATCCAGGGGTGGCGGGTGACTTGGGTTGGGATTGAATTTGAC
Ebola IC '94                AGATCTTGAAAAAGGGCTGGTTCTGAATGACCTTTGCACTCTCTCAGTGGCCCAGACGGTCCAGGGATGGAAGGTTACCTGGGCTGGGATTGAATTTGAT
Ebola Zaire '76             GGACCTGGAGAAAGGGGTTGTCTTAAGCGACCTCTGTAACTTCTTAGTTAGCCAAACTATTCAGGGGTGGAAGGTTTATTGGGCTGGTATTGAGTTTGAT 10610     10620     10630     10640     10650     10660     10670     10680     10690     10700
                            ....|....|....|....|....|....|....|....|....|....|....|....|....|....|....|....|....|....|....|....|
Ebola Bundibugyo '07        ATCGCCCAGAAAGGGATGGCTCTACTGCATCGGTTAAAAACTGCTGACTTCGCTCCTGCATGGTCGATGACAAGGAATTTATTTCCTCATTTATTTCAAA
Ebola IC '94                GTTACACAGAAAGGGATGGCCTTATTGCACAGGCTCAAGACCAGTGATTTTGCTCCAGCCTGGTCAATGACCAGGAACTTATTTCCACATCTCTTTCAAA
Ebola Zaire '76             GTGACTCACAAAGGAATGGCCCTATTGCATAGACTGAAAACTAATGACTTTGCCCCTGCATGGTCAATGACAAGGAATCTCTTTCCTCATTTATTTCAAA 10710     10720     10730     10740     10750     10760     10770     10780     10790     10800
                            ....|....|....|....|....|....|....|....|....|....|....|....|....|....|....|....|....|....|....|....|
Ebola Bundibugyo '07        ATTCAAATTCTACTATTGAGTCTCCCCTCTGGGCATTACGAGTGATTCTGGCAGCTGGTATTCAAGACCAGTTAATTGACCAATCCTTGGTAGAACCGTT
Ebola IC '94                ACCCGAACTCTACAATTGAGTCGCCACTTTGGGCACTGCGGGTCATACTAGCAGCAGGTATTCAAGATCAGCTAATTGATCAATCGTTGATCGAACCCTT
Ebola Zaire '76             ATCCGAATTCCACAATTGAATCACCGCTGTGGGCATTGAGAGTCATCCTTGCAGCAGGGATACAGGACCAGCTGATTGACCAGTCTTTGATTGAACCCTT 10810     10820     10830     10840     10850     10860     10870     10880     10890     10900
                            ....|....|....|....|....|....|....|....|....|....|....|....|....|....|....|....|....|....|....|....|
Ebola Bundibugyo '07        GGCCGGAGCCCTGAGCTTAGTCTCCGATTGGCTTCTTACAACAAACACAAACCATTTTCAAATGCGCACGCAGCACGCTAAAGAGCAACTGAGCTTGAAG
Ebola IC '94                GGCAGGAGCGCTAGGCTTAATTGCTGATTGGCTTCTTACTACTGGAACAAACCACTTTCAAATGCGCACACAACAGGCTAAGGAGCAACTAAGTCTAAAA
Ebola Zaire '76             AGCAGGAGCCCTTGGTCTGATCTCTGATTGGCTGCTAACAACCAACACTAACCATTTCAACATGCGAACACAACGTGTCAAGGAACAATTGAGCCTAAAA 10910     10920     10930     10940     10950     10960     10970     10980     10990     11000
                            ....|....|....|....|....|....|....|....|....|....|....|....|....|....|....|....|....|....|....|....|
Ebola Bundibugyo '07        ATGCTATCATTAGTGCGCTCTAATATCTTGAAATTCATCAGTCAATTGGACGCACTACATGTCGTGAACTACAATGGACTCTTGAGCAGTATCGAAATTG
Ebola IC '94                ATGTTGTCCCTGGTGCGATCAAACATCCTAAAGTTCATCAACCAACTAGATGCACTACATGTTGTGAATTACAATGGACTTCTCAGTAGCATTGAAATTG
Ebola Zaire '76             ATGCTGTCGTTGATTCGATCCAATATTCTCAAGTTTATTAACAAATTGGATGCTCTACATGTCGTGAACTACAACGGATTGTTGAGCAGTATTGAAATTG 11010     11020     11030     11040     11050     11060     11070     11080     11090     11100
                            ....|....|....|....|....|....|....|....|....|....|....|....|....|....|....|....|....|....|....|....|
Ebola Bundibugyo '07        GCACTAGAAATCATACCATTATCATCACAAGAACCAACATGGGTTTCCTGGTAGAATTACAGGAGCCTGATAAATCTGCCATGAATCAAAAGAAACCAGG
Ebola IC '94                GCACCAAAAGCCATACAATTATAATTACCCGGACAAATATGGGTTTTTTGGTAGAGTTGCAAGAGCCTGACAAATCAGCCATGAACACCAGAAAACCAGG
Ebola Zaire '76             GAACTCAAAATCATACAATCATCATAACTCGAACTAACATGGGTTTTCTGGTGGAGCTCCAAGAACCCGACAAATCGGCAATGAACCGCATGAAGCCTGG
```

```
                              12610     12620     12630     12640     12650     12660     12670     12680     12690     12700
                          ....|....|....|....|....|....|....|....|....|....|....|....|....|....|....|....|....|....|....|....|
Ebola Bundibugyo '07      CTATGTTTAGCTAAGATCCAATTGTGCTCAAATTACACTGAGAGGAAAGGGAGATTCCTTACTCAAATGCATTTGGCCGTTAATCACACACTTGAAGAAC
Ebola IC '94              TTATGCTTAGCAAAGATCCAACTCTGCTCAAATTACACTGAGAGGAAAGGAAGATTCCTCACTCAAATGCATTTAGCTGTAAATCATACACTTGAGGAAC
Ebola Zaire '76           TTGTGCTTGGCCAAAATTCAATTATGCTCAAAGTACACTGAGAGGAAGGGCCGATTCTTAACACAAATGCATTTAGCTGTAAATCACACCCTAGAAGAAA 12710     12720     12730     12740     12750     12760     12770     12780     12790     12800
                          ....|....|....|....|....|....|....|....|....|....|....|....|....|....|....|....|....|....|....|....|
Ebola Bundibugyo '07      TTATTGAGGGCCGGGGATTGAAGTCACAACAAGACTGGAAGATGAGGGAATTTCACCGAATCTTAGTAAATTTAAAGTCAACACCACAACAACTCTGTGA
Ebola IC '94              TTACAGGGTCCCGAGAATTAAGGCCACAACAGATTCGGAAGGTAAGGGAATTCCATCAAATGCTGATAAACCTTAAGGCAACTCCTCAACAACTCTGTGA
Ebola Zaire '76           TTACAGAAATGCGTGCACTAAAGCCTTCACAGGCTCAAAAGATCCGTGAATTCCATAGAACATTGATAAGGCTGGAGATGACGCCACAACAACTTTGTGA 12810     12820     12830     12840     12850     12860     12870     12880     12890     12900
                          ....|....|....|....|....|....|....|....|....|....|....|....|....|....|....|....|....|....|....|....|
Ebola Bundibugyo '07      ATTGTTTTCAGTGCAAAAGCATTGGGGGCATCCTGTGCTACATAGCGAGAAGGCTATTCAGAAAGTAAAGAAACATGCAACCGTAATAAAAGCATTGCGT
Ebola IC '94              GTTGTTTTCAGTGCAAAAGCATTGGGGGCACCCTGTCTTGCATAGCGAAAAGGCTATCCAAAAAGTAAAGAAGCATGCAACAGTGATAAAAGCATTGCGC
Ebola Zaire '76           GCTATTTTCCATTCAAAAACACTGGGGGCATCCTGTGCTACATAGTGAAACAGCAATCCAAAAAGTTAAAAAACATGCTACGGTGCTAAAAGCATTACGC 12910     12920     12930     12940     12950     12960     12970     12980     12990     13000
                          ....|....|....|....|....|....|....|....|....|....|....|....|....|....|....|....|....|....|....|....|
Ebola Bundibugyo '07      CCCGTAATCATCTTTGAGACATATTGTGTGTTCAAGTACAGCATTGCCAAACATTATTTTGATAGCCAAGGGTCATGGTATAGTGTAATCTCAGATAAAC
Ebola IC '94              CCAATAATAATCTTTGAAACATATTGTGTGTTTAAATACAGCATTGCAAAACATTATTTTGATAGTCAGGGTACGTGGTACAGTGTGACTTCTGACAGAT
Ebola Zaire '76           CCTATAGTGATTTTCGAGACATACTGTGTTTTTAAATATAGTATTGCCAAACATTATTTTGATAGTCAAGGATCTTGGTACAGTGTTACTTCAGATAGGA 13010     13020     13030     13040     13050     13060     13070     13080     13090     13100
                          ....|....|....|....|....|....|....|....|....|....|....|....|....|....|....|....|....|....|....|....|
Ebola Bundibugyo '07      ATCTAACACCAGGTTTACACTCTTACATTAAGAGGAACCAATTTCCGCCACTGCCTATGATTAAAGACTTATTGTGGGAATTCTATCACCTTGATCATCC
Ebola IC '94              GCTTAACACCAGGCCTTTCCTCTTACATCAAAAGAAACCAATTTCCTCCACTACCTATGATCAAAGAACTTTTGTGGGAATTTTATCACTTAGATCATCC
Ebola Zaire '76           ATCTAACACCGGGTCTTAATTCTTATATCAAAAGAAATCAATTCCCTCCGTTGCCAATGATTAAAGAACTACTATGGGAATTTTACCACCTTGACCACCC 13110     13120     13130     13140     13150     13160     13170     13180     13190     13200
                          ....|....|....|....|....|....|....|....|....|....|....|....|....|....|....|....|....|....|....|....|
Ebola Bundibugyo '07      TCCCTTATTTTCCACCAAGATTATTAGTGACTTGAGTATTTTCATTAAGGATCGCGCTACCGCAGTGGAAAAAACATGTTGGGATGCAGTTTTCGAGCCT
Ebola IC '94              TCCGTTATTCTCCACCAAAGTGATTAGTGATTTGAGTATCTTTATTAAAGATCGTGCTACTGCAGTCGAGAAAACATGCTGGGACGCAGTTTTTGAACCC
Ebola Zaire '76           TCCACTTTTCTCAACCAAAATTATTAGTGACTTAAGTATTTTTATAAAAGACAGAGCTACCGCAGTAGAAAGGACATGCTGGGATGCAGTATTCGAGCCT 13210     13220     13230     13240     13250     13260     13270     13280     13290     13300
                          ....|....|....|....|....|....|....|....|....|....|....|....|....|....|....|....|....|....|....|....|
Ebola Bundibugyo '07      AATGTTCTTGGATATAGTCCTCCAAACAAGTTCTCAACTAAGAGGGTTCCTGAACAGTTTCTTGAACAAGAAAATTTCTCGATTGATAGTGTTCTCACTT
Ebola IC '94              AATGTTCTTGGTTATAACCCACCGAATAAATTTGCTACAAAAAGGGTACCTGAGCAATTCCTTGAACAGGAGAATTTCTCAATAGAGAGTGTCCTACATT
Ebola Zaire '76           AATGTTCTAGGATATAATCCACCTCACAAATTTAGTACTAAACGTGTACCGGAACAATTTTTAGAGCAAGAAAACTTTTCTATTGAGAATGTTCTTTCCT 13310     13320     13330     13340     13350     13360     13370     13380     13390     13400
                          ....|....|....|....|....|....|....|....|....|....|....|....|....|....|....|....|....|....|....|....|
Ebola Bundibugyo '07      ATGCCCAGCGCCTGGATTATCTACTTCCACAATACCGGAATTTTTCTTTCTCACTTAAGGAAAAAGAATTAAATGTAGGACGAGCTTTTGGTAAGCTACC
Ebola IC '94              ATGCTCAACGTCTGGAATATCTTCTCCCGGAGTACCGGAACTTCTCTTTTTCACTCAAGGAGAAGGAGTTAAACATTGGACGAGCTTTTGGGAAATTGCC
Ebola Zaire '76           ACGCACAAAAACTCGAGTATCTACTACCACAATATCGGAACTTTTCTTTCTCATTGAAAGAGAAAGAGTTGAATGTAGGTAGAACCTTCGGAAAATTGCC
```

FIG. 2R

```
                            13410     13420     13430     13440     13450     13460     13470     13480     13490     13500
                        ....|....|....|....|....|....|....|....|....|....|....|....|....|....|....|....|....|....|....|....|
Ebola Bundibugyo '07    TTATCCTACACGTAATGTTCAAACTTGTAAGCCTTATTGGCAGATGGATTAGCTAAAGCCTTTCCTAGTAACATGATGGTTGTAACAGAGCGTGAG
Ebola IC '94            ATATCCAACACGCAATGTTCAAACTCTGTGCGAAGCTTTGTTGTTAGCAGATGATGGTTTGGCGAAAGCATTCCAAGCAATATGATGGTTGACAGAGAGCGGAG
Ebola Zaire '76         TTATCCGACTCGCAATGTTCAAACACTTTGTCAAACTCTGTGAAGCTCTGTTAGCTGATGGTCTTGCTAAAGCATTTCCTAGCAATATGCAATATGATGGTTACGGAACGTGAG 13510     13520     13530     13540     13550     13560     13570     13580     13590     13600
                        ....|....|....|....|....|....|....|....|....|....|....|....|....|....|....|....|....|....|....|....|
Ebola Bundibugyo '07    CAGAAGGAAAGCCTCTTGCACCAGGCGTCGTGGCACCACCAACAAGTGACGATTTCGGTGAGAATGCCACTGTTAGAGGCAGCAGTTTGTTGTTACCGACCTAG
Ebola IC '94            CAAAAAGAAAGCCTTTTGCATCAGCCGTCTTGCCATCACCACCAAGTGATGATTTTGGTGAGAATGCTACTGTTAGAGGCCAGCAGTAGTTTTGTAACAGACTTGG
Ebola Zaire '76         CAAAAAGAAAGTTATTGCATCAAGCATCATGGCCACCACACCACCAAGTGATGATTTGTGAACATGCCACAGTGCCACAGTTAGAGGGAGTAGCTTGTAACTGATTTAG 13610     13620     13630     13640     13650     13660     13670     13680     13690     13700
                        ....|....|....|....|....|....|....|....|....|....|....|....|....|....|....|....|....|....|....|....|
Ebola Bundibugyo '07    AAAAATACAACTTGGCATTTAGAATATGAGTTTACAGCTCCATTTATTAGTGAATACTGTAATCGATGTTATATGGTGTAAAAAATTTATTCAATTGGATGCATTA
Ebola IC '94            AAAAATACAATTTAGCATTCCGATATGAGTTTACAGCTCCATTTATTACTGAGTAATACTGTGTTACAAGTCGTTGTTAGGTAAGAAATTTGTTAATTGGATGCACTA
Ebola Zaire '76         AGAAATACAATCCTGCATTTAGAATATGAGTTTACAGCACCCTTTTATAGAATATTGCAACCGTTGCTATGGTGTTAAGAATGTTTTAATTGGATGCATTA 13710     13720     13730     13740     13750     13760     13770     13780     13790     13800
                        ....|....|....|....|....|....|....|....|....|....|....|....|....|....|....|....|....|....|....|....|
Ebola Bundibugyo '07    TACGATACCGCAATGTTTATATACATGTAAGTGATTATTATAATCCCCTCATGGAGTTTCGCTAGAAAATCGGAAGATCCCCGGAAGCCCTAGCTCT
Ebola IC '94            CACTATACCACAGTGTTATATACATGTGAGTGATTATTATAACCCCCACACATGAGTCTCTCGACACATGGAATTGGATAGAATAAATCCACCAGAAGGTCCAAGCTCT
Ebola Zaire '76         TACAATCCCACAGTGTTATATGCCAGTGCAGTGATTATTATAATCCACCACATAACCCTGAATCGGAGAATCGAGACAACCCCCGAAGGCCTAGTTCA 13810     13820     13830     13840     13850     13860     13870     13880     13890     13900
                        ....|....|....|....|....|....|....|....|....|....|....|....|....|....|....|....|....|....|....|....|
Ebola Bundibugyo '07    TACCGTGGTCATCTTGGGGAATTGAGGGACTCCAACAACTCTGGACCAGCATTTCATGTGCACAAATCTCATTAGTTGAGATCAAGACTGGTTCA
Ebola IC '94            TACCGTGGTCATCTAGGGCGGAGTTGAGGGATTGAGGGACTTCAACAAGAACTCTGGACAACAAACTCTGGACAAGATCTCAGATTCATGCACAGATTCATTAGTTCATTAGTTGAAATCAAACCGTTTTA
Ebola Zaire '76         TACAGGGGTCATATGGGAGGGGATTGAAGGACTGAAGGACTCTGGACAAGTAGTATTCATCAGTCGTTCAGATGTGCTCAAATTTCTTCAATTTCTTCAAGAATTAAGACTGTTTTA 13910     13920     13930     13940     13950     13960     13970     13980     13990     14000
                        ....|....|....|....|....|....|....|....|....|....|....|....|....|....|....|....|....|....|....|....|
Ebola Bundibugyo '07    AATTGAGATCTGCGGTAAATGGGTGATAATCAATGCATCACAGTTCTTCCGTATTCCTCTAGAGACAGATTCCAATGAGACAAGAGCATAGCTCCGAGGA
Ebola IC '94            AACTGCGATCTGCCGGTAAATGGGTGACAATCAATGTATAAACCTGCGTCTGTATTCCCCTCGTATTCCCGAAACTGAGTCAGTAGTCAGTAGCCAAGACTAGTCAGCAAGACAAGAGAATTAAGTCTGAAGA
Ebola Zaire '76         AGTTACGCTCAGCTGTGATGGGTGACAATGTTCATTACTGTGTTTATCAGTCGTCCCCCTTAGAGACTTCCCCCTTAGAGACTCAGAAGCTGCAGTGAACCAGCAGGAACAGAGCCAAGAA 14010     14020     14030     14040     14050     14060     14070     14080     14090     14100
                        ....|....|....|....|....|....|....|....|....|....|....|....|....|....|....|....|....|....|....|....|
Ebola Bundibugyo '07    CAATGCTGCTGCTCGCTAGCGAGGTGGCCCGAGCCAGCCAGTTAGCCAAAGTCACGAGTGCCTGTGGCATCTTCCTAAAACCAGATGAGACTTTTGTGCAATTCAGGCTTTATTTAT
Ebola IC '94            TAATGCCGCTAGAGTAGCTGCTAGCTTAGCAGCCTAGCTTAAGCCAAAAGTCACAAGTGCCTGCGGCATCCTCTTTTAAAACCTGATGAGAAACTTTGTCATCTCAGTTTCATTAT
Ebola Zaire '76         CAATGCAGCAGCGAGGTGGCCCAGCCAGCCTAGCAAGTTCAAGTTACAAGTGCCTGTGGCCTGCGGCCAGCCTGTGTGAATCTTTTAAAACCTGATGAAACCTTTGTACATTTGTACATTTCAGGTTTCAGGTTTATCTAT

FIG. 2S
```

```
                                14110     14120     14130     14140     14150     14160     14170     14180     14190     14200
                            ....|....|....|....|....|....|....|....|....|....|....|....|....|....|....|....|....|....|....|....|
Ebola Bundibugyo '07        TTCGGTAAGAAGCAATATTTAAATGGCGTTCAATTGCCACAATCACTCAAGACTGCTACCAGGATTGCTCCCTTGTCAGATGCAATCTTTGATGACCTTC
Ebola IC '94                TTTGGCAAAAAACAATATTTGAATGGAGTACAATTACCTCAATCACTGAAAACTGCTACTAGAATTGCACCCTTGTCAGATGCTATCTTTGATGATCTTC
Ebola Zaire '76             TTTGGAAAAAAACAATATTTGAATGGGGTCCAATTGCCTCAGTCCCTTAAAACGGCTACAAGAATGGCACCATTGTCTGATGCAATTTTTGATGATCTTC 14210     14220     14230     14240     14250     14260     14270     14280     14290     14300
                            ....|....|....|....|....|....|....|....|....|....|....|....|....|....|....|....|....|....|....|....|
Ebola Bundibugyo '07        AGGGAACTCTGGCTAGTATAGGAACGGCATTTGAGAGATCTATATCCGAGACTAGACATGTATACCCTTGCCGGGTGGTTGCCGCATTCCATACATTCTT
Ebola IC '94                AAGGGACACTAGCTAGCATAGGCACGGCTTTTGAAAGATCTATCTCCGAAACTAGGCACGTAGTCCCTTGTAGAGTAGCAGCTGCATTCCATACCTTTTT
Ebola Zaire '76             AAGGGACCCTGGCTAGTATAGGCACTGCTTTTGAGCGATCCATCTCTGAGACACGACATATCTTTCCTTGCAGGATAACCGCAGCTTTCCATACGTTTTT 14310     14320     14330     14340     14350     14360     14370     14380     14390     14400
                            ....|....|....|....|....|....|....|....|....|....|....|....|....|....|....|....|....|....|....|....|
Ebola Bundibugyo '07        CTCCGTTAGGATCCTCCAATACCACCACCTTGGTTTCAACAAAGGAACCGATCTAGGTCAACTATCACTAAGCAAACCGTTGGATTTCGGAACTATCACT
Ebola IC '94                TTCCGTAAGAATCTTACAATATCATCATCTTGGCTTCAACAAGGGAACAGACCTGGGTCAATTGTCATTAAGCAAGCCATTAGATTTTGGAACTATAACT
Ebola Zaire '76             TTCGGTGAGAATCTTGCAATATCATCATCTCGGGTTCAATAAAGGTTTTGACCTTGGACAGTTAACACTCGGCAAACCTCTGGATTTCGGAACAATATCA 14410     14420     14430     14440     14450     14460     14470     14480     14490     14500
                            ....|....|....|....|....|....|....|....|....|....|....|....|....|....|....|....|....|....|....|....|
Ebola Bundibugyo '07        CTTGCTTTAGCGGTACCTCAAGTTCTAGGAGGTTTATCGTTTTTAAACCCAGAGAAATGTTTTTATCGCAACCTTGGAGACCCCGTGACCTCCGGCCTAT
Ebola IC '94                TTGGCCTTGGCAGTACCACAAGTCTTGGGTGGCTTATCATTCCTAAATCCAGAAAAATGTTTTTATAGAAATCTGGGTGATCCTGTTACTTCAGGGCTGT
Ebola Zaire '76             TTGGCACTAGCGGTACCGCAGGTGCTTGGAGGGTTATCCTTCTTGAATCCTGAGAAATGTTTCTACCGGAATCTAGGAGATCCAGTTACCTCAGGCTTAT 14510     14520     14530     14540     14550     14560     14570     14580     14590     14600
                            ....|....|....|....|....|....|....|....|....|....|....|....|....|....|....|....|....|....|....|....|
Ebola Bundibugyo '07        TCCAACTTAGGACTTACCTGCAAATGATCAACATGGACGACTTATTTCTACCTTTAATTGCCAAGAACCCCGGGAACTGTAGTGCAATTGACTTTGTACT
Ebola IC '94                TTCAGCTCAAGACATATCTTCAAATGATCCACATGGATGATTTGTTTTTACCTTTGATCGCAAAGAACCCAGGGAACTGTAGCGCAATTGACTTTGTGTT
Ebola Zaire '76             TCCAGTTAAAAACTTATCTCCGAATGATTGAGATGGATGATTTATTCTTACCTTTAATTGCGAAGAACCCTGGGAACTGCACTGCCATTGACTTTGTGCT 14610     14620     14630     14640     14650     14660     14670     14680     14690     14700
                            ....|....|....|....|....|....|....|....|....|....|....|....|....|....|....|....|....|....|....|....|
Ebola Bundibugyo '07        CAACCCAAGCGGATTGAATGTCCCTGGGTCACAAGACCTAACATCTTTTTTACGTCAGATAGTGCGTAGAACAATCACATTGAGTGCAAAAAATAAGCTA
Ebola IC '94                AAACCCTAGTGGGTTAAACGTACCGGGGTCACAGGATTTGACATCCTTCCTACGTCAGATAGTGCGCCGAACAATTACTCTAAGTGCTAAAAATAAATTA
Ebola Zaire '76             AAATCCTAGCGGATTAAATGTCCCTGGGTCGCAAGACTTAACTTCATTTCTGCGCCAGATTGTACGCAGGACCATCACCCTAAGTGCGAAAAACAAACTT 14710     14720     14730     14740     14750     14760     14770     14780     14790     14800
                            ....|....|....|....|....|....|....|....|....|....|....|....|....|....|....|....|....|....|....|....|
Ebola Bundibugyo '07        ATAAACACATTGTTTCACTCCTCAGCCGATTTAGAAGATGAGATGGTATGTAAATGGCTACTTTCTTCAACACCTGTAATGAGTCGGTTTGCTGCTGATA
Ebola IC '94                ATAAACACTTTGTTCCATTCTTCTGCTGATTTAGAAGATGAAATGGTTTGCAAATGGTTGCTTTCTTCTACACCAGTCATGAGTAGGTTTGCCGCCGATA
Ebola Zaire '76             ATTAATACCTTATTTCATGCGTCAGCTGACTTCGAAGACGAAATGGTTTGTAAATGGCTATTATCATCAACTCCTGTTATGAGTCGTTTTGCGGCCGATA 14810     14820     14830     14840     14850     14860     14870     14880     14890     14900
                            ....|....|....|....|....|....|....|....|....|....|....|....|....|....|....|....|....|....|....|....|
Ebola Bundibugyo '07        TATTCTCTCGTACTCCGAGTGGGAAGCGCTTGCAGATCCTAGGTTATTTAGAAGGGACTAGAACCTTGCTAGCCTCCAAAGTCATCAATAACAATGCAGA
Ebola IC '94                TATTTTCTCGCACTCCCAGTGGGAAACGTTTACAGATCTTAGGTTACCTTGAAGGGACTAGAACATTGTTAGCCTCTAAAATTATAAATCATAATACTGA
Ebola Zaire '76             TCTTTTCACGCACGCCGAGCGGGAAGCGATTGCAAATTCTAGGATACCTGGAAGGAACACGCACATTATTAGCCTCTAAGATCATCAACAATAATACAGA
```

FIG. 2T

```
                            14910     14920     14930     14940     14950     14960     14970     14980     14990     15000
                        ....|....|....|....|....|....|....|....|....|....|....|....|....|....|....|....|....|....|....|....|
Ebola Bundibugyo '07    GACTCCTATTTTAGATAGGTTGAGGAAAATCACACTGCAGAGATGGAGTTTGTGGTTTAGCTACCTAGACCACTGTGATCAGGTTCTAGCAGATGCTTTA
Ebola IC '94            GACACCTATCCTAGATCGATTGAGGAAAATTACGCTGCAAAGGTGGAGCCTGTGGTTTAGTTATCTCGACCACTGTGATCAAGTTCTGGCTGATGCCCTA
Ebola Zaire '76         GACACCGGTTTTGGACAGACTGAGGAAAATAACATTGCAAAGGTGGAGCCTATGGTTTAGTTATCTTGATCATTGTGATAATATCCTGGCGGAGGCTTTA 15010     15020     15030     15040     15050     15060     15070     15080     15090     15100
                        ....|....|....|....|....|....|....|....|....|....|....|....|....|....|....|....|....|....|....|....|
Ebola Bundibugyo '07    ATAAAAGTTTCTTGTACAGTTGATTTGGCGCAAATTTTACGTGAATATACCTGGGCACACATACTAGAGGGAAGACAGCTCATTGGTGCAACACTTCCTT
Ebola IC '94            ACTCAGATAACCTGCACTGTGGACTTAGCACAGATTCTTCGCGAGTACACCTGGGCACACATACTAGAGGGAAGGCAGCTCATTGGAGCAACACTTCCTT
Ebola Zaire '76         ACCCAAATAACTTGCACAGTTGATTTAGCACAGATTCTGAGGGAATATTCATGGGCTCATATTTTAGAGGGAAGACCTCTTATTGGAGCCACACTCCCAT 15110     15120     15130     15140     15150     15160     15170     15180     15190     15200
                        ....|....|....|....|....|....|....|....|....|....|....|....|....|....|....|....|....|....|....|....|
Ebola Bundibugyo '07    GCATGTTAGAACAATTTAATGTGTTTTGGCTCAAATCGTACGAACAATGCCCTAAATGTGCAAAATCTAGAAATCCAAAAGGAGAGCCATTTGTGTCAAT
Ebola IC '94            GTATACTAGAACAACTAAATGTCATCTGGCTCAAACCATATGAGCATTGCCCTAAATGTGCAAAGTCAGCAAACCCTAAAGGGGAACCTTTTGTTTCTAT
Ebola Zaire '76         GTATGATTGAGCAATTCAAAGTGTTTTGGCTGAAACCCTACGAACAATGTCCGCAGTGTTCAAATGCAAAGCAACCAGGTGGGAAACCATTCGTGTCAGT 15210     15220     15230     15240     15250     15260     15270     15280     15290     15300
                        ....|....|....|....|....|....|....|....|....|....|....|....|....|....|....|....|....|....|....|....|
Ebola Bundibugyo '07    TGCAATTAAGAAACAAGTTGTGAGTGCATGGCCGAATCAGTCACGGTTAAATTGGACCATTGGGGACGGTGTACCTTACATCGGGTCTCGAACAGAGGAC
Ebola IC '94            TGCAATTAAAAAACATGTAGTAAGTGCTTGGCCTGATCAATCACGACTTAGTTGGACAATTGGAGATGGCATCCCTTATATCGGATCTCGAACAGAGGAT
Ebola Zaire '76         GGCAGTCAAGAAACATATTGTTAGTGCATGGCCGAACGCATCCCGAATAAGCTGGACTATCGGGGATGGAATCCCATACATTGGATCAAGGACAGAAGAT 15310     15320     15330     15340     15350     15360     15370     15380     15390     15400
                        ....|....|....|....|....|....|....|....|....|....|....|....|....|....|....|....|....|....|....|....|
Ebola Bundibugyo '07    AAGATTGGGCAGCCAGCAATCAAGCCTAAGTGTCCCTCTGCTGCCTTACGTGAAGCAATAGAGTTGACATCTAGACTAACATGGGTTACCCAAGGTGGTG
Ebola IC '94            AAGATTGGGCAGCCAGCCATCAAACCAAAATGCCCTTCAGCAGCCTTACGTGAAGCAATTGAGTTGACATCAAGATTGACTTGGGTTACTCAAGGTGGAG
Ebola Zaire '76         AAGATAGGACAACCTGCTATTAAACCAAAATGTCCTTCCGCAGCCTTAAGAGAGGCCATTGAATTGGCGTCCCGTTTAACATGGGTAACTCAAGGCAGTT 15410     15420     15430     15440     15450     15460     15470     15480     15490     15500
                        ....|....|....|....|....|....|....|....|....|....|....|....|....|....|....|....|....|....|....|....|
Ebola Bundibugyo '07    CCAATAGTGATTTGCTAGTTAAACCTTTTGTAGAGGCACGAGTAAACCTGAGTGTGCAGGAGATCCTTCAAATGACGCCTTCTCATTATTCAGGGAACAT
Ebola IC '94            CAAACAGCGACTTACTAGTTAAACCCTTCATAGAAGCACGAGTAAATTTAAGCGTACAGGAAATTCTCCAAATGACACCTTCTCATTACTCCGGCAACAT
Ebola Zaire '76         CGAACAGTGACTTGCTAATAAAACCATTTTTGGAAGCACGAGTAAATTTAAGTGTTCAAGAAATACTTCAAATGACCCCTTCACATTACTCAGGAAATAT 15510     15520     15530     15540     15550     15560     15570     15580     15590     15600
                        ....|....|....|....|....|....|....|....|....|....|....|....|....|....|....|....|....|....|....|....|
Ebola Bundibugyo '07    CGTACATCGGTATAATGACCAATACAGCCCTCATTCTTTCATGGCAAATAGAATGAGTAATTCCGCGACGAGATTGGTGGTGTCGACAAATACTCTCGGG
Ebola IC '94            TGTGCATCGATATAATGATCAATATAGTCCACACTCATTTATGGCAAATAGGATGAGTAATTCTGCTACTAGGTTAGTTGTTTCGACAAACACTCTTGGA
Ebola Zaire '76         TGTTCACAGGTACAACGATCAATACAGTCCTCATTCTTTCATGGCCAATCGTATGAGTAATTCAGCAACGCGATTGATTGTTTCTACAAACACTTTAGGT
```

```
                             17110     17120     17130     17140     17150     17160     17170     17180     17190     17200
                         ....|....|....|....|....|....|....|....|....|....|....|....|....|....|....|....|....|....|....|....|
Ebola Bundibugyo '07     GATACCACTGTATACTGTCGCTTTACAGGGGTTGTATCTTCAATGCATTATAAGCTTGATGAGGTTCTCTGGGAATTCGATAGTTTCAAAACTGCTGTGA
Ebola IC '94             GACACCACAATATATTGCCGCTTCACGGGAATAGTTTCTTCAATGCACTATAAGCTCGATGAAGTCCTTTGGGAATTTGATAATTTTAAGTCTGCTATAA
Ebola Zaire '76          GATACCACAGTTTATTGTAGATTTACCGGTATAGTCTCGTCCATGCATTACAAACTTGATGAGGTCCTTTGGGAAATAGAGAGTTTCAAGTCGGCTGTGA 17210     17220     17230     17240     17250     17260     17270     17280     17290     17300
                         ....|....|....|....|....|....|....|....|....|....|....|....|....|....|....|....|....|....|....|....|
Ebola Bundibugyo '07     CTCTAGCTGAAGGAGAAGGGTCAGGTGCCTTATTACTACTACAAAAATATAAGGTCAGAACAATCTTTTTTAACACTTTAGCTACAGAGCATAGCATCGA
Ebola IC '94             CACTTGCCGAAGGTGAAGGTTCGGGTGCATTACTCTTATTACAAAAATATAAAGTAGAAACCTTGTTTTTTAATACACTAGCCACAGAACACAGCATTGA
Ebola Zaire '76          CGCTAGCAGAGGGAGAAGGTGCTGGTGCCTTACTATTGATTCAGAAATACCAAGTTAAGACCTTATTTTTCAACACGCTAGCTACTGAGTCCAGTATAGA 17310     17320     17330     17340     17350     17360     17370     17380     17390     17400
                         ....|....|....|....|....|....|....|....|....|....|....|....|....|....|....|....|....|....|....|....|
Ebola Bundibugyo '07     GGCAGAAATAGTTTCTGGGACAACCACACCTCGAATGCTCCTTCCTGTAATGGCCAAACTTCATGATGATCAAATAAATGTAATATTAAACAATTCTGCT
Ebola IC '94             AGCAGAAATTATTTCTGGAATAACTACACCAAGAATGCTTCTCCCTATTATGTCTAGGTTCCATGGTGGACAAATAAAAGTCACTTTAAACAATTCTGCA
Ebola Zaire '76          GTCAGAAATAGTATCAGGAATGACTACTCCTAGGATGCTTCTACCTGTTATGTCAAAATTCCATAATGACCAAATTGAGATTATTCTTAACAACTCAGCA 17410     17420     17430     17440     17450     17460     17470     17480     17490     17500
                         ....|....|....|....|....|....|....|....|....|....|....|....|....|....|....|....|....|....|....|....|
Ebola Bundibugyo '07     AGCCAGGTTACTGATATCACTAACCCTGCATGGTTCACTGACCAGAAATCTAGAATCCCCACACAAGTTGAGATTATGACTATGGATGCTGAAACGACAG
Ebola IC '94             AGCCAGATTACCGATATTACTAATCCAAGTTGGTTGGCAGACCAAAAATCTAGGATCCCTAAGCAAGTAGAGATTATAACCATGGATGCTGAAACAACAG
Ebola Zaire '76          AGCCAAATAACAGACATAACAAATCCTACTTGGTTTAAAGACCAAAGAGCAAGGCTACCTAAGCAAGTCGAGGTTATAACCATGGATGCAGAGACAACAG 17510     17520     17530     17540     17550     17560     17570     17580     17590     17600
                         ....|....|....|....|....|....|....|....|....|....|....|....|....|....|....|....|....|....|....|....|
Ebola Bundibugyo '07     AAAATATTAATCGGTCAAAATTATATGAGGCTATTCAGCAATTAATTGTTTCACACATTGATACAAGGGTGCTAAAGATTGTTATTATAAAGGTTTTTTT
Ebola IC '94             AAAACATTAATCGGTCAAAATTGTACGAAGCAGTCCAACAGCTGATTGTCTCACATATTGATCCGAATGCACTCAAAGTTGTGGTTCTTAAAGTTTTCTT
Ebola Zaire '76          AGAATATAAACAGATCGAAATTGTACGAAGCTGTATATAAATTGATCTTACACCATATTGATCCTAGCGTATTGAAAGCAGTGGTCCTTAAAGTCTTTCT 17610     17620     17630     17640     17650     17660     17670     17680     17690     17700
                         ....|....|....|....|....|....|....|....|....|....|....|....|....|....|....|....|....|....|....|....|
Ebola Bundibugyo '07     AAGTGATATTGAAGGTCTCCTGTGGCTTAATGACCATCTTGCCCCTTTATTCGGATCCGGCTATTTAATTAAACCTATTACTTCGAGTCCAAAGTCAAGC
Ebola IC '94             AAGTGACATTGATGGAATCCTATGGCTGAATGATAACCTTACCCCTTTGTTTGGGCTGGGTTACTTGATCAAGCCGATCACCTCTAGCCCAAAATCTAGT
Ebola Zaire '76          AAGTGATACTGAGGGTATGTTATGGCTAAATGATAATTTAGCCCCGTTTTTTGCCACTGGTTATTTAATTAAGCCAATAACGTCAAGTGCTAGATCTAGT 17710     17720     17730     17740     17750     17760     17770     17780     17790     17800
                         ....|....|....|....|....|....|....|....|....|....|....|....|....|....|....|....|....|....|....|....|
Ebola Bundibugyo '07     GAATGGTACTTATGTCTTTCAAATTTCCTTTCAGCCTCTCGACGACGGCCTCATCAGGGTCATGCTACCTGTATGCAAGTCATCCAAACAGCGCTACGAC
Ebola IC '94             GAGTGGTACCTATGTCTCTCAAACCTTCTTTCAACTTCAAGACGATTACCTCATCAGAGTCATACTACTTGCATGCATGTTATTCAAACAGCACTCCAGC
Ebola Zaire '76          GAGTGGTATCTTTGTCTGACGAACTTCTTATCAACTACACGTAAGATGCCACACCAAAACCATCTCAGTTGTAAACAGGTAATACTTACGGCATTGCAAC 17810     17820     17830     17840     17850     17860     17870     17880     17890     17900
                         ....|....|....|....|....|....|....|....|....|....|....|....|....|....|....|....|....|....|....|....|
Ebola Bundibugyo '07     TCCAAGTTCAAAGGAGTTCATACTGGCTTAGCCATTTAGTGCAATATGCTGATATTAATTTGCACTTGAGTTATGTTAATTTGGGTTTCCCTTCATTGGA
Ebola IC '94             TACAAATTCAGAGGAGCTCATATTGGCTTAGCCACCTTGTCCAGTATGCCAATCATAATTTGCATTTAGATTATATTAATCTCGGTTTCCCTTCATTGGA
Ebola Zaire '76          TGCAAATTCAACGAAGCCCATACTGGCTAAGTCATTTAACTCAGTATGCTGACTGTGAGTTACATTTAAGTTATATCCGCCTTGGTTTTCCATCATTAGA
```

FIG. 2X

```
                       17910     17920     17930     17940     17950     17960     17970     17980     17990     18000
                         ....|....|....|....|....|....|....|....|....|....|....|....|....|....|....|....|....|....|....|....|
Ebola Bundibugyo '07     AAAGGTTCTTTACCATCGATATAACCTAGTTGATTCACGGAAGGGTCCACTGGTCTCGATCCTTTACCATTTAACACACTTGCAAGCAGAGATTAGAGAA
Ebola IC '94             GAGGGTTTTATACCATAGATACAAGTTAGTCGATTCTCAG

FIG. 2Z

SEQUENCE LISTING

```
<160> NUMBER OF SEQ ID NOS: 59

<210> SEQ ID NO 1
<211> LENGTH: 18940
<212> TYPE: DNA
<213> ORGANISM: Bundibugyo ebolavirus
<220> FEATURE:
<221> NAME/KEY: misc_feature
<223> OTHER INFORMATION: Full viral sequence

<400> SEQUENCE: 1
cggacacaca aaaagaatga aggattttga atctttattg tgtgcgagta actacgagga    60
agattaaaga ttttcctctc attgaaattg aaattgagat tctaatctcg acggatcgat   120
ccccaatacc aacactgaga attggcctga agaagtcatc tgctccttgg caaaaccaag   180
agcaggccca aagggccatt aggccacatc tgctgagcct gcagaacacg caggacttac   240
ttagcagaag agagcgcgtg ccgaaaccag ccaacaaatt gacacagctg ctcactctga   300
ccctgaattc ataaacaata ttaagttgac aacagagata ctaatccaat atttggatca   360
agaatcaaaa tagtgaaacg actgactatc cctccttaga attagcaaag atccttttgt   420
agactattgt gctacattct ctatccaaga cctcaaaatg gatcctcgtc caatcagaac   480
ctggatgatg cataacacat ctgaagttga agcagactac cataagattc taactgccgg   540
attgtccgtc cagcaaggca ttgtgagaca aagaatcatt cctgtttacc aaatctcaaa   600
cctggaggaa gtatgtcaac tcatcataca ggcattcgag gctggcgtcg acttccagga   660
tagtgcagat agcttttgt taatgctatg tctgcatcat gcctatcaag gggattataa   720 acaattttg gaaagtaatg cggtaaaata ccttgaaggt catggattcc gttttgagat   780
gaagaaaaag gaaggtgtca agcgcctgga ggaactactc cctgctgcct cgagtggaaa   840
gaacatcaag agaacattgg ctgcaatgcc cgaggaggaa acaacagaag caaatgctgg   900
```

```
acaatttctt tcatttgcta gtctgtttct cccaaaattg gttgtcggag aaaaggcctg    960
tctggagaag gttcaacgac aaatccaagt gcacgcagaa caaggtctga ttcaataccc   1020
gacatcttgg caatcggtgg gacatatgat ggtcatcttc agactaatgc gaaccaactt   1080
cctgattaag ttcctcctaa tacatcaagg aatgcatatg gttgcagggc atgatgctaa   1140
tgatgccgtc attgccaact ctgtagctca agctcgtttc tccggattgt tgatagtcaa   1200
aacagtgctt gatcatatcc tccaaaaaac agagcacgga gttcgcctgc atcccttggc   1260
gcgaacagcc aaagtcaaaa atgaggtgag ctcttttaag gccgctttag cctcactagc   1320
acaacatgga gaatatgccc cgtttgctcg tctgctgaat ctatctgggg ttaataatct   1380
tgagcatggg cttttccctc aactttctgc aattgctttg ggagtagcaa ctgcacatgg   1440
gagcactctg gctggagtca atgtaggaga gcaataccaa caactgcgag aagcagccac   1500
tgaggccgaa aagcagttgc agaaatatgc tgaatctcgt gaacttgatc acctaggtct   1560
tgatgatcag gaaagaaaaa tcctaaaaga cttccatcag aaaaagaatg agatcagctt   1620
ccagcagacg acagccatgg tcacactgcg gaaagagaga ttggccaaat tgaccgaagc   1680
tattacttcc acctctatcc tcaaaacagg aaggcggtat gatgatgaca atgcatacc    1740
ctttccaggg ccaatcaatg ataacgagaa ctctggtcag aacgatgacg atccaacaga   1800
ctcccaggat accacaatcc cggatgtaat aatcgatcca aacgatggtg ggtataataa   1860
ttacagcgat tatgcaaatg atgctgcaag tgctcctgat gacctagttc tttttgacct   1920
tgaggacgag gatgatgctg ataacccggc tcaaaacacg ccagaaaaaa atgatagacc   1980
agcaacaaca aagctgagaa atggacagga ccaggatgga aaccaaggcg aaactgcatc   2040
cccacgggta gcccccaacc aatacagaga caagccaatg ccacaagtac aggacagatc   2100
cgaaaatcat gaccaaaccc ttcaaacaca gtccagggtt ttgactccta tcagcgagga   2160
agcagacccc agcgaccaca acgatggtga caatgaaagc attcctcccc tggaatcaga   2220
cgacgagggt agcactgata ctactgcagc agaaacaaag cctgccactg cacctcccgc   2280
tcccgtctac cgaagtatct ccgtagatga ttctgtcccc tcagagaaca ttcccgcaca   2340
gtccaatcaa acgaacaatg aggacaatgt caggaacaat gctcagtcgg agcaatccat   2400
tgcagaaatg tatcaacata tcttgaaaac acaaggacct tttgatgcca tcctttacta   2460
ccatatgatg aaagaagagc ccatcatttt cagcactagt gatgggaagg agtatacata   2520
tccagactct cttgaagatg agtatccacc ctggctcagc gagaaggaag ccatgaacga   2580
agacaataga ttcataacca tggatggtca gcagttttac tggcctgtga tgaatcatag   2640
aaataaattc atggcaatcc tccagcatca caggtgatcc gacctctaaa actgagctcc   2700
taactacaag ctaccccatc actctgccgg aatgccagaa cctccctcca aaacagctcc   2760
acatcgagaa cctccgacgc ggtacacagg caagacaggc aacctaatga tgttcctgtt   2820
cacccacaac cgcaaccaac acttgatcga cttccaagac aactacaacc cccttagcca   2880
actccaccac agaagcacca cccataaca acaacccccaa accaacaaca ctgcatgtaa   2940
gtattgtctc acccccaagat gatccctgga caccaacaac cccctaacct ccccaagttg   3000
tcattaagaa aaaatatatg atgaagatta aaaccttcat cagagctatt tcttctacgc   3060
ttggttagga ccagtattca caaactattt tacaatccct acccaatatg acctctaaca   3120
gagcaagggt gacttacaac ccaccaccaa caaccacagg cacacgatcg tgtgggccgg   3180
aactttccgg gtggatctct gagcaattga tgacaggcaa gattccgatt accgatatct   3240
```

-continued

```
tcaatgaaat tgaaacctta cctagtataa gtccctcgat ccactccaaa atcaaaaccc   3300
caagtgttca aacacgcagt gtccagaccc aaactgaccc aaattgtaat catgattttg   3360
cagaggttgt gaaaatgcta acatctctaa cccttgtcgt acaaaaacaa acccttgcaa   3420
ctgaatcact tgagcaacgc attactgacc tggaaggtag cctgaaacca gtgtctgaga   3480
tcaccaagat tgtttctgca ctaaatagat cctgtgcaga gatggtggcc aaatatgatc   3540
ttctagtaat gacgactggt cgtgcaactg ccactgctgc agctactgaa gcatactggg   3600
cagaacatgg acgtcctcca ccggggccct cattgtacga ggaggatgca atcaggacta   3660
aaattggaaa acaaggggat atggtaccca aggaagtgca agaggccttc cgtaatctgg   3720
atagtactgc ccttctaacg gaagagaatt ttgggaaacc agacatatcc gcaaaagact   3780
tgcgcaatat catgtatgat cacctcccag gttttggcac agcatttcat caactagtgc   3840
aagttatctg caagttaggg aaggacaatt cctcacttga tgtaattcat gcagaatttc   3900
aggccagcct tgctgaagga gactctcctc agtgtgccct gattcagata accaaacgga   3960
ttcctatttt ccaagatgca gcaccacccg taatccatat tcggtcacgc ggtgatatac   4020
caaaggcgtg tcaaaagagc ctccgccctg ttccaccatc accaaagatt gatagggtt    4080
gggtatgcat attccagcta caagacggaa aaacactcgg actcaaaatc taaggtgaac   4140
aattgcgcaa cctccacagt cgcctatatt gcttccttcc ggaatcaggg tatgatcgcg   4200
taaaaaataa gcttccaaca tattgataca cgatccatat ccataatgcc atctccagga   4260
atatgagaac gcaaggccat atcaggaccc gatctcaatt ccaatgcaac ctactgttaa   4320
gaataaaata accaatgtcc tctagcctta tatgttctca aaaatacaag tgatgaagat   4380
taagaaaaag catcctttac ttgagaggag ctaattcttt atacttcatc taatctttaa   4440
gtaagttgat cactaccacc atgaggaggg caattctacc tactgcaccg ccagaataca   4500
tagaggctgt ctacccaatg agaacggtta gtactagtat caacagtact gccagtggtc   4560
cgaactttcc agcaccggat gtaatgatga gtgatacacc ctccaactca ctccgaccaa   4620
ttgctgatga taacatcgat catccaagtc atacaccaac cagtgtttca tcagccttta   4680
tactcgaggc aatggtgaat gtgatatcgg ggccgaaggt actaatgaag caaattccta   4740
tatggctccc cttgggtgtt gctgatcaaa aaacatatag ttttgactca actacagctg   4800
caattatgct cgcatcgtac accatcactc actttggcaa aacctccaat ccgcttgtga   4860
gaatcaatcg acttggtcct gggatccccg atcacccgtt gcggcttcta agaataggaa   4920
atcaagcctt cttgcaagag tttgtgctgc ctccagttca attgccgcag tatttcactt   4980
ttgacctgac ggctctaaag ctgatcactc aacctctccc ggcagcaacc tggacggatg   5040
atactccgac cggtcctaca ggaatacttc gtcctggaat ttcctttcat cccaaactga   5100
gacctatcct attgccaggg aagaccggga aaagaggatc cagctccgat cttacttctc   5160
ctgataaaat acaagcaata atgaactttc tccaagacct caaactcgtg ccgattgatc   5220
cagccaagaa cattatgggt attgaagtgc cggaactctt ggtccacaga ctaactggaa   5280
agaaaatcac aacaaaaaat ggtcaaccaa taattcctat tcttctacca aagtatattg   5340
gcatggatcc catttctcag ggagacctca caatggtcat cactcaagac tgtgacactt   5400
gccattctcc tgctagtctt cctccagtca gcgagaaatg agcatgaagt ccgaggctgc   5460
ccggcccaca cgacccccag ggccttcgtc cggctaccga accaaccatc cgaccttcat   5520
caaaaccaaa aaataccgcc acgcgaaagc taaaatgcag gaccacaatc caaccagcaa   5580
caccatccat acacaggtat caattgggct gccgcagcat atagacccaa tagcaagctg   5640
```

```
ctgtccagaa aatagttccg gaaagtaact caaccatcgc aagcccaatg cagcttttcag    5700 aaaatccgcca gcaacccaac tccactgtac ccccaatatt aacctgaatc gactaaccgc    5760
actttaattt gaagtacatt tgttcaatgg gttcattatt aacagtgttg cttttagatt    5820
gtacctttgc tcacagatag taaattgtta tggtatcaaa tcttattaag aaaaagaaca    5880
cgatgaagat taacgcgacc tagagcgctg ccttcatctc atcaatttaa cttgtcaata    5940
gagcaaccta gtttgtgatt actcatcttc cgtagttgac aaaactttg ctggttaatt    6000 gtaaatatac cacagtcatc atggttacat caggaattct acaattgccc cgtgaacgct    6060
tcagaaaaac atcattttt gtttgggtaa taatcctatt tcacaaagtt ttccctatcc    6120
cattgggcgt agttcacaac aacactctcc aggtaagtga tatagataaa ttggtgtgcc    6180
gggataaact ttcctccaca agtcagctga aatcggtcgg gcttaatcta aaggtaatg    6240 gagttgccac agatgtacca acagcaacga agagatgggg attccgagct ggtgttccac    6300
ccaaagtggt gaactacgaa gctggggagt gggctgaaaa ctgctacaac ctggacatca    6360
agaaagcaga tggtagcgaa tgcctacctg aagcccctga gggtgtaaga ggcttccctc    6420
gctgccgtta tgtgcacaag gtttctggaa cagggccgtg ccctgaaggt tacgctttcc    6480
acaaagaagg cgcttcttc ctgtatgatc gactggcatc aacaatcatc tatcgaagca    6540
ccacgttttc agaaggtgtt gtggctttct tgatcctccc cgaaactaaa aaggactttt    6600
tccaatcgcc accactacat gaaccggcca atatgacaac agacccatcc agctactacc    6660
acacagtcac acttaattat gtggctgaca atttttgggac caatatgact aactttctgt    6720
ttcaagtgga tcatctaact tatgtgcaac ttgaaccaag attcacacca caatttcttg    6780
tccaactcaa tgagaccatt tatactaatg ggcgtcgcag caacaccaca ggaacactaa    6840
tttggaaagt aaatcctact gttgacaccg gcgtaggtga atgggccttc tgggaaaata    6900
aaaaaacttc acaaaaaccc tttcaagtga agagctgtct gtcatatttg taccaagagc    6960
ccaggatcca ggcagcaacc agaagacgaa ggtcactccc accagcttcg ccaacaacca    7020
aacctccaag aaccacgaag acttggttcc agaggatccc gcttcagtgg ttcaagtgcg    7080
agacctccag agggaaaaca cagtgccgac cccaccccca gacacagtcc ccacaactct    7140
gatccccgac acaatggagg aacaaaaccac cagccactac gaaccaccaa acatttccag    7200
aaaccatcaa gagaggaaca acaccgcaca ccccgaaact ctcgccaaca atcccccaga    7260
caacacaacc ccgtcgacac cacctcaaga cggtgagcgg acaagttccc acacaacacc    7320 ctcccccgc ccagtcccaa ccagcacaat ccatcccacc acacgagaga ctcacattcc    7380
caccacaatg acaacaagcc atgacaccga cagcaatcga cccaacccaa ttgacatcag    7440
cgagtctaca gagccaggac cactcaccaa caccacaaga ggggctgcaa atctgctgac    7500
aggctcaaga agaacccgaa gggaaatcac cctgagaaca caagccaaat gcaacccaaa    7560
cctacactat tggacaaccc aagatgaagg ggctgccatt ggtttagcct ggataccta    7620 cttcgggccc gcagcagagg gaatttatac ggaagggata atgcacaatc aaaatgggct    7680
aatttgcggg ttgaggcagc tagcaaatga gacgactcaa gccctacagt tattcttgcg    7740
tgctaccacg gaattgcgca cttttctctat attgaatcga aaagccatcg acttttacat    7800
ccaaagatgg ggaggaacgt gccacatctt aggcccagat tgctgtattg agccccatga    7860
ttggactaag aacattactg acaaaatagt tcaaatcatt catgatttca ttgataaacc    7920
tctaccagat caaacagata atgacaattg gtggacaggg tggaggcaat gggttcctgc    7980
```

```
cgggatcggg atcacggggg taataatcgc agttatagca ctgctgtgta tttgcaaatt    8040
tctactctaa tctagtccga ctctgtacca gcataatggc ctctaaaata agcttttgct    8100
tctgcttcct atagttaata catttcagca aaaatcaact attaagtcaa aagaagatcc    8160
ctctaataat cctaattacc ttcaaaaatc tagaacttta ttaattctca gggtatttag    8220
aacagccaga tgacttgact aagtttgtac tgtaataaaa agatacttga tgaagattaa    8280
gaaaaagaca gtcttgtgat tgtcactaat cttcatctca aaacatatta ttttaccaga    8340
agctactata gcctacctcc ttgacacata gcaaaccttt ctcatgttga taattgtttg    8400
cctgctattt acatatttac taacttacaa aattatcttg gggatttctc tgaacatata    8460
atcagaattg gcatttaaaa cacaagttag tcctaatgga ctcatttcat gagagagggc    8520
gtagcagaac tattcgacag agtgcaagag atgggccgag tcatcaagta agaacaagat    8580
catcctccag agacagccac cgcagcgaat atcatacacc taggagctct tcccaagttc    8640
gagtcccgac tgtgtttcat cggaagcgta ctgattcttt gacagttcca ccagcaccaa    8700
aggacatatg tcctacctta aggaaaggat ttttgtgtga cagcaatttt tgtaaaaagg    8760
accatcaact agaaagttta acagataggg agctgctttt gctgattgca cggaaaacct    8820
gcggctccct tgaacaacaa ttgaacatca ctgctcctaa agatacacga ttagcaaatc    8880
caattgcaga tgatttccaa caaaaagacg gcccaaaaat tacactattg acacttttgg    8940
agactgcgga gtattggtca aaacaagata tcaagggcat tgatgactca agactaagag    9000
cattactaac cctttgtgcc gtcatgacga ggaaattctc aaaatcccag cttagtctat    9060
tgtgtgagag tcatctacga cgagaagggc taggacagga tcaatcagaa tctgttcttg    9120
aagtgtatca gcgcttacat agcgacaaag gcggaaattt tgaggcagcc ctatggcaac    9180
aatgggaccg acagtccttg atcatgttta taacagcatt tcttaatatt gctttacaat    9240
taccctgtga agttcatct gttgttattt caggattaag gctgctagtg cctcaatcag    9300
aagataccga gacctcaacc tacaccgaga acgtgcatg gtcagaggaa ggtggccccc    9360
attaacatct tccacagtcg aatctaccat aatttcccta ttcaacgcag ataagaatca    9420
gtactaaacc acaagtgcaa aaattaacaa aacaccagca taagtgaaat cctgtctgtg    9480
attagcaaca cgaatgatct tcaatcctgt tgcaattcgc cagtgataat tgtattcaca    9540
ttgtggccac aatatactgt cttttcccat tgaaaaataa ggctgaatct attacgctac    9600
acaaacttac aggattagca ccacgacggc tcaatactat acctattggt cacggctcga    9660
tgtgttaatc acttatattg tattcatttg aaattactca ttaggcaaat actttgatta    9720
agaaaaaata attggaaaac cagaaaatcc ctaggtattt aaattcctat ctccggagat    9780
ccgagataat taatcaagca atgagggaac aatggtgaac aacaacatat tgttgccccc    9840
tttagattgg tcagttccaa aaacaagtga tgaagattaa tgcagatgtc caaggaacac    9900
atatttgtga tttaaacgtt ccagttagac tctgttcaag gatcttcatc ttttgtagct    9960
ccactctgag tcacaacata attgagtttt tgctcagaac agttatcagg attaaattct   10020
ctcaaataac tgaaactact agcatcactc tcaatttcat tacttacgac aatcattatc   10080
ttaataatat ttctctaaat tactgactta attagcttgt aatcagataa tatcgaaacc   10140
aatttatcat aaggcataat ttgtataagt gatttaggat ttaccccaga agtgaaataa   10200
ttcttagaat aaaagaccga ctagaatatc cttaaggctg tctaacgtgc cacacagcta   10260
gggttagcct gacatctgga acaagatcga tactaatata gggatttgtt tcatactagc   10320
tctctgcaaa cacaatggct aaggcaacag gtaggtacaa cttggtttca cctaaaaagg   10380
```

```
acctcgagag ggggcttgtt ttgagtgatt tgtgcacgtt tttagttgat cagactatcc    10440
aggggtggcg ggtgacttgg gttgggattg aatttgacat cgcccagaaa gggatggctc    10500
tactgcatcg gttaaaaact gctgacttcg ctcctgcatg gtcgatgaca aggaatttat    10560
ttcctcattt atttcaaaat tcaaattcta ctattgagtc tccctctgg gcattacgag     10620 tgattctggc agctggtatt caagaccagt taattgacca atccttggta gaaccgttgg    10680
ccggagccct gagcttagtc tccgattggc ttcttacaac aaacacaaac cattttcaaa    10740
tgcgcacgca gcacgctaaa gagcaactga gcttgaagat gctatcatta gtgcgctcta    10800
atatcttgaa attcatcagt caattggacg cactacatgt cgtgaactac aatggactct    10860
tgagcagtat cgaaattggc actagaaatc ataccattat catcacaaga accaacatgg    10920
gtttcctggt agaattacag gagcctgata aatctgccat gaatcaaaag aaaccaggac    10980
cagtcaagtt ctccctcctg catgaatcaa ccttcaaggc tctaatcaaa aaacccgcaa    11040
ctaagatgca ggccttgatt ctggaattta acagctccct ggcaatatag tccaacgcta    11100
ccaaccatca ttttttgtaa ctgcatctct tttatttcct ttctaacttg atacaattat    11160
aatcaagatc cctaatccct tttgacgaag tgggctaatt tttgctcatt ctaataataa    11220
atcataacct gaataaaaga caccacaata ttataaccca ataacaccta gagaatttct    11280
gaattgctaa agattatata ctcgcactaa gagacaagtt aatcaatctt tacttaataa    11340
tatactaaat gctagatagc tctggctaac taacctgagt tgtggattac tccttttaaa    11400
agtctatcaa tttaagctta tcactaatat taaggaggac ttttaaata agagcaagtg     11460 ttatgtagtc ttactaagaa tgatttgagg aagattaaga aaaagtgctt gtggggtctt    11520
tccgttgtag aggacacacg agcaaacttc ttcctctaat tttaatatgg caactcaaca    11580
tacacaatat ccagatgcaa gattatcttc acccattgtc ttagatcaat gtgatcttgt    11640
cacccgtgct tgcggtctgt attcttcata ctcattaaat cctcagttga aaaattgtag    11700
actaccaaaa catatttacc gcctcaaatt tgatgctacg gttacaaaat ttttaagcga    11760
tgttccaata gttacattgc cgatagatta cttgacccct ttacttttac gaactttatc    11820
cggggagggc ttatgccctg tcgaaccaaa gtgcagccaa ttcttagatg aaatagtaag    11880
ttatgttttg caggatgcac gttttttaag atactatttt aggcatgttg gagtacacga    11940
tgacaatgtt ggaaaaaatt ttgagccaaa gattaaggct ttgatttatg ataatgaatt    12000
tctgcaacaa ttgttttatt ggtacgattt agcaatccta acgcgtagag ggcgcctgaa    12060
tcgagggaat aaccgttcaa catggtttgc aaatgacgat ttaatagaca ttctcgggta    12120
cggtgattat atttctgga aataccgtt gtcattgttg tcactcaaca cagaggggat       12180
tcctcatgca gctaaggact ggtatcacgc atcaatcttc aaagaagcgg ttcaaggtca    12240
cacacatatc gtgtcagttt ccactgcaga tgtttttaatt atgtgtaagg acatcataac    12300
ctgtcgtttc ataccacac tcattgcagc attggcaaat ttagaagatt ctatctgttc      12360
tgactatcca caacctgaaa caatctctaa tctgtataag gcaggggatt acttaatctc    12420
gatactgggt tcagaaggtt ataaggtcat aaagttttta gaaccactat gtttagctaa    12480
gatccaattg tgctcaaatt acactgagag gaaagggaga ttccttactc aaatgcattt    12540
ggccgttaat cacacacttg aagaacttat tgagggccgg ggattgaagt cacaacaaga    12600
ctggaagatg agggaatttc accgaatctt agtaaattta aagtcaacac cacaacaact    12660
ctgtgaattg ttttcagtgc aaaagcattg ggggcatcct gtgctacata gcgagaaggc    12720
```

```
tattcagaaa gtaaagaaac atgcaaccgt aataaaagca ttgcgtcccg taatcatctt   12780
tgagacatat tgtgtgttca agtacagcat tgccaaacat tattttgata gccaagggtc   12840
atggtatagt gtaatctcag ataaacatct aacaccaggt ttacactctt acattaagag   12900
gaaccaattt ccgccactgc ctatgattaa agacttattg tgggaattct atcaccttga   12960
tcatcctccc ttattttcca ccaagattat tagtgacttg agtattttca ttaaggatcg   13020
cgctaccgca gtggaaaaaa catgttggga tgcagttttc gagcctaatg ttcttggata   13080
tagtcctcca aacaagttct caactaagag ggttcctgaa cagtttcttg aacaagaaaa   13140
tttctcgatt gatagtgttc tcacttatgc ccagcgcctg gattatctac ttccacaata   13200
ccggaatttt tctttctcac ttaaggaaaa agaattaaat gtaggacgag cttttggtaa   13260
gctaccttat cctacacgta atgttcaaac tttatgtgaa gccttattgg cagatggatt   13320
agctaaagcc tttcctagta acatgatggt tgtaacagag cgtgagcaga aggaaagcct   13380
cttgcaccag gcgtcgtggc accacacaag tgacgatttc ggtgagaatg ccactgttag   13440
aggcagcagt tttgttaccg acctagaaaa atacaacttg gcatttagat atgagtttac   13500
agctccattt attgaatact gtaatcgatg ttatggtgta aaaaatttat tcaattggat   13560
gcattatacg ataccgcaat gttatataca tgtaagtgat tattataatc cccctcatgg   13620
agtttcgcta gaaaatcggg aagatccccc ggaaggccct agctcttacc gtggtcatct   13680
tgggggaatt gagggactcc aacagaaact ctggaccagc attttcatgtg cacaaatctc   13740
attagttgag atcaagactg gtttcaaatt gagatctgcg gtaatgggtg ataatcaatg   13800
catcacagtt cttttccgtat ttcctctaga gacagattcc aatgagcaag agcatagctc   13860
cgaggacaat gctgctcgcg tagcagccag tttagccaaa gtcacgagtg cctgtggcat   13920
cttcctaaaa ccagatgaga ctttttgtgca ttcaggctttt attatttcg gtaagaagca   13980
atatttaaat ggcgttcaat tgccacaatc actcaagact gctaccagga ttgctcccctt   14040
gtcagatgca atctttgatg accttcaggg aactctggct agtataggaa cggcatttga   14100
gagatctata tccgagacta gacatgtata cccttgccgg gtggttgccg cattccatac   14160
attcttctcc gttaggatcc tccaatacca ccaccttggt ttcaacaaag gaaccgatct   14220
aggtcaacta tcactaagca aaccgttgga tttcggaact atcactcttg ctttagcggt   14280
acctcaagtt ctaggaggtt tatcgttttt aaacccagag aaatgttttt atcgcaacct   14340
tggagacccc gtgacctccg gcctattcca acttaggact tacctgcaaa tgatcaacat   14400
ggacgactta tttctacctt taattgccaa gaaccccggg aactgtagtg caattgactt   14460
tgtactcaac ccaagcggat tgaatgtccc tgggtcacaa gacctaacat ctttttttacg   14520
tcagatagtg cgtagaacaa tcacattgag tgcaaaaaat aagctaataa acacattgtt   14580
tcactcctca gccgatttag aagatgagat ggtatgtaaa tggctacttt cttcaacacc   14640
tgtaatgagt cggtttgctg ctgatatatt ctctcgtact ccgagtggga agcgcttgca   14700
gatcctaggt tatttagaag ggactagaac cttgctagcc tccaaagtca tcaataacaa   14760
tgcagagact cctatttag ataggttgag gaaaatcaca ctgcagagat ggagtttgtg   14820
gtttagctac ctagaccact gtgatcaggt tctagcagat gctttaataa agtttcttg   14880
tacagttgat ttggcgcaaa ttttacgtga atatacctgg gcacacatac tagagggaag   14940
acagctcatt ggtgcaacac ttccttgcat gttagaacaa tttaatgtgt tttggctcaa   15000
atcgtacgaa caatgcccta aatgtgcaaa atctagaaat ccaaaggag agccatttgt   15060
gtcaattgca attaagaaac aagttgtgag tgcatggccg aatcagtcac ggttaaattg   15120
```

```
gaccattggg gacggtgtac cttacatcgg gtctcgaaca gaggacaaga ttgggcagcc   15180
agcaatcaag cctaagtgtc cctctgctgc cttacgtgaa gcaatagagt tgacatctag   15240
actaacatgg gttacccaag gtggtgccaa tagtgatttg ctagttaaac cttttgtaga   15300
ggcacgagta aacctgagtg tgcaggagat ccttcaaatg acgccttctc attattcagg   15360
gaacatcgta catcggtata atgaccaata cagccctcat tctttcatgg caaatagaat   15420
gagtaattcc gcgacgagat tggtggtgtc gacaaatact ctcggggagt tctcaggtgg   15480
ggggcaatca gcaagggaca gcaatatcat cttcaaaat gtaatcaatt tttcggttgc    15540
cctatttgat ttacgatttc ggaacaccga aacatcctcc attcagcata atcgtgccca   15600
tctccatctt tcacagtgtt gcacacggga agtcccagct caatacctaa cctacacgtc   15660
tacgctttcc ttggatctca caaggtaccg agagaatgag ttaatttatg ataacaatcc   15720
gttaaaaggt ggacttaatt gcaacctatc ctttgataat ccacttttca agggccaaag   15780
gctcaatatc atagaggagg atttgattag atttcctcat ctatctgggt gggaacttgc   15840
gaaaaccatc attcagtcca ttatctcaga cagcaataac tcatccacag accccattag   15900
cagtggagaa acacgatcat tcacaactca ctttctcaca tatcctaagg ttgggctcct   15960
ctatagtttc ggcgccatcg tgagttatta cttagggaat accattatta ggaccaaaaa   16020
gctagacctc agtcatttta tgtattactt aacaactcaa atccataatt tgccacatcg   16080
ctcgttgagg atacttaagc ccacctttaa acatgttagt gtgatatcaa gactaatgag   16140
tattgatcct catttttcaa tctacatcgg gggtacggca ggtgatcgag gctttcgga   16200 tgctaccaga ctattccttc gagtggccat ttcttccttc cttcaattta tcaaaaaatg   16260
gatcgtggaa tacaagacag ctattcctct gtgggttata tacccttggg agggacaaaa   16320
tccagatcca attaatagct ttctacatct gattatagcc ttactgcaaa atgaatcccc   16380
tcaaaacaac atccaattcc aagaagacag aaataatcaa cagttgtccg ataatctagt   16440
ttacatgtgc aagagcactg ccagtaattt cttccatgca tcacttgcct attggaggag   16500
ccggcacaaa ggacggccca aaaatcgatc gaccgaagaa cagacagtta aacccatacc   16560
atatgataat tttcattctg ttaaatgtgc ctcaaaccca ccaagcatcc ccaaatctaa   16620
gtcaggaact caaggttcaa gcgcatttt tgagaaactt gaatatgata agaaagaga    16680 attgccaaca gcttccacac cagccgaaca atccaagacc tatatcaagg ccctatccag   16740
ccgaatttat catggtaaaa caccatccaa tgccgcaaaa gatgattcaa caacctccaa   16800
gggctgcgat tccaaagaag aaaatgccgt tcaagcttca caccgaattg tcctaccatt   16860
ttttacattg tcacagaacg actacagaac tccctcagct aaaaagtcag agtatataac   16920
tgaaatcacc aaactaattc gacaattaaa ggcaattcca gataccactg tatactgtcg   16980
ctttacaggg gttgtatctt caatgcatta aagcttgat gaggttctct gggaattcga    17040
tagtttcaaa actgctgtga ctctagctga aggagaaggg tcaggtgcct tattactact   17100
acaaaaatat aaggtcagaa caatcttttt taacactta gctacagagc atagcatcga    17160
ggcagaaata gtttctggga caaccacacc tcgaatgctc cttcctgtaa tggccaaact   17220
tcatgatgat caaataaatg taatattaaa caattctgct agccaggtta ctgatatcac   17280
taaccctgca tggttcactg accagaaatc tagaatcccc acacaagttg agattatgac   17340
tatggatgct gaaacgacag aaaatattaa tcggtcaaaa ttatatgagg ctattcagca   17400
attaattgtt tcacacattg atacaagggt gctaaagatt gttattataa aggttttttt   17460
```

```
aagtgatatt gaaggtctcc tgtggcttaa tgaccatctt gcccctttat tcggatccgg    17520
ctatttaatt aaacctatta cttcgagtcc aaagtcaagc gaatggtact tatgtctttc    17580
aaatttcctt tcagcctctc gacgacggcc tcatcagggt catgctacct gtatgcaagt    17640
catccaaaca gcgctacgac tccaagttca aaggagttca tactggctta gccatttagt    17700
gcaatatgct gatattaatt tgcacttgag ttatgttaat ttgggtttcc cttcattgga    17760
aaaggttctt taccatcgat ataacctagt tgattcacgg aagggtccac tggtctcgat    17820
cctttaccat ttaacacact tgcaagcaga gattagagaa ttagtgtgtg actataatca    17880
gcaacgacaa agtcgaaccc aaacatacca cttcatcaaa acgacaaagg gccggattac    17940
aaaattagtc aatgactacc ttaaatttta tctcgtagtg caagcactga agcataattg    18000
tctttggcag gaagaactca gaacacttcc tgacttaatc aatgtttgca atcgatttta    18060
ccatataagg gactgctcat gtgaagatcg attttttaatt caaactcttt acttaacccg    18120
tatgcaagac tcagaagcaa aattaatgga gagattaacc gggtttctag gattgtatcc    18180
taatggtatt aacgcttaag atcccctag aggcatcgca atatgactcc aaacattaaa    18240
tgatattgct gtcaatacat ctacctgacc gagagcaagg tttattataa aaaacctata    18300
cacatgactg caatgcgtaa tttataccga aacacagtga gggctgcaca tgcaggttcc    18360
tgttgagctt taaagatca tgcaatataa aatgatattt gtatactaat catgttagta    18420
ctaactaaca gtactcactg catatactct atcaattaag aaaaattact gtggtttatg    18480
catttaaatg acatcacaga tggatataat atagttaatt cttacctaaa tgttgagtta    18540
tagtaatttg aagttataat tatgattagt gcttatacta taaataatag ctataccaag    18600
tatacacaag aagttatgat tttgtattca aattatattc acaggaactt gtgattaata    18660 ataaagtct cagttgttgg ttgttgagtt gtaaaactcc cgttaaaaat ttattttcca    18720
cttataacta ataataatca tagatcagta tgagttgagg ctattcaaac cttagaaaaa    18780
ttgtgcgatg tttttacca tgtcaatctt gatttcaatg atattggagg gcttgtcgat    18840
aaattcagta attaacatta agtcagtgtg gaacctcatt ggatatttga tcgtacacaa    18900
aatatcttta caaaattgtt ttctcttttt tgtgtgtcca                          18940
```

<210> SEQ ID NO 2
<211> LENGTH: 2210
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus L viral protein

<400> SEQUENCE: 2

```
Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
            20                  25                  30

Ser Ser Tyr Ser Leu Asn Pro Gln Leu Lys Asn Cys Arg Leu Pro Lys
        35                  40                  45

His Ile Tyr Arg Leu Lys Phe Asp Ala Thr Val Thr Lys Phe Leu Ser
    50                  55                  60

Asp Val Pro Ile Val Thr Leu Pro Ile Asp Tyr Leu Thr Pro Leu Leu
65                  70                  75                  80

Leu Arg Thr Leu Ser Gly Glu Gly Leu Cys Pro Val Glu Pro Lys Cys
                85                  90                  95
```

-continued

```
Ser Gln Phe Leu Asp Glu Ile Val Ser Tyr Val Leu Gln Asp Ala Arg
                100                 105                 110

Phe Leu Arg Tyr Tyr Phe Arg His Val Gly Val His Asp Asp Asn Val
        115                 120                 125

Gly Lys Asn Phe Glu Pro Lys Ile Lys Ala Leu Ile Tyr Asp Asn Glu
    130                 135                 140

Phe Leu Gln Gln Leu Phe Tyr Trp Tyr Asp Leu Ala Ile Leu Thr Arg
145                 150                 155                 160

Arg Gly Arg Leu Asn Arg Gly Asn Asn Arg Ser Thr Trp Phe Ala Asn
                165                 170                 175

Asp Asp Leu Ile Asp Ile Leu Gly Tyr Gly Asp Tyr Ile Phe Trp Lys
            180                 185                 190

Ile Pro Leu Ser Leu Leu Ser Leu Asn Thr Glu Gly Ile Pro His Ala
        195                 200                 205

Ala Lys Asp Trp Tyr His Ala Ser Ile Phe Lys Glu Ala Val Gln Gly
    210                 215                 220

His Thr His Ile Val Ser Val Ser Thr Ala Asp Val Leu Ile Met Cys
225                 230                 235                 240

Lys Asp Ile Ile Thr Cys Arg Phe Asn Thr Thr Leu Ile Ala Ala Leu
                245                 250                 255

Ala Asn Leu Glu Asp Ser Ile Cys Ser Asp Tyr Pro Gln Pro Glu Thr
            260                 265                 270

Ile Ser Asn Leu Tyr Lys Ala Gly Asp Tyr Leu Ile Ser Ile Leu Gly
        275                 280                 285

Ser Glu Gly Tyr Lys Val Ile Lys Phe Leu Glu Pro Leu Cys Leu Ala
    290                 295                 300

Lys Ile Gln Leu Cys Ser Asn Tyr Thr Glu Arg Lys Gly Arg Phe Leu
305                 310                 315                 320

Thr Gln Met His Leu Ala Val Asn His Thr Leu Glu Glu Leu Ile Glu
                325                 330                 335

Gly Arg Gly Leu Lys Ser Gln Gln Asp Trp Lys Met Arg Glu Phe His
            340                 345                 350

Arg Ile Leu Val Asn Leu Lys Ser Thr Pro Gln Gln Leu Cys Glu Leu
        355                 360                 365

Phe Ser Val Gln Lys His Trp Gly His Pro Val Leu His Ser Glu Lys
370                 375                 380

Ala Ile Gln Lys Val Lys Lys His Ala Thr Val Ile Lys Ala Leu Arg
385                 390                 395                 400

Pro Val Ile Ile Phe Glu Thr Tyr Cys Val Phe Lys Tyr Ser Ile Ala
                405                 410                 415

Lys His Tyr Phe Asp Ser Gln Gly Ser Trp Tyr Ser Val Ile Ser Asp
            420                 425                 430

Lys His Leu Thr Pro Gly Leu His Ser Tyr Ile Lys Arg Asn Gln Phe
        435                 440                 445

Pro Pro Leu Pro Met Ile Lys Asp Leu Leu Trp Glu Phe Tyr His Leu
    450                 455                 460

Asp His Pro Pro Leu Phe Ser Thr Lys Ile Ile Ser Asp Leu Ser Ile
465                 470                 475                 480

Phe Ile Lys Asp Arg Ala Thr Ala Val Glu Lys Thr Cys Trp Asp Ala
                485                 490                 495

Val Phe Glu Pro Asn Val Leu Gly Tyr Ser Pro Pro Asn Lys Phe Ser
            500                 505                 510

Thr Lys Arg Val Pro Glu Gln Phe Leu Glu Gln Glu Asn Phe Ser Ile
```

```
            515                 520                 525
Asp Ser Val Leu Thr Tyr Ala Gln Arg Leu Asp Tyr Leu Leu Pro Gln
            530                 535                 540

Tyr Arg Asn Phe Ser Phe Ser Leu Lys Glu Lys Glu Leu Asn Val Gly
545                 550                 555                 560

Arg Ala Phe Gly Lys Leu Pro Tyr Pro Thr Arg Asn Val Gln Thr Leu
                    565                 570                 575

Cys Glu Ala Leu Leu Ala Asp Gly Leu Ala Lys Ala Phe Pro Ser Asn
            580                 585                 590

Met Met Val Val Thr Glu Arg Glu Gln Lys Glu Ser Leu Leu His Gln
            595                 600                 605

Ala Ser Trp His His Thr Ser Asp Asp Phe Gly Glu Asn Ala Thr Val
            610                 615                 620

Arg Gly Ser Ser Phe Val Thr Asp Leu Glu Lys Tyr Asn Leu Ala Phe
625                 630                 635                 640

Arg Tyr Glu Phe Thr Ala Pro Phe Ile Glu Tyr Cys Asn Arg Cys Tyr
                    645                 650                 655

Gly Val Lys Asn Leu Phe Asn Trp Met His Tyr Thr Ile Pro Gln Cys
            660                 665                 670

Tyr Ile His Val Ser Asp Tyr Tyr Asn Pro Pro His Gly Val Ser Leu
            675                 680                 685

Glu Asn Arg Glu Asp Pro Pro Glu Gly Pro Ser Ser Tyr Arg Gly His
            690                 695                 700

Leu Gly Gly Ile Glu Gly Leu Gln Gln Lys Leu Trp Thr Ser Ile Ser
705                 710                 715                 720

Cys Ala Gln Ile Ser Leu Val Glu Ile Lys Thr Gly Phe Lys Leu Arg
                    725                 730                 735

Ser Ala Val Met Gly Asp Asn Gln Cys Ile Thr Val Leu Ser Val Phe
            740                 745                 750

Pro Leu Glu Thr Asp Ser Asn Glu Gln Glu His Ser Ser Glu Asp Asn
            755                 760                 765

Ala Ala Arg Val Ala Ala Ser Leu Ala Lys Val Thr Ser Ala Cys Gly
            770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                    805                 810                 815

Lys Thr Ala Thr Arg Ile Ala Pro Leu Ser Asp Ala Ile Phe Asp Asp
            820                 825                 830

Leu Gln Gly Thr Leu Ala Ser Ile Gly Thr Ala Phe Glu Arg Ser Ile
            835                 840                 845

Ser Glu Thr Arg His Val Tyr Pro Cys Arg Val Val Ala Ala Phe His
            850                 855                 860

Thr Phe Phe Ser Val Arg Ile Leu Gln Tyr His His Leu Gly Phe Asn
865                 870                 875                 880

Lys Gly Thr Asp Leu Gly Gln Leu Ser Leu Ser Lys Pro Leu Asp Phe
                    885                 890                 895

Gly Thr Ile Thr Leu Ala Leu Ala Val Pro Gln Val Leu Gly Gly Leu
            900                 905                 910

Ser Phe Leu Asn Pro Glu Lys Cys Phe Tyr Arg Asn Leu Gly Asp Pro
            915                 920                 925

Val Thr Ser Gly Leu Phe Gln Leu Arg Thr Tyr Leu Gln Met Ile Asn
            930                 935                 940
```

-continued

```
Met Asp Asp Leu Phe Leu Pro Leu Ile Ala Lys Asn Pro Gly Asn Cys
945                 950                 955                 960

Ser Ala Ile Asp Phe Val Leu Asn Pro Ser Gly Leu Asn Val Pro Gly
            965                 970                 975

Ser Gln Asp Leu Thr Ser Phe Leu Arg Gln Ile Val Arg Arg Thr Ile
        980                 985                 990

Thr Leu Ser Ala Lys Asn Lys Leu Ile Asn Thr Leu Phe His Ser Ser
            995                 1000                1005

Ala Asp Leu Glu Asp Glu Met Val Cys Lys Trp Leu Leu Ser Ser
    1010                1015                1020

Thr Pro Val Met Ser Arg Phe Ala Ala Asp Ile Phe Ser Arg Thr
    1025                1030                1035

Pro Ser Gly Lys Arg Leu Gln Ile Leu Gly Tyr Leu Glu Gly Thr
    1040                1045                1050

Arg Thr Leu Leu Ala Ser Lys Val Ile Asn Asn Asn Ala Glu Thr
    1055                1060                1065

Pro Ile Leu Asp Arg Leu Arg Lys Ile Thr Leu Gln Arg Trp Ser
    1070                1075                1080

Leu Trp Phe Ser Tyr Leu Asp His Cys Asp Gln Val Leu Ala Asp
    1085                1090                1095

Ala Leu Ile Lys Val Ser Cys Thr Val Asp Leu Ala Gln Ile Leu
    1100                1105                1110

Arg Glu Tyr Thr Trp Ala His Ile Leu Glu Gly Arg Gln Leu Ile
    1115                1120                1125

Gly Ala Thr Leu Pro Cys Met Leu Glu Gln Phe Asn Val Phe Trp
    1130                1135                1140

Leu Lys Ser Tyr Glu Gln Cys Pro Lys Cys Ala Lys Ser Arg Asn
    1145                1150                1155

Pro Lys Gly Glu Pro Phe Val Ser Ile Ala Ile Lys Lys Gln Val
    1160                1165                1170

Val Ser Ala Trp Pro Asn Gln Ser Arg Leu Asn Trp Thr Ile Gly
    1175                1180                1185

Asp Gly Val Pro Tyr Ile Gly Ser Arg Thr Glu Asp Lys Ile Gly
    1190                1195                1200

Gln Pro Ala Ile Lys Pro Lys Cys Pro Ser Ala Ala Leu Arg Glu
    1205                1210                1215

Ala Ile Glu Leu Thr Ser Arg Leu Thr Trp Val Thr Gln Gly Gly
    1220                1225                1230

Ala Asn Ser Asp Leu Leu Val Lys Pro Phe Val Glu Ala Arg Val
    1235                1240                1245

Asn Leu Ser Val Gln Glu Ile Leu Gln Met Thr Pro Ser His Tyr
    1250                1255                1260

Ser Gly Asn Ile Val His Arg Tyr Asn Asp Gln Tyr Ser Pro His
    1265                1270                1275

Ser Phe Met Ala Asn Arg Met Ser Asn Ser Ala Thr Arg Leu Val
    1280                1285                1290

Val Ser Thr Asn Thr Leu Gly Glu Phe Ser Gly Gly Gln Ser
    1295                1300                1305

Ala Arg Asp Ser Asn Ile Ile Phe Gln Asn Val Ile Asn Phe Ser
    1310                1315                1320

Val Ala Leu Phe Asp Leu Arg Phe Arg Asn Thr Glu Thr Ser Ser
    1325                1330                1335
```

-continued

```
Ile Gln His Asn Arg Ala His Leu His Leu Ser Gln Cys Cys Thr
1340                1345                1350

Arg Glu Val Pro Ala Gln Tyr Leu Thr Tyr Thr Ser Thr Leu Ser
1355                1360                1365

Leu Asp Leu Thr Arg Tyr Arg Glu Asn Glu Leu Ile Tyr Asp Asn
1370                1375                1380

Asn Pro Leu Lys Gly Gly Leu Asn Cys Asn Leu Ser Phe Asp Asn
1385                1390                1395

Pro Leu Phe Lys Gly Gln Arg Leu Asn Ile Ile Glu Glu Asp Leu
1400                1405                1410

Ile Arg Phe Pro His Leu Ser Gly Trp Glu Leu Ala Lys Thr Ile
1415                1420                1425

Ile Gln Ser Ile Ile Ser Asp Ser Asn Asn Ser Ser Thr Asp Pro
1430                1435                1440

Ile Ser Ser Gly Glu Thr Arg Ser Phe Thr Thr His Phe Leu Thr
1445                1450                1455

Tyr Pro Lys Val Gly Leu Leu Tyr Ser Phe Gly Ala Ile Val Ser
1460                1465                1470

Tyr Tyr Leu Gly Asn Thr Ile Ile Arg Thr Lys Lys Leu Asp Leu
1475                1480                1485

Ser His Phe Met Tyr Tyr Leu Thr Thr Gln Ile His Asn Leu Pro
1490                1495                1500

His Arg Ser Leu Arg Ile Leu Lys Pro Thr Phe Lys His Val Ser
1505                1510                1515

Val Ile Ser Arg Leu Met Ser Ile Asp Pro His Phe Ser Ile Tyr
1520                1525                1530

Ile Gly Gly Thr Ala Gly Asp Arg Gly Leu Ser Asp Ala Thr Arg
1535                1540                1545

Leu Phe Leu Arg Val Ala Ile Ser Ser Phe Leu Gln Phe Ile Lys
1550                1555                1560

Lys Trp Ile Val Glu Tyr Lys Thr Ala Ile Pro Leu Trp Val Ile
1565                1570                1575

Tyr Pro Leu Glu Gly Gln Asn Pro Asp Pro Ile Asn Ser Phe Leu
1580                1585                1590

His Leu Ile Ile Ala Leu Leu Gln Asn Glu Ser Pro Gln Asn Asn
1595                1600                1605

Ile Gln Phe Gln Glu Asp Arg Asn Asn Gln Gln Leu Ser Asp Asn
1610                1615                1620

Leu Val Tyr Met Cys Lys Ser Thr Ala Ser Asn Phe Phe His Ala
1625                1630                1635

Ser Leu Ala Tyr Trp Arg Ser Arg His Lys Gly Arg Pro Lys Asn
1640                1645                1650

Arg Ser Thr Glu Glu Gln Thr Val Lys Pro Ile Pro Tyr Asp Asn
1655                1660                1665

Phe His Ser Val Lys Cys Ala Ser Asn Pro Pro Ser Ile Pro Lys
1670                1675                1680

Ser Lys Ser Gly Thr Gln Gly Ser Ser Ala Phe Phe Glu Lys Leu
1685                1690                1695

Glu Tyr Asp Lys Glu Arg Glu Leu Pro Thr Ala Ser Thr Pro Ala
1700                1705                1710

Glu Gln Ser Lys Thr Tyr Ile Lys Ala Leu Ser Ser Arg Ile Tyr
1715                1720                1725

His Gly Lys Thr Pro Ser Asn Ala Ala Lys Asp Asp Ser Thr Thr
```

-continued

```
            1730                1735                1740

Ser Lys Gly Cys Asp Ser Lys Glu Glu Asn Ala Val Gln Ala Ser
    1745                1750                1755

His Arg Ile Val Leu Pro Phe Phe Thr Leu Ser Gln Asn Asp Tyr
    1760                1765                1770

Arg Thr Pro Ser Ala Lys Lys Ser Glu Tyr Ile Thr Glu Ile Thr
    1775                1780                1785

Lys Leu Ile Arg Gln Leu Lys Ala Ile Pro Asp Thr Thr Val Tyr
    1790                1795                1800

Cys Arg Phe Thr Gly Val Val Ser Ser Met His Tyr Lys Leu Asp
    1805                1810                1815

Glu Val Leu Trp Glu Phe Asp Ser Phe Lys Thr Ala Val Thr Leu
    1820                1825                1830

Ala Glu Gly Glu Gly Ser Gly Ala Leu Leu Leu Leu Gln Lys Tyr
    1835                1840                1845

Lys Val Arg Thr Ile Phe Phe Asn Thr Leu Ala Thr Glu His Ser
    1850                1855                1860

Ile Glu Ala Glu Ile Val Ser Gly Thr Thr Thr Pro Arg Met Leu
    1865                1870                1875

Leu Pro Val Met Ala Lys Leu His Asp Asp Gln Ile Asn Val Ile
    1880                1885                1890

Leu Asn Asn Ser Ala Ser Gln Val Thr Asp Ile Thr Asn Pro Ala
    1895                1900                1905

Trp Phe Thr Asp Gln Lys Ser Arg Ile Pro Thr Gln Val Glu Ile
    1910                1915                1920

Met Thr Met Asp Ala Glu Thr Thr Glu Asn Ile Asn Arg Ser Lys
    1925                1930                1935

Leu Tyr Glu Ala Ile Gln Gln Leu Ile Val Ser His Ile Asp Thr
    1940                1945                1950

Arg Val Leu Lys Ile Val Ile Ile Lys Val Phe Leu Ser Asp Ile
    1955                1960                1965

Glu Gly Leu Leu Trp Leu Asn Asp His Leu Ala Pro Leu Phe Gly
    1970                1975                1980

Ser Gly Tyr Leu Ile Lys Pro Ile Thr Ser Ser Pro Lys Ser Ser
    1985                1990                1995

Glu Trp Tyr Leu Cys Leu Ser Asn Phe Leu Ser Ala Ser Arg Arg
    2000                2005                2010

Arg Pro His Gln Gly His Ala Thr Cys Met Gln Val Ile Gln Thr
    2015                2020                2025

Ala Leu Arg Leu Gln Val Gln Arg Ser Ser Tyr Trp Leu Ser His
    2030                2035                2040

Leu Val Gln Tyr Ala Asp Ile Asn Leu His Leu Ser Tyr Val Asn
    2045                2050                2055

Leu Gly Phe Pro Ser Leu Glu Lys Val Leu Tyr His Arg Tyr Asn
    2060                2065                2070

Leu Val Asp Ser Arg Lys Gly Pro Leu Val Ser Ile Leu Tyr His
    2075                2080                2085

Leu Thr His Leu Gln Ala Glu Ile Arg Glu Leu Val Cys Asp Tyr
    2090                2095                2100

Asn Gln Gln Arg Gln Ser Arg Thr Gln Thr Tyr His Phe Ile Lys
    2105                2110                2115

Thr Thr Lys Gly Arg Ile Thr Lys Leu Val Asn Asp Tyr Leu Lys
    2120                2125                2130
```

```
Phe Tyr Leu Val Val Gln Ala Leu Lys His Asn Cys Leu Trp Gln
    2135            2140                2145

Glu Glu Leu Arg Thr Leu Pro Asp Leu Ile Asn Val Cys Asn Arg
2150            2155                2160

Phe Tyr His Ile Arg Asp Cys Ser Cys Glu Asp Arg Phe Leu Ile
    2165            2170                2175

Gln Thr Leu Tyr Leu Thr Arg Met Gln Asp Ser Glu Ala Lys Leu
    2180            2185                2190

Met Glu Arg Leu Thr Gly Phe Leu Gly Leu Tyr Pro Asn Gly Ile
    2195            2200                2205

Asn Ala
    2210

<210> SEQ ID NO 3
<211> LENGTH: 739
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus NP viral protein

<400> SEQUENCE: 3

Met Asp Pro Arg Pro Ile Arg Thr Trp Met Met His Asn Thr Ser Glu
1               5                   10                  15

Val Glu Ala Asp Tyr His Lys Ile Leu Thr Ala Gly Leu Ser Val Gln
            20                  25                  30

Gln Gly Ile Val Arg Gln Arg Ile Ile Pro Val Tyr Gln Ile Ser Asn
        35                  40                  45

Leu Glu Glu Val Cys Gln Leu Ile Ile Gln Ala Phe Glu Ala Gly Val
    50                  55                  60

Asp Phe Gln Asp Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
                85                  90                  95

Lys Tyr Leu Glu Gly His Gly Phe Arg Phe Glu Met Lys Lys Lys Glu
            100                 105                 110

Gly Val Lys Arg Leu Glu Glu Leu Leu Pro Ala Ala Ser Ser Gly Lys
        115                 120                 125

Asn Ile Lys Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ser Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
```

```
                260             265             270
Val Lys Asn Glu Val Ser Ser Phe Lys Ala Leu Ala Ser Leu Ala
            275             280             285
Gln His Gly Glu Tyr Ala Pro Phe Ala Arg Leu Leu Asn Leu Ser Gly
            290             295             300
Val Asn Asn Leu Glu His Gly Leu Phe Pro Gln Leu Ser Ala Ile Ala
305             310             315             320
Leu Gly Val Ala Thr Ala His Gly Ser Thr Leu Ala Gly Val Asn Val
                325             330             335
Gly Glu Gln Tyr Gln Gln Leu Arg Glu Ala Ala Thr Glu Ala Glu Lys
            340             345             350
Gln Leu Gln Lys Tyr Ala Glu Ser Arg Glu Leu Asp His Leu Gly Leu
            355             360             365
Asp Asp Gln Glu Lys Lys Ile Leu Lys Asp Phe His Gln Lys Lys Asn
            370             375             380
Glu Ile Ser Phe Gln Gln Thr Thr Ala Met Val Thr Leu Arg Lys Glu
385             390             395             400
Arg Leu Ala Lys Leu Thr Glu Ala Ile Thr Ser Thr Ile Leu Lys
            405             410             415
Thr Gly Arg Arg Tyr Asp Asp Asp Asn Asp Ile Pro Phe Pro Gly Pro
            420             425             430
Ile Asn Asp Asn Glu Asn Ser Gly Gln Asn Asp Asp Pro Thr Asp
            435             440             445
Ser Gln Asp Thr Thr Ile Pro Asp Val Ile Ile Asp Pro Asn Asp Gly
            450             455             460
Gly Tyr Asn Asn Tyr Ser Asp Tyr Ala Asn Asp Ala Ala Ser Ala Pro
465             470             475             480
Asp Asp Leu Val Leu Phe Asp Leu Glu Asp Asp Asp Ala Asp Asn
            485             490             495
Pro Ala Gln Asn Thr Pro Glu Lys Asn Asp Arg Pro Ala Thr Thr Lys
            500             505             510
Leu Arg Asn Gly Gln Asp Gln Asp Gly Asn Gln Gly Glu Thr Ala Ser
            515             520             525
Pro Arg Val Ala Pro Asn Gln Tyr Arg Asp Lys Pro Met Pro Gln Val
            530             535             540
Gln Asp Arg Ser Glu Asn His Asp Gln Thr Leu Gln Thr Gln Ser Arg
545             550             555             560
Val Leu Thr Pro Ile Ser Glu Glu Ala Asp Pro Ser Asp His Asn Asp
                565             570             575
Gly Asp Asn Glu Ser Ile Pro Pro Leu Glu Ser Asp Asp Glu Gly Ser
            580             585             590
Thr Asp Thr Thr Ala Ala Glu Thr Lys Pro Ala Thr Ala Pro Pro Ala
            595             600             605
Pro Val Tyr Arg Ser Ile Ser Val Asp Asp Ser Val Pro Ser Glu Asn
            610             615             620
Ile Pro Ala Gln Ser Asn Gln Thr Asn Asn Glu Asp Asn Val Arg Asn
625             630             635             640
Asn Ala Gln Ser Glu Gln Ser Ile Ala Glu Met Tyr Gln His Ile Leu
                645             650             655
Lys Thr Gln Gly Pro Phe Asp Ala Ile Leu Tyr Tyr His Met Met Lys
            660             665             670
Glu Glu Pro Ile Ile Phe Ser Thr Ser Asp Gly Lys Glu Tyr Thr Tyr
            675             680             685
```

```
Pro Asp Ser Leu Glu Asp Glu Tyr Pro Pro Trp Leu Ser Glu Lys Glu
    690             695                 700

Ala Met Asn Glu Asp Asn Arg Phe Ile Thr Met Asp Gly Gln Gln Phe
705             710                 715                     720

Tyr Trp Pro Val Met Asn His Arg Asn Lys Phe Met Ala Ile Leu Gln
            725                 730                 735

His His Arg

<210> SEQ ID NO 4
<211> LENGTH: 373
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus SGP viral protein

<400> SEQUENCE: 4

Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
            20                  25                  30

Ile Pro Leu Gly Val Val His Asn Asn Thr Leu Gln Val Ser Asp Ile
        35                  40                  45

Asp Lys Leu Val Cys Arg Asp Lys Leu Ser Ser Thr Ser Gln Leu Lys
50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
        115                 120                 125

Val Arg Gly Phe Pro Arg Cys Arg Tyr Val His Lys Val Ser Gly Thr
130                 135                 140

Gly Pro Cys Pro Glu Gly Tyr Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Glu Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
            260                 265                 270

Leu Ile Trp Lys Val Asn Pro Thr Val Asp Thr Gly Val Gly Glu Trp
        275                 280                 285

Ala Phe Trp Glu Asn Lys Lys Thr Ser Gln Lys Pro Phe Gln Val Lys
290                 295                 300
```

-continued

Ser Cys Leu Ser Tyr Leu Tyr Gln Glu Pro Arg Ile Gln Ala Ala Thr
305                 310                 315                 320

Arg Arg Arg Arg Ser Leu Pro Pro Ala Ser Pro Thr Thr Lys Pro Pro
            325                 330                 335

Arg Thr Thr Lys Thr Trp Phe Gln Arg Ile Pro Leu Gln Trp Phe Lys
        340                 345                 350

Cys Glu Thr Ser Arg Gly Lys Thr Gln Cys Arg Pro His Pro Gln Thr
            355                 360                 365

Gln Ser Pro Gln Leu
        370

<210> SEQ ID NO 5
<211> LENGTH: 251
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus VP24 viral protein

<400> SEQUENCE: 5

Met Ala Lys Ala Thr Gly Arg Tyr Asn Leu Val Ser Pro Lys Lys Asp
1               5                   10                  15

Leu Glu Arg Gly Leu Val Leu Ser Asp Leu Cys Thr Phe Leu Val Asp
            20                  25                  30

Gln Thr Ile Gln Gly Trp Arg Val Thr Trp Val Gly Ile Glu Phe Asp
        35                  40                  45

Ile Ala Gln Lys Gly Met Ala Leu Leu His Arg Leu Lys Thr Ala Asp
50                  55                  60

Phe Ala Pro Ala Trp Ser Met Thr Arg Asn Leu Phe Pro His Leu Phe
65                  70                  75                  80

Gln Asn Ser Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Val
            100                 105                 110

Glu Pro Leu Ala Gly Ala Leu Ser Leu Val Ser Asp Trp Leu Leu Thr
        115                 120                 125

Thr Asn Thr Asn His Phe Gln Met Arg Thr Gln His Ala Lys Glu Gln
130                 135                 140

Leu Ser Leu Lys Met Leu Ser Leu Val Arg Ser Asn Ile Leu Lys Phe
145                 150                 155                 160

Ile Ser Gln Leu Asp Ala Leu His Val Val Asn Tyr Asn Gly Leu Leu
                165                 170                 175

Ser Ser Ile Glu Ile Gly Thr Arg Asn His Thr Ile Ile Thr Arg
            180                 185                 190

Thr Asn Met Gly Phe Leu Val Glu Leu Gln Glu Pro Asp Lys Ser Ala
        195                 200                 205

Met Asn Gln Lys Lys Pro Gly Pro Val Lys Phe Ser Leu Leu His Glu
210                 215                 220

Ser Thr Phe Lys Ala Leu Ile Lys Lys Pro Ala Thr Lys Met Gln Ala
225                 230                 235                 240

Leu Ile Leu Glu Phe Asn Ser Ser Leu Ala Ile
                245                 250

<210> SEQ ID NO 6
<211> LENGTH: 289
<212> TYPE: PRT

<213> ORGANISM: Bundibugyo ebolavirus
<220> FEATURE:
<221> NAME/KEY: misc_feature
<223> OTHER INFORMATION: Bundibugyo ebolavirus VP30 viral protein

<400> SEQUENCE: 6

Met Asp Ser Phe His Glu Arg Gly Arg Ser Arg Thr Ile Arg Gln Ser
1               5                   10                  15

Ala Arg Asp Gly Pro Ser His Gln Val Arg Thr Arg Ser Ser Ser Arg
            20                  25                  30

Asp Ser His Arg Ser Glu Tyr His Thr Pro Arg Ser Ser Ser Gln Val
        35                  40                  45

Arg Val Pro Thr Val Phe His Arg Lys Arg Thr Asp Ser Leu Thr Val
    50                  55                  60

Pro Pro Ala Pro Lys Asp Ile Cys Pro Thr Leu Arg Lys Gly Phe Leu
65                  70                  75                  80

Cys Asp Ser Asn Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Leu
            100                 105                 110

Glu Gln Gln Leu Asn Ile Thr Ala Pro Lys Asp Thr Arg Leu Ala Asn
        115                 120                 125

Pro Ile Ala Asp Asp Phe Gln Gln Lys Asp Gly Pro Lys Ile Thr Leu
    130                 135                 140

Leu Thr Leu Leu Glu Thr Ala Glu Tyr Trp Ser Lys Gln Asp Ile Lys
145                 150                 155                 160

Gly Ile Asp Asp Ser Arg Leu Arg Ala Leu Leu Thr Leu Cys Ala Val
                165                 170                 175

Met Thr Arg Lys Phe Ser Lys Ser Gln Leu Ser Leu Leu Cys Glu Ser
            180                 185                 190

His Leu Arg Arg Glu Gly Leu Gly Gln Asp Gln Ser Glu Ser Val Leu
        195                 200                 205

Glu Val Tyr Gln Arg Leu His Ser Asp Lys Gly Gly Asn Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ser Val
                245                 250                 255

Val Ile Ser Gly Leu Arg Leu Leu Val Pro Gln Ser Glu Asp Thr Glu
            260                 265                 270

Thr Ser Thr Tyr Thr Glu Thr Arg Ala Trp Ser Glu Glu Gly Gly Pro
        275                 280                 285

His

<210> SEQ ID NO 7
<211> LENGTH: 341
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus VP35 viral protein

<400> SEQUENCE: 7

Met Thr Ser Asn Arg Ala Arg Val Thr Tyr Asn Pro Pro Thr Thr
1               5                   10                  15

Thr Gly Thr Arg Ser Cys Gly Pro Glu Leu Ser Gly Trp Ile Ser Glu
            20                  25                  30

Gln Leu Met Thr Gly Lys Ile Pro Ile Thr Asp Ile Phe Asn Glu Ile
                35                  40                  45

Glu Thr Leu Pro Ser Ile Ser Pro Ser Ile His Ser Lys Ile Lys Thr
 50                  55                  60

Pro Ser Val Gln Thr Arg Ser Val Gln Thr Gln Thr Asp Pro Asn Cys
 65                  70                  75                  80

Asn His Asp Phe Ala Glu Val Val Lys Met Leu Thr Ser Leu Thr Leu
                 85                  90                  95

Val Val Gln Lys Gln Thr Leu Ala Thr Glu Ser Leu Glu Gln Arg Ile
                100                 105                 110

Thr Asp Leu Glu Gly Ser Leu Lys Pro Val Ser Glu Ile Thr Lys Ile
                115                 120                 125

Val Ser Ala Leu Asn Arg Ser Cys Ala Glu Met Val Ala Lys Tyr Asp
130                 135                 140

Leu Leu Val Met Thr Thr Gly Arg Ala Thr Ala Thr Ala Ala Ala Thr
145                 150                 155                 160

Glu Ala Tyr Trp Ala Glu His Gly Arg Pro Pro Pro Gly Pro Ser Leu
                165                 170                 175

Tyr Glu Glu Asp Ala Ile Arg Thr Lys Ile Gly Lys Gln Gly Asp Met
                180                 185                 190

Val Pro Lys Glu Val Gln Glu Ala Phe Arg Asn Leu Asp Ser Thr Ala
                195                 200                 205

Leu Leu Thr Glu Glu Asn Phe Gly Lys Pro Asp Ile Ser Ala Lys Asp
                210                 215                 220

Leu Arg Asn Ile Met Tyr Asp His Leu Pro Gly Phe Gly Thr Ala Phe
225                 230                 235                 240

His Gln Leu Val Gln Val Ile Cys Lys Leu Gly Lys Asp Asn Ser Ser
                245                 250                 255

Leu Asp Val Ile His Ala Glu Phe Gln Ala Ser Leu Ala Glu Gly Asp
                260                 265                 270

Ser Pro Gln Cys Ala Leu Ile Gln Ile Thr Lys Arg Ile Pro Ile Phe
                275                 280                 285

Gln Asp Ala Ala Pro Val Ile His Ile Arg Ser Arg Gly Asp Ile
                290                 295                 300

Pro Lys Ala Cys Gln Lys Ser Leu Arg Pro Val Pro Pro Ser Pro Lys
305                 310                 315                 320

Ile Asp Arg Gly Trp Val Cys Ile Phe Gln Leu Gln Asp Gly Lys Thr
                325                 330                 335

Leu Gly Leu Lys Ile
                340

<210> SEQ ID NO 8
<211> LENGTH: 326
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus VP40 viral protein

<400> SEQUENCE: 8

Met Arg Arg Ala Ile Leu Pro Thr Ala Pro Pro Glu Tyr Ile Glu Ala
 1               5                  10                  15

Val Tyr Pro Met Arg Thr Val Ser Thr Ser Ile Asn Ser Thr Ala Ser
                20                  25                  30

Gly Pro Asn Phe Pro Ala Pro Asp Val Met Met Ser Asp Thr Pro Ser

```
            35                  40                  45
Asn Ser Leu Arg Pro Ile Ala Asp Asp Asn Ile Asp His Pro Ser His
 50                  55                  60

Thr Pro Thr Ser Val Ser Ser Ala Phe Ile Leu Glu Ala Met Val Asn
 65                  70                  75                  80

Val Ile Ser Gly Pro Lys Val Leu Met Lys Gln Ile Pro Ile Trp Leu
                 85                  90                  95

Pro Leu Gly Val Ala Asp Gln Lys Thr Tyr Ser Phe Asp Ser Thr Thr
                100                 105                 110

Ala Ala Ile Met Leu Ala Ser Tyr Thr Ile Thr His Phe Gly Lys Thr
                115                 120                 125

Ser Asn Pro Leu Val Arg Ile Asn Arg Leu Gly Pro Gly Ile Pro Asp
130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
                180                 185                 190

Asp Asp Thr Pro Thr Gly Pro Thr Gly Ile Leu Arg Pro Gly Ile Ser
                195                 200                 205

Phe His Pro Lys Leu Arg Pro Ile Leu Leu Pro Gly Lys Thr Gly Lys
210                 215                 220

Arg Gly Ser Ser Asp Leu Thr Ser Pro Asp Lys Ile Gln Ala Ile
225                 230                 235                 240

Met Asn Phe Leu Gln Asp Leu Lys Leu Val Pro Ile Asp Pro Ala Lys
                245                 250                 255

Asn Ile Met Gly Ile Glu Val Pro Glu Leu Leu Val His Arg Leu Thr
                260                 265                 270

Gly Lys Lys Ile Thr Thr Lys Asn Gly Gln Pro Ile Ile Pro Ile Leu
                275                 280                 285

Leu Pro Lys Tyr Ile Gly Met Asp Pro Ile Ser Gln Gly Asp Leu Thr
290                 295                 300

Met Val Ile Thr Gln Asp Cys Asp Thr Cys His Ser Pro Ala Ser Leu
305                 310                 315                 320

Pro Pro Val Ser Glu Lys
                325

<210> SEQ ID NO 9
<211> LENGTH: 676
<212> TYPE: PRT
<213> ORGANISM: Bundibugyo ebolavirus
<220> FEATURE:
<221> NAME/KEY: misc_feature
<223> OTHER INFORMATION: Bundibugyo ebolavirus GP viral protein

<400> SEQUENCE: 9

Met Val Thr Ser Gly Ile Leu Gln Leu Pro Arg Glu Arg Phe Arg Lys
 1               5                  10                  15

Thr Ser Phe Phe Val Trp Val Ile Ile Leu Phe His Lys Val Phe Pro
                20                  25                  30

Ile Pro Leu Gly Val Val His Asn Asn Thr Leu Gln Val Ser Asp Ile
                35                  40                  45

Asp Lys Leu Val Cys Arg Asp Lys Leu Ser Ser Thr Ser Gln Leu Lys
 50                  55                  60
```

```
Ser Val Gly Leu Asn Leu Glu Gly Asn Gly Val Ala Thr Asp Val Pro
 65                  70                  75                  80

Thr Ala Thr Lys Arg Trp Gly Phe Arg Ala Gly Val Pro Pro Lys Val
                 85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
        115                 120                 125

Val Arg Gly Phe Pro Arg Cys Arg Tyr Val His Lys Val Ser Gly Thr
    130                 135                 140

Gly Pro Cys Pro Glu Gly Tyr Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Glu Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
    210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
            260                 265                 270

Leu Ile Trp Lys Val Asn Pro Thr Val Asp Thr Gly Val Gly Glu Trp
        275                 280                 285

Ala Phe Trp Glu Asn Lys Lys Asn Phe Thr Lys Thr Leu Ser Ser Glu
    290                 295                 300

Glu Leu Ser Val Ile Phe Val Pro Arg Ala Gln Asp Pro Gly Ser Asn
305                 310                 315                 320

Gln Lys Thr Lys Val Thr Pro Thr Ser Phe Ala Asn Asn Gln Thr Ser
                325                 330                 335

Lys Asn His Glu Asp Leu Val Pro Glu Asp Pro Ala Ser Val Val Gln
            340                 345                 350

Val Arg Asp Leu Gln Arg Glu Asn Thr Val Pro Thr Pro Pro Pro Asp
        355                 360                 365

Thr Val Pro Thr Thr Leu Ile Pro Asp Thr Met Glu Glu Gln Thr Thr
    370                 375                 380

Ser His Tyr Glu Pro Pro Asn Ile Ser Arg Asn His Gln Glu Arg Asn
385                 390                 395                 400

Asn Thr Ala His Pro Glu Thr Leu Ala Asn Asn Pro Pro Asp Asn Thr
                405                 410                 415

Thr Pro Ser Thr Pro Pro Gln Asp Gly Glu Arg Thr Ser Ser His Thr
            420                 425                 430

Thr Pro Ser Pro Arg Pro Val Pro Thr Ser Thr Ile His Pro Thr Thr
        435                 440                 445

Arg Glu Thr His Ile Pro Thr Thr Met Thr Thr Ser His Asp Thr Asp
    450                 455                 460

Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
```

```
                    485              490              495
Arg Arg Thr Arg Arg Glu Ile Thr Leu Arg Thr Gln Ala Lys Cys Asn
                500              505              510

Pro Asn Leu His Tyr Trp Thr Thr Gln Asp Glu Gly Ala Ala Ile Gly
            515              520              525

Leu Ala Trp Ile Pro Tyr Phe Gly Pro Ala Ala Glu Gly Ile Tyr Thr
        530              535              540

Glu Gly Ile Met His Asn Gln Asn Gly Leu Ile Cys Gly Leu Arg Gln
545              550              555              560

Leu Ala Asn Glu Thr Thr Gln Ala Leu Gln Leu Phe Leu Arg Ala Thr
                565              570              575

Thr Glu Leu Arg Thr Phe Ser Ile Leu Asn Arg Lys Ala Ile Asp Phe
            580              585              590

Leu Leu Gln Arg Trp Gly Gly Thr Cys His Ile Leu Gly Pro Asp Cys
        595              600              605

Cys Ile Glu Pro His Asp Trp Thr Lys Asn Ile Thr Asp Lys Ile Asp
        610              615              620

Gln Ile Ile His Asp Phe Ile Asp Lys Pro Leu Pro Asp Gln Thr Asp
625              630              635              640

Asn Asp Asn Trp Trp Thr Gly Trp Arg Gln Trp Val Pro Ala Gly Ile
                645              650              655

Gly Ile Thr Gly Val Ile Ile Ala Val Ile Ala Leu Leu Cys Ile Cys
            660              665              670

Lys Phe Leu Leu
        675

<210> SEQ ID NO 10
<211> LENGTH: 18935
<212> TYPE: DNA
<213> ORGANISM: Cote dIvoire ebolavirus

<400> SEQUENCE: 10
cggacacaca aaagaaaga aggtttttg atctttattg tgtgcgaata actatgagga      60
agattaataa ttttcctctc attgacactt acattaagat taagattctc attgatctgt    120
tacttactct gaggataata attggtgttc agaagtaccc cattccccag tgggggcaaa    180
gacagtccaa aagactcaac ttgtcctatt caactaatct gttttgtctc agtagttcac    240
atattgatca tacccaggag ttggacctaa ttccaaagct tagagtggga cctagtgtat    300
cctcggggct gtaatataat cagccattta acacataaca agccctactg ttttcttgtt    360
ttgccgtgca tttagaataa gagacaactt aaacctccga ttcggcaaca cagggaataa    420
tctcaccaga cccggcagtg tcttcaggct tcatagcccc aagatggaga gtcgggccca    480
caaagcatgg atgacgcaca ccgcatcagg tttcgaaaca gattaccata agattttaac    540
agcaggattg tcagtccaac aaggcattgt gagacaacgg tcattcaag tccaccaggt     600 tacaaaccta gaagaaatat gccaattgat cattcaagcc tttgaagctg gtgttgattt    660
tcaagagagt gcagacagtt tcttgctgat gctatgttta catcatgctt atcagggtga    720
ctacaagcaa ttcttggaaa gcaatgcagt caagtacctt gagggtcatg gctttcgctt    780
tgaggtcagg aaaaaggaag gagtcaagcg actcgaagaa ttgcttcctg ctgcatccag    840 tgcaagagc atcaggagaa cactggctgc aatgcctgaa gaggagacaa cagaagcaaa     900
tgccggacag ttcctctctt ttgctagctt atttcttcct aagctagttg tcggagaaaa    960
agcctgtcta gaaaaggtgc agcggcaaat tcaagttcat tctgagcagg gattgatcca   1020
```

```
atacccaca gcctggcagt cagttggaca catgatggtc attttcagac tgatgagaac    1080
aaattttcta attaagttcc tccttataca tcaagggatg catatggtag caggacacga    1140
tgctaacgat gctgtcatcg caaactctgt agctcaagca cgttttcag gattattgat     1200 cgttaaaaca gtgctagatc acatccttca gaaaacagag cacggagtgc gtcttcatcc    1260
tttggcaaga actgctaagg tcaagaacga agtaaattcc tttaaggctg cccttagctc    1320
gctagcacaa catggagagt atgctccttt tgctcgcttg ctgaatcttt ctggagtcaa    1380
caatctcgag cacggactgt ttcctcagct ttctgcaatt gccctaggtg tcgcaacggc    1440
acacggcagt accctggcag gagtaaatgt gggggaacag tatcagcaac tacgagaagc    1500
agccactgag gcagaaaaac aattgcagaa atacgctgaa tctcgcgagc ttgaccatct    1560
aggtctcgat gatcaagaga agaagatctt gaaagacttc catcagaaga aaatgaaat    1620 cagcttccag cagacaacag ccatggtcac actacggaag gaaaggctag ccaagctcac    1680
tgaggcaatc acctccacat cccttctcaa gacaggaaaa cagtatgatg atgacaacga    1740 tatcccttt cctgggccca tcaatgataa cgaaaactca gaacagcaag acgatgatcc     1800
aacagattct caggacacta ccatccctga tatcattgtt gacccggatg atggcagata    1860
caacaattat ggagactatc ctagtgagac ggcgaatgcc cctgaagacc ttgttctttt    1920
tgaccttgaa gatggtgacg aggatgatca ccgaccgtca agttcatcag agaacaacaa    1980
caaacacagt cttacaggaa ctgacagtaa caaaacaagt aactggaatc gaaacccgac    2040
taatatgcca agaaaagact ccacacaaaa caatgacaat cctgcacagc gggctcaaga    2100
atacgccagg gataacatcc aggatacacc aacaccccat cgagctctaa ctcccatcag    2160
cgaagaaacc ggctccaatg gtcacaatga agatgacatt gatagcatcc ctcctttgga    2220
atcagacgaa gaaacaacaa ctgagacaac cattaccacc acaaaaaata ccactgctcc    2280
accagcacct gtttatcgga gtaattcaga aaaggagccc ctcccgcaag aaaaatccca    2340
gaagcaacca aaccaagtga gtggtagtga gaataccgac aataaacctc actcagagca    2400
atcagtggaa gaaatgtatc gacacatcct ccaaacacaa ggaccatttg atgccatcct    2460
atactattac atgatgacgg aggagccgat tgtctttagc actagtgatg ggaaagaata    2520
cgtataccct gattctcttg aaggggagca tccaccgtgg ctcagtgaaa agaggccttt    2580
gaatgaggac aataggttta tcacaatgga tgatcaacaa ttctactggc ctgtaatgaa    2640
tcacaggaac aaattcatgg ctatccttca gcaccacaag taatttcttc ataatgacag    2700
atcattgtaa ggttattacc accatccctg caacaaagca tgaaaccac actcaacaac     2760 gccctaccac aggataccct ggagaccata caccaagatc agcagctgtg caaccacccc    2820
catgcgaatc caccaccaca accaccaaac aataatccca agaccaaacc gcacacatcc    2880
agatcaaccc aaaccctcaa acaccacccc actccgcgat cccagaccaa actccgcccc    2940
agacaagcac cccacccatc ccagaaaccg cacggccgag aatcgatccc cagcattcaa    3000
aatgcgttat taagaaaaaa catatgatga agattaaaac cttcatcaac attgcacaga    3060
ctttgatcct taggagttta ttctagctat ctacaaaacg ggtccaaaac ggaatgattt    3120
ccactagggc tgcagcaatc aatgatcctt cattaccaat cagaaccag tgtacacgtg      3180 gccctgaact atcaggatgg atctccgaac aattaatgac aggcaaaatt ccggtacatg    3240
aaatcttcaa cgacactgag ccccacataa gctcagggtc cgactgcctt ccagacccca    3300
aaaacacggc ccccggact cgcaacaccc agacacagac cgatccggtt tgcaatcaca      3360
```

```
attttgaaga cgttacacaa gcactaacat cattaaccaa tgtcatacaa aaacaggctc    3420
ttaacttaga gtctctcgaa caacgcatca tagatctaga gaatggctta aagccaatgt    3480
atgacatggc taaagtcatt tctgcattga atagatcttg tgctgagatg gtagcaaaat    3540
atgatctcct ggtgatgaca actggccgcg caaccgccac cgccgctgca actgaggctt    3600
attgggagga acatggacaa ccaccacctg gaccatcact ttatgaagag agtgcgatta    3660
gaggcaagat taacaagcaa gaggataaag tacctaagga agttcaagaa gcttttcgta    3720
atctggacag taccagctca ctaacagaag agaactttgg caagccagat atatctgcaa    3780
aggacctacg agacatcatg tatgaccacc taccaggctt cggtacggct tttcaccaac    3840
tggtccaggt aatttgcaag ctaggaaaag acaattctgc attggacatt attcatgctg    3900
agttccaagc cagccttgct gaaggtgatt ctccccaatg tgccctgatc caaataacaa    3960
aacggatccc catcttccag gatgccactc cgcccacaat tcacatccgc tctcgtggtg    4020
acatcccacg tgcctgccaa aaagtctcc gtccagttcc tccatcacca aaaatagaca    4080
gaggttgggt ttgcattttc caattgcagg acgggaagac acttgggctc aagatatagg    4140 gtccccagt caaagacacg tgcggtccca tcctccctca ccttcagaca tcaacgcatg    4200
gcagtcccaa acaccggtga gggaggcgcc cggcgacaac acatgatgat aggctgatct    4260
tcgggataag agacatgaaa aaccaaaaag ccgtttacat ccagatccaa gatcaagagt    4320
ggcttggaaa taaggggcac ttgttctttg tctcaaagga cttacaaaaa caagggtgat    4380
gaagattaag aaaaagcctc cttcagttgc aaggagctaa ttcttaaaac ttcatctaga    4440
ctaaggataa atcgattcca atcacgatga ggagaatcat cctacccacg gcaccacctg    4500
aatacatgga ggctgtttac ccaatgagaa caatgaattc tggtgcagac aacactgcca    4560
gtggccctaa ttacacaaca actggtgtga tgacaaatga tactccctct aattcactcc    4620
gaccagttgc agatgataat attgatcatc gagccacac gcctaacagt gttgcctctg    4680
catttatatt ggaagctatg gtgaatgtaa tatctggccc gaaagtgctg atgaagcaaa    4740
tcccaatctg gcttcctctg ggtgtctctg accagaagac atatagcttt gattcaacca    4800
ctgctgccat tatgctagca tcatatacca tcactcattt tggcaaaacc tcaaatcccc    4860
ttgtgagaat caaccgactt ggtcctggca tacctgatca cccactacga ctcctaagaa    4920
taggaaatca agccttccta caagagtttg tgctacctcc tgtacaactg ccacaatact    4980
tcacttttga tctgacagcg ctgaagctga tcacccagcc actcccagcg caacctgga    5040 cagatgaaac tccagctgtg tcaactggca cgctccgccc agggatctca ttccatccca    5100
aattaaggcc tatcctgcta ccaggaagag ctggaaagaa gggctccaac tccgatctaa    5160
catctcctga caaaatccag gctataatga atttcctaca agacctcaaa attgtaccaa    5220
tcgatccaac caagaatatc atgggtattg aagtgccaga actcctggtt cacaggctga    5280 ctggaagaa gacaactacc aagaatggtc aaccaatcat tccaattctg ctaccaaagt    5340
acattggtct tgatcctcta tctcaaggtg atctcacaat ggtgatcact caggactgtg    5400
attcctgcca ctccccggcc agtcttcccc cagtcaatga aaaatgacca tgagactcaa    5460
catcacactg ccagagcacc tcaccgcaag tctatacaac aatcaacccc ggcatctaca    5520
acctgcaaaa accagcccat ctgatactcc tggcatcggg ggcaagacaa ggcagccaag    5580
cagcagcccc cgagccgagc ccaaacccat tacacccgag cccaacaccc atccagcaac    5640
ccacaaccgt caaacgcaca gatggacaag caaagaacat caagccagga gcaacacaga    5700
ccccaagtct aagctgatca accctcccg caatcccacc aacgccagca aaaatccccc    5760
```

```
aactcgatac caaccccaag caaatcagct caaaccgtct atctctcccc gcttcactcc    5820
acaccccaga ttcagcaaac gatcaacgca cttcttatgc cacagcttat attaagaaaa    5880
agaacttgat gaagattaag gcaaccagtg gtgctatctt catctctttg atttgagtct    5940
taagtgaata cacaggttct aatactgttc ttctgtccaa cggtataatt cagccaggcc    6000
taagacagta gctaatcaca gtcatcatgg gagcgtcagg gattctgcaa ttgccccgtg    6060
agcgcttcag gaaaacatct ttctttgttt gggtaataat cctattccat aaagtctttt    6120
caatcccgtt gggggttgta cacaacaata ccctacaagt gagtgatatt gacaagtttg    6180
tgtgccgaga caaactctct tcaactagcc aattgaagtc agtcgggttg aacttggagg    6240
gcaatggagt agcaactgat gtaccaacgg caaccaaaag atggggtttt cgagctggtg    6300
ttccaccaaa ggtggtaaat tgcgaagctg agaatgggc tgagaactgt tataacctgg    6360
ctataaagaa agttgatggt agtgagtgcc taccagaagc ccctgaggga gtagggatt    6420 ttccccgttg ccgctatgta cacaaagtct caggaactgg accatgccca ggaggactcg    6480
cctttcacaa agaaggagcc ttcttcctgt atgaccgact cgcatcaaca atcatttatc    6540
ggggtacaac ctttgccgaa ggagttattg catttctgat cttgcctaag gcgcgaaagg    6600
attttttcca gtctcctcca ttgcatgagc ctgccaacat gaccacggat ccctccagtt    6660
actatcacac gacaacaata aactacgtgg ttgataattt tggaaccaac accacagagt    6720
ttctgttcca agtcgatcat ttgacgtatg tgcagctcga ggcaagattc acaccacaat    6780
tccttgtcct cctaaatgaa accatctact ctgataaccg cagaagtaac acaacaggaa    6840
aactaatctg gaaaataaat cccactgttg ataccagcat gggtgagtgg gctttctggg    6900
aaaataaaaa aacttcacaa aaacccttc aagtgaagag ttgtctttcg tacctgtacc    6960
agaaacccag aaccaggtcc ttgacacgac agcgacggtc tctcctccca tctccgccca    7020
caaccacgca gccgaagacc acaaagaatt ggtttcagag gattccactc cagtggttca    7080
gatgcaaaac atcaagggaa aggacacaat gccaaccaca gtgacgggtg taccaacaac    7140
cacaccctct ccatttccaa tcaatgctcg caacactgat cataccaaat catttatcgg    7200
cctggagggg ccccaagaag accacagcac cacacagcct gccaagacca ccagccaacc    7260
aaccaacagc acagaatcga cgacactaaa cccaacatca gagccctcca gtagaggcac    7320
gggaccatcc agcccacgg tccccaacac cacagaaagc cacgccgaac ttggcaagac    7380
aaccccaacc acactcccag aacagcacac tgccgccagt gccattccaa gagccgtgca    7440
ccccgacgaa ctcagtggac ctggcttcct gacgaacaca atacgggggg ttacaaatct    7500
cctgacagga tccagaagaa agcgaaggga tgtcactccc aatacacaac ccaaatgcaa    7560
cccaaacctg cactattgga cagccttgga tgagggtgct gccataggtt tagcctggat    7620
accatacttc gggccagcag ctgagggaat ttacactgaa ggcataatgg agaatcaaaa    7680
tggattgatc tgtggattga ggcagctggc caacgaaacg acacaagctc ttcaattgtt    7740
cttaagggca actactgagt tgcgtacatt ctctatacta aatcggaaag caatagactt    7800
cttgctccaa agatggggag gaacatgtca cattctaggg cctgattgtt gcattgaacc    7860
ccaagattgg accaaaaata tcactgataa aattgatcaa ataatccatg actttgtcga    7920
taataatctt ccaaatcaga atgatggcag caactggtgg actggatgga acaatgggt    7980 tcctgctgga ataggaatca caggagtaat cattgctatt attgctttgc tgtgcatttg    8040
caaattcatg ctttgaacta atatagcatc atactttcta atattccccc aatatgaatt    8100
```

```
tttgttttcg attttattta atgatatatc ctctgtatac ctcactaatg tactcgagca    8160
taatttccct gatagacttg attgtatttg atgattaagg acctcacaaa attcctgggg    8220
attgaaaaga actggataac tcaataaatt ttatgctagg accacaaata cacttgatga    8280
agattaagaa aaagataatc ttatgattat cattgatctt catctatacc ttaaatactc    8340
tattcaagga gagtatgaca aaaccaagta gtattggata aacttgtcct gcattcaaat    8400
ctgaagacat acggcttatc tattcactat tgtattagaa atctaggga atatcatttg    8460
aaactaatta gtgactaaaa cacacaactc aagtcggcca gaatggaagt tgttcatgaa    8520
agaggtcgct ccaggatctc ccgacaaaac acaagggatg gacctagtca tttagtacgg    8580
gcgagatcat cctctcgagc tagttatcga agtgaatacc atacaccaag gagtgcctcg    8640
cagatccgtg tccccactgt ctttcatcgg aaaaagacag atttattgac agttccacca    8700
gcacctaaag atgtatgccc gactttaaag aaagggtttc tatgtgacag caatttctgt    8760
aaaaaggatc accaacttga aagcttaaca gatagagagt tactcttgct gattgcacgc    8820
aagacatgtg gatccacgga acaacaacta agcatagttg ctccaaaaga ttcacgtctg    8880
gctaatccta ttgctgagga tttccaacaa aaagatgggc ctaaggtaac actgtcgatg    8940
cttatagaga cagcagagta ttggtccaaa caggacatta gaacatcga tgattcaaga    9000
ttaagagctt tattgaccct ttgtgctgtt atgacgcgca aattttcaaa atctcaactt    9060
agcttgctat gtgaaagcca cttacggcga gaaggacttg gtcaagacca atcagagtca    9120
gttctggagg tatatcaacg cttacacagc gataaaggtg ggaatttcga ggcagcacta    9180
tggcagcagt gggatcggca atcattgata atgttcataa cagcattttt aaatattgca    9240
ttacaattac catgtgagag ttcatctgtt gttatttcag gtttgagaat gctgataccc    9300
cagtcggaag ccactgaggt tgtaaccccc tccgaaacct gcacatggtc agaaggagga    9360
agttcccatt gaagccccaa atcacaaggc gagctaaaaa atccctttg aacatgcata    9420
acatcacata caatttcaaa ggcattggaa taaatggtga tttcaggaag attagtgttt    9480
gccctcaaaa tcagatccga gcaataatca tctactctac agccagttaa tttctaatat    9540
aaaggttaaa aaaatgctgc aggccagcta ttgttccaca ggtcccaatt cttcttgtta    9600
aattgtagga gctagcacaa gtgatgcaat taaatgatac tagtatatac aatgccacca    9660
acttaattct aagattttgt atatctcgga aattcaaaat taaatgctac gttattgatt    9720
caattaagaa aaagacaatg gaccatcaaa attagttcaa tacctgaact aatgcactta    9780
tagaaacagg agaaccagcc agacagcaga caaataacaa tgaaccacaa tatgttactg    9840
ctataatgaa gttcgttaat tcaaaaacaa atgatgaaga ttaatgcaga tgtctaaagg    9900
ataaacactc catgcatcag tgttataatt gggctctgta gaaaatcttc atctcctcca    9960
acctacctca agaaggatt ttaccgcgat tgggagttat aacgacaata gggacaacca    10020
cctttgacac tagccaagct tgtcgtgggc acacagcatt ttatcttgca acgtcgacat    10080
tcccatcaat ctgaggagta acagctatca aaacaacgca tatgtagaca ttgtcggtaa    10140
tagtactgcc taagacaact atttataata acagttggaa ttcattttt cacccaagct    10200
attctcaagt taacagttga aacaggactc gacccaggac aactccggat acgtaacata    10260
agaaaagaac aaccccttgac ccagagtgaa caagctcata ctatcaaggc taatcctcgg    10320
gcctgcctgg agtccacaat ggccaaggct actgggaggt acaaccttat ctccccaaag    10380
aaagatcttg aaaagggct ggttctgaat gacctttgca ctctctcagt ggcccagacg    10440
gtccagggat ggaaggttac ctgggctggg attgaatttg atgttacaca gaaagggatg    10500
```

```
gccttattgc acaggctcaa gaccagtgat tttgctccag cctggtcaat gaccaggaac  10560
ttatttccac atctctttca aaacccgaac tctacaattg agtcgccact ttgggcactg  10620
cgggtcatac tagcagcagg tattcaagat cagctaattg atcaatcgtt gatcgaaccc  10680
ttggcaggag cgctaggctt aattgctgat tggcttctta ctactggaac aaaccacttt  10740
caaatgcgca cacaacaggc taaggagcaa ctaagtctaa aaatgttgtc cctggtgcga  10800
tcaaacatcc taaagttcat caaccaacta gatgcactac atgttgtgaa ttacaatgga  10860
cttctcagta gcattgaaat tggcaccaaa agccatacaa ttataattac ccggacaaat  10920
atgggttttt tggtagagtt gcaagagcct gacaaatcag ccatgaacac cagaaaacca  10980
ggaccagtca aattctccct cctccatgaa tcaaccttga agacacttgc taaaaaacct  11040
gcgacccaga tgcaagcact aatcttagaa ttcaatagtt ctctcgctat ttaactcaac  11100
tcatcaaaat gctaacttgt gatccttaag ctgcacctta gacttttgat aagaatacta  11160
actattgatg attgtctttg acatgaggat aagaacactg cccattagat agatggggtt  11220
caccattaat acacaattac ccaatcatgt taacagcagt tagatccctc aagtatatca  11280
agttcattct acccttttgca ttgtcactct aattaaatca cctgatacaa ttatgttaat  11340
tagctagatt ctctcatttt tagacttgtt tgctagaata attgatcatc cacttgatta  11400
cacatccaac tagggtctag ttcatagatt gctaataatc tttagttcaa tactaatgac  11460
aaagagatta gattagctat agcttgagga agattaagaa aaagtgtctg tggggtcttt  11520
ccgtgtagaa gggcacacag ccataattct tcctctttat acaacatggc tacacaaacat  11580 acgcaatatc cagacgcaag gttatcatca cctatagttt tagatcagtg tgatcttgtc  11640
actcgtgctt gtggattgta ttccgcatac tccttaaatc cccaactaaa gaactgtaga  11700
ctaccgaaac atatataccg actaaaatat gacaccactg ttacagagtt tttgagtgat  11760
gtgccggtag caacattgcc agcggatttt ttagtaccta catttcttag gactctatca  11820
ggaaatggtt cttgtccaat tgatccaaaa tgcagtcaat ttttagaaga aattgtcaat  11880
tatactctac aagatattcg cttcctaaac tattacctca atcgagccgg agtgcataac  11940
gatcatgtgg atagggattt tggacaaaaa attcgcaatc taatttgcga caatgaggtt  12000
ttacatcaaa tgtttcactg gtatgatctt gcaattctag cacgtagagg gcgactaaat  12060
agagggaata atcgctcaac atggtttgca agtgataatt tggtagatat cctaggttat  12120
ggagattata tttttttggaa ataccattat tcactactac cagtggatac acaaggcctc  12180
ccacatgcag ccaaggactg gtatcatgaa tcggttttca aggaggctat tcaaggccat  12240
acacacatcg tgtccatctc tacagcagat gtcttaatca tgtgtaagga cataatcacc  12300
tgtcgattta atactttact gattgctgct gtggcaaatc tagaggattc agttcattca  12360 gattacccctt taccagaaac agtgtctgac ctatacaaag caggagatta tttaatctca  12420
ttgctaggat cagaaggtta caaagtcata aaattccttg agccgttatg cttagcaaag  12480
atccaactct gctcaaatta cactgagagg aaaggaagat tcctcactca aatgcattta  12540
gctgtaaatc atacttga ggaacttaca gggtcccgag aattaaggcc acaacagatt  12600
cggaaggtaa gggaattcca tcaaatgctg ataaacctta aggcaactcc tcaacaactc  12660
tgtgagttgt tttcagtgca aaagcattgg gggcaccctg tcttgcatag cgaaaaggct  12720
atccaaaaag taaagaagca tgcaacagtg ataaaagcat gcgcccaat aataatctttt  12780 gaaacatatt gtgtgtttaa atacagcatt gcaaacatt attttgatag tcagggtacg  12840
```

```
tggtacagtg tgacttctga cagatgctta acaccaggcc tttcctctta catcaaaaga    12900
aaccaatttc ctccactacc tatgatcaaa gaacttttgt gggaatttta tcacttagat    12960
catcctccgt tattctccac caaagtgatt agtgatttga gtatcttat taaagatcgt     13020 gctactgcag tcgagaaaac atgctgggac gcagttttg aacccaatgt tcttggttat     13080
aacccaccga ataaatttgc tacaaaaagg gtacctgagc aattccttga acaggagaat    13140
ttctcaatag agagtgtcct acattatgct caacgtctgg aatatcttct cccggagtac    13200
cggaacttct ctttttcact caaggagaag gagttaaaca ttggacgagc ttttgggaaa    13260
ttgccatatc caacacgcaa tgttcaaact ctgtgcgaag ctttgttagc agatggtttg    13320
gcgaaagcat tcccaagcaa tatgatggtt gtgacagagc gcgagcaaaa agaaagcctt    13380
ttgcatcaag cgtcttggca tcacacaagt gatgattttg gtgagaatgc tactgttaga    13440
ggcagtagtt ttgtaacaga cttggaaaaa tacaatttag cattccgata tgagtttaca    13500 gctccttttta ttgaatactg taatcgttgt tacggtgtaa gaaatttgtt taattggatg    13560
cactacacta taccacagtg ttatatacat gtgagtgatt attataaccc cccacatgga    13620
gtctctctcg aaaaccgaga aaatccacca gaaggtccaa gctcttaccg tggtcatcta    13680
ggcgggattg agggacttca acaaaaactc tggacaagca tctcatgtgc acagatttca    13740
ttagttgaaa tcaaaaccgg ttttaaactg cgatctgcgg taatgggtga caatcaatgt    13800
ataactgtac tctctgtatt tcccctcgaa actgagtcta gtgagcaaga attaagttct    13860
gaagataatg ccgctagagt agctgctagc ttagcaaaag tcacaagtgc ctgcggcatc    13920 ttttaaaac ctgatgaaac ttttgttcac tcaggtttca tttattttgg caaaaaacaa     13980
tatttgaatg gagtacaatt acctcaatca ctgaaaactg ctactagaat tgcacccttg    14040
tcagatgcta tctttgatga tcttcaaggg acactagcta gcataggcac ggcttttgaa    14100
agatctatct ccgaaactag gcacgtagtc ccttgtagag tagcagctgc attccatacc    14160 ttttttccg taagaatctt acaatatcat catcttggct tcaacaaggg aacagacctg    14220
ggtcaattgt cattaagcaa gccattagat tttggaacta taactttggc cttggcagta    14280
ccacaagtct tgggtggctt atcattccta aatccagaaa aatgttttta tagaaatctg    14340
ggtgatcctg ttacttcagg gctgtttcag ctcaagacat atcttcaaat gatccacatg    14400
gatgatttgt ttttaccttt gatcgcaaag aacccaggga actgtagcgc aattgacttt    14460
gtgttaaacc ctagtgggtt aaacgtaccg gggtcacagg atttgacatc cttcctacgt    14520
cagatagtgc gccgaacaat tactctaagt gctaaaaata aattaataaa cactttgttc    14580
cattcttctg ctgatttaga agatgaaatg gtttgcaaat ggttgctttc ttctacacca    14640
gtcatgagta ggtttgccgc cgatatattt tctcgcactc ccagtgggaa acgtttacag    14700
atcttaggtt accttgaagg gactagaaca ttgttagcct ctaaaattat aaatcataat    14760
actgagacac ctatcctaga tcgattgagg aaaattacgc tgcaaaggtg gagcctgtgg    14820
tttagttatc tcgaccactg tgatcaagtt ctggctgatg ccctaactca gataacctgc    14880
actgtggact tagcacagat tcttcgcgag tacacctggg cacacatact agagggaagg    14940
cagctcattg gagcaacact tccttgtata ctagaacaac taaatgtcat ctggctcaaa    15000
ccatatgagc attgccctaa atgtgcaaag tcagcaaacc ctaaagggga accttttgtt    15060
tctattgcaa ttaaaaaaca tgtagtaagt gcttggcctg atcaatcacg acttagttgg    15120
acaattggag atggcatccc ttatatcgga tctcgaacag aggataagat tgggcagcca    15180
gccatcaaac caaaatgccc ttcagcagcc ttacgtgaag caattgagtt gacatcaaga    15240
```

```
ttgacttggg ttactcaagg tggagcaaac agcgacttac tagttaaacc cttcatagaa   15300
gcacgagtaa atttaagcgt acaggaaatt ctccaaatga caccttctca ttactccggc   15360
aacattgtgc atcgatataa tgatcaatat agtccacact catttatggc aaataggatg   15420
agtaattctg ctactaggtt agttgtttcg acaaacactc ttggagaatt tcaggagga    15480 ggtcagtcag caagagatag taatattatc ttccagaatg tcattaattt tgctgttgca   15540 cttttgatc tacgatttag gaacgtggct acttcttcta acaacatca tcgggctcat     15600 cttcatttgt caaagtgttg cacgcgagag gttccagccc aatatttagt ttatacatca   15660
acattgccat tggaccttac acggtatcgg gataatgagt tgatttacga tgacaatcca   15720
ttaagaggtg gtttaaattg caatctttct tttgataatc cgcttttcaa gggccagaga   15780
cttaacataa ttgaagaaga cttgattaga ctaccttact tatcaggatg ggagctagct   15840
aaaactgtta tccaatctat aatttctgac agcaacaatt catcaacgga tccaatcagt   15900
agtggggaaa cacgatcatt caccactcac ttcttgacat atcctaagat tggactacta   15960
tatagttttg gtgcactcat cagttattat ctaggcaaca ccattattag aaccaaaaaa   16020
ttgactctta acaacttcat atattaccta gctactcaaa tacataattt acctcatcgc   16080
tcgttgagaa tccttaaacc tactttgaaa cacgctagtg ttatctcgag attaataagt   16140
attgactctc acttctcaat ttatattgga ggaactgctg gtgatcgagg acttccgat    16200 gcggcaagat tgtttcttag aactgccatt actgtcttcc ttcaattcgt tagaaagtgg   16260
atagttgaac gcaagacagc tattccactg tgggtcatct accctctaga aggtcaaagt   16320
cctagtccga tcaacagttt tctacaccac gtcatcgcat tgttgcaaca tgagtcctcc   16380
cacgatcatg tttgtgctgc agaagcccac agtcgagtgg agacatttga taatttagtt   16440
tatatgtgta aaagcacagc aagtaacttc tttcatgctt cattagcata ctggagaagt   16500
cgatctaaaa atcaagacaa aagagagatg acaaagatat tatctttgac gcaaacggaa   16560
aagaaaaatt cattcggcta tacagcacat ccagaaagca ctgctgttct tggttccctc   16620
cagaccagcc ttgctccacc tccatctgct gacgaggcta catatgatag gaaaaacaaa   16680
gttttgaaag cttccagacc tggcaagtat tcccagaata caaccaaagc cccacccaac   16740
caaaccagtt gtcgcgatgt atctcccaat atcacaggca cagatgggtg cccttctgcc   16800
aatgagggtt ctaacagcaa taacaataat ttagtctcgc acagaattgt actgccgttt   16860
tttacattgt ctcataatta taacgaaaga ccctctatca gaaagtctga ggggacaaca   16920
gagattgtaa ggcttactcg gcagctgagg gcaataccag acaccacaat atattgccgc   16980
ttcacgggaa tagtttcttc aatgcactat aagctcgatg aagtcctttg ggaatttgat   17040
aattttaagt ctgctataac acttgccgaa ggtgaaggtt cgggtgcatt actcttatta   17100
caaaaatata agtagaaac cttgtttttt aatacactag ccacagaaca cagcattgaa    17160
gcagaaatta tttctggaat aactacacca agaatgcttc tccctattat gtctaggttc   17220
catggtggac aaataaaagt cactttaaac aattctgcaa gccagattac cgatattact   17280
aatccaagtt ggttggcaga ccaaaaatct aggatcccta agcaagtaga gattataacc   17340
atggatgctg aaacaacaga aaacattaat cggtcaaaat tgtacgaagc agtccaacag   17400
ctgattgtct cacatattga tccgaatgca ctcaaagttg tggttcttaa agttttctta   17460
agtgacattg atggaatcct atggctgaat gataacctta ccccttttgtt tgggctgggt  17520 tacttgatca agccgatcac ctctagccca aaatctagtg agtggtacct atgtctctca   17580
```

-continued

```
aaccttcttt caacttcaag acgattacct catcagagtc atactacttg catgcatgtt    17640
attcaaacag cactccagct acaaattcag aggagctcat attggcttag ccaccttgtc    17700
cagtatgcca atcataattt gcatttagat tatattaatc tcggtttccc ttcattggag    17760
agggttttat accatagata caatttagtc gattctcaga aaggcccttt gacttccatt    17820
gtccaacatc tagcgcacct gcagaccgag attagggagt tggttaatga ctataatcaa    17880
caaagacaaa gtcgaaccca acatatcat ttcattaaaa caataaaagg tcgtattaca    17940
aaattggtaa atgattacct taagttcttt ctaataatac aagccttaaa gcacaattgc    18000
acatggcaag aggaactaag agctcttcca gatctaatta gtgtctgcac tcgattctat    18060
catactcgaa actgttcatg tgaaaaccgg ttcctagtac agactttata cttatcacgc    18120
atgcaggatt cggaaatcaa actaatagat agattgaccg gccttcttag tctatgtcca    18180
aatggttttt ttcggtaagg actcttgacg tacaaactcc acatagttat acaatggtac    18240
caggacacta tatgtaaatt gaccctaaga aagagtaatt cgacacacag agttctcaag    18300
tgaaacccct catctcagat tatctgtggt tgcaattcta atatccgatt gttacccgt    18360 gagtataact ccagattaat ataagaaaat acctttgtc ctgcaaattt atcttaaatt     18420
caagtacata cgctccaaat cgtataaaat attaagaaaa agttaatctg cttgctttaa    18480
ttataacttt aatattcgac aaatagttaa cggtctcatc actcaaaaat ttcattaaca    18540
aaagaagtac tctgagtata ttcacatatc atatgtgatt aacatataag caacgcatga    18600
tgcgccttcc tcttacttat tgtgttgtca cgcagtcgtt gtactacctc gaaaattcca    18660
aacaataaat cgtgtctatc ccgcatttag tgtctttaat ttaagatctc aaatccaaaa    18720
aactgggttt atgttgatgt aaatcaataa taccgaaatt gcttgatatt aaaataaagc    18780
ttaaaggatt tttccttaaa cggtgatgtt aggtatatag gaaagctcga tcacgatgtc    18840
ccttactcag aaaaagaaaa acggaagccc tattggccat ttaatcgtac acaaaaatat    18900
ctttaccaaa ttgttttctc tttttgtgt gtcca                                18935
```

<210> SEQ ID NO 11
<211> LENGTH: 739
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus NP protein

<400> SEQUENCE: 11

```
Met Glu Ser Arg Ala His Lys Ala Trp Met Thr His Thr Ala Ser Gly
1               5                   10                  15

Phe Glu Thr Asp Tyr His Lys Ile Leu Thr Ala Gly Leu Ser Val Gln
            20                  25                  30

Gln Gly Ile Val Arg Gln Arg Val Ile Gln Val His Gln Val Thr Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
                85                  90                  95

Lys Tyr Leu Glu Gly His Gly Phe Arg Phe Glu Val Arg Lys Lys Glu
            100                 105                 110

Gly Val Lys Arg Leu Glu Glu Leu Leu Pro Ala Ala Ser Ser Gly Lys
```

```
                115                 120                 125
Ser Ile Arg Arg Thr Leu Ala Ala Met Pro Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ser Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Gln His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Lys Tyr Ala Glu Ser Arg Glu Leu Asp His Leu Gly Leu
        355                 360                 365

Asp Asp Gln Glu Lys Lys Ile Leu Lys Asp Phe His Gln Lys Lys Asn
    370                 375                 380

Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Thr Ser Leu Leu Lys
                405                 410                 415

Thr Gly Lys Gln Tyr Asp Asp Asp Asn Asp Ile Pro Phe Pro Gly Pro
            420                 425                 430

Ile Asn Asp Asn Glu Asn Ser Glu Gln Gln Asp Asp Pro Thr Asp
        435                 440                 445

Ser Gln Asp Thr Thr Ile Pro Asp Ile Ile Val Asp Pro Asp Asp Gly
    450                 455                 460

Arg Tyr Asn Asn Tyr Gly Asp Tyr Pro Ser Glu Thr Ala Asn Ala Pro
465                 470                 475                 480

Glu Asp Leu Val Leu Phe Asp Leu Glu Asp Gly Asp Glu Asp His
                485                 490                 495

Arg Pro Ser Ser Ser Ser Glu Asn Asn Asn Lys His Ser Leu Thr Gly
            500                 505                 510

Thr Asp Ser Asn Lys Thr Ser Asn Trp Asn Arg Asn Pro Thr Asn Met
        515                 520                 525

Pro Lys Lys Asp Ser Thr Gln Asn Asn Asp Asn Pro Ala Gln Arg Ala
    530                 535                 540
```

Gln Glu Tyr Ala Arg Asp Asn Ile Gln Asp Thr Pro Thr His Arg
545                 550                 555                 560

Ala Leu Thr Pro Ile Ser Glu Glu Thr Gly Ser Asn Gly His Asn Glu
                565                 570                 575

Asp Asp Ile Asp Ser Ile Pro Pro Leu Glu Ser Asp Glu Asn Asn
            580                 585                 590

Thr Glu Thr Thr Ile Thr Thr Thr Lys Asn Thr Thr Ala Pro Pro Ala
                595                 600                 605

Pro Val Tyr Arg Ser Asn Ser Glu Lys Glu Pro Leu Pro Gln Glu Lys
            610                 615                 620

Ser Gln Lys Gln Pro Asn Gln Val Ser Gly Ser Glu Asn Thr Asp Asn
625                 630                 635                 640

Lys Pro His Ser Glu Gln Ser Val Glu Met Tyr Arg His Ile Leu
                645                 650                 655

Gln Thr Gln Gly Pro Phe Asp Ala Ile Leu Tyr Tyr Met Met Thr
                660                 665                 670

Glu Glu Pro Ile Val Phe Ser Thr Ser Asp Gly Lys Glu Tyr Val Tyr
            675                 680                 685

Pro Asp Ser Leu Glu Gly Glu His Pro Pro Trp Leu Ser Glu Lys Glu
            690                 695                 700

Ala Leu Asn Glu Asp Asn Arg Phe Ile Thr Met Asp Asp Gln Gln Phe
705                 710                 715                 720

Tyr Trp Pro Val Met Asn His Arg Asn Lys Phe Met Ala Ile Leu Gln
                725                 730                 735

His His Lys

<210> SEQ ID NO 12
<211> LENGTH: 341
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus VP35 NP protein

<400> SEQUENCE: 12

Met Ile Ser Thr Arg Ala Ala Ile Asn Asp Pro Ser Leu Pro Ile
1               5                   10                  15

Arg Asn Gln Cys Thr Arg Gly Pro Glu Leu Ser Gly Trp Ile Ser Glu
                20                  25                  30

Gln Leu Met Thr Gly Lys Ile Pro Val His Glu Ile Phe Asn Asp Thr
                35                  40                  45

Glu Pro His Ile Ser Ser Gly Ser Asp Cys Leu Pro Arg Pro Lys Asn
    50                  55                  60

Thr Ala Pro Arg Thr Arg Asn Thr Gln Thr Gln Thr Asp Pro Val Cys
65                  70                  75                  80

Asn His Asn Phe Glu Asp Val Thr Gln Ala Leu Thr Ser Leu Thr Asn
                85                  90                  95

Val Ile Gln Lys Gln Ala Leu Asn Leu Glu Ser Leu Glu Gln Arg Ile
                100                 105                 110

Ile Asp Leu Glu Asn Gly Leu Lys Pro Met Tyr Asp Met Ala Lys Val
            115                 120                 125

Ile Ser Ala Leu Asn Arg Ser Cys Ala Glu Met Val Ala Lys Tyr Asp
    130                 135                 140

Leu Leu Val Met Thr Thr Gly Arg Ala Thr Ala Thr Ala Ala Ala Thr
145                 150                 155                 160

Glu Ala Tyr Trp Glu Glu His Gly Gln Pro Pro Gly Pro Ser Leu
            165                 170                 175

Tyr Glu Glu Ser Ala Ile Arg Gly Lys Ile Asn Lys Gln Glu Asp Lys
            180                 185                 190

Val Pro Lys Glu Val Gln Glu Ala Phe Arg Asn Leu Asp Ser Thr Ser
            195                 200                 205

Ser Leu Thr Glu Glu Asn Phe Gly Lys Pro Asp Ile Ser Ala Lys Asp
        210                 215                 220

Leu Arg Asp Ile Met Tyr Asp His Leu Pro Gly Phe Gly Thr Ala Phe
225                 230                 235                 240

His Gln Leu Val Gln Val Ile Cys Lys Leu Gly Lys Asp Asn Ser Ala
            245                 250                 255

Leu Asp Ile Ile His Ala Glu Phe Gln Ala Ser Leu Ala Glu Gly Asp
            260                 265                 270

Ser Pro Gln Cys Ala Leu Ile Gln Ile Thr Lys Arg Ile Pro Ile Phe
        275                 280                 285

Gln Asp Ala Thr Pro Thr Ile His Ile Arg Ser Arg Gly Asp Ile
            290                 295                 300

Pro Arg Ala Cys Gln Lys Ser Leu Arg Pro Val Pro Ser Pro Lys
305                 310                 315                 320

Ile Asp Arg Gly Trp Val Cys Ile Phe Gln Leu Gln Asp Gly Lys Thr
            325                 330                 335

Leu Gly Leu Lys Ile
            340

<210> SEQ ID NO 13
<211> LENGTH: 326
<212> TYPE: PRT
<213> ORGANISM: Bundibugyo ebolavirus
<220> FEATURE:
<221> NAME/KEY: misc_feature
<223> OTHER INFORMATION: Cote d'Ivoire ebolavirus VP40 NP protein

<400> SEQUENCE: 13

Met Arg Arg Ile Ile Leu Pro Thr Ala Pro Pro Glu Tyr Met Glu Ala
1               5                   10                  15

Val Tyr Pro Met Arg Thr Met Asn Ser Gly Ala Asp Asn Thr Ala Ser
            20                  25                  30

Gly Pro Asn Tyr Thr Thr Thr Gly Val Met Thr Asn Asp Thr Pro Ser
        35                  40                  45

Asn Ser Leu Arg Pro Val Ala Asp Asp Asn Ile Asp His Pro Ser His
    50                  55                  60

Thr Pro Asn Ser Val Ala Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ser Asp Gln Lys Thr Tyr Ser Phe Asp Ser Thr Thr
            100                 105                 110

Ala Ala Ile Met Leu Ala Ser Tyr Thr Ile Thr His Phe Gly Lys Thr
        115                 120                 125

Ser Asn Pro Leu Val Arg Ile Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu

```
                    165                 170                 175
Thr Ala Leu Lys Leu Ile Thr Gln Pro Leu Pro Ala Thr Trp Thr
                180                 185                 190

Asp Glu Thr Pro Ala Val Ser Thr Gly Thr Leu Arg Pro Gly Ile Ser
            195                 200                 205

Phe His Pro Lys Leu Arg Pro Ile Leu Leu Pro Gly Arg Ala Gly Lys
        210                 215                 220

Lys Gly Ser Asn Ser Asp Leu Thr Ser Pro Asp Lys Ile Gln Ala Ile
225                 230                 235                 240

Met Asn Phe Leu Gln Asp Leu Lys Ile Val Pro Ile Asp Pro Thr Lys
                245                 250                 255

Asn Ile Met Gly Ile Glu Val Pro Glu Leu Leu Val His Arg Leu Thr
            260                 265                 270

Gly Lys Lys Thr Thr Lys Asn Gly Gln Pro Ile Ile Pro Ile Leu
        275                 280                 285

Leu Pro Lys Tyr Ile Gly Leu Asp Pro Leu Ser Gln Gly Asp Leu Thr
        290                 295                 300

Met Val Ile Thr Gln Asp Cys Asp Ser Cys His Ser Pro Ala Ser Leu
305                 310                 315                 320

Pro Pro Val Asn Glu Lys
                325

<210> SEQ ID NO 14
<211> LENGTH: 676
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus GP NP protein

<400> SEQUENCE: 14

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
                20                  25                  30

Ile Pro Leu Gly Val Val His Asn Asn Thr Leu Gln Val Ser Asp Ile
            35                  40                  45

Asp Lys Phe Val Cys Arg Asp Lys Leu Ser Ser Thr Ser Gln Leu Lys
        50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
        130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190
```

Phe Phe Gln Ser Pro Pro Leu His Glu Pro Ala Asn Met Thr Thr Asp
            195                 200                 205

Pro Ser Ser Tyr Tyr His Thr Thr Ile Asn Tyr Val Val Asp Asn
        210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Ser Asn Thr Thr Gly Lys
            260                 265                 270

Leu Ile Trp Lys Ile Asn Pro Thr Val Asp Thr Ser Met Gly Glu Trp
        275                 280                 285

Ala Phe Trp Glu Asn Lys Lys Asn Phe Thr Lys Thr Leu Ser Ser Glu
    290                 295                 300

Glu Leu Ser Phe Val Pro Val Pro Glu Thr Gln Asn Gln Val Leu Asp
305                 310                 315                 320

Thr Thr Ala Thr Val Ser Pro Pro Ile Ser Ala His Asn His Ala Ala
                325                 330                 335

Glu Asp His Lys Glu Leu Val Ser Glu Asp Ser Thr Pro Val Val Gln
            340                 345                 350

Met Gln Asn Ile Lys Gly Lys Asp Thr Met Pro Thr Val Thr Gly
        355                 360                 365

Val Pro Thr Thr Thr Pro Ser Pro Phe Pro Ile Asn Ala Arg Asn Thr
    370                 375                 380

Asp His Thr Lys Ser Phe Ile Gly Leu Glu Gly Pro Gln Glu Asp His
385                 390                 395                 400

Ser Thr Thr Gln Pro Ala Lys Thr Thr Ser Gln Pro Thr Asn Ser Thr
                405                 410                 415

Glu Ser Thr Thr Leu Asn Pro Thr Ser Glu Pro Ser Ser Arg Gly Thr
            420                 425                 430

Gly Pro Ser Ser Pro Thr Val Pro Asn Thr Thr Glu Ser His Ala Glu
        435                 440                 445

Leu Gly Lys Thr Thr Pro Thr Thr Leu Pro Glu Gln His Thr Ala Ala
450                 455                 460

Ser Ala Ile Pro Arg Ala Val His Pro Asp Glu Leu Ser Gly Pro Gly
465                 470                 475                 480

Phe Leu Thr Asn Thr Ile Arg Gly Val Thr Asn Leu Leu Thr Gly Ser
                485                 490                 495

Arg Arg Lys Arg Arg Asp Val Thr Pro Asn Thr Gln Pro Lys Cys Asn
            500                 505                 510

Pro Asn Leu His Tyr Trp Thr Ala Leu Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Ile Met Glu Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro Gln Asp Trp Thr Lys Asn Ile Thr Asp Lys Ile Asp

```
                610                615                620
Gln Ile Ile His Asp Phe Val Asp Asn Asn Leu Pro Asn Gln Asn Asp
625                630                635                640

Gly Ser Asn Trp Trp Thr Gly Trp Lys Gln Trp Val Pro Ala Gly Ile
                645                650                655

Gly Ile Thr Gly Val Ile Ala Ile Ala Leu Leu Cys Ile Cys
                660                665                670

Lys Phe Met Leu
        675

<210> SEQ ID NO 15
<211> LENGTH: 365
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus SGP NP protein

<400> SEQUENCE: 15

Met Gly Ala Ser Gly Ile Leu Gln Leu Pro Arg Glu Arg Phe Arg Lys
1               5                  10                  15

Thr Ser Phe Phe Val Trp Val Ile Ile Leu Phe His Lys Val Phe Ser
                20                  25                  30

Ile Pro Leu Gly Val Val His Asn Asn Thr Leu Gln Val Ser Asp Ile
            35                  40                  45

Asp Lys Phe Val Cys Arg Asp Lys Leu Ser Ser Thr Ser Gln Leu Lys
50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
            115                 120                 125

Val Arg Asp Phe Pro Arg Cys Arg Tyr Val His Lys Val Ser Gly Thr
130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Leu His Glu Pro Ala Asn Met Thr Thr Asp
            195                 200                 205

Pro Ser Ser Tyr Tyr His Thr Thr Ile Asn Tyr Val Val Asp Asn
            210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
            275                 280                 285
```

-continued

```
Ala Phe Trp Glu Asn Lys Lys Thr Ser Gln Lys Pro Phe Gln Val Lys
    290                 295                 300

Ser Cys Leu Ser Tyr Leu Tyr Gln Lys Pro Arg Thr Arg Ser Leu Thr
305                 310                 315                 320

Arg Gln Arg Arg Ser Leu Leu Pro Ser Pro Thr Thr Thr Gln Pro
                325                 330                 335

Lys Thr Thr Lys Asn Trp Phe Gln Arg Ile Pro Leu Gln Trp Phe Arg
            340                 345                 350

Cys Lys Thr Ser Arg Glu Arg Thr Gln Cys Gln Pro Gln
                355                 360                 365

<210> SEQ ID NO 16
<211> LENGTH: 302
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus SSGP NP protein

<400> SEQUENCE: 16

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
                20                  25                  30

Ile Pro Leu Gly Val Val His Asn Asn Thr Leu Gln Val Ser Asp Ile
            35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
    130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Thr Thr Ile Asn Tyr Val Val Asp Asn
    210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
        275                 280                 285
```

```
Ala Phe Trp Glu Asn Lys Lys Leu His Lys Asn Pro Phe Lys
        290                 295                 300

<210> SEQ ID NO 17
<211> LENGTH: 289
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus VP30 NP protein

<400> SEQUENCE: 17

Met Glu Val Val His Glu Arg Gly Arg Ser Arg Ile Ser Arg Gln Asn
1               5                   10                  15

Thr Arg Asp Gly Pro Ser His Leu Val Arg Ala Arg Ser Ser Ser Arg
            20                  25                  30

Ala Ser Tyr Arg Ser Glu Tyr His Thr Pro Arg Ser Ala Ser Gln Ile
        35                  40                  45

Arg Val Pro Thr Val Phe His Arg Lys Lys Thr Asp Leu Leu Thr Val
    50                  55                  60

Pro Pro Ala Pro Lys Asp Val Cys Pro Thr Leu Lys Lys Gly Phe Leu
65                  70                  75                  80

Cys Asp Ser Asn Phe Cys Lys Lys Asp His Gln Leu Glu Ser Leu Thr
                85                  90                  95

Asp Arg Glu Leu Leu Leu Ile Ala Arg Lys Thr Cys Gly Ser Thr
            100                 105                 110

Glu Gln Gln Leu Ser Ile Val Ala Pro Lys Asp Ser Arg Leu Ala Asn
        115                 120                 125

Pro Ile Ala Glu Asp Phe Gln Gln Lys Asp Gly Pro Lys Val Thr Leu
    130                 135                 140

Ser Met Leu Ile Glu Thr Ala Glu Tyr Trp Ser Lys Gln Asp Ile Lys
145                 150                 155                 160

Asn Ile Asp Asp Ser Arg Leu Arg Ala Leu Leu Thr Leu Cys Ala Val
                165                 170                 175

Met Thr Arg Lys Phe Ser Lys Ser Gln Leu Ser Leu Leu Cys Glu Ser
            180                 185                 190

His Leu Arg Arg Glu Gly Leu Gly Gln Asp Gln Ser Glu Ser Val Leu
        195                 200                 205

Glu Val Tyr Gln Arg Leu His Ser Asp Lys Gly Gly Asn Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ser Val
                245                 250                 255

Val Ile Ser Gly Leu Arg Met Leu Ile Pro Gln Ser Glu Ala Thr Glu
            260                 265                 270

Val Val Thr Pro Ser Glu Thr Cys Thr Trp Ser Glu Gly Gly Ser Ser
        275                 280                 285

His

<210> SEQ ID NO 18
<211> LENGTH: 251
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus VP24 NP protein
```

<400> SEQUENCE: 18

Met Ala Lys Ala Thr Gly Arg Tyr Asn Leu Ile Ser Pro Lys Lys Asp
1               5                   10                  15

Leu Glu Lys Gly Leu Val Leu Asn Asp Leu Cys Thr Leu Ser Val Ala
            20                  25                  30

Gln Thr Val Gln Gly Trp Lys Val Thr Trp Ala Gly Ile Glu Phe Asp
        35                  40                  45

Val Thr Gln Lys Gly Met Ala Leu Leu His Arg Leu Lys Thr Ser Asp
    50                  55                  60

Phe Ala Pro Ala Trp Ser Met Thr Arg Asn Leu Phe Pro His Leu Phe
65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ala Asp Trp Leu Leu Thr
        115                 120                 125

Thr Gly Thr Asn His Phe Gln Met Arg Thr Gln Gln Ala Lys Glu Gln
130                 135                 140

Leu Ser Leu Lys Met Leu Ser Leu Val Arg Ser Asn Ile Leu Lys Phe
145                 150                 155                 160

Ile Asn Gln Leu Asp Ala Leu His Val Val Asn Tyr Asn Gly Leu Leu
                165                 170                 175

Ser Ser Ile Glu Ile Gly Thr Lys Ser His Thr Ile Ile Ile Thr Arg
            180                 185                 190

Thr Asn Met Gly Phe Leu Val Glu Leu Gln Glu Pro Asp Lys Ser Ala
        195                 200                 205

Met Asn Thr Arg Lys Pro Gly Pro Val Lys Phe Ser Leu Leu His Glu
    210                 215                 220

Ser Thr Leu Lys Thr Leu Ala Lys Lys Pro Ala Thr Gln Met Gln Ala
225                 230                 235                 240

Leu Ile Leu Glu Phe Asn Ser Ser Leu Ala Ile
                245                 250

<210> SEQ ID NO 19
<211> LENGTH: 2210
<212> TYPE: PRT
<213> ORGANISM: Bundibugyo ebolavirus
<220> FEATURE:
<221> NAME/KEY: misc_feature
<223> OTHER INFORMATION: Cote dIvoire ebolavirus L NP protein

<400> SEQUENCE: 19

Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
            20                  25                  30

Ser Ala Tyr Ser Leu Asn Pro Gln Leu Lys Asn Cys Arg Leu Pro Lys
        35                  40                  45

His Ile Tyr Arg Leu Lys Tyr Asp Thr Thr Val Thr Glu Phe Leu Ser
    50                  55                  60

Asp Val Pro Val Ala Thr Leu Pro Ala Asp Phe Leu Val Pro Thr Phe
65                  70                  75                  80

Leu Arg Thr Leu Ser Gly Asn Gly Ser Cys Pro Ile Asp Pro Lys Cys
                85                  90                  95

Ser Gln Phe Leu Glu Glu Ile Val Asn Tyr Thr Leu Gln Asp Ile Arg
            100                 105                 110

Phe Leu Asn Tyr Tyr Leu Asn Arg Ala Gly Val His Asn Asp His Val
            115                 120                 125

Asp Arg Asp Phe Gly Gln Lys Ile Arg Asn Leu Ile Cys Asp Asn Glu
130                 135                 140

Val Leu His Gln Met Phe His Trp Tyr Asp Leu Ala Ile Leu Ala Arg
145                 150                 155                 160

Arg Gly Arg Leu Asn Arg Gly Asn Asn Arg Ser Thr Trp Phe Ala Ser
                165                 170                 175

Asp Asn Leu Val Asp Ile Leu Gly Tyr Gly Asp Tyr Ile Phe Trp Lys
            180                 185                 190

Ile Pro Leu Ser Leu Leu Pro Val Asp Thr Gln Gly Leu Pro His Ala
            195                 200                 205

Ala Lys Asp Trp Tyr His Glu Ser Val Phe Lys Glu Ala Ile Gln Gly
            210                 215                 220

His Thr His Ile Val Ser Ile Ser Thr Ala Asp Val Leu Ile Met Cys
225                 230                 235                 240

Lys Asp Ile Ile Thr Cys Arg Phe Asn Thr Leu Leu Ile Ala Ala Val
                245                 250                 255

Ala Asn Leu Glu Asp Ser Val His Ser Asp Tyr Pro Leu Pro Glu Thr
            260                 265                 270

Val Ser Asp Leu Tyr Lys Ala Gly Asp Tyr Leu Ile Ser Leu Leu Gly
            275                 280                 285

Ser Glu Gly Tyr Lys Val Ile Lys Phe Leu Glu Pro Leu Cys Leu Ala
            290                 295                 300

Lys Ile Gln Leu Cys Ser Asn Tyr Thr Glu Arg Lys Gly Arg Phe Leu
305                 310                 315                 320

Thr Gln Met His Leu Ala Val Asn His Thr Leu Glu Glu Leu Thr Gly
                325                 330                 335

Ser Arg Glu Leu Arg Pro Gln Gln Ile Arg Lys Val Arg Glu Phe His
            340                 345                 350

Gln Met Leu Ile Asn Leu Lys Ala Thr Pro Gln Gln Leu Cys Glu Leu
            355                 360                 365

Phe Ser Val Gln Lys His Trp Gly His Pro Val Leu His Ser Glu Lys
            370                 375                 380

Ala Ile Gln Lys Val Lys Lys His Ala Thr Val Ile Lys Ala Leu Arg
385                 390                 395                 400

Pro Ile Ile Ile Phe Glu Thr Tyr Cys Val Phe Lys Tyr Ser Ile Ala
                405                 410                 415

Lys His Tyr Phe Asp Ser Gln Gly Thr Trp Tyr Ser Val Thr Ser Asp
            420                 425                 430

Arg Cys Leu Thr Pro Gly Leu Ser Ser Tyr Ile Lys Arg Asn Gln Phe
            435                 440                 445

Pro Pro Leu Pro Met Ile Lys Glu Leu Leu Trp Glu Phe Tyr His Leu
450                 455                 460

Asp His Pro Pro Leu Phe Ser Thr Lys Val Ile Ser Asp Leu Ser Ile
465                 470                 475                 480

Phe Ile Lys Asp Arg Ala Thr Ala Val Glu Lys Thr Cys Trp Asp Ala
                485                 490                 495

Val Phe Glu Pro Asn Val Leu Gly Tyr Asn Pro Pro Asn Lys Phe Ala
            500                 505                 510

Thr Lys Arg Val Pro Glu Gln Phe Leu Glu Gln Glu Asn Phe Ser Ile
            515                 520                 525

Glu Ser Val Leu His Tyr Ala Gln Arg Leu Glu Tyr Leu Leu Pro Glu
530                 535                 540

Tyr Arg Asn Phe Ser Phe Ser Leu Lys Glu Lys Glu Leu Asn Ile Gly
545                 550                 555                 560

Arg Ala Phe Gly Lys Leu Pro Tyr Pro Thr Arg Asn Val Gln Thr Leu
                565                 570                 575

Cys Glu Ala Leu Leu Ala Asp Gly Leu Ala Lys Ala Phe Pro Ser Asn
            580                 585                 590

Met Met Val Val Thr Glu Arg Glu Gln Lys Glu Ser Leu Leu His Gln
            595                 600                 605

Ala Ser Trp His His Thr Ser Asp Asp Phe Gly Glu Asn Ala Thr Val
610                 615                 620

Arg Gly Ser Ser Phe Val Thr Asp Leu Glu Lys Tyr Asn Leu Ala Phe
625                 630                 635                 640

Arg Tyr Glu Phe Thr Ala Pro Phe Ile Glu Tyr Cys Asn Arg Cys Tyr
                645                 650                 655

Gly Val Arg Asn Leu Phe Asn Trp Met His Tyr Thr Ile Pro Gln Cys
            660                 665                 670

Tyr Ile His Val Ser Asp Tyr Tyr Asn Pro Pro His Gly Val Ser Leu
            675                 680                 685

Glu Asn Arg Glu Asn Pro Pro Glu Gly Pro Ser Ser Tyr Arg Gly His
            690                 695                 700

Leu Gly Gly Ile Glu Gly Leu Gln Gln Lys Leu Trp Thr Ser Ile Ser
705                 710                 715                 720

Cys Ala Gln Ile Ser Leu Val Glu Ile Lys Thr Gly Phe Lys Leu Arg
                725                 730                 735

Ser Ala Val Met Gly Asp Asn Gln Cys Ile Thr Val Leu Ser Val Phe
            740                 745                 750

Pro Leu Glu Thr Glu Ser Ser Glu Gln Glu Leu Ser Ser Glu Asp Asn
            755                 760                 765

Ala Ala Arg Val Ala Ala Ser Leu Ala Lys Val Thr Ser Ala Cys Gly
            770                 775                 780

Ile Phe Leu Lys Pro Asp Glu Thr Phe Val His Ser Gly Phe Ile Tyr
785                 790                 795                 800

Phe Gly Lys Lys Gln Tyr Leu Asn Gly Val Gln Leu Pro Gln Ser Leu
                805                 810                 815

Lys Thr Ala Thr Arg Ile Ala Pro Leu Ser Asp Ala Ile Phe Asp Asp
            820                 825                 830

Leu Gln Gly Thr Leu Ala Ser Ile Gly Thr Ala Phe Glu Arg Ser Ile
            835                 840                 845

Ser Glu Thr Arg His Val Val Pro Cys Arg Val Ala Ala Ala Phe His
850                 855                 860

Thr Phe Phe Ser Val Arg Ile Leu Gln Tyr His His Leu Gly Phe Asn
865                 870                 875                 880

Lys Gly Thr Asp Leu Gly Gln Leu Ser Leu Ser Lys Pro Leu Asp Phe
                885                 890                 895

Gly Thr Ile Thr Leu Ala Leu Ala Val Pro Gln Val Leu Gly Gly Leu
            900                 905                 910

Ser Phe Leu Asn Pro Glu Lys Cys Phe Tyr Arg Asn Leu Gly Asp Pro
            915                 920                 925

Val Thr Ser Gly Leu Phe Gln Leu Lys Thr Tyr Leu Gln Met Ile His

```
                930             935             940
Met Asp Asp Leu Phe Leu Pro Leu Ile Ala Lys Asn Pro Gly Asn Cys
945                 950             955             960

Ser Ala Ile Asp Phe Val Leu Asn Pro Ser Gly Leu Asn Val Pro Gly
            965             970             975

Ser Gln Asp Leu Thr Ser Phe Leu Arg Gln Ile Val Arg Thr Ile
                980             985             990

Thr Leu Ser Ala Lys Asn Lys Leu Ile Asn Thr Leu Phe His Ser Ser
            995             1000            1005

Ala Asp Leu Glu Asp Glu Met Val Cys Lys Trp Leu Leu Ser Ser
    1010            1015            1020

Thr Pro Val Met Ser Arg Phe Ala Ala Asp Ile Phe Ser Arg Thr
    1025            1030            1035

Pro Ser Gly Lys Arg Leu Gln Ile Leu Gly Tyr Leu Glu Gly Thr
    1040            1045            1050

Arg Thr Leu Leu Ala Ser Lys Ile Ile Asn His Asn Thr Glu Thr
    1055            1060            1065

Pro Ile Leu Asp Arg Leu Arg Lys Ile Thr Leu Gln Arg Trp Ser
    1070            1075            1080

Leu Trp Phe Ser Tyr Leu Asp His Cys Asp Gln Val Leu Ala Asp
    1085            1090            1095

Ala Leu Thr Gln Ile Thr Cys Thr Val Asp Leu Ala Gln Ile Leu
    1100            1105            1110

Arg Glu Tyr Thr Trp Ala His Ile Leu Glu Gly Arg Gln Leu Ile
    1115            1120            1125

Gly Ala Thr Leu Pro Cys Ile Leu Glu Gln Leu Asn Val Ile Trp
    1130            1135            1140

Leu Lys Pro Tyr Glu His Cys Pro Lys Cys Ala Lys Ser Ala Asn
    1145            1150            1155

Pro Lys Gly Glu Pro Phe Val Ser Ile Ala Ile Lys Lys His Val
    1160            1165            1170

Val Ser Ala Trp Pro Asp Gln Ser Arg Leu Ser Trp Thr Ile Gly
    1175            1180            1185

Asp Gly Ile Pro Tyr Ile Gly Ser Arg Thr Glu Asp Lys Ile Gly
    1190            1195            1200

Gln Pro Ala Ile Lys Pro Lys Cys Pro Ser Ala Ala Leu Arg Glu
    1205            1210            1215

Ala Ile Glu Leu Thr Ser Arg Leu Thr Trp Val Thr Gln Gly Gly
    1220            1225            1230

Ala Asn Ser Asp Leu Leu Val Lys Pro Phe Ile Glu Ala Arg Val
    1235            1240            1245

Asn Leu Ser Val Gln Glu Ile Leu Gln Met Thr Pro Ser His Tyr
    1250            1255            1260

Ser Gly Asn Ile Val His Arg Tyr Asn Asp Gln Tyr Ser Pro His
    1265            1270            1275

Ser Phe Met Ala Asn Arg Met Ser Asn Ser Ala Thr Arg Leu Val
    1280            1285            1290

Val Ser Thr Asn Thr Leu Gly Glu Phe Ser Gly Gly Gly Gln Ser
    1295            1300            1305

Ala Arg Asp Ser Asn Ile Ile Phe Gln Asn Val Ile Asn Phe Ala
    1310            1315            1320

Val Ala Leu Phe Asp Leu Arg Phe Arg Asn Val Ala Thr Ser Ser
    1325            1330            1335
```

-continued

Ile Gln His His Arg Ala His Leu His Leu Ser Lys Cys Cys Thr
1340                1345                1350

Arg Glu Val Pro Ala Gln Tyr Leu Val Tyr Thr Ser Thr Leu Pro
1355                1360                1365

Leu Asp Leu Thr Arg Tyr Arg Asp Asn Glu Leu Ile Tyr Asp Asp
1370                1375                1380

Asn Pro Leu Arg Gly Gly Leu Asn Cys Asn Leu Ser Phe Asp Asn
1385                1390                1395

Pro Leu Phe Lys Gly Gln Arg Leu Asn Ile Ile Glu Glu Asp Leu
1400                1405                1410

Ile Arg Leu Pro Tyr Leu Ser Gly Trp Glu Leu Ala Lys Thr Val
1415                1420                1425

Ile Gln Ser Ile Ile Ser Asp Ser Asn Asn Ser Thr Asp Pro
1430                1435                1440

Ile Ser Ser Gly Glu Thr Arg Ser Phe Thr Thr His Phe Leu Thr
1445                1450                1455

Tyr Pro Lys Ile Gly Leu Leu Tyr Ser Phe Gly Ala Leu Ile Ser
1460                1465                1470

Tyr Tyr Leu Gly Asn Thr Ile Ile Arg Thr Lys Lys Leu Thr Leu
1475                1480                1485

Asn Asn Phe Ile Tyr Tyr Leu Ala Thr Gln Ile His Asn Leu Pro
1490                1495                1500

His Arg Ser Leu Arg Ile Leu Lys Pro Thr Leu Lys His Ala Ser
1505                1510                1515

Val Ile Ser Arg Leu Ile Ser Ile Asp Ser His Phe Ser Ile Tyr
1520                1525                1530

Ile Gly Gly Thr Ala Gly Asp Arg Gly Leu Ser Asp Ala Ala Arg
1535                1540                1545

Leu Phe Leu Arg Thr Ala Ile Thr Val Phe Leu Gln Phe Val Arg
1550                1555                1560

Lys Trp Ile Val Glu Arg Lys Thr Ala Ile Pro Leu Trp Val Ile
1565                1570                1575

Tyr Pro Leu Glu Gly Gln Ser Pro Ser Pro Ile Asn Ser Phe Leu
1580                1585                1590

His His Val Ile Ala Leu Leu Gln His Glu Ser Ser His Asp His
1595                1600                1605

Val Cys Ala Ala Glu Ala His Ser Arg Val Glu Thr Phe Asp Asn
1610                1615                1620

Leu Val Tyr Met Cys Lys Ser Thr Ala Ser Asn Phe Phe His Ala
1625                1630                1635

Ser Leu Ala Tyr Trp Arg Ser Arg Ser Lys Asn Gln Asp Lys Arg
1640                1645                1650

Glu Met Thr Lys Ile Leu Ser Leu Thr Gln Thr Glu Lys Lys Asn
1655                1660                1665

Ser Phe Gly Tyr Thr Ala His Pro Glu Ser Thr Ala Val Leu Gly
1670                1675                1680

Ser Leu Gln Thr Ser Leu Ala Pro Pro Pro Ser Ala Asp Glu Ala
1685                1690                1695

Thr Tyr Asp Arg Lys Asn Lys Val Leu Lys Ala Ser Arg Pro Gly
1700                1705                1710

Lys Tyr Ser Gln Asn Thr Thr Lys Ala Pro Pro Asn Gln Thr Ser
1715                1720                1725

-continued

```
Cys Arg Asp Val Ser Pro Asn Ile Thr Gly Thr Asp Gly Cys Pro
1730                1735                1740

Ser Ala Asn Glu Gly Ser Asn Ser Asn Asn Asn Leu Val Ser
1745                1750                1755

His Arg Ile Val Leu Pro Phe Phe Thr Leu Ser His Asn Tyr Asn
1760                1765                1770

Glu Arg Pro Ser Ile Arg Lys Ser Glu Gly Thr Thr Glu Ile Val
1775                1780                1785

Arg Leu Thr Arg Gln Leu Arg Ala Ile Pro Asp Thr Thr Ile Tyr
1790                1795                1800

Cys Arg Phe Thr Gly Ile Val Ser Ser Met His Tyr Lys Leu Asp
1805                1810                1815

Glu Val Leu Trp Glu Phe Asp Asn Phe Lys Ser Ala Ile Thr Leu
1820                1825                1830

Ala Glu Gly Glu Gly Ser Gly Ala Leu Leu Leu Gln Lys Tyr
1835                1840                1845

Lys Val Glu Thr Leu Phe Phe Asn Thr Leu Ala Thr Glu His Ser
1850                1855                1860

Ile Glu Ala Glu Ile Ile Ser Gly Ile Thr Thr Pro Arg Met Leu
1865                1870                1875

Leu Pro Ile Met Ser Arg Phe His Gly Gly Gln Ile Lys Val Thr
1880                1885                1890

Leu Asn Asn Ser Ala Ser Gln Ile Thr Asp Ile Thr Asn Pro Ser
1895                1900                1905

Trp Leu Ala Asp Gln Lys Ser Arg Ile Pro Lys Gln Val Glu Ile
1910                1915                1920

Ile Thr Met Asp Ala Glu Thr Thr Glu Asn Ile Asn Arg Ser Lys
1925                1930                1935

Leu Tyr Glu Ala Val Gln Gln Leu Ile Val Ser His Ile Asp Pro
1940                1945                1950

Asn Ala Leu Lys Val Val Val Leu Lys Val Phe Leu Ser Asp Ile
1955                1960                1965

Asp Gly Ile Leu Trp Leu Asn Asp Asn Leu Thr Pro Leu Phe Gly
1970                1975                1980

Leu Gly Tyr Leu Ile Lys Pro Ile Thr Ser Ser Pro Lys Ser Ser
1985                1990                1995

Glu Trp Tyr Leu Cys Leu Ser Asn Leu Leu Ser Thr Ser Arg Arg
2000                2005                2010

Leu Pro His Gln Ser His Thr Thr Cys Met His Val Ile Gln Thr
2015                2020                2025

Ala Leu Gln Leu Gln Ile Gln Arg Ser Ser Tyr Trp Leu Ser His
2030                2035                2040

Leu Val Gln Tyr Ala Asn His Asn Leu His Leu Asp Tyr Ile Asn
2045                2050                2055

Leu Gly Phe Pro Ser Leu Glu Arg Val Leu Tyr His Arg Tyr Asn
2060                2065                2070

Leu Val Asp Ser Gln Lys Gly Pro Leu Thr Ser Ile Val Gln His
2075                2080                2085

Leu Ala His Leu Gln Thr Glu Ile Arg Glu Leu Val Asn Asp Tyr
2090                2095                2100

Asn Gln Gln Arg Gln Ser Arg Thr Gln Thr Tyr His Phe Ile Lys
2105                2110                2115

Thr Ile Lys Gly Arg Ile Thr Lys Leu Val Asn Asp Tyr Leu Lys
```

```
                2120                2125                2130
Phe  Phe  Leu  Ile  Ile  Gln  Ala  Leu  Lys  His  Asn  Cys  Thr  Trp  Gln
          2135                2140                2145

Glu  Glu  Leu  Arg  Ala  Leu  Pro  Asp  Leu  Ile  Ser  Val  Cys  Thr  Arg
     2150                2155                2160

Phe  Tyr  His  Thr  Arg  Asn  Cys  Ser  Cys  Glu  Asn  Arg  Phe  Leu  Val
     2165                2170                2175

Gln  Thr  Leu  Tyr  Leu  Ser  Arg  Met  Gln  Asp  Ser  Glu  Ile  Lys  Leu
     2180                2185                2190

Ile  Asp  Arg  Leu  Thr  Gly  Leu  Leu  Ser  Leu  Cys  Pro  Asn  Gly  Phe
     2195                2200                2205

Phe  Arg
     2210

<210> SEQ ID NO 20
<211> LENGTH: 18959
<212> TYPE: DNA
<213> ORGANISM: Zaire ebolavirus
<220> FEATURE:
<221> NAME/KEY: misc_feature
<223> OTHER INFORMATION: Full viral sequence

<400> SEQUENCE: 20
cggacacaca aaagaaaga agaatttttta ggatcttttg tgtgcgaata actatgagga       60
agattaataa ttttcctctc attgaaattt atatcggaat ttaaattgaa attgttactg      120
taatcacacc tggtttgttt cagagccaca tcacaaagat agagaacaac ctaggtctcc      180
gaagggagca agggcatcag tgtgctcagt tgaaaatccc ttgtcaacac ctaggtctta      240
tcacatcaca agttccacct cagactctgc agggtgatcc aacaacctta atagaaacat      300
tattgttaaa ggacagcatt agttcacagt caaacaagca agattgagaa ttaaccttgg      360
ttttgaactt gaacacttag gggattgaag attcaacaac cctaaagctt ggggtaaaac      420
attggaaata gttaaaagac aaattgctcg gaatcacaaa attccgagta tggattctcg      480
tcctcagaaa atctggatgg cgccgagtct cactgaatct gacatggatt accacaagat      540
cttgacagca ggtctgtccg ttcaacaggg gattgttcgg caaagagtca tcccagtgta      600
tcaagtaaac aatcttgaag aaatttgcca acttatcata caggcctttg aagcaggtgt      660
tgattttcaa gagagtgcgg acagtttcct tctcatgctt gtcttcatc atgcgtacca       720
gggagattac aaacttttct tggaaagtgg cgcagtcaag tatttggaag gcacgggtt       780
ccgttttgaa gtcaagaagc gtgatggagt gaagcgcctt gaggaattgc tgccagcagt      840
atctagtgga aaaacatta agagaacact tgctgccatg ccggaagagg agacaactga       900
agctaatgcc ggtcagtttc tctcctttgc aagtctattc cttccgaaat ggtagtagg       960
agaaaaggct tgccttgaga aggttcaaag gcaaattcaa gtacatgcag agcaaggact     1020
gatacaatat ccaacagctt ggcaatcagt aggacacatg atggtgattt ccgtttgat      1080
gcgaacaaat tttctgatca aatttctcct aatacaccaa gggatgcaca tggttgccgg     1140
gcatgatgcc aacgatgctg tgatttcaaa ttcagtggct caagctcgtt tttcaggctt     1200
attgattgtc aaaacagtac ttgatcatat cctacaaaag acagaacgag gagttcgtct     1260
ccatcctctt gcaaggaccg ccaaggtaaa aaatgaggtg aactcctta aggctgcact      1320
cagctccctg gccaagcatg agagtatgc tcctttcgcc cgactttga acctttctgg       1380
agtaaataat cttgagcatg gtctttcc tcaactatcg gcaattgcac tcggagtcgc       1440
```

```
cacagcacac gggagtaccc tcgcaggagt aaatgttgga gaacagtatc aacaactcag  1500
agaggctgcc actgaggctg agaagcaact ccaacaatat gcagagtctc gcgaacttga  1560
ccatcttgga cttgatgatc aggaaaagaa aattcttatg aacttccatc agaaaaagaa  1620
cgaaatcagc ttccagcaaa caaacgctat ggtaactcta agaaaagagc gcctggccaa  1680
gctgacagaa gctatcactg ctgcgtcact gcccaaaaca agtggacatt acgatgatga  1740
tgacgacatt ccctttccag gacccatcaa tgatgacgac aatcctggcc atcaagatga  1800
tgatccgact gactcacagg atacgaccat tcccgatgtg gtggttgatc ccgatgatgg  1860
aagctacggc gaataccaga gttactcgga aaacggcatg aatgcaccag atgacttggt  1920
cctattcgat ctagacgagg acgacgagga cactaagcca gtgcctaata gatcgaccaa  1980
gggtggacaa cagaagaaca gtcaaaaggg ccagcatata gagggcagac agacacaatc  2040
caggccaatt caaaatgtcc caggccctca cagaacaatc caccacgcca gtgcgccact  2100
cacggacaat gacagaagaa atgaaccctc cggctcaacc agccctcgca tgctgacacc  2160
aattaacgaa gaggcagacc cactggacga tgccgacgac gagacgtcta gccttccgcc  2220
cttggagtca gatgatgaag agcaggacag ggacggaact tccaaccgca cacccactgt  2280
cgccccaccg gctcccgtat acagagatca ctctgaaaag aaagaactcc cgcaagacga  2340
gcaacaagat caggaccaca ctcaagaggc caggaaccag gacagtgaca acacccagtc  2400
agaacactct tttgaggaga tgtatcgcca cattctaaga tcacaggggc catttgatgc  2460
tgttttgtat tatcatatga tgaaggatga gcctgtagtt ttcagtacca gtgatggcaa  2520
agagtacacg tatccagact cccttgaaga ggaatatcca ccatggctca ctgaaaaaga  2580
ggctatgaat gaagagaata gatttgttac attggatggt caacaatttt attggccggt  2640
gatgaatcac aagaataaat tcatggcaat cctgcaacat catcagtgaa tgagcatgga  2700
acaatgggat gattcaaccg acaaatagct aacattaagt agtcaaggaa cgaaaacagg  2760
aagaattttt gatgtctaag gtgtgaatta ttatcacaat aaaagtgatt cttatttttg  2820
aatttaaagc tagcttatta ttactagccg ttttcaaag ttcaatttga gtcttaatgc  2880
aaataggcgt taagccacag ttatagccat aattgtaact caatattcta actagcgatt  2940
tatctaaatt aaattacatt atgcttttat aacttaccta ctagcctgcc caacatttac  3000
acgatcgttt tataattaag aaaaaactaa tgatgaagat taaaaccttc atcatcctta  3060
cgtcaattga attctctagc actcgaagct tattgtcttc aatgtaaaag aaaagctggt  3120
ctaacaagat gacaactaga acaaagggca ggggccatac tgcggccacg actcaaaacg  3180
acagaatgcc aggccctgag cttcgggct ggatctctga gcagctaatg accggaagaa  3240
ttcctgtaag cgacatcttc tgtgatattg agaacaatcc aggattatgc tacgcatccc  3300
aaatgcaaca aacgaagcca aacccgaaga cgcgcaacag tcaaacccaa acggacccaa  3360
tttgcaatca tagttttgag gaggtagtac aaacattggc ttcattggct actgttgtgc  3420
aacaacaaac catcgcatca gaatcattag aacaacgcat tacgagtctt gagaatggtc  3480
taaagccagt ttatgatatg gcaaaaacaa tctcctcatt gaacagggtt tgtgctgaga  3540
tggttgcaaa atatgatctt ctggtgatga caaccggtcg ggcaacagca accgctgcgg  3600
caactgaggc ttattgggcc gaacatggtc aaccaccacc tggaccatca ctttatgaag  3660
aaagtgcgat tcggggtaag attgaatcta gagatgagac cgtccctcaa agtgttaggg  3720
aggcattcaa caatctaaac agtaccactt cactaactga ggaaaatttt gggaaacctg  3780
acatttcggc aaaggatttg agaaacatta tgtatgatca cttgcctggt tttggaactg  3840
```

```
ctttccacca attagtacaa gtgatttgta aattgggaaa agatagcaac tcattggaca    3900
tcattcatgc tgagttccag gccagcctgg ctgaaggaga ctctcctcaa tgtgccctaa    3960
ttcaaattac aaaaagagtt ccaatcttcc aagatgctgc tccacctgtc atccacatcc    4020
gctctcgagg tgacattccc cgagcttgcc agaaaagctt gcgtccagtc ccaccatcgc    4080
ccaagattga tcgaggttgg gtatgtgttt ttcagcttca agatggtaaa acacttggac    4140
tcaaaatttg agccaatctc ccttccctcc gaaagaggcg aataatagca gaggcttcaa    4200
ctgctgaact atagggtacg ttacattaat gatacacttg tgagtatcag ccctggataa    4260
tataagtcaa ttaaacgacc aagataaaat tgttcatatc tcgctagcag cttaaaatat    4320
aaatgtaata ggagctatat ctctgacagt attataatca attgttatta agtaacccaa    4380
accaaaagtg atgaagatta agaaaaacct acctcggctg agagagtgtt ttttcattaa    4440
ccttcatctt gtaaacgttg agcaaaattg ttaaaaatat gaggcgggtt atattgccta    4500
ctgctcctcc tgaatatatg gaggccatat accctgtcag gtcaaattca acaattgcta    4560
gaggtggcaa cagcaataca ggcttcctga caccggagtc agtcaatggg gacactccat    4620
cgaatccact caggccaatt gccgatgaca ccatcgacca tgccagccac acaccaggca    4680
gtgtgtcatc agcattcatc cttgaagcta tggtgaatgt catatcgggc cccaaagtgc    4740
taatgaagca aattccaatt tggcttcctc taggtgtcgc tgatcaaaag acctacagct    4800
ttgactcaac tacggccgcc atcatgcttg cttcatacac tatcacccat ttcggcaagg    4860
caaccaatcc acttgtcaga gtcaatcggc tgggtcctgg aatcccggat catcccctca    4920
ggctcctgcg aattggaaac caggctttcc tccaggagtt cgttcttccg ccagtccaac    4980
taccccagta tttcaccttt gatttgacag cactcaaact gatcacccaa ccactgcctg    5040
ctgcaacatg gaccgatgac actccaacag gatcaaatgg agcgttgcgt ccaggaattt    5100
catttcatcc aaaacttcgc cccattcttt tacccaacaa aagtgggaag aaggggaaca    5160
gtgccgatct aacatctccg gagaaaatcc aagcaataat gacttcactc caggacttta    5220
agatcgttcc aattgatcca accaaaaata tcatgggaat cgaagtgcca gaaactctgg    5280
tccacaagct gaccggtaag aaggtgactt ctaaaaatgg acaaccaatc atccctgttc    5340
ttttgccaaa gtacattggg ttggacccgg tggctccagg agacctcacc atggtaatca    5400
cacaggattg tgacacgtgt cattctcctg caagtcttcc agctgtgatt gagaagtaat    5460
tgcaataatt gactcagatc cagtttata gaatcttctc agggatagtg ataacatcta    5520
tttagtaatc cgtccattag aggagacact tttaattgat caatatacta aaggtgcttt    5580
acaccattgt cttttttctc tcctaaatgt agaacttaac aaaagactca taatatactt    5640
gttttaaag gattgattga tgaaagatca taactaataa cattcaaaat aatcctacta    5700
taatcaatac ggtgattcaa atgttaatct ttctcattgc acatactttt tgcccttatc    5760
ctcaaattgc ctgcatgctt acatctgagg atagccagtg tgacttggat tggaaatgtg    5820
gagaaaaaat cgggacccat tctaggttg ttcacaatcc aagtacagac attgcccttc    5880
taattaagaa aaaatcggcg atgaagatta agccgacagt gagcgtaatc ttcatctctc    5940
ttagattatt tgttttccag agtaggggtc gtcaggtcct tttcaatcgt gtaaccaaaa    6000
taaactccac tagaaggata ttgtggggca acaacacaat gggcgttaca ggaatattgc    6060
agttacctcg tgatcgattc aagaggacat cattctttct ttgggtaatt atcctttttcc    6120
aaagaacatt ttccatccca cttggagtca tccacaatag cacattacag gttagtgatg    6180
```

-continued

```
tcgacaaact agtttgtcgt gacaaactgt catccacaaa tcaattgaga tcagttggac    6240
tgaatctcga agggaatgga gtggcaactg acgtgccatc tgcaactaaa agatggggct    6300
tcaggtccgg tgtcccacca aggtggtca attatgaagc tggtgaatgg gctgaaaact    6360
gctacaatct tgaaatcaaa aaacctgacg ggagtgagtg tctaccagca gcgccagacg    6420
ggattcgggg cttcccccgg tgccggtatg tgcacaaagt atcaggaacg ggaccgtgtg    6480
ccggagactt tgccttccat aaagagggtg ctttcttcct gtatgatcga cttgcttcca    6540
cagttatcta ccgaggaacg actttcgctg aaggtgtcgt tgcatttctg atactgcccc    6600
aagctaagaa ggacttcttc agctcacacc ccttgagaga gccggtcaat gcaacgagg     6660
acccgtctag tggctactat tctaccacaa ttagatatca ggctaccggt tttggaacca    6720
atgagacaga gtacttgttc gaggttgaca atttgaccta cgtccaactt gaatcaagat    6780
tcacaccaca gtttctgctc cagctgaatg agacaatata tacaagtggg aaaaggagca    6840
ataccacggg aaaactaatt tggaaggtca accccgaaat tgatacaaca atcggggagt    6900
gggccttctg ggaaactaaa aaaacctcac tagaaaaatt cgcagtgaag agttgtcttt    6960
cacagttgta tcaaacggag ccaaaaacat cagtggtcag agtccggcgc gaacttcttc    7020
cgacccaggg accaacacaa caactgaaga ccacaaaatc atggcttcag aaaattcctc    7080
tgcaatggtt caagtgcaca gtcaaggaag ggaagctgca gtgtcgcatc taacaaccct    7140
tgccacaatc tccacgagtc cccaatccct cacaaccaaa ccaggtccgg acaacagcac    7200
ccataataca cccgtgtata aacttgacat ctctgaggca actcaagttg aacaacatca    7260
ccgcagaaca gacaacgaca gcacagcctc cgacactccc tctgccacga ccgcagccgg    7320
accccccaaaa gcagagaaca ccaacacgag caagagcact gacttcctgg accccgccac    7380
cacaacaagt cccccaaaacc acagcgagac cgctggcaac aacaacactc atcaccaaga    7440
taccggagaa gagagtgcca gcagcgggaa gctaggctta attaccaata ctattgctgg    7500
agtcgcagga ctgatcacag gcgggagaag aactcgaaga gaagcaattg tcaatgctca    7560
acccaaatgc aaccctaatt tacattactg gactactcag gatgaaggtg ctgcaatcgg    7620
actggcctgg ataccatatt tcgggccagc agccgaggga atttacatag agggctaat    7680
gcacaatcaa gatggtttaa tctgtgggtt gagacagctg gccaacgaga cgactcaagc    7740
tcttcaactg ttcctgagag ccacaactga gctacgcacc ttttcaatcc tcaaccgtaa    7800
ggcaattgat ttcttgctgc agcgatgggg cggcacatgc cacattctgg gaccggactg    7860
ctgtatcgaa ccacatgatt ggaccaagaa cataacagac aaaattgatc agattattca    7920
tgattttgtt gataaaaccc ttccggacca gggggacaat gacaattggt ggacaggatg    7980
gagacaatgg ataccggcag gtattggagt tacaggcgtt ataattgcag ttatcgcttt    8040
attctgtata tgcaaatttg tcttttagtt tttcttcaga ttgcttcatg gaaaagctca    8100
gcctcaaatc aatgaaacca ggatttaatt atatggatta cttgaatcta agattacttg    8160
acaaatgata atataataca ctggagcttt aaacatagcc aatgtgattc taactccttt    8220
aaactcacag ttaatcataa acaaggtttg acatcaatct agttatctct tgagaatga    8280
taaacttgat gaagattaag aaaaaggtaa tctttcgatt atctttaatc ttcatccttg    8340
attctacaat catgacagtt gtctttagtg acaagggaaa gaagcctttt tattaagttg    8400
taataatcag atctgcgaac cggtagagtt tagttgcaac ctaacacaca taaagcattg    8460
gtcaaaaagt caatagaaat ttaaacgtg agtggagaca acttttaaat ggaagcttca    8520
tatgagagag gacgcccacg agctgccaga cagcattcaa gggatggaca cgaccaccat    8580
```

```
gttcgagcac gatcatcatc cagagagaat tatcgaggtg agtaccgtca atcaaggagc   8640
gcctcacaag tgcgcgttcc tactgtattt cataagaaga gagttgaacc attaacagtt   8700
cctccagcac ctaaagacat atgtccgacc ttgaaaaaag gattttttgtg tgacagtagt   8760
ttttgcaaaa aagatcacca gttggagagt ttaactgata gggaattact cctactaatc   8820
gcccgtaaga cttgtggatc agtagaacaa caattaaata taactgcacc caaggactcg   8880
cgcttagcaa atccaacggc tgatgatttc cagcaagagg aaggtccaaa aattaccttg   8940
ttgacactga tcaagacggc agaacactgg gcgagacaag acatcagaac catagaggat   9000
tcaaaattaa gagcattgtt gactctatgt gctgtgatga cgaggaaatt ctcaaaatcc   9060
cagctgagtc ttttatgtga gacacaccta aggcgcgagg ggcttgggca agatcaggca   9120
gaacccgttc tcgaagtata tcaacgatta cacagtgata aaggaggcag ttttgaagct   9180
gcactatggc aacaatggga ccgacaatcc ctaattatgt ttatcactgc attcttgaat   9240
attgctctcc agttaccgtg tgaaagttct gctgtcgttg tttcagggtt aagaacattg   9300
gttcctcaat cagataatga ggaagcttca accaacccgg ggacatgctc atggtctgat   9360
gagggtaccc cttaataagg ctgactaaaa cactatataa ccttctactt gatcacaata   9420
ctccgtatac ctatcatcat atatttaatc aagacgatat cctttaaaac ttattcagta   9480
ctataatcac tctcgtttca aattaataag atgtgcatga ttgccctaat atatgaagag   9540
gtatgataca accctaacag tgatcaaaga aaatcataat ctcgtatcgc tcgtaatata   9600
acctgccaag cataccctctt gcacaaagtg attcttgtac acaaataatg ttttactcta   9660
caggaggtag caacgatcca tcccatcaaa aaataagtat ttcatgactt actaatgatc   9720
tcttaaaata ttaagaaaaa ctgacggaac ataaattctt tatgcttcaa gctgtggagg   9780
aggtgtttgg tattggctat tgttatatta caatcaataa caagcttgta aaaatattgt   9840
tcttgtttca agaggtagat tgtgaccgga aatgctaaac taatgatgaa gattaatgcg   9900
gaggtctgat aagaataaac cttattattc agattaggcc ccaagaggca ttcttcatct   9960
ccttttagca aagtactatt tcagggtagt ccaattagtg gcacgtcttt tagctgtata  10020
tcagtcgccc ctgagatacg ccacaaaagt gtctctaagc taaattggtc tgtacacatc  10080
ccatacattg tattaggggc aataatatct aattgaactt agccgtttaa aatttagtgc  10140
ataaatctgg gctaacacca ccaggtcaac tccattggct gaaaagaagc ttacctacaa  10200
cgaacatcac tttgagcgcc ctcacaatta aaaaatagga acgtcgttcc aacaatcgag  10260
cgcaaggttt caaggttgaa ctgagagtgt ctagacaaca aaatattgat actccagaca  10320
ccaagcaaga cctgagaaaa aaccatggct aaagctacgg gacgatacaa tctaatatcg  10380
cccaaaaagg acctggagaa aggggttgtc ttaagcgacc tctgtaactt cttagttagc  10440
caaactattc aggggtggaa ggtttattgg gctggtattg agtttgatgt gactcacaaa  10500
ggaatggccc tattgcatag actgaaaact aatgactttg cccctgcatg gtcaatgaca  10560
aggaatctct ttcctcattt atttcaaaat ccgaattcca caattgaatc accgctgtgg  10620
gcattgagag tcatccttgc agcagggata caggaccagc tgattgacca gtctttgatt  10680
gaacccttag caggagccct tggtctgatc tctgattggc tgctaacaac caacactaac  10740
catttcaaca tgcgaacaca acgtgtcaag gaacaattga gcctaaaaat gctgtcgttg  10800
attcgatcca atattctcaa gtttattaac aaattggatg ctctacatgt cgtgaactac  10860
aacggattgt tgagcagtat tgaaattgga actcaaaatc atacaatcat cataactcga  10920
```

| | |
|---|---|
| actaacatgg gttttctggt ggagctccaa gaacccgaca atcggcaat gaaccgcatg | 10980 |
| aagcctgggc cggcgaaatt ttccctcctt catgagtcca cactgaaagc atttacacaa | 11040 |
| ggatcctcga cacgaatgca agtttgatt cttgaattta atagctctct tgctatctaa | 11100 |
| ctaaggtaga atacttcata ttgagctaac tcatatatgc tgactcaata gttatcttga | 11160 |
| catctctgct ttcataatca gatatataag cataataaat aaatactcat atttcttgat | 11220 |
| aatttgttta accacagata atcctcact gtaagccagc ttccaagttg acacccttac | 11280 |
| aaaaaccagg actcagaatc cctcaaacaa gagattccaa gacaacatca tagaattgct | 11340 |
| ttattatatg aataagcatt ttatcaccag aaatcctata tactaaatgg ttaattgtaa | 11400 |
| ctgaacccgc aggtcacatg tgttaggttt cacagattct atatattact aactctatac | 11460 |
| tcgtaattaa cattagataa gtagattaag aaaaagcct gaggaagatt aagaaaaact | 11520 |
| gcttattggg tctttccgtg ttttagatga agcagttgaa attcttcctc ttgatattaa | 11580 |
| atggctacac aacatacca ataccccagac gctaggttat catcaccaat tgtattggac | 11640 |
| caatgtgacc tagtcactag agcttgcggg ttatattcat catactccct taatccgcaa | 11700 |
| ctacgcaact gtaaactccc gaaacatatc taccgtttga aatacgatgt aactgttacc | 11760 |
| aagttcttga gtgatgtacc agtggcgaca ttgcccatag atttcatagt cccagttctt | 11820 |
| ctcaaggcac tgtcaggcaa tggattctgt cctgttgagc cgcggtgcca acagttctta | 11880 |
| gatgaaatca ttaagtacac aatgcaagat gctctcttct tgaaatatta tctcaaaaat | 11940 |
| gtgggtgctc aagaagactg tgttgatgaa cactttcaag agaaatctt atcttcaatt | 12000 |
| cagggcaatg aattttaca tcaaatgttt ttctggtatg atctggctat tttaactcga | 12060 |
| aggggtagat taaatcgagg aaactctaga tcaacatggt ttgttcatga tgatttaata | 12120 |
| gacatcttag gctatgggga ctatgttttt tggaagatcc caatttcaat gttaccactg | 12180 |
| aacacacaag gaatcccca tgctgctatg gactggtatc aggcatcagt attcaaagaa | 12240 |
| gcggttcaag gcatacaca cattgtttct gtttctactg ccgacgtctt gataatgtgc | 12300 |
| aaagatttaa ttacatgtcg attcaacaca actctaatct caaaaatagc agagattgag | 12360 |
| gatccagttt gttctgatta tcccaatttt aagattgtgt ctatgcttta ccagagcgga | 12420 |
| gattacttac tctccatatt agggtctgat gggtataaaa ttattaagtt cctcgaacca | 12480 |
| ttgtgcttgg ccaaaattca attatgctca aagtacactg agaggaaggg ccgattctta | 12540 |
| acacaaatgc atttagctgt aaatcacacc ctagaagaaa ttacagaaat gcgtgcacta | 12600 |
| aagccttcac aggctcaaaa gatccgtgaa ttccatagaa cattgataag gctggagatg | 12660 |
| acgccacaac aactttgtga gctattttcc attcaaaaac actgggggca tcctgtgcta | 12720 |
| catagtgaaa cagcaatcca aaagttaaa aaacatgcta cggtgctaaa agcattacgc | 12780 |
| cctatagtga ttttcgagac atactgtgtt tttaaatata gtattgccaa acattatttt | 12840 |
| gatagtcaag gatcttggta cagtgttact tcagatagga atctaacacc gggtcttaat | 12900 |
| tcttatatca aaagaaatca attccctccg ttgccaatga ttaaagaact actatgggaa | 12960 |
| ttttaccacc ttgaccaccc tccacttttc tcaaccaaaa ttattagtga cttaagtatt | 13020 |
| tttataaaag acagagctac cgcagtgaaa aggacatgct gggatgcagt attcgagcct | 13080 |
| aatgttctag gatataatcc acctcacaaa tttagtacta acgtgtacc ggaacaattt | 13140 |
| ttagagcaag aaaactttc tattgagaat gttctttcct acgcacaaaa actcgagtat | 13200 |
| ctactaccac aatatcggaa cttttctttc tcattgaaag agaaagagtt gaatgtaggt | 13260 |
| agaaccttcg gaaaattgcc ttatccgact cgcaatgttc aaacactttg tgaagctctg | 13320 |

```
ttagctgatg gtcttgctaa agcatttcct agcaatatga tggtagttac ggaacgtgag   13380
caaaaagaaa gcttattgca tcaagcatca tggcaccaca caagtgatga ttttggtgaa   13440
catgccacag ttagagggag tagctttgta actgatttag agaaatacaa tcttgcattt   13500
agatatgagt ttacagcacc tttttatagaa tattgcaacc gttgctatgg tgttaagaat   13560
gtttttaatt ggatgcatta tacaatccca cagtgttata tgcatgtcag tgattattat   13620
aatccaccac ataacctcac actggagaat cgagacaacc cccccgaagg gcctagttca   13680
tacaggggtc atatgggagg gattgaagga ctgcaacaaa aactctggac aagtatttca   13740
tgtgctcaaa tttctttagt tgaaattaag actggtttta agttacgctc agctgtgatg   13800
ggtgacaatc agtgcattac tgttttatca gtcttcccct tagagactga cgcagacgag   13860
caggaacaga gcgccgaaga caatgcagcg agggtggccg ccagcctagc aaaagttaca   13920
agtgcctgtg aatcttttt aaaacctgat gaaacatttg tacattcagg ttttatctat   13980
tttgaaaaaa aacaatattt gaatggggtc caattgcctc agtcccttaa aacggctaca   14040
agaatggcac cattgtctga tgcaattttt gatgatcttc aagggaccct ggctagtata   14100
ggcactgctt ttgagcgatc catctctgag acacgacata tctttccttg caggataacc   14160
gcagctttcc atacgttttt ttcggtgaga atcttgcaat atcatcatct cgggttcaat   14220
aaaggttttg accttggaca gttaacactc ggcaaacctc tggatttcgg aacaatatca   14280
ttggcactag cggtaccgca ggtgcttgga gggttatcct tcttgaatcc tgagaaatgt   14340
ttctaccgga atctaggaga tccagttacc tcaggcttat tccagttaaa aacttatctc   14400
cgaatgattg agatggatga tttattctta cctttaattg cgaagaaccc tgggaactgc   14460
actgccattg actttgtgct aaatcctagc ggattaaatg tccctgggtc gcaagactta   14520
acttcatttc tgcgccagat tgtacgcagg accatcaccc taagtgcgaa aaacaaactt   14580
attaatacct tatttcatgc gtcagctgac ttcgaagacg aaatggtttg taaatggcta   14640
ttatcatcaa ctcctgttat gagtcgtttt gcggccgata tctttttcacg cacgccgagc   14700 gggaagcgat tgcaaattct aggatacctg gaaggaacac gcacattatt agcctctaag   14760
atcatcaaca ataatacaga gacaccggtt ttggacagac tgaggaaaat aacattgcaa   14820
aggtggagcc tatggtttag ttatcttgat cattgtgata atatcctggc ggaggcttta   14880
acccaaataa cttgcacagt tgatttagca cagattctga gggaatattc atgggctcat   14940
attttagagg gaagacctct tattggagcc acactcccat gtatgattga gcaattcaaa   15000
gtgttttggc tgaaaccccta cgaacaatgt ccgcagtgtt caaatgcaaa gcaaccaggt   15060
gggaaaccat tcgtgtcagt ggcagtcaag aaacatattg ttagtgcatg gccgaacgca   15120
tcccgaataa gctggactat cggggatgga atcccataca ttggatcaag gacagaagat   15180
aagataggac aacctgctat taaaccaaaa tgtccttccg cagccttaag agaggccatt   15240
gaattggcgt cccgtttaac atgggtaact caaggcagtt cgaacagtga cttgctaata   15300
aaaccatttt tggaagcacg agtaaattta agtgttcaag aaatacttca aatgacccct   15360
tcacattact caggaaatat tgttcacagg tacaacgatc aatacagtcc tcattctttc   15420
atggccaatc gtatgagtaa ttcagcaacg cgattgattg tttctacaaa cacttttaggt   15480 gagttttcag gaggtggcca gtctgcacgc gacagcaata ttattttcca gaatgttata   15540
aattatgcag ttgcactgtt cgatattaaa tttagaaaca ctgaggctac agatatccaa   15600
tataatcgtg ctcaccttca tctaactaag tgttgcaccc gggaagtacc agctcagtat   15660
```

```
ttaacataca catctacatt ggatttagat ttaacaagat accgagaaaa cgaattgatt    15720
tatgacagta atcctctaaa aggaggactc aattgcaata tctcattcga taatccattt    15780
ttccaaggta aacggctgaa cattatagaa gatgatctta ttcgactgcc tcacttatct    15840
ggatgggagc tagccaagac catcatgcaa tcaattattt cagatagcaa caattcatct    15900
acagacccaa ttagcagtgg agaaacaaga tcattcacta cccatttctt aacttatccc    15960
aagataggac ttctgtacag ttttggggcc tttgtaagtt attatcttgg caatacaatt    16020
cttcggacta agaaattaac acttgacaat tttttatatt acttaactac tcaaattcat    16080
aatctaccac atcgctcatt gcgaatactt aagccaacat tcaaacatgc aagcgttatg    16140
tcacggttaa tgagtattga tcctcatttt tctatttaca taggcggtgc tgcaggtgac    16200
agaggactct cagatgcggc caggttattt ttgagaacgt ccatttcatc tttcttaca    16260
tttgtaaaag aatggataat taatcgcgga acaattgtcc ctttatggat agtatatccg    16320
ctagagggtc aaaacccaac acctgtgaat aattttctct atcagatcgt agaactgctg    16380
gtgcatgatt catcaagaca acaggctttt aaaactacca taagtgatca tgtacatcct    16440
cacgacaatc ttgtttacac atgtaagagt acagccagca atttcttcca tgcatcattg    16500
gcgtactgga ggagcagaca cagaaacagc aaccgaaaat acttggcaag agactcttca    16560
actggatcaa gcacaaacaa cagtgatggt catattgaga gaagtcaaga acaaaccacc    16620
agagatccac atgatggcac tgaacggaat ctagtcctac aaatgagcca tgaaataaaa    16680
agaacgacaa ttccacaaga aaacacgcac cagggtccgt cgttccagtc ctttctaagt    16740
gactctgctt gtggtacagc aaatccaaaa ctaaatttcg atcgatcgag acacaatgtg    16800
aaatttcagg atcataactc ggcatccaag agggaaggtc atcaaataat ctcacaccgt    16860
ctagtcctac ctttctttac attatctcaa gggacacgcc aattaacgtc atccaatgag    16920
tcacaaaccc aagacgagat atcaaagtac ttacggcaat tgagatccgt cattgatacc    16980
acagtttatt gtagatttac cggtatagtc tcgtccatgc attacaaact tgatgaggtc    17040
ctttgggaaa tagagagttt caagtcggct gtgacgctag cagagggaga aggtgctggt    17100
gccttactat tgattcagaa ataccaagtt aagaccttat ttttcaacac gctagctact    17160
gagtccagta tagagtcaga aatagtatca ggaatgacta ctcctaggat gcttctacct    17220
gttatgtcaa aattccataa tgaccaaatt gagattattc ttaacaactc agcaagccaa    17280
ataacagaca taacaaatcc tacttggttt aaagaccaaa gagcaaggct acctaagcaa    17340
gtcgaggtta taaccatgga tgcagagaca acagagaata taaacagatc gaaattgtac    17400
gaagctgtat ataaattgat cttacaccat attgatccta gcgtattgaa agcagtggtc    17460
cttaaagtct ttctaagtga tactgagggt atgttatggc taaatgataa tttagccccg    17520
ttttttgcca ctggttattt aattaagcca ataacgtcaa gtgctagatc tagtgagtgg    17580
tatctttgtc tgacgaactt cttatcaact acacgtaaga tgccacacca aaaccatctc    17640
agttgtaaac aggtaatact tacggcattg caactgcaaa ttcaacgaag cccatactgg    17700
ctaagtcatt taactcagta tgctgactgt gagttacatt taagttatat ccgccttggt    17760
tttccatcat tagagaaagt actataccac aggtataacc tcgtcgattc aaaaagaggt    17820
ccactagtct ctatcactca gcacttagca catcttagag cagagattcg agaattaact    17880
aatgattata atcaacagcg acaaagtcgg actcaaacat atcactttat tcgtactgca    17940
aaaggacgaa tcacaaaact agtcaatgat tatttaaaat tctttcttat tgtgcaagca    18000
ttaaaacata atgggacatg gcaagctgag tttaagaaat taccagagtt gattagtgtg    18060
```

-continued

```
tgcaataggt tctaccatat tagagattgc aattgtgaag aacgtttctt agttcaaacc    18120
ttatatttac atagaatgca ggattctgaa gttaagctta tcgaaaggct gacagggctt    18180
ctgagtttat ttccggatgg tctctacagg tttgattgaa ttaccgtgca tagtatcctg    18240
atacttgcaa aggttggtta ttaacataca gattataaaa aactcataaa ttgctctcat    18300
acatcatatt gatctaatct caataaacaa ctatttaaat aacgaaagga gtccctatat    18360
tatatactat atttagcctc tctccctgcg tgataatcaa aaaattcaca atgcagcatg    18420
tgtgacatat tactgccgca atgaatttaa cgcaacataa taaactctgc actctttata    18480
attaagcttt aacgaaaggt ctgggctcat attgttattg atataataat gttgtatcaa    18540
tatcctgtca gatggaatag tgttttggtt gataacacaa cttcttaaaa caaaattgat    18600
ctttaagatt aagttttta taattatcat tactttaatt tgtcgttta aaaacggtga    18660 tagccttaat ctttgtgtaa aataagagat taggtgtaat aaccttaaca tttttgtcta    18720
gtaagctact atttcataca gaatgataaa attaaaagaa aaggcaggac tgtaaaatca    18780 gaaataccttt ctttacaata tagcagacta gataataatc ttcgtgttaa tgataattaa    18840
gacattgacc acgctcatca gaaggctcgc cagaataaac gttgcaaaaa ggattcctgg    18900
aaaaatggtc gcacacaaaa atttaaaaat aaatctatt cttctttttt gtgtgtcca     18959
```

<210> SEQ ID NO 21
<211> LENGTH: 20
<212> TYPE: DNA
<213> ORGANISM: Artificial Sequence
<220> FEATURE:
<223> OTHER INFORMATION: PCR forward primer for Sudan ebola BMG
<220> FEATURE:
<221> NAME/KEY: modified_base
<222> LOCATION: (8)..(8)
<220> FEATURE:
<221> NAME/KEY: misc_feature
<222> LOCATION: (8)..(8)
<223> OTHER INFORMATION: n is a, c, g, or t

<400> SEQUENCE: 21
gccatggntt caggtttgag                                               20

<210> SEQ ID NO 22
<211> LENGTH: 22
<212> TYPE: DNA
<213> ORGANISM: Artificial Sequence
<220> FEATURE:
<223> OTHER INFORMATION: PCR reverse primer for Sudan ebola BMG
<220> FEATURE:
<221> NAME/KEY: modified_base
<222> LOCATION: (4)..(4)
<223> OTHER INFORMATION: I
<220> FEATURE:
<221> NAME/KEY: misc_feature
<222> LOCATION: (4)..(4)
<223> OTHER INFORMATION: n is a, c, g, or t

<400> SEQUENCE: 22
ggtnacattg ggcaacaatt ca                                            22

<210> SEQ ID NO 23
<211> LENGTH: 26
<212> TYPE: DNA
<213> ORGANISM: Artificial Sequence
<220> FEATURE:
<223> OTHER INFORMATION: PCR probe for Sudan ebola BMG
<220> FEATURE:
<221> NAME/KEY: misc_feature

```
<222> LOCATION: (1)..(1)
<223> OTHER INFORMATION: Fluorescein (FAM)
<220> FEATURE:
<221> NAME/KEY: misc_feature
<222> LOCATION: (26)..(26)
<223> OTHER INFORMATION: Black hole quencher dye (BHQ1)

<400> SEQUENCE: 23
acggtgcaca ttctcctttt ctcgga                                          26

<210> SEQ ID NO 24
<211> LENGTH: 22
<212> TYPE: DNA
<213> ORGANISM: Artificial Sequence
<220> FEATURE:
<223> OTHER INFORMATION: PCR forward primer for Ebola Bundibugyo
      fragment A

<400> SEQUENCE: 24
gtgagacaaa gaatcattcc tg                                              22

<210> SEQ ID NO 25
<211> LENGTH: 23
<212> TYPE: DNA
<213> ORGANISM: Artificial Sequence
<220> FEATURE:
<223> OTHER INFORMATION: PCR reverse primer for Ebola Bundibugyo
      fragment A

<400> SEQUENCE: 25
catcaattgc tcagagatcc acc                                             23

<210> SEQ ID NO 26
<211> LENGTH: 21
<212> TYPE: DNA
<213> ORGANISM: Artificial Sequence
<220> FEATURE:
<223> OTHER INFORMATION: PCR forward primer for Ebola Bundibugyo
      fragment B

<400> SEQUENCE: 26
ccaacaacac tgcatgtaag t                                               21

<210> SEQ ID NO 27
<211> LENGTH: 20
<212> TYPE: DNA
<213> ORGANISM: Artificial Sequence
<220> FEATURE:
<223> OTHER INFORMATION: PCR reverse primer for Ebola Bundibugyo
      fragment B

<400> SEQUENCE: 27
aggtcgcgtt aatcttcatc                                                 20

<210> SEQ ID NO 28
<211> LENGTH: 21
<212> TYPE: DNA
<213> ORGANISM: Artificial Sequence
<220> FEATURE:
<223> OTHER INFORMATION: PCR forward primer for Ebola Bundibugyo
      fragment C

<400> SEQUENCE: 28
gatggttgag ttactttccg g                                               21

<210> SEQ ID NO 29
<211> LENGTH: 20
```

```
<212> TYPE: DNA
<213> ORGANISM: Artificial Sequence
<220> FEATURE:
<223> OTHER INFORMATION: PCR reverse primer for Ebola Bundibugyo
      fragment C

<400> SEQUENCE: 29
gtcttgagtc atcaatgccc                                              20

<210> SEQ ID NO 30
<211> LENGTH: 18
<212> TYPE: DNA
<213> ORGANISM: Artificial Sequence
<220> FEATURE:
<223> OTHER INFORMATION: PCR forward primer for Ebola Bundibugyo
      fragment D

<400> SEQUENCE: 30
ccaccagcac caaaggac                                                18

<210> SEQ ID NO 31
<211> LENGTH: 22
<212> TYPE: DNA
<213> ORGANISM: Artificial Sequence
<220> FEATURE:
<223> OTHER INFORMATION: PCR reverse primer for Ebola Bundibugyo
      fragment D

<400> SEQUENCE: 31
ctatcggcaa tgtaactatt gg                                           22

<210> SEQ ID NO 32
<211> LENGTH: 19
<212> TYPE: DNA
<213> ORGANISM: Artificial Sequence
<220> FEATURE:
<223> OTHER INFORMATION: PCR forward primer for Ebola Bundibugyo
      fragment E

<400> SEQUENCE: 32
gccgttgtag aggacacac                                               19

<210> SEQ ID NO 33
<211> LENGTH: 26
<212> TYPE: DNA
<213> ORGANISM: Artificial Sequence
<220> FEATURE:
<223> OTHER INFORMATION: PCR reverse primer for Ebola Bundibugyo
      fragment E

<400> SEQUENCE: 33
cacattaaat tgttctaaca tgcaag                                       26

<210> SEQ ID NO 34
<211> LENGTH: 23
<212> TYPE: DNA
<213> ORGANISM: Artificial Sequence
<220> FEATURE:
<223> OTHER INFORMATION: PCR forward primer for Ebola Bundibugyo
      fragment F

<400> SEQUENCE: 34
cctaggttat ttagaaggga cta                                          23

<210> SEQ ID NO 35
<211> LENGTH: 24
<212> TYPE: DNA
```

```
<213> ORGANISM: Artificial Sequence
<220> FEATURE:
<223> OTHER INFORMATION: PCR reverse primer for Ebola Bundibugyo
      fragment F

<400> SEQUENCE: 35
ggtagatgta ttgacagcaa tatc                                              24

<210> SEQ ID NO 36
<211> LENGTH: 21
<212> TYPE: DNA
<213> ORGANISM: Artificial Sequence
<220> FEATURE:
<223> OTHER INFORMATION: PCR primer for Ebola Uganda 692(-)

<400> SEQUENCE: 36
acaaaaagct atctgcacta t                                                 21

<210> SEQ ID NO 37
<211> LENGTH: 20
<212> TYPE: DNA
<213> ORGANISM: Artificial Sequence
<220> FEATURE:
<223> OTHER INFORMATION: PCR primer for Ebola Uganda 18269(+)

<400> SEQUENCE: 37
ctcagaagca aaattaatgg                                                   20

<210> SEQ ID NO 38
<211> LENGTH: 23
<212> TYPE: DNA
<213> ORGANISM: Artificial Sequence
<220> FEATURE:
<223> OTHER INFORMATION: PCR forward primer for Cote dIviore ebola virus
      fragment A

<400> SEQUENCE: 38
gtgtgcgaat aactatgagg aag                                               23

<210> SEQ ID NO 39
<211> LENGTH: 22
<212> TYPE: DNA
<213> ORGANISM: Artificial Sequence
<220> FEATURE:
<223> OTHER INFORMATION: PCR reverse primer for Cote dIviore ebola virus
      fragment A

<400> SEQUENCE: 39
gtctgtgcaa tgttgatgaa gg                                                22

<210> SEQ ID NO 40
<211> LENGTH: 22
<212> TYPE: DNA
<213> ORGANISM: Artificial Sequence
<220> FEATURE:
<223> OTHER INFORMATION: PCR forward primer for Cote dIviore ebola virus
      fragment B

<400> SEQUENCE: 40
catgaaaacc acactcaaca ac                                                22

<210> SEQ ID NO 41
<211> LENGTH: 24
<212> TYPE: DNA
<213> ORGANISM: Artificial Sequence
<220> FEATURE:
<223> OTHER INFORMATION: PCR reverse primer for Cote dIviore ebola virus
``` fragment B

<400> SEQUENCE: 41
gttgccttaa tcttcatcaa gttc                                              24

<210> SEQ ID NO 42
<211> LENGTH: 22
<212> TYPE: DNA
<213> ORGANISM: Artificial Sequence
<220> FEATURE:
<223> OTHER INFORMATION: PCR forward primer for Cote dIviore ebola virus
      fragment C

<400> SEQUENCE: 42
ggctataatg aatttcctcc ag                                                22

<210> SEQ ID NO 43
<211> LENGTH: 22
<212> TYPE: DNA
<213> ORGANISM: Artificial Sequence
<220> FEATURE:
<223> OTHER INFORMATION: PCR reverse primer for ebola cote dIviore virus
      fragment C

<400> SEQUENCE: 43
caagtgtatt tgtggtccta gc                                                22

<210> SEQ ID NO 44
<211> LENGTH: 20
<212> TYPE: DNA
<213> ORGANISM: Artificial Sequence
<220> FEATURE:
<223> OTHER INFORMATION: PCR reverse primer for Cote dIviore ebola virus
      fragment C

<400> SEQUENCE: 44
gctggaatag gaatcacagg                                                   20

<210> SEQ ID NO 45
<211> LENGTH: 21
<212> TYPE: DNA
<213> ORGANISM: Artificial Sequence
<220> FEATURE:
<223> OTHER INFORMATION: PCR reverse primer for Cote dIviore ebola virus
      fragment D

<400> SEQUENCE: 45
cggtagtcta cagttctttta g                                                21

<210> SEQ ID NO 46
<211> LENGTH: 25
<212> TYPE: DNA
<213> ORGANISM: Artificial Sequence
<220> FEATURE:
<223> OTHER INFORMATION: PCR forward primer for Cote dIviore ebola virus
      fragment E

<400> SEQUENCE: 46
gacaaagaga ttagattagc tatag                                             25

<210> SEQ ID NO 47
<211> LENGTH: 22
<212> TYPE: DNA
<213> ORGANISM: Artificial Sequence
<220> FEATURE:
<223> OTHER INFORMATION: PCR reverse primer for Cote dIviore ebola virus
      fragment E

<400> SEQUENCE: 47
gtaatgagaa ggtgtcattt gg                                              22

<210> SEQ ID NO 48
<211> LENGTH: 22
<212> TYPE: DNA
<213> ORGANISM: Artificial Sequence
<220> FEATURE:
<223> OTHER INFORMATION: PCR forward primer for Cote dIviore ebola virus
      fragment F

<400> SEQUENCE: 48
cacgacttag ttggacaatt gg                                              22

<210> SEQ ID NO 49
<211> LENGTH: 23
<212> TYPE: DNA
<213> ORGANISM: Artificial Sequence
<220> FEATURE:
<223> OTHER INFORMATION: PCR reverse primer for Cote dIviore ebola virus
      fragment F

<400> SEQUENCE: 49
cagacactaa ttagatctgg aag                                             23

<210> SEQ ID NO 50
<211> LENGTH: 21
<212> TYPE: DNA
<213> ORGANISM: Artificial Sequence
<220> FEATURE:
<223> OTHER INFORMATION: PCR forward primer for Cote dIviore ebola virus
      fragment G

<400> SEQUENCE: 50
cggacacaca aaaagaawra a                                               21

<210> SEQ ID NO 51
<211> LENGTH: 21
<212> TYPE: DNA
<213> ORGANISM: Artificial Sequence
<220> FEATURE:
<223> OTHER INFORMATION: PCR reverse primer for Cote dIviore ebola virus
      fragment G

<400> SEQUENCE: 51
cgttcttgac cttagcagtt c                                               21

<210> SEQ ID NO 52
<211> LENGTH: 22
<212> TYPE: DNA
<213> ORGANISM: Artificial Sequence
<220> FEATURE:
<223> OTHER INFORMATION: PCR forward primer for Cote dIviore ebola virus
      fragment H

<400> SEQUENCE: 52
gcactataag ctcgatgaag tc                                              22

<210> SEQ ID NO 53
<211> LENGTH: 20
<212> TYPE: DNA
<213> ORGANISM: Artificial Sequence
<220> FEATURE:
<223> OTHER INFORMATION: PCR reverse primer for Cote dIviore ebola virus
      fragment H -continued

```
<400> SEQUENCE: 53
tggacacaca aaaargaraa                                                    20

<210> SEQ ID NO 54
<211> LENGTH: 21
<212> TYPE: DNA
<213> ORGANISM: Artificial Sequence
<220> FEATURE:
<223> OTHER INFORMATION: PCR forward primer for Cote dIviore ebola virus
      gap between fragments C and D

<400> SEQUENCE: 54
ctgagaggat ccagaagaaa g                                                  21

<210> SEQ ID NO 55
<211> LENGTH: 22
<212> TYPE: DNA
<213> ORGANISM: Artificial Sequence
<220> FEATURE:
<223> OTHER INFORMATION: PCR reverse primer for Cote d'Iviore ebola
      virus gap between fragments C and D

<400> SEQUENCE: 55
gtgtaagcgt tgatatacct cc                                                 22

<210> SEQ ID NO 56
<211> LENGTH: 22
<212> TYPE: DNA
<213> ORGANISM: Artificial Sequence
<220> FEATURE:
<223> OTHER INFORMATION: PCR forward primer for ebola uganda virus
      EboU965(+)

<400> SEQUENCE: 56
gagaaaaggc ctgtctggag aa                                                 22

<210> SEQ ID NO 57
<211> LENGTH: 24
<212> TYPE: DNA
<213> ORGANISM: Artificial Sequence
<220> FEATURE:
<223> OTHER INFORMATION: PCR forward primer for ebola uganda virus
      EboU1039(-)

<400> SEQUENCE: 57
tcgggtattg aatcagacct tgtt                                               24

<210> SEQ ID NO 58
<211> LENGTH: 26
<212> TYPE: DNA
<213> ORGANISM: Artificial Sequence
<220> FEATURE:
<223> OTHER INFORMATION: PCR probe for ebola uganda virus EboU989

<400> SEQUENCE: 58
ttcaacgaca aatccaagtg cacgca                                             26

<210> SEQ ID NO 59
<211> LENGTH: 302
<212> TYPE: PRT
<213> ORGANISM: Bundibugyo ebolavirus
<220> FEATURE:
<221> NAME/KEY: misc_feature
<223> OTHER INFORMATION: SSGP viral protein

<400> SEQUENCE: 59
```

```
Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
            20                  25                  30

Ile Pro Leu Gly Val Val His Asn Asn Thr Leu Gln Val Ser Asp Ile
            35              40                  45

Asp Lys Leu Val Cys Arg Asp Lys Leu Ser Ser Thr Ser Gln Leu Lys
        50                  55              60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
            115                 120                 125

Val Arg Gly Phe Pro Arg Cys Arg Tyr Val His Lys Val Ser Gly Thr
            130                 135                 140

Gly Pro Cys Pro Glu Gly Tyr Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Glu Thr Lys Lys Asp
                180                 185                 190

Phe Phe Gln Ser Pro Pro Leu His Glu Pro Ala Asn Met Thr Thr Asp
                195                 200                 205

Pro Ser Ser Tyr Tyr His Thr Val Thr Leu Asn Tyr Val Ala Asp Asn
            210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
                260                 265                 270

Leu Ile Trp Lys Val Asn Pro Thr Val Asp Thr Gly Val Gly Glu Trp
                275                 280                 285

Ala Phe Trp Glu Asn Lys Lys Leu His Lys Asn Pro Phe Lys
                290                 295                 300
```

HUMAN EBOLA VIRUS SPECIES AND COMPOSITIONS AND METHODS THEREOF

CROSS-REFERENCE TO RELATED APPLICATIONS

This application is a divisional of U.S. application Ser. No. 13/125,890, filed Apr. 25, 2011, now abandoned, which is the U.S. national phase of application PCT/US2009/062079, filed Oct. 26, 2009, which claims priority benefit of U.S. Provisional Application 61/108,175 filed 24 Oct. 2008; the contents of which are hereby incorporated by reference.

DEPOSIT STATEMENT

The invention provides the isolated human Ebola (hEbola) viruses denoted as *Bundibugyo* (EboBun) deposited with the Centers for Disease Control and Prevention ("CDC"; Atlanta, Ga., United States of America) on Nov. 26, 2007 and accorded an accession number 200706291. This deposit was not made to an International Depository Authority (IDA) as established under the Budapest Treaty on the International Recognition of the Deposit of Microorganisms for the Purposes of Patent Procedure, and is a non-Budapest treaty deposit. The deposited organism is not acceptable by American Type Culture Collection (ATCC), Manassas, Va., an International Depository Authority (IDA) as established under the Budapest Treaty on the International Recognition of the Deposit of Microorganisms for the Purposes of Patent Procedure. Samples of the stated Deposit Accession No. 200706291 will be made available to approved facilities for thirty years from the date of deposit, and for the lifetime of the patent issuing from, or claiming priority to this application.

FIELD OF THE INVENTION

The invention is related to compositions and methods directed to a novel species of human Ebola (hEbola) virus.

BACKGROUND OF THE INVENTION

The family Filoviridae consists of two genera, *Marburgvirus* and *Ebolavirus*, which have likely evolved from a common ancestor[1]. The genus *Ebolavirus* includes four species: Zaire, Sudan, Reston and Côte d'Ivoire (Ivory Coast) *ebolaviruses*, which have, with the exception of Reston and Côte d'Ivoire *ebolaviruses*, been associated with large hemorrhagic fever (HF) outbreaks in Africa with high case fatality (53-90%)[2].

Viruses of each species have genomes that are at least 30-40% divergent from one another, a level of diversity that presumably reflects differences in the ecologic niche they occupy and in their evolutionary history. Identification of the natural reservoir of *ebolaviruses* remains somewhat elusive, although recent PCR and antibody data suggest that three species of arboreal fruit bats may be carriers of Zaire *ebolavirus*[3]. No data has yet been published to suggest reservoirs for the Sudan, Reston and Côte d'Ivoire *ebolavirus* species. However, a cave-dwelling fruit bat has been recently implicated as a natural host for *marburgvirus*[4, 5], supporting the hypothesis that different bat species may be the reservoir hosts for the various filoviruses.

Filovirus outbreaks are sporadic, sometimes interspersed by years or even decades of no apparent disease activity. The last new species of *ebolavirus* was discovered 14 years ago (1994), in Cote d'Ivoire (Ivory Coast), and involved a single non-fatal case, a veterinarian who performed an autopsy on an infected chimpanzee found in the Tai Forest[6]. No further disease reports have been associated with Côte d'Ivoire *ebolavirus*, in contrast to Zaire and Sudan *ebolaviruses* which have each caused multiple large outbreaks over the same time period.

In late November 2007, HF cases were reported in the townships of Bundibugyo and Kikyo in Bundibugyo District, Western Uganda. The outbreak continued through January 2008, and resulted in approximately 149 cases and 37 deaths[2]. Laboratory investigation of the initial 29 suspect-case blood specimens by classic methods (antigen capture, IgM and IgG ELISA) and a recently developed random-primed pyrosequencing approach identified this to be an Ebola HF outbreak associated with a new discovered *ebolavirus* species. These specimens were negative when initially tested with highly sensitive real-time RT-PCR assays specific for all known Zaire and Sudan *ebolaviruses* and Marburg viruses. This new species is referred to herein as "the *Bundibugyo* species", abbreviated "EboBun".

Accordingly, compositions and methods directed to the new Ebola virus species are described herein and the most closely related Ebola Ivory Coast species, which compositions and methods are useful for diagnosis and prevention of human Ebola virus infection; including related vaccine development, and prevention of hemorrhagic fever in a human population.

SUMMARY OF THE INVENTION

The present invention is based upon the isolation and identification of a new human Ebola virus species, EboBun. EboBun was isolated from the patients suffering from hemorrhagic fever in a recent outbreak in Uganda. The isolated virus is a member of the Filoviridae family, a family of negative sense RNA viruses. Accordingly, the invention relates to the isolated EboBun virus that morphologically and phylogenetically relates to known members filoviridae.

In one aspect, the invention provides the isolated EboBun virus deposited with the Centers for Disease Control and Prevention ("CDC"; Atlanta, Ga., United States of America) on Nov. 26, 2007 and accorded an accession number 200706291, as stated in the paragraph entitled "DEPOSIT STATEMENT" supra.

In another aspect, the invention provides an isolated hEbola EboBun virus comprising a nucleic acid molecule comprising a nucleotide sequence selected from the group consisting of: a) a nucleotide sequence set forth in SEQ ID NO: 1; b) a nucleotide sequence that hybridizes to the sequence set forth in SEQ ID NO: 1 under stringent conditions; and c) a nucleotide sequence that has at least 70%, 75%, 80%, 85%, 90%, 95%, 96%, 97%, 98%, or 99% identity to the SEQ ID NO: 1. In another aspect, the invention provides the complete genomic sequence of the hEbola virus EboBun.

In a related aspect, the invention provides nucleic acid molecules isolated from EboBun, or fragments thereof.

In another aspect, the invention provides proteins or polypeptides that are isolated from the EboBun, including viral proteins isolated from cells infected with the virus but not present in comparable uninfected cells; or fragments thereof. In one embodiment of the present invention, the amino acid sequences of the proteins or polypeptides are set forth in SEQ ID NOS: 2-9 and 59, or fragments thereof.

In a related aspect, the invention provides an isolated polypeptide encoded by the nucleic acid molecule of the inventive hEbola EboIC (Sequence ID No. 10) virus described above.

In another aspect, the invention provides an isolated hEbola EboIC virus comprising a nucleic acid molecule comprising a nucleotide sequence selected from the group consisting of: a) a nucleotide sequence set forth in SEQ ID NO: 10; b) a nucleotide sequence that hybridizes to the sequence set forth in SEQ ID NO: 10 under stringent conditions; and c) a nucleotide sequence that has at least 70%, 75%, 80%, 85%, 90%, 95%, 96%, 97%, 98%, or 99% identity to the SEQ ID NO: 10. In another aspect, the invention provides the complete genomic sequence of the hEbola virus EboIC.

In a related aspect, the invention provides nucleic acid molecules isolated from EboIC, or fragments thereof.

In another aspect, the invention provides proteins or polypeptides that are isolated from the EboIC, including viral proteins isolated from cells infected with the virus but not present in comparable uninfected cells; or fragments thereof. In one embodiment of the present invention, the amino acid sequences of the proteins or polypeptides are set forth in SEQ ID NOs: 11-19, or fragments thereof.

In a related aspect, the invention provides an isolated polypeptide encoded by the nucleic acid molecule of the inventive hEbola EboIC virus described above.

In other aspects, the invention relates to the use of the isolated hEbola virus for diagnostic and therapeutic methods based on EbBun, EboIC, or a combination thereof. In one embodiment, the invention provides a method of detecting in a biological sample an antibody immunospecific for the genus of West Afrin Ebola Species constituting hEbola. EbBun and EboIC virus using at least one the inventive isolated hEbola virus described herein, or any of the inventive proteins or polypeptides as described herein. In another specific embodiment, the invention provides a method of screening for an antibody which immunospecifically binds and neutralizes hEbola EboBun. Such an antibody is useful for a passive immunization or immunotherapy of a subject infected with hEbola.

In another aspect, the invention provides an isolated antibody or an antigen-binding fragment thereof which immunospecifically binds to the hEbola virus of the invention described above.

In other aspects, the invention provides methods for detecting the presence, activity or expression of the clade of Bundibungyo-Ivory Coast hEbola virus in a biological material, such as cells, blood, saliva, urine, feces and so forth; and specifically at least one of EbBun or EboIC.

In a related aspect, the invention provides a method for detecting the presence of the inventive hEbola virus described above in a biological sample, the method includes (a) contacting the sample with an agent that selectively binds to a West African hEbola virus; and (b) detecting whether the compound binds to the West African hEbola virus in the sample.

In another aspect, the invention provides a method for detecting the presence of the inventive polypeptide described above, in a biological sample, said method includes (a) contacting the biological sample with an agent that selectively binds to the polypeptide; and (b) detecting whether the agent binds to the polypeptide in the sample. In another aspect, the invention provides a method for detecting the presence of a first nucleic acid molecule derived from the inventive hEbola virus described above in a biological sample, the method comprising: (a) contacting the biological sample with an agent that selectively binds to the polypeptide; and (b) detecting whether the agent binds to the polypeptide in the sample.

In another aspect, the invention provides a method for propagating the hEbola virus in host cells comprising infecting the host cells with the inventive isolated hEbola virus described above, culturing the host cells to allow the virus to multiply, and harvesting the resulting virions. Also provided by the present invention are host cells infected with the inventive hEbola virus described above.

In another aspect, the invention provides a method of detecting in a biological sample the presence of an antibody that immunospecifically binds hEbola virus, the method comprising: (a) contacting the biological sample with the inventive host cell host described above; and (b) detecting the antibody bound to the cell.

In another aspect, the invention provides vaccine preparations, comprising the inventive hEbola virus, including recombinant and chimeric forms of the virus, nucleic acid molecules comprised by the virus, or protein subunits of the virus. The invention also provides a vaccine formulation comprising a therapeutically or prophylactically effective amount of the inventive hEbola virus described above, and a pharmaceutically acceptable carrier. In one embodiment, the invention provides a vaccine formulation comprising a therapeutically or prophylactically effective amount of a protein extract of the inventive hEbola virus described above, or a subunit thereof; and a pharmaceutically acceptable carrier. In another, the invention provides a vaccine formulation comprising a therapeutically or prophylactically effective amount of a nucleic acid molecule comprising the nucleotide sequence of SEQ ID NO: 1 or a complement thereof, and a pharmaceutically acceptable carrier. In another, the invention provides a vaccine formulation comprising a therapeutically or prophylactically effective amount of a nucleic acid molecule comprising any of inventive the nucleotide sequences as described above, or a complement thereof, and a pharmaceutically acceptable carrier.

In a related aspect, the invention provides an immunogenic formulation comprising an immunogenically effective amount of the inventive hEbola virus described above, and a pharmaceutically acceptable carrier. In another related aspect, the invention provides an immunogenic formulation comprising an immunogenically effective amount of a protein extract of the inventive hEbola virus described above or a subunit thereof, and a pharmaceutically acceptable carrier. In another related aspect, the invention provides an immunogenic formulation comprising an immunogenically effective amount of a nucleic acid molecule comprising the nucleotide sequence of SEQ ID NO: 1 or a complement thereof, and a pharmaceutically acceptable carrier. In another related aspect, the invention provides an immunogenic formulation comprising an immunogenically effective amount of a nucleic acid molecule comprising the inventive nucleotide sequence as described above or a complement thereof, and a pharmaceutically acceptable carrier. In another related aspect, the invention provides an immunogenic formulation comprising an immunogenically effective amount of any of the inventive polypeptides described above.

In another aspect, the present invention provides pharmaceutical compositions comprising antiviral agents of the present invention and a pharmaceutically acceptable carrier. In a specific embodiment, the antiviral agent of the invention is an antibody that immunospecifically binds hEbola virus or any hEbola epitope. In another specific embodiment, the antiviral agent is a polypeptide or protein of the present invention or nucleic acid molecule of the invention.

In a related aspect, the invention provides a pharmaceutical composition comprising a prophylactically or therapeutically effective amount of an anti-hEbola EboBun agent and a pharmaceutically acceptable carrier.

The invention also provides kits containing compositions and formulations of the present invention. Thus, in another aspect, the invention provides a kit comprising a container containing the inventive immunogenic formulation described above. In another aspect, the invention provides a kit comprising a container containing the inventive vaccine formulation described above. In another, the invention provides a kit comprising a container containing the inventive pharmaceutical composition described above. In another, the invention provides a kit comprising a container containing the inventive vaccine formulation described above. In another, the invention provides a method for identifying a subject infected with the inventive hEbola virus described above, comprising: (a) obtaining total RNA from a biological sample obtained from the subject; (b) reverse transcribing the total RNA to obtain cDNA; and (c) amplifying the cDNA using a set of primers derived from a nucleotide sequence of the inventive hEbola virus described above.

The invention further relates to the use of the sequence information of the isolated virus for diagnostic and therapeutic methods.

In another aspect, the present invention provides methods for screening antiviral agents that inhibit the infectivity or replication of hEbola virus or variants thereof.

The invention further provides methods of preparing recombinant or chimeric forms of hEbola.

BRIEF DESCRIPTION OF THE DRAWINGS

Figure 1:
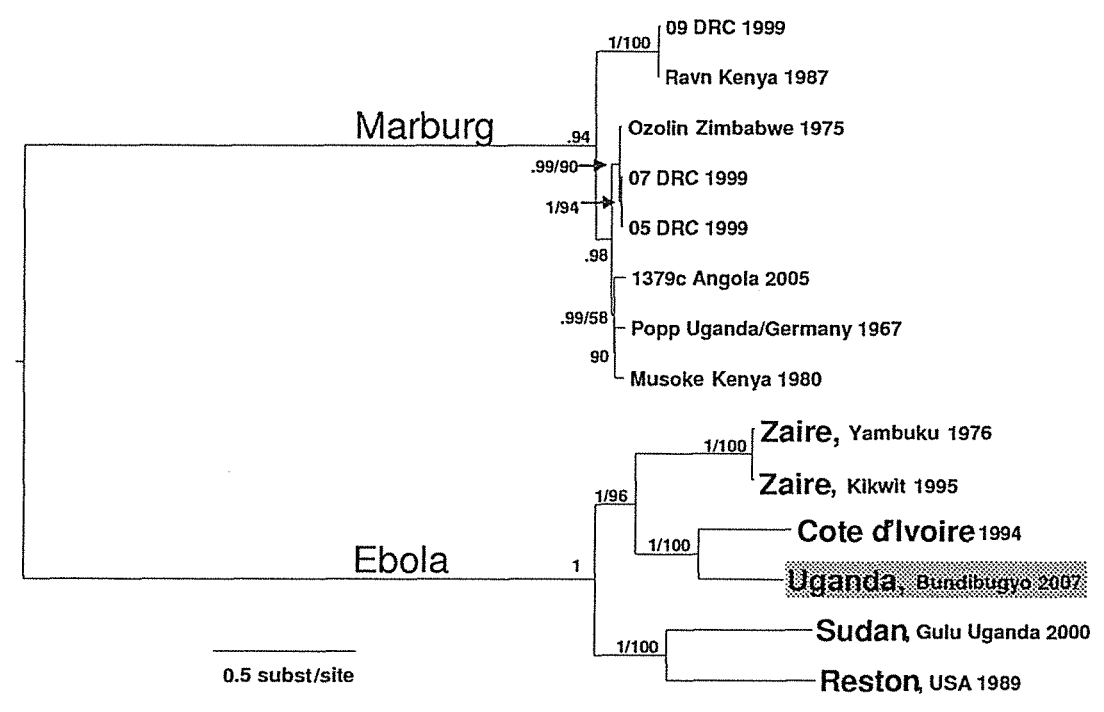

FIG. 1 represents a Phylogenetic tree comparing full-length genomes of *Ebolavirus* and Marburg virus by Bayesian analysis;

Figure 2A:
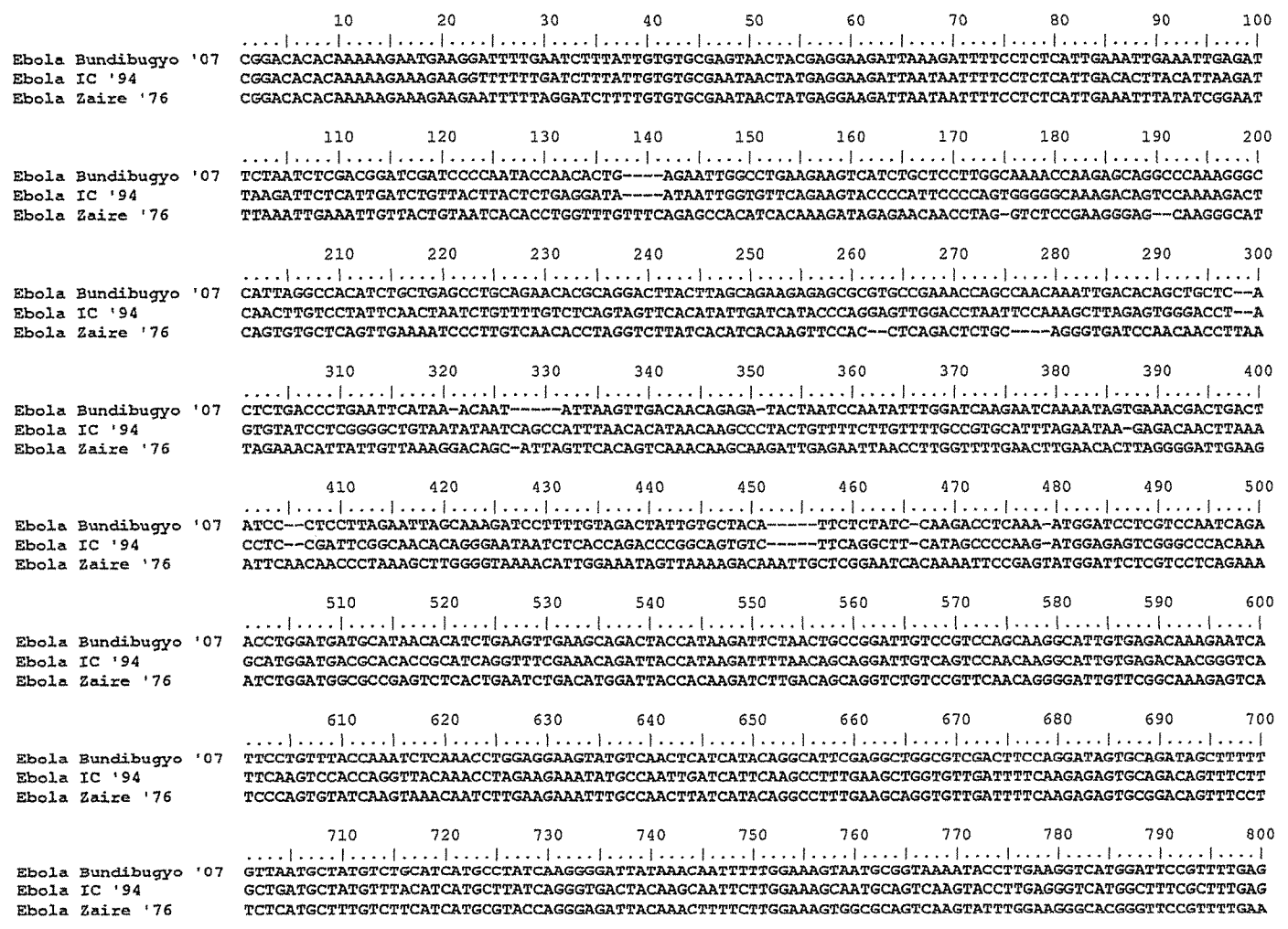
Figure 2C:
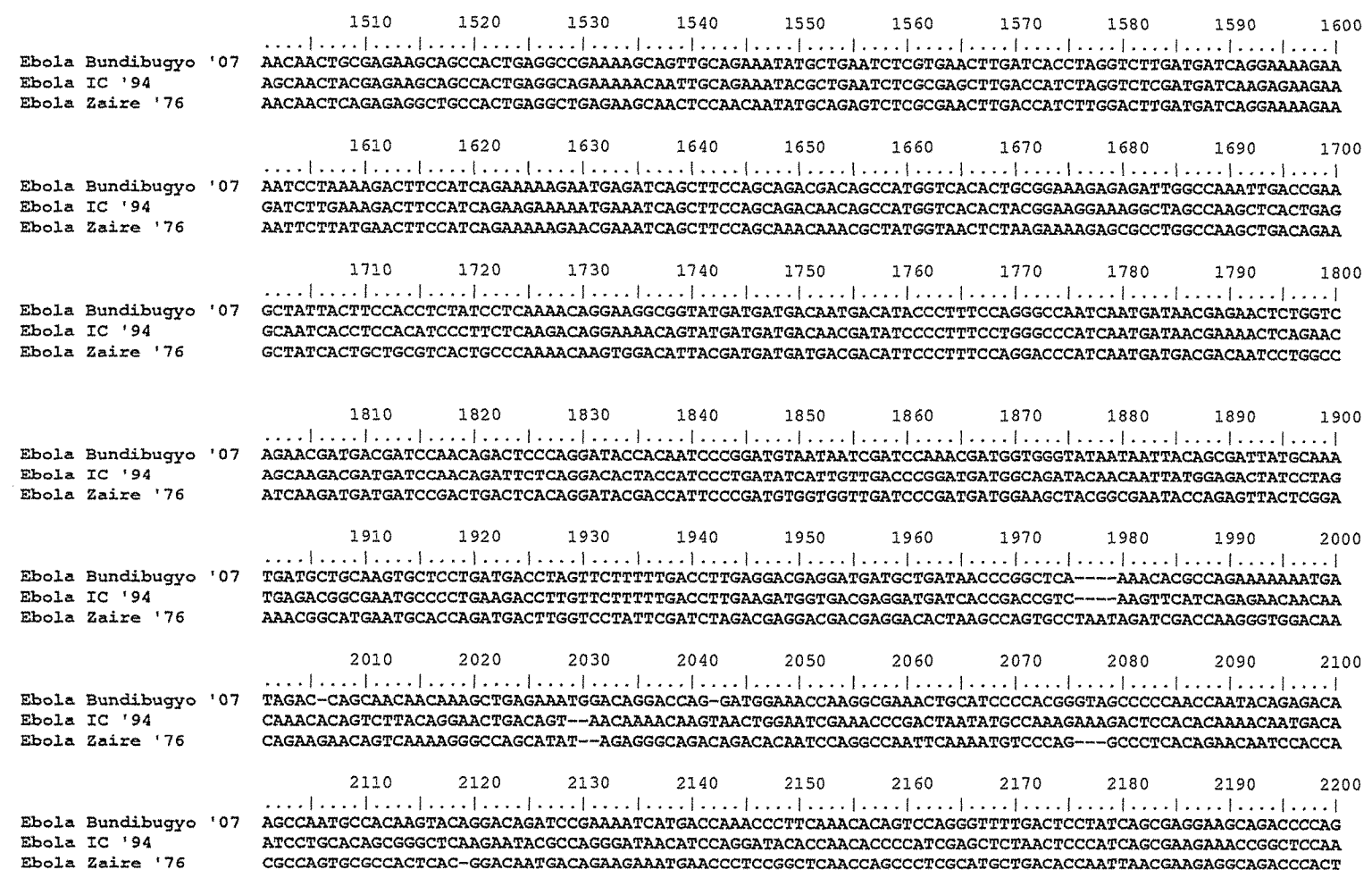
Figure 2D:
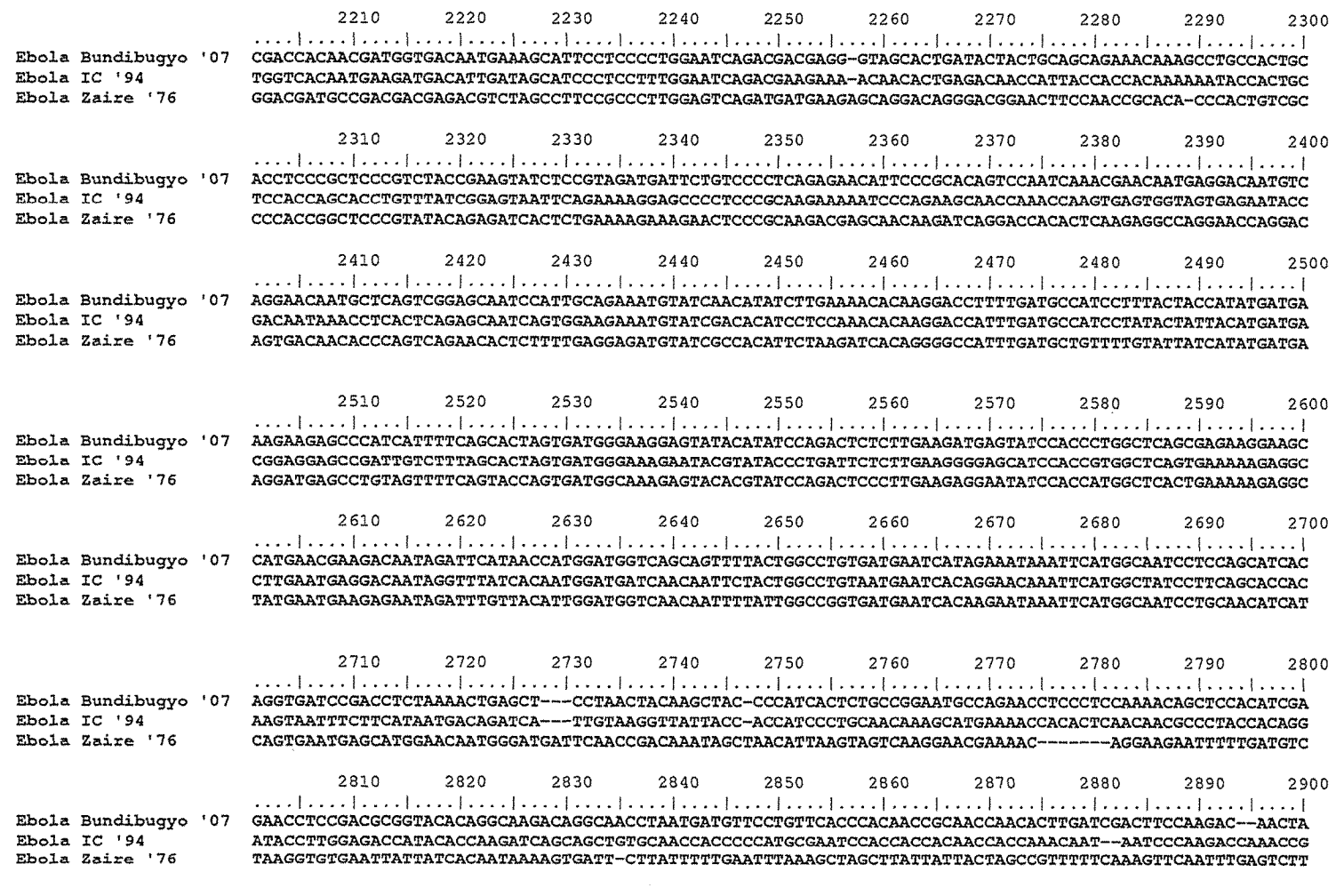
Figure 2F:
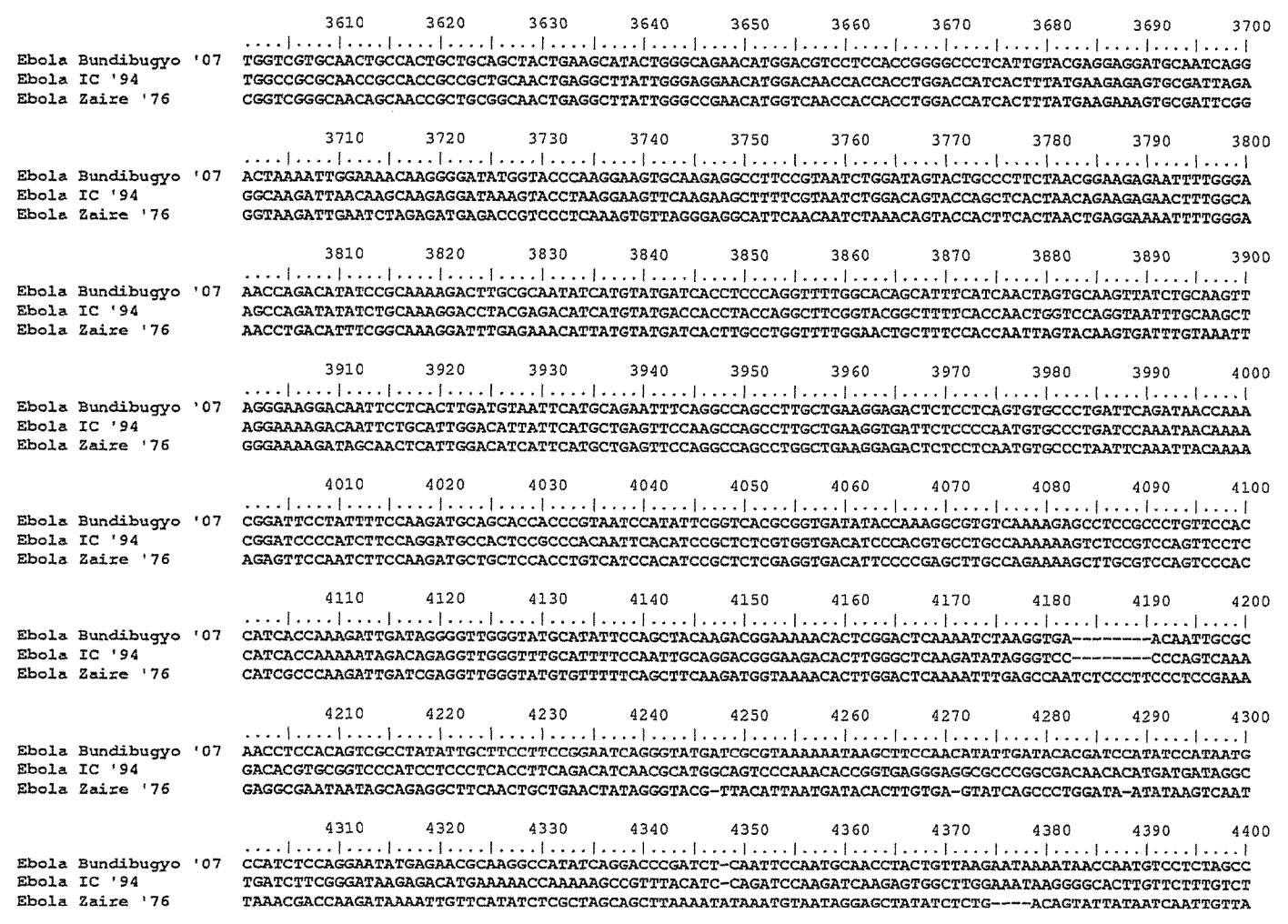
Figure 2G:
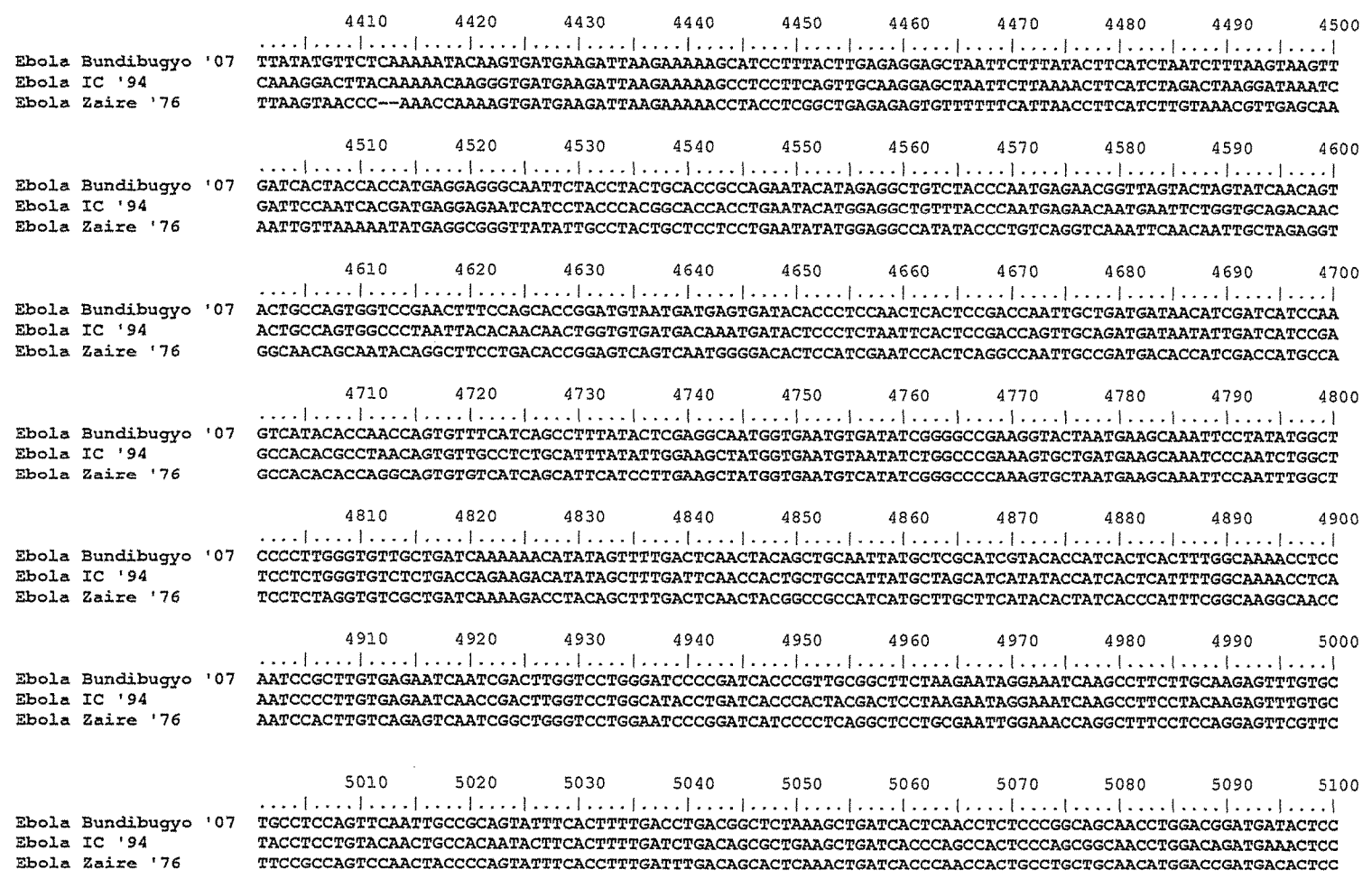
Figure 2H:
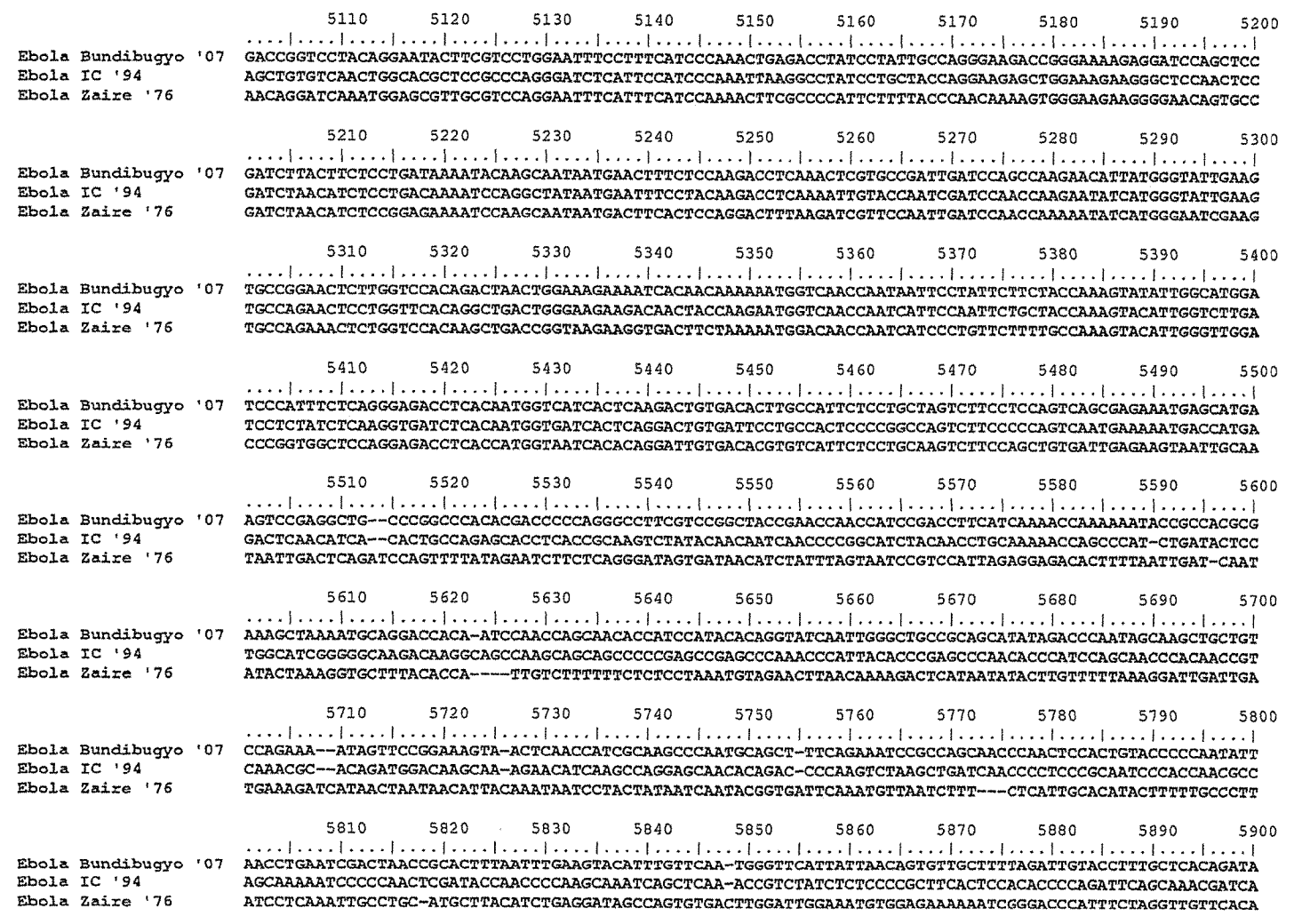
Figure 2J:
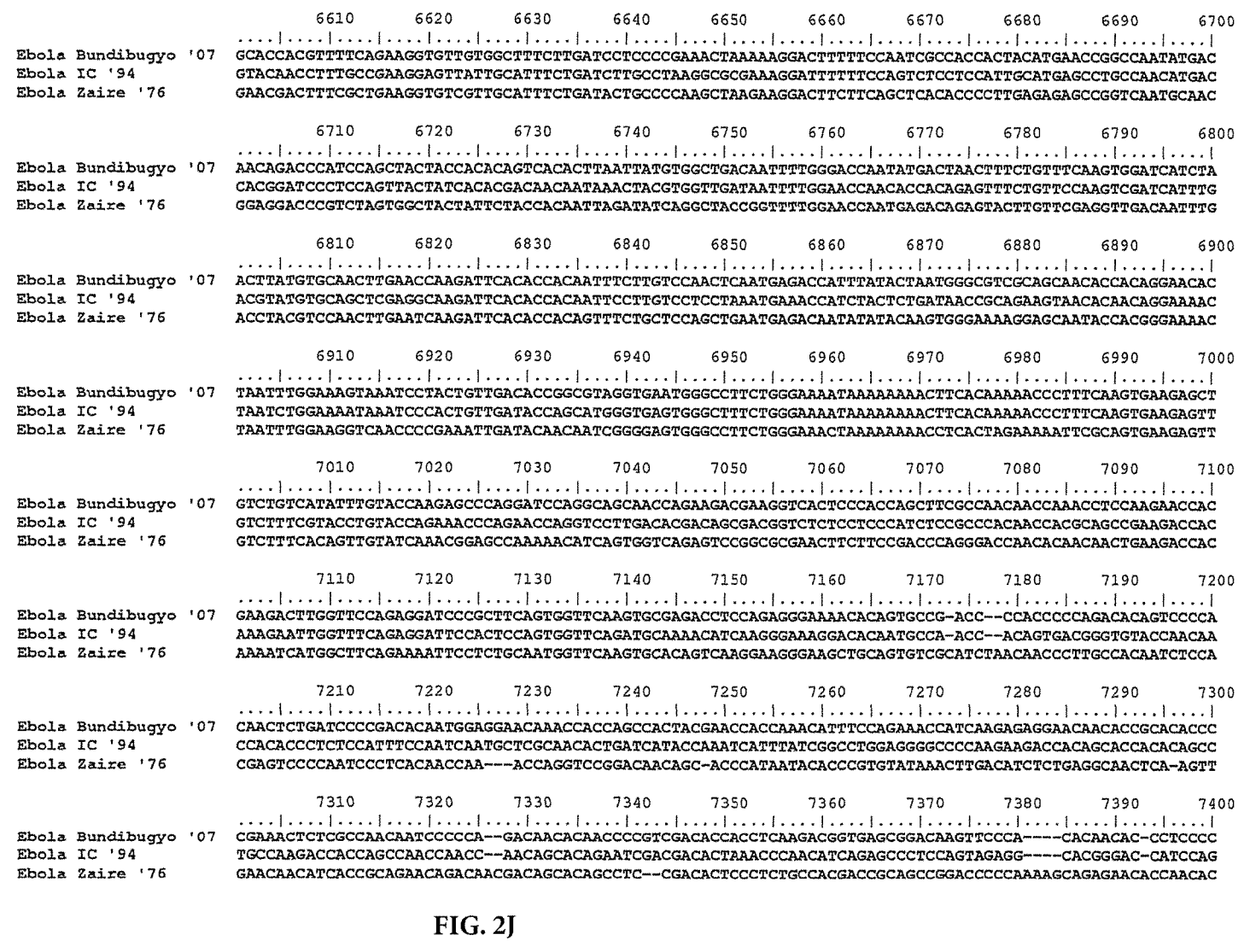
Figure 2K:
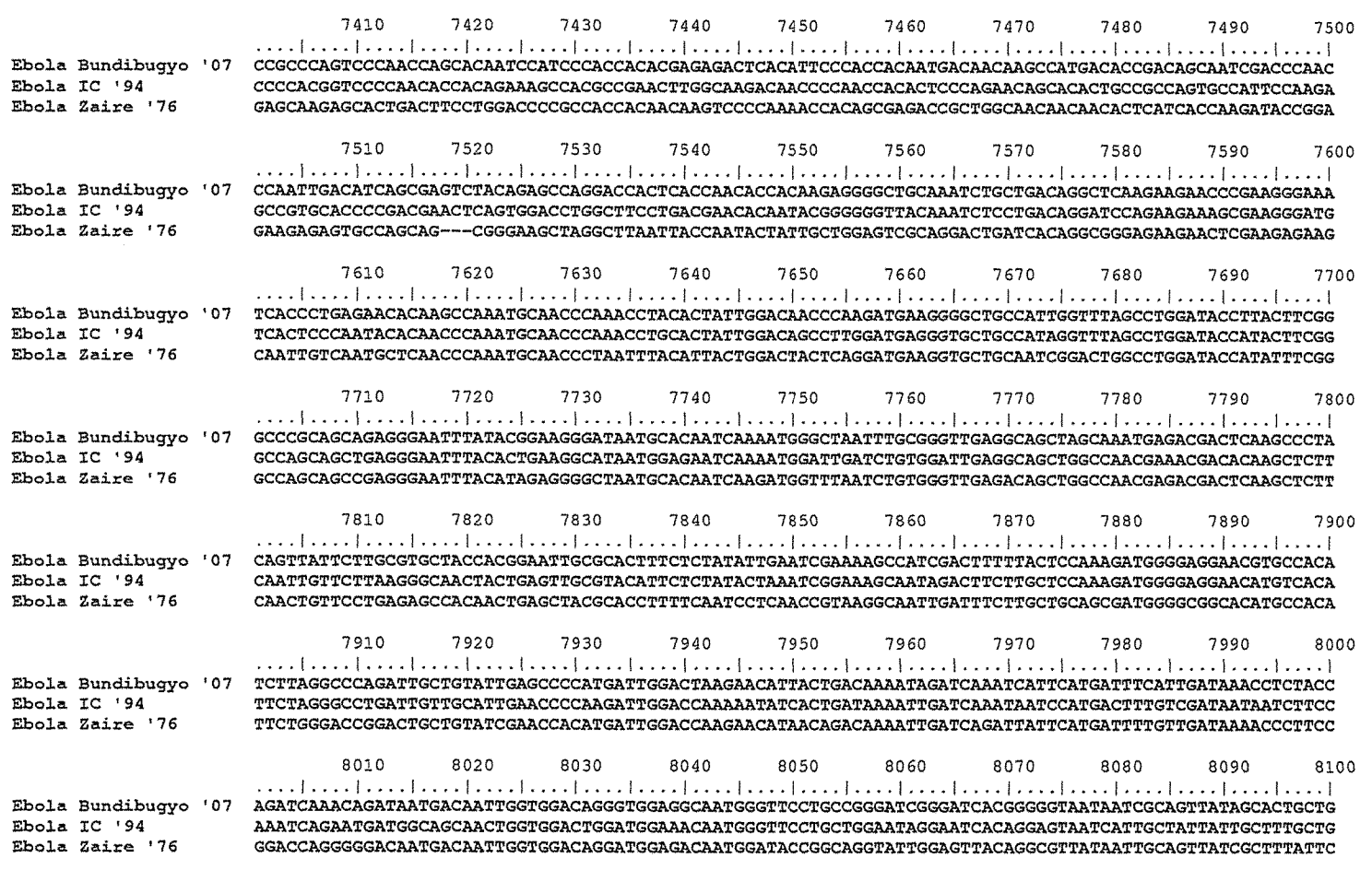
Figure 2L:
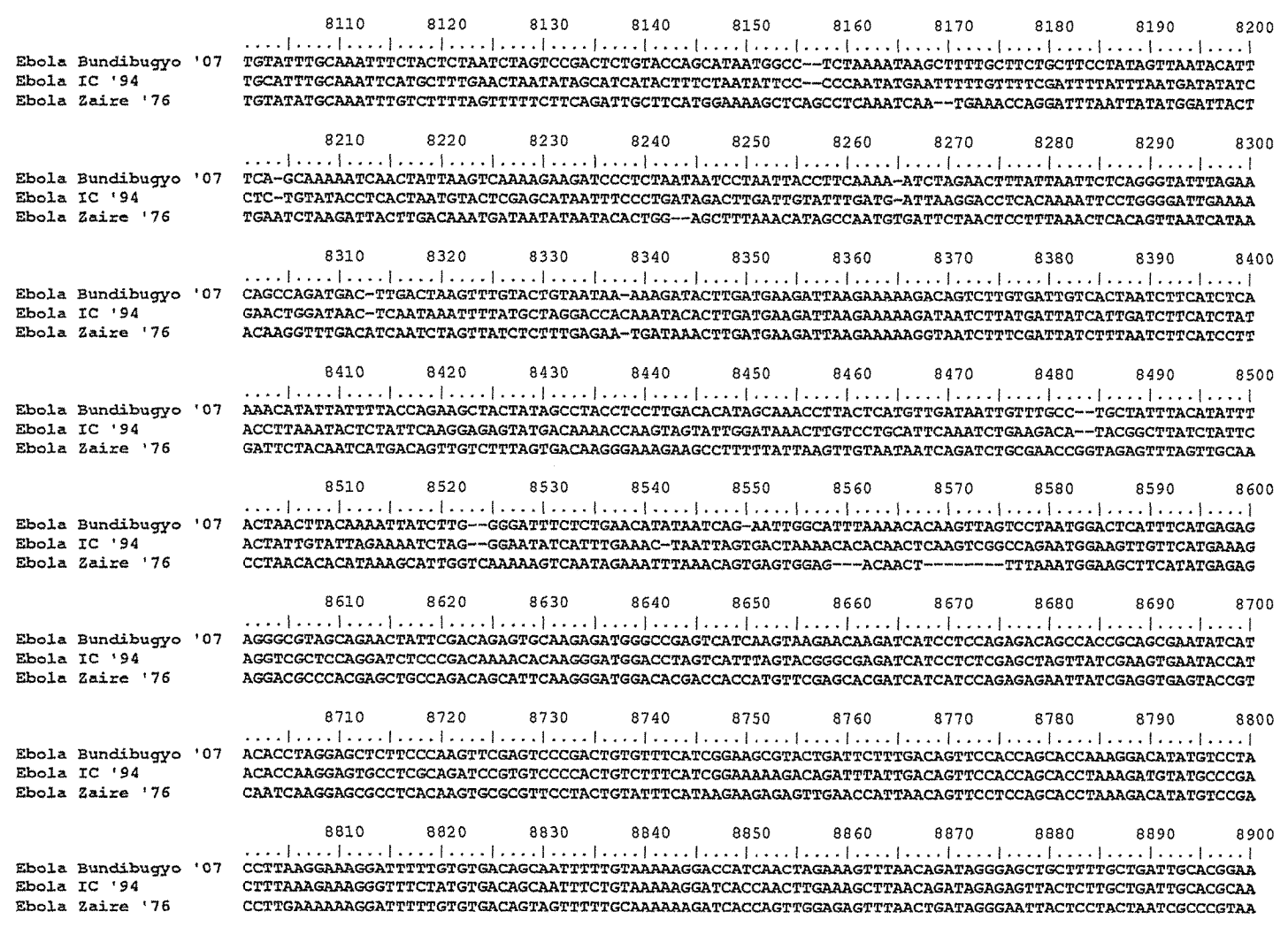
Figure 2M:
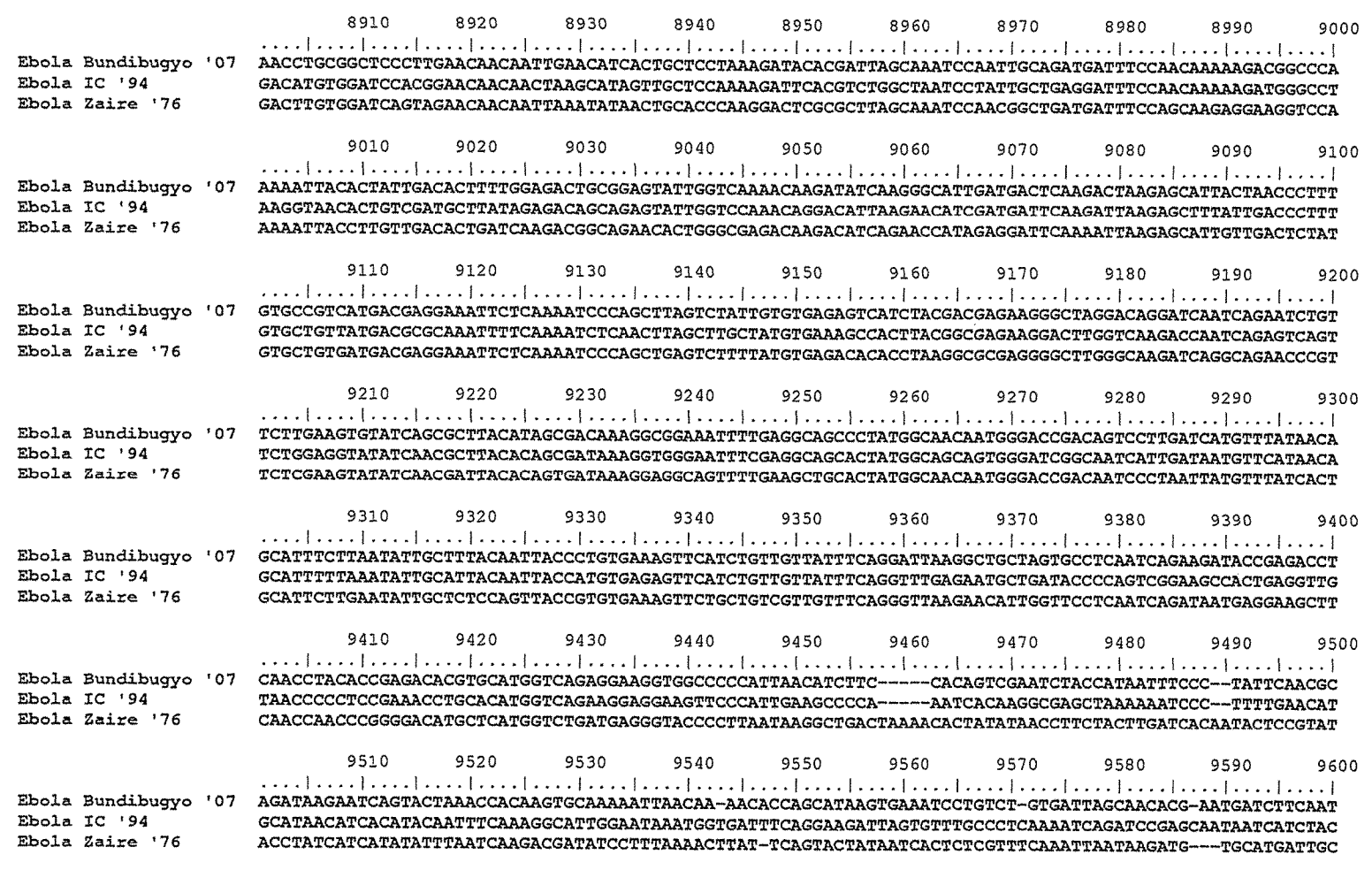
Figure 2N:
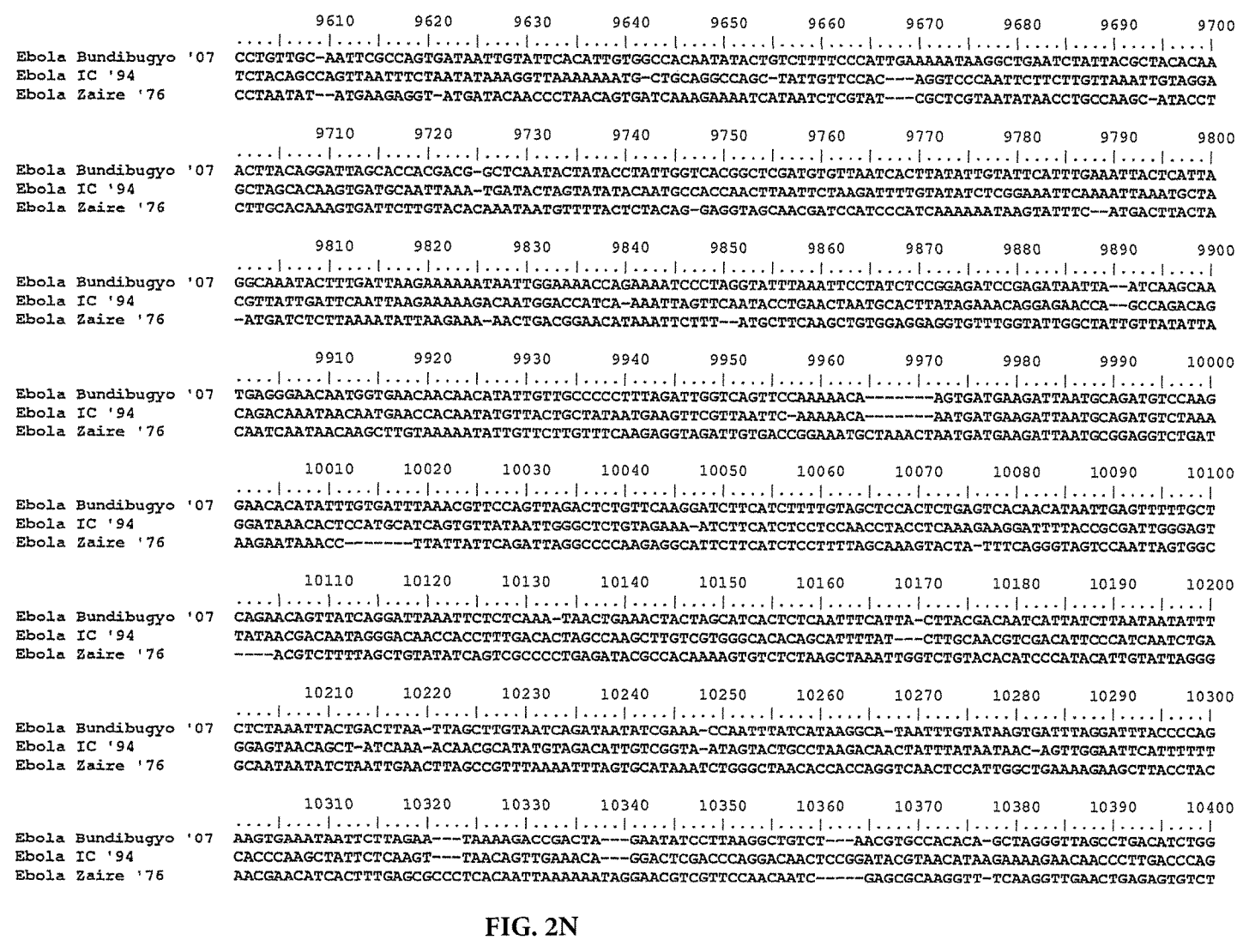
Figure 2P:
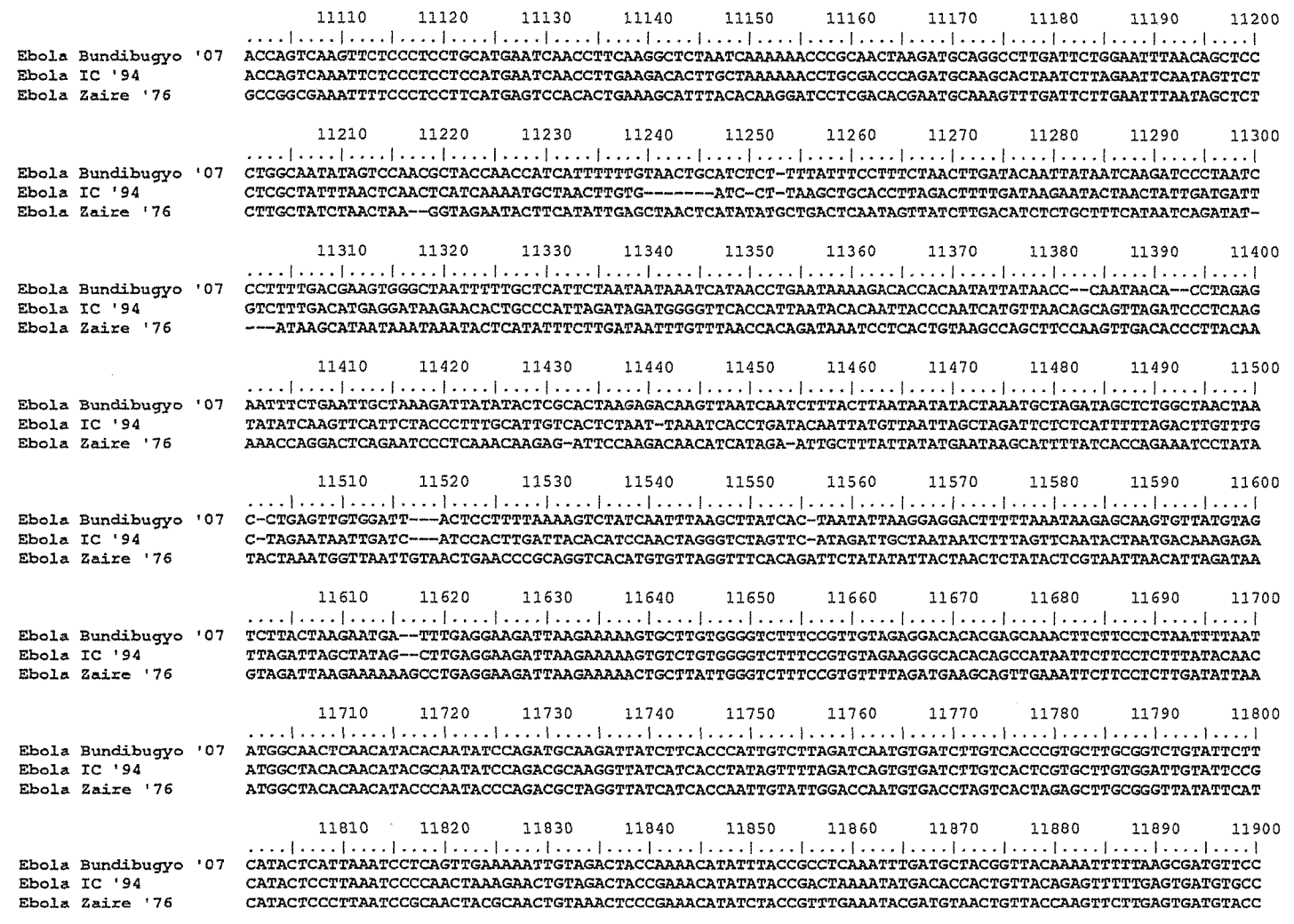
Figure 2Q:
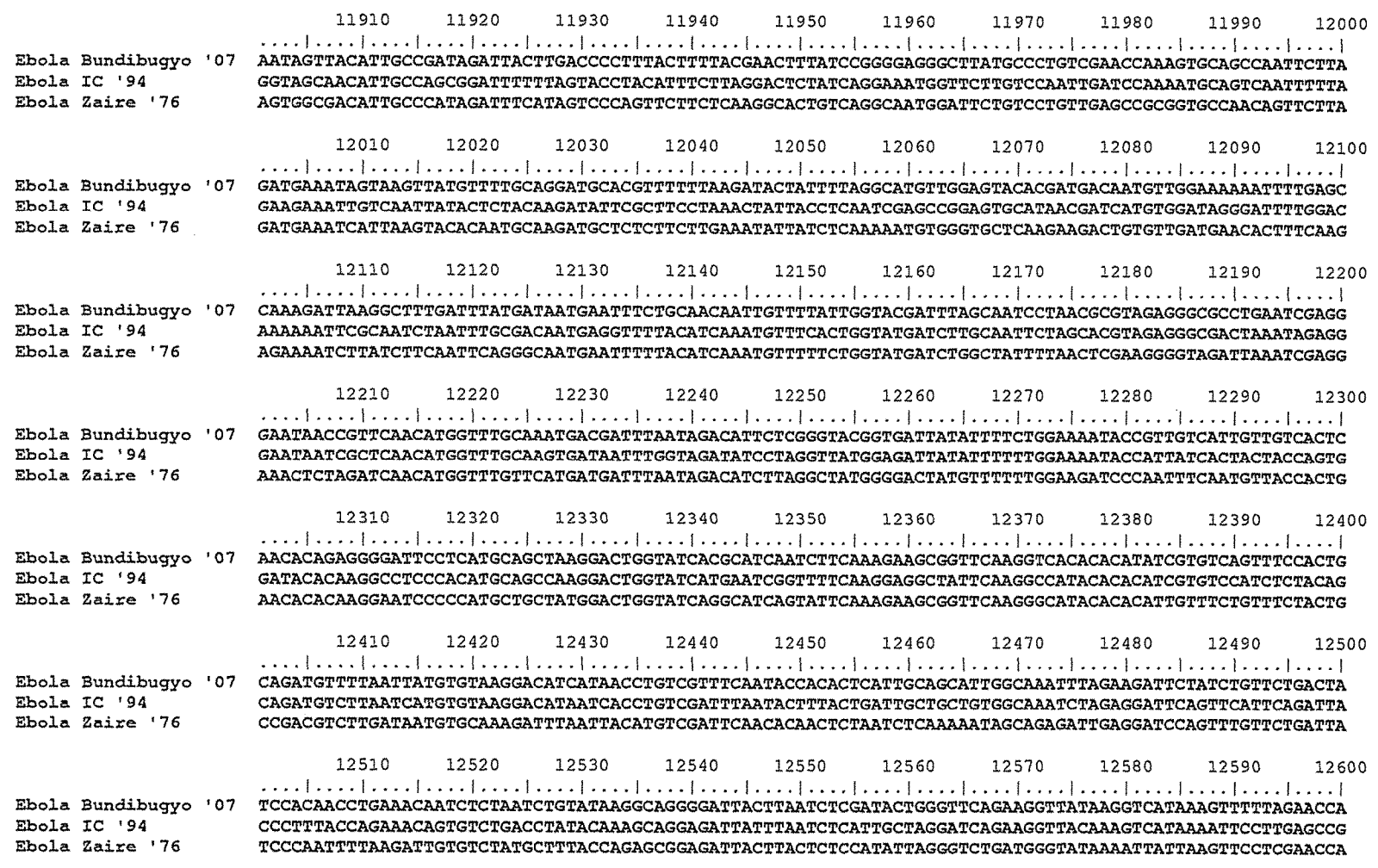
Figure 2V:
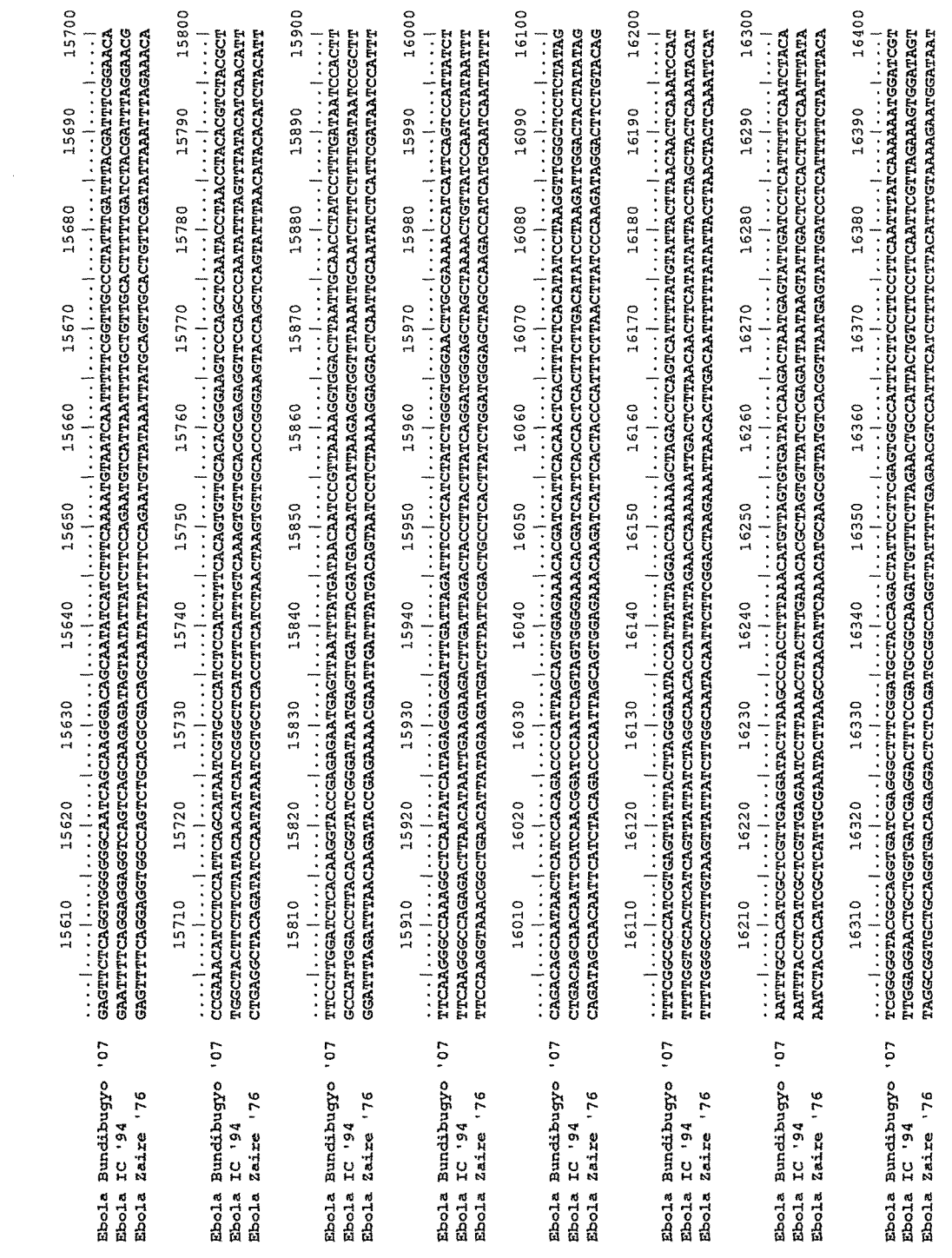
Figure 2W:
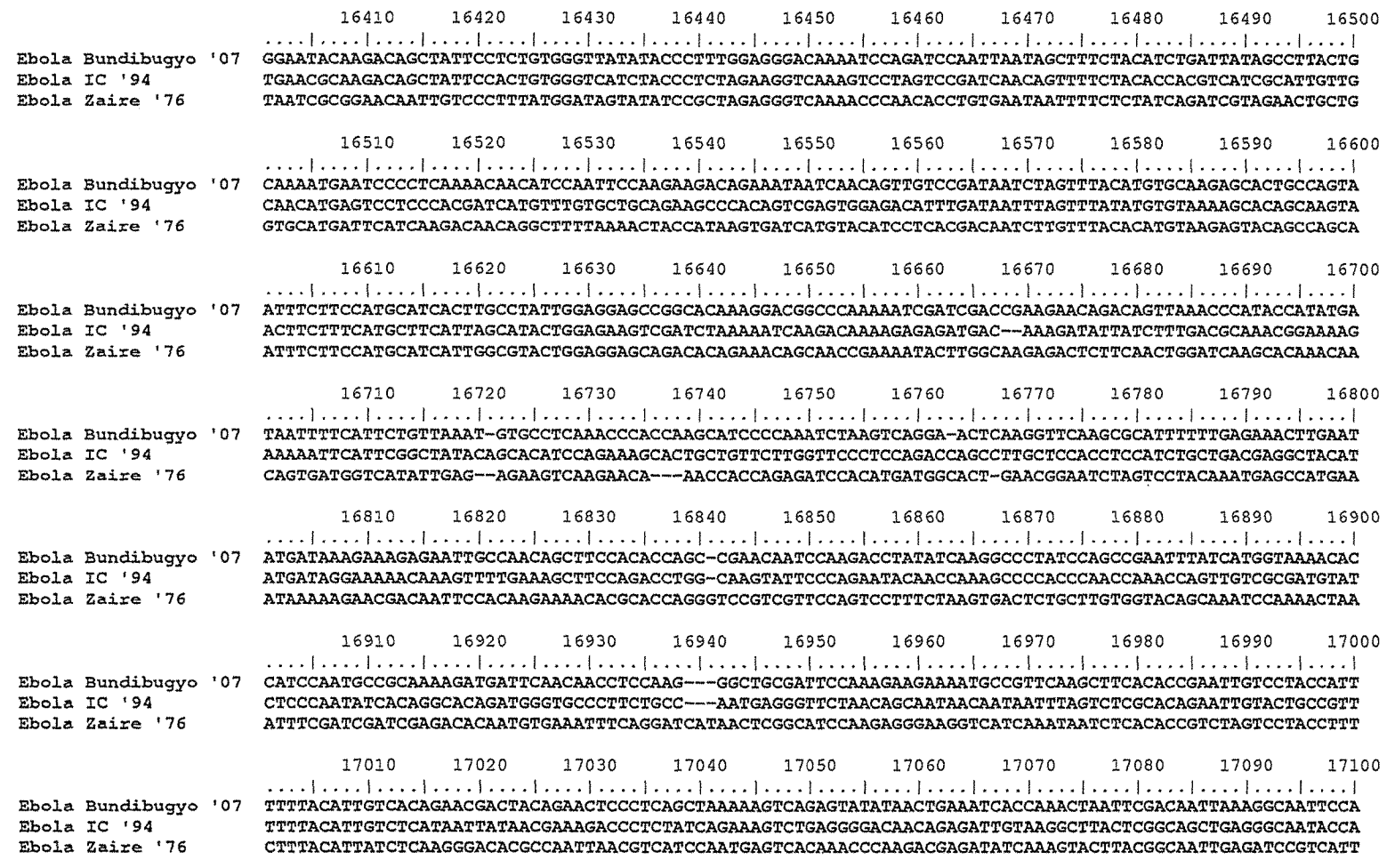
Figure 2Z:
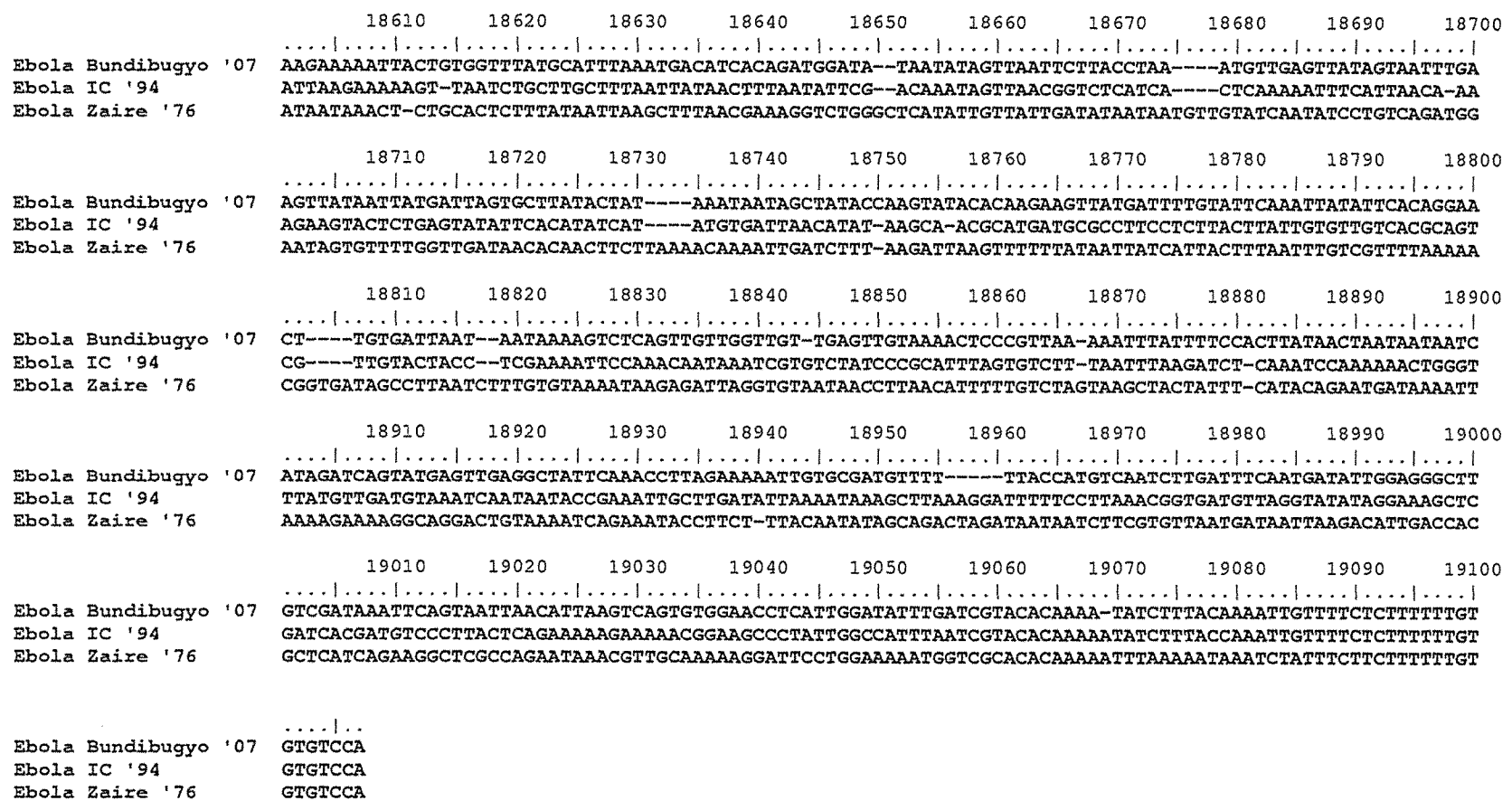

FIGS. 2A-2Z represent an alignment of genomes of novel hEbola EboBun (SEQ ID NO: 1) referred to below as "Ebola *Bundibugyo* " or "EboBun", and hEbola Zaire (SEQ ID NO: 20); referred to below as "Ebola Zaire '76" or "EboZ" and hEbola Ivory Coast (SEQ ID NO: 10) also referred to below as "EboIC".

DETAILED DESCRIPTION OF THE PREFERRED EMBODIMENTS

It is to be understood that the present invention is not limited to particular embodiments described, as such may, of course, vary. It is also to be understood that the terminology used herein is for the purpose of describing particular embodiments only, and is not intended to be limiting.

Due to the sequence divergence of EboBun relative to all previously recognized *ebolaviruses*, the present invention has utility in design of diagnostic assays to monitor Ebola HF disease in humans and animals, and develop effective antivirals and vaccines.

The EboBun virus of the present invention is genetically distinct, differing by more than 30% at the genome level from all other known *ebolavirus* species. The unique nature of this virus created challenges for traditional filovirus molecular based diagnostic assays and genome sequencing approaches. Instead, over 70% of the virus genome was sequenced using a recently developed random-primed pyrosequencing approach which allowed the rapid development of molecular detection assay which were deployed in the disease outbreak response. This random-primed pyrosequencing draft sequence allowed faster completion of the whole genome sequence using traditional primer walking approach and confirmation that the EboBun virus represented a new *ebolavirus* species.

Definitions

The definitions herein provided are operative throughout the entire description of the invention set forth herein, including the Summary of the Invention.

The term "an antibody or an antibody fragment that immunospecifically binds a polypeptide of the invention" as used herein refers to an antibody or a fragment thereof that immunospecifically binds to the polypeptide encoded by the nucleotide sequence of SEQ ID NO: 1 (EboBun), or a fragment thereof, and does not non-specifically bind to other polypeptides. An antibody or a fragment thereof that immunospecifically binds to the polypeptide of the invention may cross-react with other antigens. Preferably, an antibody or a fragment thereof that immunospecifically binds to a polypeptide of the invention does not cross-react with other antigens. An antibody or a fragment thereof that immunospecifically binds to the polypeptide of the invention can be identified by, for example, immunoassays or other techniques known to those skilled in the art, or otherwise as described herein.

An "isolated" or "purified" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1% (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment of the invention, nucleic acid molecules encoding polypeptides/proteins of the invention are isolated or purified. The term "isolated" nucleic acid molecule does not include a nucleic acid that is a member of a library that has not been purified away from other library clones containing other nucleic acid molecules.

The term "portion" or "fragment" as used herein includes the specified fragment lengths, and all integers in between, inclusive of the specified end points in a specified range, and inclusive of any length up to the full length of a protein, polypeptide, or nucleic acid.

The term "having a biological activity of the protein" or "having biological activities of the polypeptides of the invention" refers to the characteristics of the polypeptides or proteins having a common biological activity, similar or identical structural domain, and/or having sufficient amino acid identity to the polypeptide encoded by the nucleotide sequence of SEQ ID NO: 1 (EboBun). Such common biological activities of the polypeptides of the invention include antigenicity and immunogenicity.

The term "under stringent condition" refers to hybridization and washing conditions under which nucleotide sequences having at least 70%, at least 75%, at least 80%, at least 85%, at least 90%, or at least 95% identity to each other remain hybridized to each other. Such hybridization conditions are described in, for example but not limited to, Current Protocols in Molecular Biology, John Wiley & Sons, NY (1989), 6.3.1-6.3.6.; Basic Methods in Molecular Biology, Elsevier Science Publishing Co., Inc., NY (1986), pp. 75-78, and 84-87; and Molecular Cloning, Cold Spring Harbor Laboratory, NY (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C., followed by one or more washes in 0.2×SSC, 0.1% SDS at about 50-65° C.

The term "variant" as used herein refers either to a naturally occurring genetic mutant of hEbola EboBun, or hEbola EboIC, or a recombinantly prepared variation of these hEbola species, each of which contain one or more mutations in its genome compared to the hEbola of SEQ ID NO: 1 or 10. The term "variant" may also refer either to a naturally occurring variation of a given peptide or a recombinantly prepared variation of a given peptide or protein in which one or more amino acid residues have been modified by amino acid substitution, addition, or deletion.

"Homology" refers to sequence similarity or, alternatively, sequence identity, between two or more polynucleotide sequences or two or more polypeptide sequences.

The terms "percent identity" and "% identity," as applied to polynucleotide sequences, refer to the percentage of identical nucleotide matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using one or more computer algorithms or programs known in the art or described herein. For example, percent identity can be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison, Wis.). CLUSTAL V is described in Higgins, D. G. and P. M. Sharp (1989; CABIOS 5:151-153) and in Higgins, D. G. et al. (1992; CABIOS 8:189-191). For pairwise alignments of polynucleotide sequences, the default parameters are set as follows: Ktuple=2, gap penalty=5, window=4, and "diagonals saved"=4. The "weighted" residue weight table is selected as the default.

Alternatively, a suite of commonly used and freely available sequence comparison algorithms which can be used is provided by the National Center for Biotechnology Information (NCBI) Basic Local Alignment Search Tool (BLAST) (Altschul, S. F. et al. (1990) J. Mol. Biol. 215: 403-410), which is available from several sources, including the NCBI, Bethesda, Md., and on the NCBI World Wide Web site available on the Internet. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively on the Internet via the NCBI World Wide Web site as well. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example: Matrix:BLOSUM62; Reward for match: 1; Penalty for mismatch: −2; Open Gap: 5 and Extension Gap: 2 penalties; Gap x drop-off: 50; Expect: 10; Word Size: 11; Filter: on.

Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or sequence listing, may be used to describe a length over which percentage identity may be measured.

The phrases "percent identity" and "% identity", as applied to polypeptide sequences, refer to the percentage of identical residue matches between at least two polypeptide sequences aligned using a standardized algorithm. Methods of polypeptide sequence alignment are well known. Some alignment methods take into account conservative amino acid substitutions. Such conservative substitutions, explained in more detail above, generally preserve the charge and hydrophobicity at the site of substitution, thus preserving the structure (and therefore function) of the polypeptide. The phrases "percent similarity" and "% similarity", as applied to polypeptide sequences, refer to the percentage of residue matches, including identical residue matches and conservative substitutions, between at least two polypeptide sequences aligned using a standardized algorithm. In contrast, conservative substitutions are not included in the calculation of percent identity between polypeptide sequences.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example: Matrix: BLOSUM62; Open Gap: 11 and Extension Gap: 1 penalties; Gap x drop-off: 50; Expect: 10; Word Size: 3; Filter: on.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or sequence listing, may be used to describe a length over which percentage identity may be measured.

The term "agent" encompasses any chemical, biochemical, or biological molecule; such as small molecules, proteins, polypeptides, antibodies, nucleic acid molecules including DNA or RNA, and the like.

Methods and Compositions Related to the Inventive hEbola

The present invention is based upon the isolation and identification of a new human Ebola virus species, EboBun and the sequencing of the only other known West African Ebola species EboIC. EboBun was isolated from the patients suffering from hemorrhagic fever in a recent outbreak in Uganda. The isolated virus is a member of the Filoviridae family, a family of negative sense RNA viruses. Accordingly, the invention relates to the isolated EboBun or EBOIC virus that morphologically and phylogenetically relates to known members filoviridae.

In another aspect, the invention provides an isolated hEbola virus including a nucleic acid molecule with a nucleotide sequence that is preferably: a) a nucleotide sequence set forth in SEQ ID NO: 1; b) a nucleotide sequence that hybridizes to the sequence set forth in SEQ ID NO: 1 under stringent conditions; or c) a nucleotide sequence that has at least 70%, 75%, 80%, 85%, 90%, 95%, 96%, 97%, 98%, or 99% identity to the SEQ ID NO: 1. In one embodiment of the present invention, the hEbola virus is killed. In another, the virus is attenuated. In another, the infectivity of the attenuated hEbola virus is reduced. In another, the infectivity is reduced by at least 5-fold, 10-fold, 25-fold, 50-fold, 100-fold, 250-fold, 500-fold, or 10,000-fold. In another, the replication ability of the attenuated hEbola virus is reduced. In another, the replication ability of the attenuated virus is educed by at least 5-fold, 10-fold, 25-fold, 50-fold, 100-fold, 250-fold, 500-fold, 1,000-fold, or 10,000-fold. In another, the protein synthesis ability of the attenuated virus is reduced. In another, the protein synthesis ability is reduced by at least 5-fold, 10-fold, 25-fold, 50-fold, 100-fold, 250-fold, 500-fold, 1,000-fold, or 10,000-fold. In another, the assembling ability of the attenuated hEbola virus is reduced. In another, the assembling ability of the attenuated virus is reduced by at least 5-fold, 10-fold, 25-fold, 50-fold, 100-fold, 250-fold, 500-fold, 1,000-fold, or 10,000-fold. In another, the cytopathic effect of the attenuated hEbola virus is reduced. In another, the cytopathic effect is reduced by at least 5-fold, 10-fold, 25-fold, 50-fold, 100-fold, 250-fold, 500-fold, 1,000-fold, or 10,000-fold.

In another aspect, the invention provides the complete genomic sequence of the hEbola virus EboBun or EboIC. In a specific embodiment, the virus includes a nucleotide sequence of SEQ ID NOs: 1 or 10, respectively.

In a related aspect, the invention provides nucleic acid molecules isolated from EboBun, EboIC, or fragments thereof. In one embodiment of the present invention, the isolated nucleic acid molecule includes the nucleotide sequence of SEQ ID NOs: 1 or 10, or a complement thereof. In another, the nucleic acid molecule includes a nucleotide sequence having at least 4, 5, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, 4600, 4700, 4800, or 4900 contiguous nucleotides of the nucleotide sequence of SEQ ID NO: 1, or a complement thereof; with the proviso that the nucleotide sequence is not comprised by the nucleotide sequence set forth in SEQ ID NO: 20 (Ebola Zaire nucleotide sequence); or at least 5000, 5500, 5600, 5700, 5800, 5900, 6000, 6100, 6200, 6300, 6400, 6500, or 6600 contiguous nucleotides of the nucleotide sequence of SEQ ID NOs: 1 or 10, or a complement thereof. In another embodiment, the isolated nucleic acid molecule includes a nucleotide sequence that encodes the EboBun amino acid sequence of SEQ ID NOs: 2-9 or 59, the EboIC amino acid sequence of SEQ ID NOs: 11-19, or a complement of the nucleotide sequence that encodes the EboBun amino acid sequences of SEQ ID NOs: 2-9 or 59 or the EboIC amino acid sequences of SEQ ID NOs: 11-19. In another, the isolated nucleic acid molecule hybridizes under stringent conditions to a nucleic acid molecule having the nucleotide sequence of SEQ ID NOs: 1 or 10 or a complement thereof, wherein the nucleic acid molecule encodes an amino acid sequence which has a biological activity exhibited by a polypeptide encoded by the nucleotide sequence of SEQ ID NOs: 1 or 10. In another, nucleic acid molecule is RNA. In another, nucleic acid molecule is DNA.

In another aspect, the invention provides proteins or polypeptides that are isolated from the EboBun, including viral proteins isolated from cells infected with the virus but not present in comparable uninfected cells. In one embodiment of the present invention, the amino acid sequences of the proteins or polypeptides are set forth in SEQ ID NOs: 2-9, 59, or 11-19, or fragments thereof. In one embodiment, polypeptides or proteins of the present invention have a biological activity of the protein (including antigenicity and/or immunogenicity) encoded by the sequence of SEQ ID NOs: 1 or 10. In another, the polypeptides or the proteins of the present invention have a biological activity of at least one protein having the amino acid sequence (including antigenicity and/or immunogenicity) set forth in SEQ ID NOS: 2-9, 59, or 11-19, or a fragment thereof.

In a related aspect, the invention provides an isolated polypeptide encoded by the nucleic acid molecule of the invention described above. In one embodiment of the present invention, the isolated polypeptide includes the amino acid sequence selected from the group consisting of: a) an amino acid sequence set forth in SEQ ID NO: 2, 3, 4, 5, 6, 7, 8, or 9; 11, 12, 13, 14, 15, 16, 17, 18 or 19; and b) an amino acid sequence that has 70%, 75%, 80%, 85%, 90%, 95%, 96%, 97%, 98%, or 99% homology to the amino acid sequence according to a). In another, the isolated polypeptide comprises the amino acid sequence having at least 5, 10, 15, 20, 25, 30, 35, 40, 45, 50, 60, 70, 80, 90, 100, 150, 200, 210, 220, 230, 240 or 250 contiguous amino acid residues of the amino acid sequence of SEQ ID NOs: 5 or 18 (VP24); 5, 10, 15, 20, 25, 30, 35, 40, 45, 50, 60, 70, 80, 90, 100, 150, 200, 210, 220, 230, 240, 250, 260, 270, 280 contiguous amino acid residues of the amino acid sequence of SEQ ID NOs: 6 or 17 (VP30); 5, 10, 15, 20, 25, 30, 35, 40, 45, 50, 60, 70, 80, 90, 100, 150, 200, 250, 300, 310, or 320 contiguous amino acid residues of the amino acid sequence of SEQ ID NOs: 8 or 13 (VP40); 5, 10, 15, 20, 25, 30, 35, 40, 45, 50, 60, 70, 80, 90, 100, 150, 200, 250, 300, 310, 320, 330, or 340 contiguous amino acid residues of the amino acid sequence of SEQ ID NOs: 7 or 12 (VP35); 5, 10, 15, 20, 25, 30, 35, 40, 45, 50, 60, 70, 80, 90, 100, 150, 200, 250, 300, 310, 320, 330, 340, 350, 360, or 370 contiguous amino acid residues of the amino acid sequence of SEQ ID NOs: 4 or 15 (SGP); 5, 10, 15, 20, 25, 30, 35, 40, 45, 50, 60, 70, 80, 90, 100, 150, 200, 250, 300, 310, 320, 330, 340, 350, 360, or 370 contiguous amino acid residues of the amino acid sequence of SEQ ID NOs: 59 or 16 (SSGP); 5, 10, 15, 20, 25, 30, 35, 40, 45, 50, 60, 70, 80, 90, 100, 150, 200, 250, 300, 350, 400, 450, 450, 500, 550, 600, 610, 620, 630, 640, 650, 660, or 670 contiguous amino acid residues of the amino acid sequence of SEQ ID NOs: 9 or 14 (GP); 5, 10, 15, 20, 25, 30, 35, 40, 45, 50, 60, 70, 80, 90, 100, 150, 200, 250, 300, 350, 400, 450, 450, 500, 550, 600, 650, 700, 710, 720, or 730 contiguous amino acid residues of the amino acid sequence of SEQ ID NOs: 3 or 11 (NP); or 5, 10, 15, 20, 25, 30, 35, 40, 45, 50, 60, 70, 80, 90, 100, 150, 200, 250, 300, 350, 400, 450, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2160, 2170, 2180, 2190, or 2200 contiguous amino acid residues of the amino acid sequence of SEQ ID NOs: 2 or 19 (L).

In other aspects, the invention relates to the use of an isolated West African hEbola virus for diagnostic and therapeutic methods. In one embodiment, the invention provides a method of detecting in a biological sample an antibody immunospecific for the hEbola virus using the inventive isolated hEbola virus described herein, or any of the inventive proteins or polypeptides as described herein. In another specific embodiment, the invention provides a method of screening for an antibody which immunospecifically binds and neutralizes hEbola EboBun or EboIC or a combination thereof. Such an antibody is useful for a passive immunization or immunotherapy of a subject infected with hEbola.

In another aspect, the invention provides an isolated antibody or an antigen-binding fragment thereof which immunospecifically binds to a West African genus hEbola virus of the invention described above, and illustratively including EboBun or EboIC. In one embodiment of the present invention, the isolated antibody or an antigen-binding fragment thereof neutralizes a West African genus hEbola virus. In another, the isolated antibody or an antigen-binding fragment thereof immunospecifically binds to the inventive polypeptide described above. The invention further provides antibodies that specifically bind a polypeptide of the invention encoded by the nucleotide sequence of SEQ ID NOs: 1 (EboBun) or 10 (EboIC), a fragment thereof, or encoded by a nucleic acid comprising a nucleotide sequence that hybridizes under stringent conditions to the nucleotide sequence of SEQ ID NOs: 1 (EboBun) or 10 (EboIC) and/or any hEbola EboBun epitope, having one or more biological activities of a polypeptide of the invention. These polypeptides include those shown in SEQ ID NOs: 2-9, 59, and 11-19. Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, intrabodies and fragments containing either a VL or VH domain or even a complementary determining region (CDR) that specifically binds to a polypeptide of the invention.

In other aspects, the invention provides methods for detecting the presence, activity or expression of the hEbola virus of the invention in a biological material, such as cells, blood, saliva, urine, and so forth. The increased or decreased activity or expression of the hEbola virus in a sample relative to a control sample can be determined by contacting the biological material with an agent which can detect directly or indirectly the presence, activity or expression of the hEbola virus. In one embodiment of the present invention, the detecting agents are the antibodies or nucleic acid molecules of the present invention. Antibodies of the invention can also be used to treat hemorrhagic fever.

In a related aspect, the invention provides a method for detecting the presence of the inventive hEbola virus described above in a biological sample, the method comprising: (a) contacting the sample with an agent that selectively binds to the hEbola virus; and (b) detecting whether the compound binds to the hEbola virus in the sample. In one embodiment of the present invention, the biological sample is selected from the group consisting of cells; blood; serum; plasma; feces; rectal, vaginal and conjunctival swabs In another, the agent that binds to the virus is an antibody. In another, the agent that binds to the virus is a nucleic acid molecule comprising the nucleotide sequence of SEQ ID NO: 1 or a complement thereof. In another, the agent that binds to the virus is a nucleic acid molecule comprising a nucleotide sequence having at least 4, 5, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, 4600, 4700, 4800, 4900, 5000, 5500, 5600, 5700, 5800, 5900, 6000, 6100, 6200, 6300, 6400, 6500, or 6600 contiguous nucleotides of the nucleotide sequence of SEQ ID NOs: 1 or 10, or a complement thereof.

In another aspect, the invention provides a method for detecting the presence of the inventive polypeptide described above, in a biological sample, the method comprising: (a) contacting the biological sample with an agent that selectively binds to the polypeptide; and (b) detecting whether the agent binds to the polypeptide in the sample. In one embodiment of the present invention, the biological sample is selected from the group consisting of cells; blood; serum; plasma; feces; rectal, vaginal and conjunctival swabs. In another, the agent that binds to the polypeptide is an antibody or an antigen-binding fragment thereof.

In another aspect, the invention provides a method for detecting the presence of a first nucleic acid molecule derived from the inventive hEbola virus described above in a biological sample, the method includes (a) contacting the biological sample with an agent that selectively binds to the nucleic acid; and (b) detecting whether the agent binds to the nucleotide in the sample. In one embodiment of the present invention, the agent that binds to the first nucleic acid molecule is a second nucleic acid molecule comprising the nucleotide sequence of SEQ ID NO: 1 or a complement thereof. In another, the second nucleic acid molecule comprises at least 4, 5, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, 4600, 4700, 4800, 4900, 5000, 5500, 5600, 5700, 5800, 5900, 6000, 6100, 6200, 6300, 6400, 6500, or 6600 contiguous nucleotides of the nucleotide sequence of SEQ ID NOs: 1 or 10, or a complement thereof.

In another aspect, the invention provides a method for propagating the hEbola virus in host cells comprising infecting the host cells with an inventive isolated West African hEbola virus described above, culturing the host cells to allow the virus to multiply, and harvesting the resulting virions. Also provided by the present invention are host cells infected with the inventive hEbola virus described above. In one embodiment of the present invention, the host cell is a primate cell.

In another aspect, the invention provides a method of detecting in a biological sample e the presence of an antibody that immunospecifically binds hEbola virus, the method includes: (a) contacting the biological sample with the inventive host cell described above; and (b) detecting the antibody bound to the cell.

In another aspect, the invention provides vaccine preparations, including the inventive hEbola virus, including recombinant and chimeric forms of the virus, nucleic acid molecules comprised by the virus, or protein subunits of the virus. In one embodiment, the vaccine preparations of the present invention includes live but attenuated hEbola virus with or without pharmaceutically acceptable carriers, including adjuvants. In another, the vaccine preparations of the invention comprise an inactivated or killed hEbola EboBun virus, EboIC virus, or a combination thereof, with or without pharmaceutically acceptable carriers, including adjuvants. Such attenuated or inactivated viruses may be prepared by a series of passages of the virus through the host cells or by preparing recombinant or chimeric forms of virus. Accordingly, the present invention further provides methods of preparing recombinant or chimeric forms of the inventive hEbola viruses described herein.

In another specific embodiment, the invention provides a vaccine formulation comprising a therapeutically or prophylactically effective amount of the inventive hEbola virus described above, and a pharmaceutically acceptable carrier. In another, the invention provides a vaccine formulation comprising a therapeutically or prophylactically effective amount of a protein extract of the inventive hEbola virus described above, or a subunit thereof; and a pharmaceutically acceptable carrier. In another aspect, the invention provides a vaccine formulation comprising a therapeutically or prophylactically effective amount of a nucleic acid molecule comprising the nucleotide sequence of SEQ ID NOs: 1 or 10, or a complement thereof, and a pharmaceutically acceptable carrier. In another, the invention provides a vaccine formulation comprising a therapeutically or prophylactically effective amount of a nucleic acid molecule comprising any of inventive the nucleotide sequences as described above, or a complement thereof, and a pharmaceutically acceptable carrier. In another aspect, the invention provides a vaccine formulation comprising a therapeutically or prophylactically effective amount of a protein extract of the inventive hEbola virus described above, or a subunit thereof; and a pharmaceutically acceptable carrier. In another aspect, the invention provides a vaccine formulation comprising a therapeutically or prophylactically effective amount of a nucleic acid molecule comprising the nucleotide sequence of SEQ ID NOs: 1 or 10, or a complement thereof, and a pharmaceutically acceptable carrier. In another, the invention provides a vaccine formulation comprising a therapeutically or prophylactically effective amount of a nucleic acid molecule comprising any of inventive the nucleotide sequences as described above, or a complement thereof, and a pharmaceutically acceptable carrier.

In yet another specific embodiment, the vaccine preparations of the present invention comprise a nucleic or fragment of the hEbola virus, e.g., the virus having Accession No. 200706291, or nucleic acid molecules having the sequence of SEQ ID NOs: 1 or 10, or a fragment thereof. In another, the vaccine preparations comprise a polypeptide of the invention encoded by the nucleotide sequence of SEQ ID NOs: 1 or 10 or a fragment thereof. In a specific embodiment, the vaccine preparations comprise polypeptides of the invention as shown in SEQ ID NOs: 2-9, 59, or 11-19, or encoded by the nucleotide sequence of SEQ ID NOs: 1 or 10, or a fragment thereof.

Furthermore, the present invention provides methods for treating, ameliorating, managing or preventing hemorrhagic fever by administering the vaccine preparations or antibodies of the present invention alone or in combination with adjuvants, or other pharmaceutically acceptable excipients. Furthermore, the present invention provides methods for treating, ameliorating, managing, or preventing hemorrhagic fever by administering the inventive compositions and formulations including the vaccine preparations or antibodies of the present invention alone or in combination with antivirals [e.g., amantadine, rimantadine, gancyclovir, acyclovir, ribavirin, penciclovir, oseltamivir, foscarnet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons, etc.], steroids and corticosteroids such as prednisone, cortisone, fluticasone and glucocorticoid, antibiotics, analgesics, bronchodilators, or other treatments for respiratory and/or viral infections.

In a related aspect, the invention provides an immunogenic formulation comprising an immunogenically effective amount of the inventive hEbola virus described above, and a pharmaceutically acceptable carrier.

In another related aspect, the invention provides an immunogenic formulation comprising an immunogenically effective amount of a protein extract of the inventive hEbola virus described above or a subunit thereof, and a pharmaceutically acceptable carrier.

In another related aspect, the invention provides an immunogenic formulation comprising an immunogenically effective amount of a nucleic acid molecule comprising the nucleotide sequence of SEQ ID NOs: 1, 10, a combination thereof, or a complement thereof, and a pharmaceutically acceptable carrier.

In another related aspect, the invention provides an immunogenic formulation comprising an immunogenically effective amount of a nucleic acid molecule comprising the inventive nucleotide sequence as described above or a complement thereof, and a pharmaceutically acceptable carrier.

In another related aspect, the invention provides an immunogenic formulation comprising an immunogenically effective amount of any of the inventive polypeptides described above.

In another aspect, the present invention provides pharmaceutical compositions comprising antiviral agents of the present invention and a pharmaceutically acceptable carrier. In a specific embodiment, the antiviral agent of the invention is an antibody that immunospecifically binds hEbola virus or any hEbola epitope. In another specific embodiment, the antiviral agent is a polypeptide or protein of the present invention or nucleic acid molecule of the invention.

In a related aspect, the invention provides a pharmaceutical composition comprising a prophylactically or therapeutically effective amount of an anti-hEbola EboBun agent and a pharmaceutically acceptable carrier. In one embodiment of the present invention, the anti-hEbola EboBun agent is an antibody or an antigen-binding fragment thereof which immunospecifically binds to the hEbola virus of Deposit Accession No. 200706291, or polypeptides or protein derived therefrom. In another, the anti-hEbola agent is a nucleic acid molecule comprising the nucleotide sequence of SEQ ID NOs: 1, 10, a combination thereof, or a fragment thereof. In another, the anti-hEbola agent is a polypeptide encoded by a nucleic acid molecule comprising the nucleotide sequence of SEQ ID NOs: 1, 10, a combination thereof, or a fragment thereof having a biological activity of the polypeptide.

The invention also provides kits containing compositions and formulations of the present invention. Thus, in another aspect, the invention provides a kit comprising a container containing the inventive immunogenic formulation described above.

In another aspect, the invention provides a kit includes a container containing the inventive vaccine formulation described above.

In another aspect, the invention provides a kit including a container containing the inventive pharmaceutical composition described above.

In another aspect, the invention provides a kit including a container containing the inventive vaccine formulation described above.

In another aspect, the invention provides a method for identifying a subject infected with the inventive hEbola virus described above, including: (a) obtaining total RNA from a biological sample obtained from the subject; (b) reverse transcribing the total RNA to obtain cDNA; and (c) amplifying the cDNA using a set of primers derived from a nucleotide sequence of the inventive hEbola virus described above.

In one embodiment of the present invention, the set of primers are derived from the nucleotide sequence of the genome of the hEbola virus of Deposit Accession No. 200706291. In another, the set of primers are derived from the nucleotide sequence of SEQ ID NOs: 1 or 10 or any of the inventive nucleotide sequences as described above, or a complement thereof.

The invention further relates to the use of the sequence information of the isolated virus for diagnostic and therapeutic methods. In a specific embodiment, the invention provides nucleic acid molecules which are suitable for use as primers consisting of or including the nucleotide sequence of SEQ ID NOs: 1 or 10, or a complement thereof, or at least a portion of the nucleotide sequence thereof. In another specific embodiment, the invention provides nucleic acid molecules which are suitable for hybridization to the inventive hEbola nucleic acid; including, but not limited to PCR primers, Reverse Transcriptase primers, probes for Southern analysis or other nucleic acid hybridization analysis for the detection of hEbola nucleic acids, e.g., consisting of or including the nucleotide sequence of SEQ ID NOs: 1, 10 a combination thereof, a complement thereof, or a portion thereof. The invention further encompasses chimeric or recombinant viruses encoded in whole or in part by the nucleotide sequences.

In another aspect, the present invention provides methods for screening antiviral agents that inhibit the infectivity or replication of hEbola virus or variants thereof.

The invention further provides methods of preparing recombinant or chimeric forms of hEbola.

In another aspect, the invention provides vaccine preparations including the hEbola virus, including recombinant and chimeric forms of the virus, or subunits of the virus. The present invention encompasses recombinant or chimeric viruses encoded by viral vectors derived from the genome of the inventive hEbola virus described herein or natural variants thereof. In a specific embodiment, a recombinant virus is one derived from the hEbola virus of Deposit Accession No. 200706291. It is recognized that natural variants of the inventive hEbola viruses described herein comprise one or more mutations, including, but not limited to, point mutations, rearrangements, insertions, deletions etc., to the genomic sequence. It is recognized that the mutations may or may not result in a phenotypic change.

In another specific embodiment, a chimeric virus of the invention is a recombinant hEbola EboBun or EboIC virus which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

According to the present invention, the chimeric viruses are encoded by the viral vectors of the invention which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different species or variants of hEbola virus. In particular, the chimeric virus is encoded by nucleotide sequences that encode antigenic polypeptides derived from different species or variants of hEbola virus.

A chimeric virus may be of particular use for the generation of recombinant vaccines protecting against two or more viruses (Tao et al., J. Virol. 72, 2955-2961; Durbin et al., 2000, J. Virol. 74, 6821-6831; Skiadopoulos et al., 1998, J. Virol. 72, 1762-1768 (1998); Teng et al., 2000, J. Virol. 74, 9317-9321). For example, it can be envisaged that a virus vector derived from the hEbola virus expressing one or more proteins of variants of hEbola virus including hEbola EboBun, or vice versa, will protect a subject vaccinated with such vector against infections by both the native hEbola and the variant. Attenuated and replication-defective viruses may be of use for vaccination purposes with live vaccines as has been suggested for other viruses. (See, for example, PCT WO 02/057302, at pp. 6 and 23; and United States Patent Application Publication 2008/0069838 incorporated by reference herein).

In accordance with the present invention the heterologous sequence to be incorporated into the viral vectors encoding the recombinant or chimeric viruses of the invention include sequences obtained or derived from different species or variants of hEbola.

In certain embodiments, the chimeric or recombinant viruses of the invention are encoded by viral vectors derived from viral genomes wherein one or more sequences, intergenic regions, termini sequences, or portions or entire ORF have been substituted with a heterologous or non-native sequence. In certain embodiments of the invention, the chimeric viruses of the invention are encoded by viral vectors derived from viral genomes wherein one or more heterologous sequences have been inserted or added to the vector.

The selection of the viral vector may depend on the species of the subject that is to be treated or protected from a viral infection. If the subject is human, then an attenuated hEbola virus can be used to provide the antigenic sequences.

In accordance with the present invention, the viral vectors can be engineered to provide antigenic sequences which confer protection against infection by the inventive hEbola and natural variants thereof. The viral vectors may be engineered to provide one, two, three or more antigenic sequences. In accordance with the present invention the antigenic sequences may be derived from the same virus, from different species or variants of the same type of virus, or from different viruses.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. One way to achieve this goal involves modifying existing hEbola genes to contain foreign sequences in their respective external domains. Where the heterologous sequences are epitopes or antigens of pathogens, these chimeric viruses may be used to induce a protective immune response against the disease agent from which these determinants are derived. In particular, the chimeric virions of the present invention may be engineered to create vaccines for the protection of a subject from infections with hEbola virus and variants thereof.

Thus, the present invention further relates to the use of viral vectors and recombinant or chimeric viruses to formulate vaccines against a broad range of viruses and/or antigens. The present invention also encompasses recombinant viruses including a viral vector derived from the hEbola or variants thereof which contains sequences which result in a virus having a phenotype more suitable for use in vaccine formulations, e.g., attenuated phenotype or enhanced antigenicity. The mutations and modifications can be in coding regions, in intergenic regions and in the leader and trailer sequences of the virus.

The invention provides a host cell including a nucleic acid or a vector according to the invention. Plasmid or viral vectors containing the polymerase components of hEbola virus are generated in prokaryotic cells for the expression of the components in relevant cell types (bacteria, insect cells, eukaryotic cells). Plasmid or viral vectors containing full-length or partial copies of the hEbola genome will be generated in prokaryotic cells for the expression of viral nucleic acids in vitro or in vivo. The latter vectors optionally contain other viral sequences for the generation of chimeric viruses or chimeric virus proteins, optionally lack parts of the viral genome for the generation of replication defective virus, and optionally contain mutations, deletions or insertions for the generation of attenuated viruses. In addition, the present invention provides a host cell infected with hEbola virus of Deposit Accession No. 200706291, Infectious copies of West African hEbola (being wild type, attenuated, replication-defective or chimeric) are optionally produced upon co-expression of the polymerase components according to the state-of-the-art technologies described above.

In addition, eukaryotic cells, transiently or stably expressing one or more full-length or partial hEbola proteins are optionally used. Such cells are preferably made by transfection (proteins or nucleic acid vectors), infection (viral vectors) or transduction (viral vectors) and are useful for complementation of mentioned wild type, attenuated, replication-defective or chimeric viruses.

The viral vectors and chimeric viruses of the present invention optionally modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents.

Formulation of Vaccines and Antivirals

In a preferred embodiment, the invention provides a proteinaceous molecule or hEbola virus specific viral protein or functional fragment thereof encoded by a nucleic acid according to the invention. Useful proteinaceous molecules are for example derived from any of the genes or genomic fragments derivable from the virus according to the invention, preferably the GP, L, NP, sGP, VP24, VP30, VP35, and VP 40 proteins described herein. Such molecules, or antigenic fragments thereof, as provided herein, are for example useful in diagnostic methods or kits and in pharmaceutical compositions such as subunit vaccines. Particularly useful are polypeptides encoded by the nucleotide sequence of SEQ ID NOs: 1 or 10; or antigenic fragments thereof for inclusion as antigen or subunit immunogen, but inactivated whole virus can also be used. Particularly useful are also those proteinaceous substances that are encoded by recombinant nucleic acid fragments of the hEbola genome, of course preferred are those that are within the preferred bounds and metes of ORFs, in particular, for eliciting hEbola specific antibody or T cell responses, whether in vivo (e.g. for protective or therapeutic purposes or for providing diagnostic antibodies) or in vitro (e.g. by phage display technology or another technique useful for generating synthetic antibodies).

It is recognized that numerous variants, analogues, or homologues of EboBun polypeptides are within the scope of the present invention including amino acid substitutions, alterations, modifications, or other amino acid changes that increase, decrease, or do not alter the function or immunogenic propensity of the inventive immunogen or vaccine. Several post-translational modifications are similarly envisioned as within the scope of the present invention illustratively including incorporation of a non-naturally occurring amino acid(s), phosphorylation, glycosylation, sulfation, and addition of pendent groups such as biotynlation, fluorophores, lumiphores, radioactive groups, antigens, or other molecules.

Methods of expressing and purifying natural or recombinant peptides and proteins are well known in the art. Illustratively, peptides and proteins are recombinantly expressed in eukaryotic cells. Exemplary eukaryotic cells include yeast, HeLa cells, 293 cells, COS cells, Chinese hamster ovary cells (CHO), and many other cell types known in the art. Both eukaryotic and prokaryotic expression systems and cells are available illustratively from Invitrogen Corp., Carlsbad, Calif. It is appreciated that cell-free expression systems are similarly operable.

In a preferred embodiment an immunogenic polypeptide is a full length EboBun protein. Preferably, an immunogen is a full length EboBun protein of SEQ ID NOs: 2-9 or 59, or EboIC SEQ ID NOs: 11-19, or a fragment thereof as described herein. Preferably, an immunogen is has a minimum of 5 amino acids. As used herein an immunogen is preferably a polypeptide. In the context of an immunogenic polypeptide the terms immunogen, polypeptide, and antigen are used interchangeably.

Modifications and changes can be made in the structure of the inventive immunogens that are the subject of the application and still obtain a molecule having similar or improved characteristics as the wild-type sequence (e.g., a conservative amino acid substitution). For example, certain amino acids are optionally substituted for other amino acids in a sequence without appreciable loss of immunogenic activity. Because it is the interactive capacity and nature of a polypeptide that defines that polypeptide's biological functional activity, certain amino acid sequence substitutions can be made in a polypeptide sequence and nevertheless obtain a polypeptide with like or improved properties. Optionally, a polypeptide is used that has less or more immunogenic activity compared to the wild-type sequence.

In making such changes, the hydropathic index of amino acids is preferably considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent immunogen. In such changes, the substitution of amino acids whose hydropathic indices are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide and immunogen as set forth above. In particular, embodiments of the polypeptides and immunogens optionally include variants having about 50%, 60%, 70%, 80%, 90%, and 95% sequence identity to the polypeptide of interest.

The invention provides vaccine formulations for the prevention and treatment of infections with hEbola virus. In certain embodiments, the vaccine of the invention comprises recombinant and chimeric viruses of the hEbola virus. In certain embodiments, the virus is attenuated.

In another embodiment of this aspect of the invention, inactivated vaccine formulations are prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly or intranasally.

Inactivated viruses are optionally formulated with a suitable adjuvant in order to enhance the immunological response. Such adjuvants illustratively include but are not limited to mineral gels, e.g., aluminum hydroxide; surface active substances such as lysolecithin, pluronic polyols, polyanions; peptides; oil emulsions; and potentially useful human adjuvants such as BCG and *Corynebacterium parvum*.

In another aspect, the present invention also provides DNA vaccine formulations including a nucleic acid or fragment of the inventive hEbola virus, e.g., the virus having Accession No. 200706291, or nucleic acid molecules having the sequence of SEQ ID NOs: 1 or 10, or a fragment thereof. In another specific embodiment, the DNA vaccine formulations of the present invention comprise a nucleic acid or fragment thereof encoding the antibodies which immunospecifically bind hEbola viruses. In DNA vaccine formulations, a vaccine DNA comprises a viral vector, such as that derived from the hEbola virus, bacterial plasmid, or other expression vector, bearing an insert including a nucleic acid molecule of the present invention operably linked to one or more control elements, thereby allowing expression of the vaccinating proteins encoded by the nucleic acid molecule in a vaccinated subject. Such vectors can be prepared by recombinant DNA technology as recombinant or chimeric viral vectors carrying a nucleic acid molecule of the present invention.

A nucleic acid as used herein refers to single- or double-stranded molecules which are optionally DNA, including the nucleotide bases A, T, C and G, or RNA, including the bases A, U (substitutes for T), C, and G. The nucleic acid may represent a coding strand or its complement. Nucleic acids are optionally identical in sequence to the sequence which is naturally occurring or include alternative codons which encode the same amino acid as that which is found in the naturally occurring sequence. Furthermore, nucleic acids optionally include codons which represent conservative substitutions of amino acids as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids is illustratively accomplished by techniques such as cell lysis followed by phenol plus chloroform extraction, followed by ethanol precipitation of the nucleic acids. The nucleic acids of this invention are illustratively isolated from cells according to methods well known in the art for isolating nucleic acids. Alternatively, the nucleic acids of the present invention are optionally synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention is optionally part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct including a nucleic acid encoding a polypeptide of this invention.

Generally, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered" and "recombinant" cells are synonymous with "host" cells and are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. A host cell preferably does not possess a naturally occurring gene encoding RSV G protein. Engineered cells are, thus, cells having a gene or genes introduced through the hand of man. Recombinant cells illustratively include those having an introduced cDNA or genomic DNA, and also include genes positioned adjacent to a promoter not naturally associated with the particular introduced gene.

To express a recombinant encoded polypeptide in accordance with the present invention one optionally prepares an expression vector that comprises a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts illustratively include *E. coli* strain RR1, *E. coli* LE392, *E. coli* B, *E. coli* 1776 (ATCC No. 31537) as well as *E. coli* W3110 (F-, lambda-, prototrophic, ATCC No. 273325); bacilli such as *Bacillus subtilis*; and other *enterobacteria* such as *Salmonella typhimurium, Serratia* marcescens, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage may also contain, or be modified to contain, promoters that can be used by the microbial organism for expression of its own proteins.

In addition, phage vectors containing replicon and control sequences that are compatible with the host microorganism are optionally used as transforming vectors in connection with these hosts. For example, the phage lambda is optionally utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors illustratively include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also preferably ligated into the expression vector 3' of the sequence desired to be expressed to provide polyadenylation of the mRNA and termination.

Other suitable promoters, which have the additional advantage of transcription controlled by growth conditions, illustratively include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms are also operable as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter).

Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines include VERO and HeLa cells, Chinese hamster ovary (CHO) cell lines, W138, BHK, COS-7, 293, HepG2, NIH3T3, RIN and MDCK cell lines. In addition, a host cell is preferably chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems are preferably chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication is preferably provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters are optionally derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems are operable herein, for example, commonly used promoters are derived from polyoma, Adenovirus 2, Adenovirus 5, cytomegalovirus and Simian Virus 40 (SV40). The early and late promoters of SV40 virus are useful because both are obtained easily from the virus as a fragment which also contains the SV40 viral origin of replication. Smaller or larger SV40 fragments are also operable, particularly when there is included the approximately 250 bp sequence extending from the HindIII site toward the BglI site located in the viral origin of replication.

In cases where an adenovirus is used as an expression vector, the coding sequences are preferably ligated to an adenovirus transcription/translation control complex, e.g., the late promoter and tripartite leader sequence. This chimeric gene is then optionally inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons are optionally of a variety of origins, both natural and synthetic. The efficiency of expression is optionally enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins are engineered. Rather than using expression vectors that contain viral origins of replication, host cells are preferably transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems are illustratively used, including, but not limited, to the herpes simplex virus thymidine kinase, hypoxanthine-guanine phosphoribosyltransferase and adenine phosphoribosyltransferase genes, in tk-, hgprt- or aprt-cells, respectively. Also, antimetabolite resistance is optionally used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

The nucleic acids encoding the peptides and polypeptides of this invention are optionally administered as nucleic acid vaccines. For the purposes of vaccine delivery, a nucleic acid encoding a peptide or polypeptide of this invention is preferably in an expression vector that includes viral nucleic acid including, but not limited to, vaccinia virus, adenovirus, retrovirus and/or adeno-associated virus nucleic acid. The nucleic acid or vector of this invention is optionally in a liposome or a delivery vehicle which can be taken up by a cell via receptor-mediated or other type of endocytosis. The nucleic acid vaccines of this invention are preferably in a pharmaceutically acceptable carrier or administered with an adjuvant. The nucleic acids encoding the peptides and polypeptides of this invention can also be administered to cells in vivo or ex vivo.

It is contemplated that the isolated nucleic acids of the disclosure are optionally "overexpressed", i.e., expressed in increased levels relative to its natural expression in cells of its indigenous organism, or even relative to the expression of other proteins in the recombinant host cell. Such overexpression is assessed by a variety of methods illustratively including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural in transfected cells is indicative of overexpression, as is a relative abundance of the specific protein in relation to the other proteins produced by the host cell and, e.g., visible on a gel.

Various heterologous vectors are described for DNA vaccinations against viral infections. For example, the vectors described in the following references, incorporated herein by reference, may be used to express hEbola sequences instead of the sequences of the viruses or other pathogens described; in particular, vectors described for hepatitis B virus (Michel, M. L. et al., 1995, DAN-mediated immunization to the hepatitis B surface antigen in mice: Aspects of the humoral response mimic hepatitis B viral infection in humans, Proc. Natl. Aca. Sci. USA 92:5307-5311; Davis, H. L. et al., 1993, DNA-based immunization induces continuous secretion of hepatitis B surface antigen and high levels of circulating antibody, Human Molec. Genetics 2:1847-1851), HIV virus (Wang, B. et al., 1993, Gene inoculation generates immune responses against human immunodeficiency virus type 1, Proc. Natl. Acad. Sci. USA 90:4156-4160; Lu, S. et al., 1996, Simian immunodeficiency virus DNA vaccine trial in Macques, J. Virol. 70:3978-3991; Letvin, N. L. et al., 1997, Potent, protective anti-HIV immune responses generated by bimodal HIV envelope DNA plus protein vaccination, Proc Natl Acad Sci USA. 94(17):9378-83), and influenza viruses (Robinson, H L et al., 1993, Protection against a lethal influenza virus challenge by immunization with a haemagglutinin-expressing plasmid DNA, Vaccine 11:957-960; Ulmer, J. B. et al., Heterologous protection against influenza by injection of DNA encoding a viral protein, Science 259:1745-1749), as well as bacterial infections, such as tuberculosis (Tascon, R. E. et al., 1996, Vaccination against tuberculosis by DNA injection, Nature Med. 2:888-892; Huygen, K. et al., 1996, Immunogenicity and protective efficacy of a tuberculosis DNA vaccine, Nature Med., 2:893-898), and parasitic infection, such as malaria (Sedegah, M., 1994, Protection against malaria by immunization with plasmid DNA encoding circumsporozoite protein, Proc. Natl. Acad. Sci. USA 91:9866-9870; Doolan, D. L. et al., 1996, Circumventing genetic restriction of protection against malaria with multigene DNA immunization: CD8+T cell-interferon .delta., and nitric oxide-dependent immunity, J. Exper. Med., 1183:1739-1746).

Many methods are optionally used to introduce the vaccine formulations described above. These include, but are not limited to, oral, intradermal, intramuscular, intraperitoneal, intravenous, subcutaneous, and intranasal routes. Alternatively, in a preferred embodiment the chimeric virus vaccine formulation is introduced via the natural route of infection of the pathogen for which the vaccine is designed. The DNA vaccines of the present invention are optionally administered in saline solutions by injections into muscle or skin using a syringe and needle (Wolff J. A. et al., 1990, Direct gene transfer into mouse muscle in vivo, Science 247:1465-1468; Raz, E., 1994, Intradermal gene immunization: The possible role of DNA uptake in the induction of cellular immunity to viruses, c. Natl. Acd. Sci. USA 91:9519-9523). Another way to administer DNA vaccines operable herein is called the "gene gun" method, whereby microscopic gold beads coated with the DNA molecules of interest is fired into cells (Tang, D. et al., 1992, Genetic immunization is a simple method for eliciting an immune response, Nature 356:152-154). For general reviews of the methods for DNA vaccines, see Robinson, H. L., 1999, DNA vaccines: basic mechanism and immune responses (Review), Int. J. Mol. Med. 4(5):549-555; Barber, B., 1997, Introduction: Emerging vaccine strategies, Seminars in Immunology 9(5):269-270; and Robinson, H. L. et al., 1997, DNA vaccines, Seminars in Immunology 9(5):271-283.

Attenuation of hEbola Virus or Variants Thereof

The hEbola virus or variants thereof of the invention are optionally genetically engineered to exhibit an attenuated phenotype. In particular, the viruses of the invention exhibit an attenuated phenotype in a subject to which the virus is administered as a vaccine. Attenuation can be achieved by any method known to a skilled artisan. Without being bound by theory, the attenuated phenotype of the viruses of the invention is caused, e.g., by using a virus that naturally does not replicate well in an intended host species, for example, by reduced replication of the viral genome, by reduced ability of the virus to infect a host cell, or by reduced ability of the viral proteins to assemble to an infectious viral particle relative to the wild type species of the virus.

The attenuated phenotypes of hEbola virus or variants thereof are optionally tested by any method known to the artisan. A candidate virus, for example, is optionally tested for its ability to infect a host or for the rate of replication in a cell culture system. In certain embodiments, growth curves at different temperatures are used to test the attenuated phenotype of the virus. For example, an attenuated virus is able to grow at 35° C., but not at 39° C. or 40° C. In certain embodiments, different cell lines are used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In a specific embodiment, the plaque reduction neutralization assay or ELISA is carried out at a low dose. In certain embodiments, the ability of the hEbola virus to elicit pathological symptoms in an animal model is tested. A reduced ability of the virus to elicit pathological symptoms in an animal model system is indicative of its attenuated phenotype. In a specific embodiment, the candidate viruses are tested in a monkey model for nasal infection, indicated by mucus production.

The viruses of the invention are optionally attenuated such that one or more of the functional characteristics of the virus are impaired. In certain embodiments, attenuation is measured in comparison to the wild type species of the virus from which the attenuated virus is derived. In other embodiments, attenuation is determined by comparing the growth of an attenuated virus in different host systems. Thus, for a non-limiting example, hEbola virus or a variant thereof is attenuated when grown in a human host if the growth of the hEbola or variant thereof in the human host is reduced compared to the non-attenuated hEbola or variant thereof.

In certain embodiments, the attenuated virus of the invention is capable of infecting a host, is capable of replicating in a host such that infectious viral particles are produced. In comparison to the wild type species, however, the attenuated species grows to lower titers or grows more slowly. Any technique known to the skilled artisan can be used to determine the growth curve of the attenuated virus and compare it to the growth curve of the wild type virus.

In certain embodiments, the attenuated virus of the invention (e.g., a recombinant or chimeric hEbola) cannot replicate in human cells as well as the wild type virus (e.g., wild type hEbola) does. However, the attenuated virus can replicate well in a cell line that lacks interferon functions, such as Vero cells.

In other embodiments, the attenuated virus of the invention is capable of infecting a host, of replicating in the host, and of causing proteins of the virus of the invention to be inserted into the cytoplasmic membrane, but the attenuated virus does not cause the host to produce new infectious viral particles. In certain embodiments, the attenuated virus infects the host, replicates in the host, and causes viral proteins to be inserted in the cytoplasmic membrane of the host with the same efficiency as the wild type hEbola. In other embodiments, the ability of the attenuated virus to cause viral proteins to be inserted into the cytoplasmic membrane into the host cell is reduced compared to the wild type virus. In certain embodiments, the ability of the attenuated hEbola virus to replicate in the host is reduced compared to the wild type virus. Any technique known to the skilled artisan can be used to determine whether a virus is capable of infecting a mammalian cell, of replicating within the host, and of causing viral proteins to be inserted into the cytoplasmic membrane of the host.

In certain embodiments, the attenuated virus of the invention is capable of infecting a host. In contrast to the wild type hEbola, however, the attenuated hEbola cannot be replicated in the host. In a specific embodiment, the attenuated hEbola virus can infect a host and can cause the host to insert viral proteins in its cytoplasmic membranes, but the attenuated virus is incapable of being replicated in the host. Any method known to the skilled artisan can be used to test whether the attenuated hEbola has infected the host and has caused the host to insert viral proteins in its cytoplasmic membranes.

In certain embodiments, the ability of the attenuated virus to infect a host is reduced compared to the ability of the wild type virus to infect the same host. Any technique known to the skilled artisan can be used to determine whether a virus is capable of infecting a host.

In certain embodiments, mutations (e.g., missense mutations) are introduced into the genome of the virus, for example, into the sequence of SEQ ID NOs: 1 or 10, or to generate a virus with an attenuated phenotype. Mutations (e.g., missense mutations) can be introduced into the structural genes and/or regulatory genes of the hEbola. Mutations are optionally additions, substitutions, deletions, or combinations thereof. Such variant of hEbola can be screened for a predicted functionality, such as infectivity, replication ability, protein synthesis ability, assembling ability, as well as cytopathic effect in cell cultures. In a specific embodiment, the missense mutation is a cold-sensitive mutation. In another embodiment, the missense mutation is a heat-sensitive mutation. In another embodiment, the missense mutation prevents a normal processing or cleavage of the viral proteins.

In other embodiments, deletions are introduced into the genome of the hEbola virus, which result in the attenuation of the virus.

In certain embodiments, attenuation of the virus is achieved by replacing a gene of the wild type virus with a gene of a virus of a different species, of a different subgroup, or of a different variant. In another aspect, attenuation of the virus is achieved by replacing one or more specific domains of a protein of the wild type virus with domains derived from the corresponding protein of a virus of a different species. In certain other embodiments, attenuation of the virus is achieved by deleting one or more specific domains of a protein of the wild type virus.

When a live attenuated vaccine is used, its safety should also be considered. The vaccine preferably does not cause disease. Any techniques known in the art for improving vaccine safety are operable in the present invention. In addition to attenuation techniques, other techniques are optionally be used. One non-limiting example is to use a soluble heterologous gene that cannot be incorporated into the virion membrane. For example, a single copy of the soluble version of a viral transmembrane protein lacking the transmembrane and cytosolic domains thereof is used.

Various assays are optionally used to test the safety of a vaccine. For example, sucrose gradients and neutralization assays are used to test the safety. A sucrose gradient assay is optionally used to determine whether a heterologous protein is inserted in a virion. If the heterologous protein is inserted in the virion, the virion is preferably tested for its ability to cause symptoms in an appropriate animal model since the virus may have acquired new, possibly pathological, properties.

5.4 Adjuvants and Carrier Molecules hEbola-associated antigens are administered with one or more adjuvants. In one embodiment, the hEbola-associated antigen is administered together with a mineral salt adjuvants or mineral salt gel adjuvant. Such mineral salt and mineral salt gel adjuvants include, but are not limited to, aluminum hydroxide (ALHYDROGEL, REHYDRAGEL), aluminum phosphate gel, aluminum hydroxyphosphate (ADJU-PHOS), and calcium phosphate.

In another embodiment, hEbola-associated antigen is administered with an immunostimulatory adjuvant. Such class of adjuvants include, but are not limited to, cytokines (e.g., interleukin-2, interleukin-7, interleukin-12, granulocyte-macrophage colony stimulating factor (GM-CSF), interferon-γ interleukin-1β (IL-1 β), and IL-1 β peptide or Sclavo Peptide), cytokine-containing liposomes, triterpenoid glycosides or saponins (e.g., QuilA and QS-21, also sold under the trademark STIMULON, ISCOPREP), Muramyl Dipeptide (MDP) derivatives, such as N-acetyl-muramyl-L-threonyl-D-isoglutamine (Threonyl-MDP, sold under the trademark TERMURTIDE), GMDP, N-acetyl-nor-muramyl-L-alanyl-D-isoglutamine, N-acetylmuramyl-L-alanyl-D-isoglutaminyl-L-alanine-2-(1'-2'-dipalmitoyl-s-n-glycero-3-hydroxy phosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid. A (3D-MLA sold under the trademark MPL), and polyphosphazenes.

In another embodiment, the adjuvant used is a particular adjuvant, including, but not limited to, emulsions, e.g., Freund's Complete Adjuvant, Freund's Incomplete Adjuvant, squalene or squalane oil-in-water adjuvant formulations, such as SAF and MF59, e.g., prepared with block-copolymers, such as L-121 (polyoxypropylene/polyoxyetheylene) sold under the trademark PLURONIC L-121, Liposomes, Virosomes, cochleates, and immune stimulating complex, which is sold under the trademark ISCOM.

In another embodiment, a microparticular adjuvant is used. Microparticular adjuvants include, but are not limited to, biodegradable and biocompatible polyesters, homo- and copolymers of lactic acid (PLA) and glycolic acid (PGA), poly(lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatitis B surface antigen (HbsAg).

Yet another class of adjuvants that are optionally used include mucosal adjuvants, including but not limited to heat-labile enterotoxin from *Escherichia coli* (LT), cholera holotoxin (CT) and cholera Toxin B Subunit (CTB) from *Vibrio cholerae*, mutant toxins (e.g., LTK63 and LTR72), microparticles, and polymerized liposomes.

In other embodiments, any of the above classes of adjuvants are optionally used in combination with each other or with other adjuvants. For example, non-limiting examples of combination adjuvant preparations used to administer the hEbola-associated antigens of the invention include liposomes containing immunostimulatory protein, cytokines, T-cell and/or B-cell peptides, or microbes with or without entrapped IL-2 or microparticles containing enterotoxin. Other adjuvants known in the art are also included within the scope of the invention (see Vaccine Design: The Subunit and Adjuvant Approach, Chap. 7, Michael F. Powell and Mark J. Newman (eds.), Plenum Press, New York, 1995, which is incorporated herein in its entirety).

The effectiveness of an adjuvant is illustratively determined by measuring the induction of antibodies directed against an immunogenic polypeptide containing a hEbola polypeptide epitope, the antibodies resulting from administration of this polypeptide in vaccines which are also comprised of the various adjuvants.

The polypeptides are optionally formulated into the vaccine as neutral or salt forms. Pharmaceutically acceptable salts include the acid additional salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups are optionally derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention are preferably multivalent or univalent. Multivalent vaccines are made from recombinant viruses that direct the expression of more than one antigen.

Many methods are operable herein to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but is also optionally a non-human animal including but not limited to lower primates, cows, horses, sheep, pigs, fowl (e.g., chickens), goats, cats, dogs, hamsters, mice and rats.

Preparation of Antibodies

Antibodies that specifically recognize a polypeptide of the invention, such as, but not limited to, polypeptides including the sequence of SEQ ID NOs: 2-9, 59, or 11-19 and other polypeptides as described herein, or hEbola epitope or antigen-binding fragments thereof are used in a preferred embodiment for detecting, screening, and isolating the polypeptide of the invention or fragments thereof, or similar sequences that might encode similar enzymes from the other organisms. For example, in one specific embodiment, an antibody which immunospecifically binds hEbola epitope, or a fragment thereof, is used for various in vitro detection assays, including enzyme-linked immunosorbent assays (ELISA), radioimmunoassays, western blot, etc., for the detection of a polypeptide of the invention or, preferably, hEbola, in samples, for example, a biological material, including cells, cell culture media (e.g., bacterial cell culture media, mammalian cell culture media, insect cell culture media, yeast cell culture media, etc.), blood, plasma, serum, tissues, sputum, naseopharyngeal aspirates, etc.

Antibodies specific for a polypeptide of the invention or any epitope of hEbola are optionally generated by any suitable method known in the art. Polyclonal antibodies to an antigen of interest, for example, the hEbola virus from Deposit Accession No. 200706291, or including a nucleotide sequence of SEQ ID NOs: 1 or 10, are optionally produced by various procedures well known in the art. For example, an antigen is optionally administered to various host animals including, but not limited to, rabbits, mice, rats, etc., to induce the production of antisera containing polyclonal antibodies specific for the antigen. Various adjuvants are optionally used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art.

Monoclonal antibodies are optionally prepared using a wide variety of techniques known in the art including the use of hybridoma, recombinant, and phage display technologies, or a combination thereof. In one example, monoclonal antibodies are produced using hybridoma techniques including those known in the art and taught, for example, in Harlow et al., Antibodies: A Laboratory Manual (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice are immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, is optionally generated by inoculating mice intraperitoneally with positive hybridoma clones.

Antibody fragments which recognize specific epitopes are optionally generated by known techniques. For example, Fab and F(ab')$_2$ fragments are illustratively produced by proteolytic cleavage of immunoglobulin molecules, using enzymes such as papain (to produce Fab fragments) or pepsin (to produce F(ab')$_2$ fragments). F(ab')$_2$ fragments preferably contain the complete light chain, and the variable region, the CH1 region and the hinge region of the heavy chain.

The antibodies of the invention or fragments thereof are optionally produced by any method known in the art for the synthesis of antibodies, in particular, by chemical synthesis or preferably, by recombinant expression techniques.

The nucleotide sequence encoding an antibody is obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR are optionally then cloned into replicable cloning vectors using any method known in the art.

Once the nucleotide sequence of the antibody is determined, the nucleotide sequence of the antibody is optionally manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule is optionally produced by recombinant DNA technology using techniques known in the art as discussed in the previous sections. Methods which are known to those skilled in the art are optionally used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody are optionally cloned into such a vector for expression. Thus, prepared expression vector is optionally then introduced into appropriate host cells for the expression of the antibody. Accordingly, the invention includes host cells containing a polynucleotide encoding an antibody specific for the polypeptides of the invention or fragments thereof.

The host cell is optionally co-transfected with two expression vectors of the invention, the first vector encoding a heavy chain derived polypeptide and the second vector encoding a light chain derived polypeptide. The two vectors illustratively contain identical selectable markers which enable equal expression of heavy and light chain polypeptides or different selectable markers to ensure maintenance of both plasmids. Alternatively, a single vector is optionally used which encodes, and is capable of expressing, both heavy and light chain polypeptides. In such situations, the light chain should be placed before the heavy chain to avoid an excess of toxic free heavy chain (Proudfoot, Nature, 322:52, 1986; and Kohler, Proc. Natl. Acad. Sci. USA, 77:2 197, 1980). The coding sequences for the heavy and light chains optionally include cDNA or genomic DNA.

In another embodiment, antibodies are generated using various phage display methods known in the art. In phage display methods, functional antibody domains are displayed on the surface of phage particles which carry the polynucleotide sequences encoding them. In a particular embodiment, such phage is utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest is optionally selected or identified with antigen, e.g., using labeled antigen or antigen bound or captured to a solid surface or bead. Phages used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage is optionally isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments are optionally employed using methods known in the art such as those disclosed in PCT publication. WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques operable to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, or otherwise known in the art, it is then optionally purified by any method known in the art for purification of an immunoglobulin molecule, for example, by chromatography (e.g., ion exchange, affinity, particularly by affinity for the specific antigen after Protein A or Protein G purification, and sizing column chromatography), centrifligation, differential solubility, or by any other standard technique(s) for the purification of proteins. Further, the antibodies of the present invention or fragments thereof are optionally fused to heterologous polypeptide sequences described herein or otherwise known in the art to facilitate purification. Illustrative examples include 6× His tag, FLAG tag, biotin, avidin, or other system.

For some uses, including in vivo use of antibodies in humans and in vitro detection assays, it is preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., Nature, 332:323, 1988, which are incorporated herein by reference in their entireties. Antibodies are humanized using a variety of techniques known in the art including, for example, CDR-grafting (EP 239,400; PCT publication WO 91/09967; U.S. Pat. Nos. 5,225,539; 5,530,101 and 5,585, 089), veneering or resurfacing (EP 592,106; EP 519,596; Padlan, Molecular Immunology, 28(4/5):489-498, 1991; Studnicka et al., Protein Engineering, 7(6):805-814, 1994; Roguska et al., Proc Natl. Acad. Sci. USA, 91:969-973, 1994), and chain shuffling (U.S. Pat. No. 5,565,332), all of which are hereby incorporated by reference in their entireties.

Completely human antibodies are particularly desirable for therapeutic treatment of human patients. Human antibodies are made by a variety of methods known in the art illustratively including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies are also illustratively produced using transgenic mice which are incapable of expressing functional endogenous immunoglobulins, but which can express human immunoglobulin genes. For an overview of this technology for producing human antibodies, see Lonberg and Huszar, Int. Rev. Immunol., 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.), Medarex (NJ) and Genpharm (San Jose, Calif.) can be engaged to provide human antibodies directed against a selected antigen using technology similar to that described above.

Completely human antibodies which recognize a selected epitope are optionally generated using a technique referred to as "guided selection." In this approach a selected non-human monoclonal antibody, e.g., a mouse antibody, is used to guide the selection of a completely human antibody recognizing the same epitope. (Jespers et al., Bio/technology, 12:899-903, 1988).

Antibodies fused or conjugated to heterologous polypeptides are optionally used in in vitro immunoassays and in purification methods (e.g., affinity chromatography) known in the art. See e.g., PCT publication No. WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties.

Antibodies may also be illustratively attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

Pharmaceutical Compositions and Kits

The present invention encompasses pharmaceutical compositions including antiviral agents of the present invention. In a specific embodiment, the antiviral agent is preferably an antibody which immunospecifically binds and neutralizes the hEbola virus or variants thereof, or any proteins derived therefrom. In another specific embodiment, the antiviral agent is a polypeptide or nucleic acid molecule of the invention. The pharmaceutical compositions have utility as an antiviral prophylactic agent are illustratively administered to a subject where the subject has been exposed or is expected to be exposed to a virus.

Various delivery systems are known and operable to administer the pharmaceutical composition of the invention, illustratively, encapsulation in liposomes, microparticles, microcapsules, recombinant cells capable of expressing the mutant viruses, and receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and optionally administered together with other biologically active agents. Administration is systemic or local. In a preferred embodiment, it is desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it is desirable to administer the pharmaceutical compositions of the invention locally to the area in need of treatment. This administration may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, the implant being of a porous, non-porous, or gelatinous material, including membranes, such as sialastic membranes, or fibers. In one embodiment, administration can be by direct injection at the site (or former site) infected tissues.

In another embodiment, the pharmaceutical composition is delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition is delivered in a controlled release system. In one embodiment, a pump is used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials are used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system is placed in proximity of the composition's target, i.e., the lung, thus, requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)) the contents of which are incorporated herein by reference.

The pharmaceutical compositions of the present invention illustratively include a therapeutically effective amount of a live attenuated, inactivated or killed West African hEbola virus, or recombinant or chimeric hEbola virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers are illustratively sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions are optionally employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, also contains wetting or emulsifying agents, or pH buffering agents. These compositions optionally take the form of solutions, suspensions, emulsion, tablets, pills, capsules, powders, sustained release formulations and the like. The composition is optionally formulated as a suppository, with traditional binders and carriers such as triglycerides. Oral formulation illustratively includes standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. The composition also includes an optional solubilizing agent and a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline is optionally provided so that the ingredients may be mixed prior to administration.

The pharmaceutical compositions of the invention are illustratively formulated as neutral or salt forms. Pharmaceutically acceptable salts illustratively include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays are optionally employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20 to 500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit including one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration. In a preferred embodiment, the kit contains an antiviral agent of the invention, e.g., an antibody specific for the polypeptides encoded by a nucleotide sequence of SEQ ID NOs: 1 or 10, or as shown in SEQ ID NOs: 2-9, 59, or 11-19, or any hEbola epitope, or a polypeptide or protein of the present invention, or a nucleic acid molecule of the invention, alone or in combination with adjuvants, antivirals, antibiotics, analgesic, bronchodilators, or other pharmaceutically acceptable excipients.

The present invention further encompasses kits including a container containing a pharmaceutical composition of the present invention and instructions for use.

Detection Assays

The present invention provides a method for detecting an antibody, which immunospecifically binds to the hEbola virus, in a biological sample, including for example blood, serum, plasma, saliva, urine, feces, etc., from a patient suffering from hEbola infection, and/or hemorrhagic fever. In a specific embodiment, the method including contacting the sample with the hEbola virus, for example, of Deposit Accession No. 200706291, or having a genomic nucleic acid sequence of SEQ ID NOs: 1 or 10, directly immobilized on a substrate and detecting the virus-bound antibody directly or indirectly by a labeled heterologous anti-isotype antibody. In another specific embodiment, the sample is contacted with a host cell which is infected by the hEbola virus, for example, of Deposit Accession No. 200706291, or having a genomic nucleic acid sequence of SEQ ID NOs: 1 or 10, and the bound antibody is optionally detected by immunofluorescent assay.

An exemplary method for detecting the presence or absence of a polypeptide or nucleic acid of the invention in a biological sample involves obtaining a biological sample from various sources and contacting the sample with a compound or an agent capable of detecting an epitope or nucleic acid (e.g., mRNA, genomic DNA) of the hEbola virus such that the presence of the hEbola virus is detected in the sample. A preferred agent for detecting hEbola mRNA or genomic RNA of the invention is a labeled nucleic acid probe capable of hybridizing to mRNA or genomic RNA encoding a polypeptide of the invention. The nucleic acid probe is, for example, a nucleic acid molecule including the nucleotide sequence of SEQ ID NOs: 1 or 10, a complement thereof, or a portion thereof, such as an oligonucleotide of at least 15, 20, 25, 30, 50, 100, 250, 500, 750, 1000 or more contiguous nucleotides in length and sufficient to specifically hybridize under stringent conditions to a hEbola mRNA or genomic RNA.

As used herein, the term "stringent conditions" describes conditions for hybridization and washing under which nucleotide sequences having at least 30%, 35%, 40%, 45%, 50%, 55%, 60%, 65%, 70%, 75%, 80%, 85%, 90%, or 95% identity to each other typically remain hybridized to each other. Such hybridization conditions are described in, for example but not limited to, Current Protocols in Molecular Biology, John Wiley & Sons, N.Y. (1989), 6.3.1 6.3.6.; Basic Methods in Molecular Biology, Elsevier Science Publishing Co., Inc., N.Y. (1986), pp. 75 78, and 84 87; and Molecular Cloning, Cold Spring Harbor Laboratory, N.Y. (1982), pp. 387 389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at 50 to 65° C.

A nucleic acid probe, polynucleotide, oligonucleotide, or other nucleic acid is preferably purified. An "isolated" or "purified" nucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1%, (by dry weight) of contaminating material. When nucleotide/oligonucleotide is produced by chemical synthesis, it is preferably substantially free of chemical precursors or other chemicals, i.e., it is separated from chemical precursors or other chemicals which are involved in the synthesis of the protein. Accordingly, such preparations of the nucleotide/oligonucleotide have less than about 30%, 20%, 10%, or 5% (by dry weight) of chemical precursors or compounds other than the nucleotide/oligonucleotide of interest. In a preferred embodiment of the present invention, the nucleotide/oligonucleotide is isolated or purified.

In another preferred specific embodiment, the presence of hEbola virus is detected in the sample by a reverse transcription polymerase chain reaction (RT-PCR) using the primers that are constructed based on a partial nucleotide sequence of the genome of hEbola virus, for example, that of Deposit Accession No. 200706291, or having a genomic nucleic acid sequence of SEQ ID NOs: 1 or 10. In a non-limiting specific embodiment, preferred primers to be used in a RT-PCR method are the primers are described in detail herein.

In more preferred specific embodiment, the present invention provides a real-time quantitative PCR assay to detect the presence of hEbola virus in a biological sample by subjecting the cDNA obtained by reverse transcription of the extracted total RNA from the sample to PCR reactions using the specific primers described in detail herein, and a fluorescence dye, such as SYBR® Green I, which fluoresces when bound nonspecifically to double-stranded DNA. The fluorescence signals from these reactions are captured at the end of extension steps as PCR product is generated over a range of the thermal cycles, thereby allowing the quantitative determination of the viral load in the sample based on an amplification plot.

A preferred agent for detecting hEbola is an antibody that specifically binds a polypeptide of the invention or any hEbola epitope, preferably an antibody with a detectable label. Antibodies are illustratively polyclonal, or more preferably, monoclonal. An intact antibody, or a fragment thereof (e.g., Fab or $F(ab')_2$) is operable herein.

The term "labeled", with regard to the probe or antibody, is intended to encompass direct labeling of the probe or antibody by coupling (i.e., physically linking) a detectable substance to the probe or antibody, optionally via a linker, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it is detectable with fluorescently labeled streptavidin. The detection method of the invention is optionally used to detect mRNA, protein (or any epitope), or genomic RNA in a sample in vitro as well as in vivo. Exemplary in vitro techniques for detection of mRNA include northern hybridizations, in situ hybridizations, RT-PCR, and RNase protection. In vitro techniques for detection of an epitope of hEbola illustratively include enzyme linked immunosorbent assays (ELISAs), western blots, immunoprecipitations and immunofluorescence. In vitro techniques for detection of genomic RNA include northern hybridizations, RT-PCT, and RNase protection. Furthermore, in vivo techniques for detection of hEbola include introducing into a subject organism a labeled antibody directed against the polypeptide. In one embodiment, the antibody is labeled with a radioactive marker whose presence and location in the subject organism is detected by standard imaging techniques, including autoradiography.

In a specific embodiment, the methods further involve obtaining a control sample from a control subject, contacting the control sample with a compound or agent capable of detecting hEbola, e.g., a polypeptide of the invention or mRNA or genomic RNA encoding a polypeptide of the invention, such that the presence of hEbola or the polypeptide or mRNA or genomic RNA encoding the polypeptide is detected in the sample, and comparing the absence of hEbola or the polypeptide or mRNA or genomic RNA encoding the polypeptide in the control sample with the presence of hEbola, or the polypeptide or mRNA or genomic DNA encoding the polypeptide in the test sample.

The invention also encompasses kits for detecting the presence of hEbola or a polypeptide or nucleic acid of the invention in a test sample. The kit illustratively includes a labeled compound or agent capable of detecting hEbola or the polypeptide or a nucleic acid molecule encoding the polypeptide in a test sample and, in certain embodiments, a means for determining the amount of the polypeptide or mRNA in the sample (e.g., an antibody which binds the polypeptide or an oligonucleotide probe which binds to DNA or mRNA encoding the polypeptide). Kits optionally include instructions for use.

For antibody-based kits, the kit illustratively includes: (1) a first antibody (e.g., attached to a solid support) which binds to a polypeptide of the invention or hEbola epitope; and, optionally, (2) a second, different antibody which binds to either the polypeptide or the first antibody and is preferably conjugated to a detectable agent.

For oligonucleotide-based kits, the kit illustratively includes: (1) an oligonucleotide, e.g., a detectably labeled oligonucleotide, which hybridizes to a nucleic acid sequence encoding a polypeptide of the invention or to a sequence within the hEbola genome; or (2) a pair of primers useful for amplifying a nucleic acid molecule containing an hEbola sequence. The kit optionally includes a buffering agent, a preservative, or a protein stabilizing agent. The kit optionally includes components necessary for detecting the detectable agent (e.g., an enzyme or a substrate). The kit optionally contains a control sample or a series of control samples which can be assayed and compared to the test sample contained. Each component of the kit is usually enclosed within an individual container and all of the various containers are within a single package along with instructions for use.

Screening Assays to Identify Antiviral Agents

The invention provides methods for the identification of a compound that inhibits the ability of hEbola virus to infect a host or a host cell. In certain embodiments, the invention provides methods for the identification of a compound that reduces the ability of hEbola virus to replicate in a host or a host cell. Any technique well known to the skilled artisan is illustratively used to screen for a compound useful to abolish or reduce the ability of hEbola virus to infect a host and/or to replicate in a host or a host cell.

In certain embodiments, the invention provides methods for the identification of a compound that inhibits the ability of hEbola virus to replicate in a mammal or a mammalian cell. More specifically, the invention provides methods for the identification of a compound that inhibits the ability of hEbola virus to infect a mammal or a mammalian cell. In certain embodiments, the invention provides methods for the identification of a compound that inhibits the ability of hEbola virus to replicate in a mammalian cell. In a specific embodiment, the mammalian cell is a human cell. 102141 In another embodiment, a cell is contacted with a test compound and infected with the hEbola virus. In certain embodiments, a control culture is infected with the hEbola virus in the absence of a test compound. The cell is optionally contacted with a test compound before, concurrently with, or subsequent to the infection with the hEbola virus. In a specific embodiment, the cell is a mammalian cell. In an even more specific embodiment, the cell is a human cell. In certain embodiments, the cell is incubated with the test compound for at least 1 minute, at least 5 minutes, at least 15 minutes, at least 30 minutes, at least 1 hour, at least 2 hours, at least 5 hours, at least 12 hours, or at least 1 day. The titer of the virus is optionally measured at any time during the assay. In certain embodiments, a time course of viral growth in the culture is determined. If the viral growth is inhibited or reduced in the presence of the test compound, the test compound is identified as being effective in inhibiting or reducing the growth or infection of the hEbola virus. In a specific embodiment, the compound that inhibits or reduces the growth of the hEbola virus is tested for its ability to inhibit or reduce the growth rate of other viruses to test its specificity for the hEbola virus.

In one embodiment, a test compound is administered to a model animal and the model animal is infected with the hEbola virus. In certain embodiments, a control model animal is infected with the hEbola virus without the administration of a test compound. The test compound is optionally administered before, concurrently with, or subsequent to the infection with the hEbola virus. In a specific embodiment, the model animal is a mammal. In an even more specific embodiment, the model animal is, but is not limited to, a cotton rat, a mouse, or a monkey. The titer of the virus in the model animal is optionally measured at any time during the assay. In certain embodiments, a time course of viral growth in the culture is determined. If the viral growth is inhibited or reduced in the presence of the test compound, the test compound is identified as being effective in inhibiting or reducing the growth or infection of the hEbola virus. In a specific embodiment, the compound that inhibits or reduces the growth of the hEbola in the model animal is tested for its ability to inhibit or reduce the growth rate of other viruses to test its specificity for the hEbola virus.

According to the method of the invention, a human or an animal is optionally treated for for EboBun or EboIC, other viral infection or bacterial infection by administering an effective amount of an inventive therapeutic composition. Preferably, a vaccine is administered prophylactically. An "effective amount" is an amount that will induce an immune response in a subject. Illustratively, an effective amount of the compositions of this invention ranges from nanogram/kg to milligram/kg amounts for young children and adults. Equivalent dosages for lighter or heavier body weights can readily be determined. The dose should be adjusted to suit the individual to whom the composition is administered and will vary with age, weight and metabolism of the individual. The exact amount of the composition required will vary from subject to subject, depending on the species, age, weight and general condition of the subject, the particular peptide or polypeptide used, its mode of administration and the like. An appropriate amount can be determined by one of ordinary skill in the art using only routine experimentation given the teachings herein. One skilled in the art will realize that dosages are best optimized by the practicing physician or veterinarian and methods for determining dose amounts and regimens and preparing dosage forms are described, for example, in Remington's Pharmaceutical Sciences, (Martin, E. W., ed., latest edition), Mack Publishing Co., Easton, Pa. Preferably, a single administration is operable to induce an immune response.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Embodiments of inventive compositions and methods are illustrated in the following detailed examples. These examples are provided for illustrative purposes and are not considered limitations on the scope of inventive compositions and methods.

EXAMPLES

Example 1

Newly Discovered Ebola Virus Associated with Hemorrhagic Fever Outbreak in Bundibugyo, Uganda In late November 2007 HF cases were reported in the townships of Bundibugyo and Kikyo in Bundibugyo District, Western Uganda (FIG. 1A). These samples were assayed as described by Towner, J S, et al., PLoS Pathog, 2008 November; 4(11): e1000212, the contents of which are incorporated herein by reference for methods, results, reagents, and all other aspects of the publication. A total of 29 blood samples were initially collected from suspect cases and showed evidence of acute ebolavirus infection in eight specimens using a broadly reactive ebolavirus antigen capture assay known to cross-react with the different ebolavirus species[7] and an IgM capture assay based on Zaire ebolavirus reagents (Table 1). These specimens were negative when initially tested with highly sensitive real-time RT-PCR assays specific for all known Zaire and Sudan ebolaviruses and marburgviruses. However, further evidence of acute ebolavirus infection was obtained using a traditionally less sensitive (relative to the real-time RT-PCR assays) but more broadly reactive filovirus L gene-specific RT-PCR assay (1 specimen) (Table 1). Sequence analysis of the PCR fragment (400 bp of the virus L gene) revealed the reason for the initial failure of the real-time RT-PCR assays, as the sequence was distinct from that of the 4 known species of ebolavirus, although distantly related to Cote d'Ivoire ebolavirus. In total, 9 of 29 specimens showed evidence of ebolavirus infection, and all tests were negative for marburgvirus (data not shown).

Approximately 70% of the virus genome was rapidly sequenced from total RNA extracted from a patient serum (#200706291) using a newly established metagenomics pyrosequencing method (454 Life Sciences) which involves successive rounds of random DNA amplification[8]. Using the newly derived draft sequence, a real-time RT-PCR assay specific for the NP gene of this virus was quickly developed and evaluated. The assay was shown to have excellent sensitivity (Table 1), finding positive all the initial six samples that tested positive by either virus antigen capture (five specimens) or virus isolation assays (four specimens). The antigen-capture, IgM, IgG and newly designed real-time PCR assays were quickly transferred to the Uganda Virus Research Institute during the course of the outbreak to facilitate rapid identification and isolation of Ebola cases in the affected area for efficient control of the outbreak. The outbreak continued through late December 2007, and resulted in 149 suspected cases and 37 deaths[9].

Table 1. Ebolavirus diagnostic results of initial 29 specimens obtained from Bundibugyo District with numerical specimen numbers assigned. RT-PCR refers to results obtained from conventional PCR using the broadly reactive Filo A/B primers[13]. Ag, IgM, and IgG refer to results from ELISA-based assays[10, 11] with Zaire ebolavirus reagents while virus isolation refers to culture attempts on Vero E6 cells[12]. Q-RT-PCR refers to results obtained using the optimized Bundibugyo ebolavirus specific real-time RT-PCR assay with cycle threshold (Ct) values of positive (Pos) samples indicated in the far right column. *Specimen #200706291 is the clinical sample from which prototype isolate #811250 was obtained.

TABLE 1

| Sample No | RT-PCR | Ag | IgM | IgG | Virus Isolation | Q-RT-PCR | Ct |
|---|---|---|---|---|---|---|---|
| 200706288 | neg | neg | neg | neg | neg | neg | 40 |
| 200706289 | neg | neg | neg | neg | neg | neg | 40 |
| 200706290 | neg | neg | neg | neg | neg | neg | 40 |
| 200706291* | Pos | Pos | neg | neg | Pos | Pos | 23.64 |
| 200706292 | neg | neg | neg | neg | neg | neg | 40 |
| 200706293 | neg | neg | neg | rneg | neg | neg | 40 |
| 200706294 | neg | neg | neg | neg | neg | neg | 40 |
| 200706295 | neg | neg | neg | neg | neg | neg | 40 |
| 200706296 | neg | neg | Pos | Pos | neg | neg | 40 |
| 200706297 | neg | neg | Pos | Pos | neg | neg | 40 |
| 200706298 | neg | Pos | Pos | Pos | neg | Pos | 34.83 |
| 200706299 | neg | neg | Pos | Pos | neg | neg | 40 |
| 200706300 | neg | neg | neg | neg | neg | neg | 40 |
| 200706301 | neg | neg | neg | neg | neg | neg | 40 |
| 200706302 | neg | Pos | Pos | neg | neg | Pos | 35.01 |
| 200706303 | neg | neg | neg | neg | neg | neg | 40 |
| 200706304 | neg | neg | neg | neg | Pos | Pos | 38.18 |
| 200706305 | neg | neg | neg | neg | neg | neg | 40 |
| 200706306 | neg | neg | neg | neg | neg | neg | 40 |
| 200706307 | neg | neg | neg | neg | neg | neg | 40 |
| 200706320 | ND | Pos | neg | neg | Pos | Pos | 30.24 |
| 200706321 | ND | neg | neg | neg | neg | neg | 40 |
| 200706322 | ND | neg | neg | neg | neg | neg | 40 |
| 200706323 | ND | neg | neg | neg | neg | neg | 40 |
| 200706324 | ND | neg | neg | neg | neg | neg | 40 |
| 200706325 | ND | neg | neg | neg | neg | neg | 40 |
| 200706326 | ND | neg | neg | neg | neg | neg | 40 |

TABLE 1-continued

| Sample No | RT-PCR | Ag | IgM | IgG | Virus Isolation | Q-RT-PCR | Ct |
|---|---|---|---|---|---|---|---|
| 200706327 | ND | Pos | neg | neg | Pos | Pos | 34.41 |
| 200706328 | ND | neg | neg | neg | neg | neg | 40 |

The entire genome sequence of this virus was completed using a classic primer walking sequencing approach on RNA. The complete genome of the Eb *ebolavirus* was not available, so it too was derived by a similar combination of random primed pyrosequencing and primer walking approaches. Acquisition of these sequences allowed for the first time the phylogenetic analysis of the complete genomes of representatives of all known species of Ebola and Marburg viruses. The analysis revealed that the newly discovered virus differed from the four existing *ebolavirus* species (FIG. 1), with approximately 32% nucleotide difference from even the closest relative, EboIC (Table 2). Similar complete genome divergence (35-45%) is seen between the previously characterized *ebolavirus* species.

Table 2. Identity matrix based on comparisons of full-length genome sequences of Zaire *ebolaviruses* 1976 (Genbank accession number NC_002549) and 1995 (Genbank accession number AY354458), Sudan *ebolavirus* 2000 (Genbank accession number NC_006432), Cote d'Ivoire *ebolavirus* 1994 (SEQ ID NO: 10), Reston *ebolavirus* 1989 (Genbank accession number NC_004161), and *Bundibugyo ebolavirus* 2007 (SEQ ID NO: 1).

TABLE 2

| | Zaire '95 | Sudan '00 | EboIC '94 | EboBun '07 | Reston '89 |
|---|---|---|---|---|---|
| Zaire '76 | .988 | .577 | .630 | .632 | .581 |
| Zaire '95 | | .577 | .631 | .633 | .581 |
| Sudan '00 | | | .577 | .577 | .609 |
| EboIC '94 | | | | .683 | .575 |
| EboBun '07 | | | | | .576 |

The material and information obtained from the discovery of the new unique virus EboBun and the realization that together with EboIC these viruses represent a clade of Bundibungyo-Ivory Coast Ebola virus species is valuable, and makes possible the development of clinical, diagnostic and research tools directed to human hEbola infection.

Material and Methods

*Ebolavirus* detection and virus isolation. Several diagnostic techniques were used for each sample: (i) antigen capture, IgG, and IgM assays were performed as previously described[11] (ii) virus isolation attempts were performed on Vero E6 cells[12] and monitored for 14 days; (iii) RNA was extracted and tested for Zaire[16] and Sudan *ebolavirus* and *marburgvirus*[4] using real-time quantitative RT-PCR assays designed to detect all known species of each respective virus species the primers/probe for the Sudan *ebolavirus* assay were EboSudBMG 1(+) 5'-GCC ATG GTT TCA GGT TTG AG-3' (SEQ ID NO: 21), EboSudBMG 1(−) 5'-GGT IAC ATT GGG CAA CAA TTC A-3' (SEQ ID NO: 22) and Ebola Sudan BMG Probe 5'FAM-AC GGT GCA CAT TCT CCT TTT CTC GGA-BHQ1 (SEQ ID NO: 23)]; (iv) the conventional RT-PCR was performed with the filo A/B primer set as previously described[16] using Superscript III (Invitrogen) according to the manufacturer's instructions. The specimen 200706291 was selected as the reference sample for further sequence analysis.

Genome sequencing. Pyrosequencing was carried out utilizing the approach developed by 454 Life Sciences, and the method described by Cox-Foster et al.[8] Subsequent virus whole genome primer walking was performed as previously described[17] but using the primers specific for *Bundibugyo ebolavirus* RT-PCR amplification. In total, the entire virus genome was amplified in six overlapping RT-PCR fragments (all primers listed 5' to 3'): fragment A (predicted size 2.7 kb) was amplified using forward-GTGAGACAAAGAATCAT-TCCTG (SEQ ID NO: 24) with reverse-CATCAATT-GCTCAGAGATCCACC (SEQ ID NO: 25); fragment B (predicted size 3.0 kb) was amplified using forward-CCAACAACACTGCATGTAAGT (SEQ ID NO: 26) with reverse-AGGTCGCGTTAATCTTCATC (SEQ ID NO: 27); fragment C (predicted size 3.5 kb) was amplified using forward-GATGGTTGAGTTACTTTCCGG (SEQ ID NO: 28) with reverse-GTCTTGAGTCATCAATGCCC (SEQ ID NO: 29); fragment D (predicted size 3.1 kb) was amplified using forward-CCACCAGCACCAAAGGAC (SEQ ID NO: 30) with reverse-CTATCGGCAATGTAACTATTGG (SEQ ID NO: 31); fragment E (predicted size 3.4 kb) was amplified using forward-GCCGTTGTAGAGGACACAC (SEQ ID NO: 32) with reverse-CACATTAAATTGT-TCTAACATGCAAG (SEQ ID NO: 33) and fragment F (predicted size 3.5 kb) was amplified using forward-CCTAGGTTATTTAGAAGGGACTA (SEQ ID NO: 34) with reverse-GGT AGA TGT ATT GAC AGC AAT ATC (SEQ ID NO: 35).

The exact 5' and 3' ends of *Bundibugyo ebolavirus* were determined by 3' RACE from virus RNA extracted from virus infected Vero E6 cell monolayers using TriPure isolation reagent. RNAs were then polyadenylated in vitro using A-Plus poly(A) polymerase tailing kit (Epicenter Biotechnologies) following the manufacturer's instructions and then purified using an RNeasy kit (Qiagen) following standard protocols. Ten microliters of in vitro polyadenylated RNA were added as template in RT-PCR reactions, using SuperScript III One-Step RT-PCR system with Platinum Taq High Fidelity (Invitrogen) following the manufacturer's protocol. Two parallel RT-PCR reactions using the oligo(dT)-containing 3'RACE-AP primer (Invitrogen) mixed with 1 of 2 viral specific primers, Ebo-U 692(−) ACAAAAAGCTATCTG-CACTAT (SEQ ID NO: 36) and Ebo-U18269(+) CTCA-GAAGCAAAATTAATGG (SEQ ID NO: 37), generated ~700 nt long fragments containing the 3' ends of either genomic and antigenomic RNAs. The resulting RT-PCR products were analyzed by agarose electrophoresis, and DNA bands of the correct sizes were purified using QIAquick Gel Extraction Kit (Qiagen) and sequenced using standard protocols (ABI).

The nucleotide sequence of the Côte d'Ivoire *ebolavirus* (EboIC) isolate RNA was initially determined using the exact same pyrosequencing strategy as that used for *Bundibugyo ebolavirus* described above. This method generated sequence for approximately 70% of the entire genome. This draft sequence was then used to design a whole genome primer walking strategy for filling any gaps and confirming the initial sequence. The following Côte d'Ivoire *ebolavirus*-specific primers were used to generate RT-PCR fragments, designated A-F, as follows: Fragment A (predicted size 3.0 kb) was amplified using forward-GTGTGCGAATAACTAT-GAGGAAG (SEQ ID NO: 38) and reverse-GTCTGTG-CAATGTTGATGAAGG (SEQ ID NO: 39); Fragment B (predicted size 3.2 kb) was amplified using forward-CAT-GAAAACCACACTCAACAAC (SEQ ID NO: 40) and reverse-GTTGCCTTAATCTTCATCAAGTTC (SEQ ID NO: 41); Fragment C (predicted size 3.0 kb) was amplified using forward-GGCTATAATGAATTTCCTCCAG (SEQ ID NO: 42) and reverse-CAAGTGTATTTGTGGTCCTAGC (SEQ ID NO: 43); fragment D (predicted size 3.5 kb) was amplified using forward-GCTGGAATAGGAATCACAGG (SEQ ID NO: 44) and reverse-CGGTAGTCTACAGT-TCTTTAG (SEQ ID NO: 45); fragment E (predicted size 4.0 kb) was amplified using forward-GACAAAGAGATTA-GATTAGCTATAG (SEQ ID NO: 46) and reverse-GTAAT-GAGAAGGTGTCATTTGG (SEQ ID NO: 47); fragment F (predicted size 2.9 kb) was amplified using forward-CAC-GACTTAGTTGGACAATTGG (SEQ ID NO: 48) and reverse-CAGACACTAATTAGATCTGGAAG (SEQ ID NO: 49); fragment G (predicted size 1.3 kb) was amplified using forward-CGGACACACAAAAAGAAWRAA (SEQ ID NO: 50) and reverse-CGTTCTTGACCTTAGCAGTTC (SEQ ID NO: 51); and fragment H (predicted size 2.5 kb) was amplified using forward-GCACTATAAGCTCGAT-GAAGTC (SEQ ID NO: 52) and reverse-TGGACACA-CAAAAARGARAA (SEQ ID NO: 53). A gap in the sequence contig was located between fragments C and D and this was resolved using the following primers to generate a predicted fragment of 1.5 kb: forward-CTGAGAG-GATCCAGAAGAAAG (SEQ ID NO: 54) and reverse-GTGTAAGCGTTGATATACCTCC (SEQ ID NO: 55). The terminal ~20 nucleotides of the sequence were not experimentally determined but were inferred by comparing with the other known Ebola genome sequences.

*Bundibugyo ebolavirus* real-time RT-PCR assay. The primers and probe used in the *Bundibugyo ebolavirus* specific Q-RT-PCR assay were as follows: EboU965(+): 5'-GA-GAAAAGGCCTGTCTGGAGAA-3' (SEQ ID NO: 56), EboU1039(−): 5'-TCGGGTATTGAATCAGACCTTGTT-3' (SEQ ID NO: 57) and EboU989 Prb: 5'Fam-TTCAACGA-CAAATCCAAGTGCACGCA-3'BHQ1 (SEQ ID NO 58). Q-RT-PCR reactions were set up using Superscript III One-Step Q-RT-PCR (Invitrogen) according to the manufacturer's instructions and run for 40 cycles with a 58° C. annealing temperature.

Phylogenetic analysis. Modeltest 3.7[18] was used to examine 56 models of nucleotide substitution to determine the model most appropriate for the data. The General Time Reversible model incorporating invariant sites and a gamma distribution (GTR+I+G) was selected using the Akaike Information Criterion (AIC). Nucleotide frequencies were A=0.3278, C=0.2101, G=0.1832, T=0.2789, the proportion of invariant sites=0.1412, and the gamma shape parameter=1.0593. A maximum likelihood analysis was subsequently performed in PAUP*4.0b10[19] using the GTR+I+G model parameters. Bootstrap support values were used to assess topological support and were calculated based on 1,000 pseudoreplicates[20].

In addition, a Bayesian phylogenetic analysis was conducted in MrBayes 3.2[21] using the GTR+I+G model of nucleotide substitution. Two simultaneous analyses, each with four Markov chains, were run for 5,000,000 generations sampling every 100 generations. Prior to termination of the run, the AWTY module was used to assess Markov Chain Monte Carlo convergence to ensure that the length of the analysis was sufficient[22]. Trees generated before the stabilization of the likelihood scores were discarded (burn in=40), and the remaining trees were used to construct a consensus tree. Nodal support was assessed by posterior probability values (≥95=statistical support).

Example 2

Immunization Against EboBun:

To determine the capability of immunogens to elicit an immune response in non-human primates (NHP), 12 cynomolgus macaques, of which 10 are immunized with VSVΔG/EboBunGP either orally (OR; n=4), intranasally (IN; n=4) or intramuscularly (IM; n=2) in accordance with all animal control and safety guidelines and essentially as described by Qiu, X, et al., PLoS ONE. 2009; 4(5): e5547. The remaining 2 control animals are vaccinated intramuscularly with VSVΔG/MARVGP. VSVΔG/MARVGP does not provide heterologous protection against EboBun, therefore these NHPs succumb to EboBun infection. Animals are acclimatized for 14 days prior to infection. Animals are fed and monitored twice daily (pre- and post-infection) and fed commercial monkey chow, treats and fruit. Husbandry enrichment consists of commercial toys and visual stimulation.

The recombinant VSVΔG/EboBun vaccines are synthesized expressing the EboBun glycoprotein (GP) (SEQ ID NO: 9), soluble glycoprotein (sGP) (SEQ ID NO: 4), or nucleoprotein (NP) (SEQ ID NO: 3). Control VSVΔG/MARVGP vaccines represent the analogous proteins from Lake victoria *marburgvirus* (MARV) (strain Musoke). The following results for GP are similar for sGP and NP. Vaccines are generated using VSV (Indiana serotype) as described previously. Garbutt, M, et al., *J Virol*, 2004; 78(10):5458-5465; Schnell, M J, et al., *PNAS USA*, 1996; 93(21):11359-11365. EboBun challenge virus is passaged in Vero E6 cells prior to challenge, as described previously Jones, S M, et al., *Nat Med*, 2005; 11(7):786-790; Jahrling, P B, et al., *J Infect Dis*, 1999; 179(Suppl 1):S224-34. An EboBun immunogen peptide pool consisting of 15 mers with 11 amino acid overlaps (Sigma-Genosys) spanning the entire sequence of the EboBun immunogens and strain Mayinga 1976 GP are used.

Twelve filovirus naïve cynomolgus monkeys randomized into four groups receive 2 ml of 1×10⁷ PFU/ml of vaccine in Dulbecco's modified Eagle's medium (DMEM). Animals in the three experimental groups are vaccinated with either: 1) 2 ml orally (OR) (n=4); 2) 1 ml dripped into each nostril, intranasally (IN) (n=4); or 3) 1 ml each into two sites intramuscularly (IM) (n=2). The two controls are injected intramuscularly with 2 ml of 1×10⁷ PFU/ml of VSVΔG/MARVGP. All animals are challenged intramuscularly 28 days later with 1,000 PFU of EboBun.

Routine examination is conducted on 0, 2, 4, 6, 10, 14 and 21 days post-vaccination, then 0, 3, 6, 10, 14, 19, 26 days, 6 and 9 months after the EboBun challenge. For the examinations animals are anaesthetized by intramuscular injection with 10 mg/kg of ketaset (Ayerst). Examinations include haematological analysis, monitoring temperature (rectal), respiration rate, lymph nodes, weight, hydration, discharges and mucous membranes. Also, swabs (throat, oral, nasal, rectal, vaginal) and blood samples are collected (4 ml from femoral vein, 1 ml in EDTA vacutainer tube; 3 ml in serum separator vacutainer tube). Cynomolgus monkey PBMCs are isolated using BD CPT sodium citrate Vacutainers (Becton Dickinson) as per manufacturer's protocol.

All VSVΔG/EboBunGP immunized animals are protected from high dose challenge. These animals show no evidence of clinical illness after vaccination or EboBun challenge. Both control animals demonstrate typical symptoms associated with EboBun HF including fever, macular rashes, lethargy, and unresponsiveness. Continued infection requires euthanization. Hematology analyses at each examination date demonstrate increases in the platelet-crit in the OR and IN groups post-challenge, however, no significant changes are observed in any NHPs post-immunization or in the VSVΔG/EboBunGP immunized NHPs post-challenge.

EboBun antibody production from humoral antibody response to vaccination and challenge is examined by a virus like particle (VLP) based ELISA assay. Generation of EboBun VLPs is performed by the protocol for ZEBOV as described by Wahl-Jensen, V., et al., J Virol, 2005; 79(4): 2413-2419. ELISA is performed by the protocol described by Qiu, X, et al., PLoS ONE. 2009; 4(5): e5547.

The VSVΔG/MARVGP immunized animals do not develop a detectable antibody response to EboBun. In contrast, potent antibody responses are detected in all VSVΔG/EboBunGP immunized animals independent of immunization route. Between days 14 and 21 post-vaccination, all VSVΔG/EboBunGP immunized NHPs develop high levels of IgA, IgM, and IgG against EboBunGP. After challenge the IgM titres do not exceed the post-vaccination levels, however, IgG and IgA antibody titres are increased peaking 14 days post-challenge then slowly decreasing before maintaining a relatively high antibody titre up to 9 months.

The level of neutralization antibodies is detected by a EboBun-GFP flow cytometric neutralization assay in serum collected at days 0 and 21 post-vaccination. Samples are assayed in duplicate for their ability to neutralize an infection with EboBun-GFP in VeroE6 cells. Serially diluted serum samples are incubated with an equal volume of EboBun-GFP in DMEM, at 37° C., 5% $CO_2$ for 1 hr followed by addition of 150 µl per well of a confluent 12 well plate of VeroE6 cells (MOI=0.0005). After 2 hours at 37° C., 5% $CO_2$, 1 ml of DMEM, 2% fetal bovine serym (FBS), 100 U/ml penicillin, 100 µg/ml streptomycin is added per well and incubated for 5 days. Cells are harvested by removing the culture supernatant, washing with 1 ml PBS, 0.04% EDTA, then adding 800 µl of PBS 0.04% EDTA for 5 minutes at 37° C. before adding 8 ml PBS, 4% paraformaldehyde (PFA) and overnight incubation. The cells are acquired (10,000 events) and analyzed with CellQuest Pro v3.3 on a Becton Dickinson FACSCalibur flow cytometer.

The OR and IN routes produce EboBunGP-specific neutralizing antibodies with the OR route producing the highest titres post-vaccination. The IM immunization produces detectable levels of neutralizing antibody. In comparison, ¾ NHPs in the OR group demonstrate a 50% reduction in EboBun-GFP positive cells at a titre of 1:40. Similarly, the IN route results in a reduction of EboBun-GFP positive cells at the 1:40 dilution.

EboBunGP-specific effector cellular immune responses are determined using IL-2 and IFN-γ ELISPOT assays as described by Qin, X, et al., PLoS ONE. 2009; 4(5): e5547 to determine the number of IL-2 and IFN-γ secreting lymphocytes. Prior to challenge on days 10 to 14 post-vaccination there is a detectable EboBun immunogen-specific IFN-γ response in all immunized animals. The IM route is the most potent, inducing approximately 2-fold more IFN-γ secreting cells than OR ($p<0.001$) or IN ($p=0.043$) routes. A strong post-challenge secondary IFN-γ response is induced in all VSVΔG/EboBun immunized animals with the IM route producing the most IFN-γ cells at day 6. By day 10 the OR group demonstrates a stronger response. The IFN-γ in the IN group rises steadily, peaking at day 26 post-challenge with 4.3 and 2 fold more EboBun specific IFN-γ secreting cells than the IM ($p=0.003$) and OR ($p=0.075$) group, respectively. All three routes produce strong EboBun-specific IFN-γ responses.

Post-vaccination, the IM group also has more EboBunGP-specific IL-2 secreting cells than either of the mucosally immunized groups. Post-challenge, the IM route continues to dominate early after challenge peaking on day 10. This difference shows a trend when compared to the IN group ($p=0.067$) and is significant when compared to the OR group ($p<0.001$). Additionally, the IN group has more IL-2 producing cells than the OR group ($p=0.090$) on day 10 post-challenge. By day 26 post-challenge all three routes continue to produce a EboBunGP-specific IL-2 response, however, the IN group response is strongest. At day 26 post-challenge the IN group has the most potent IFN-γ and IL-2 responses, as well as the highest IgA and IgG antibody titre, indicating this immunization route, followed by a EboBun challenge, results in the development of potent and sustained effector responses.

Absolute lymphocyte numbers for $CD3^+$, $CD4^+$, and $CD8^+$ ($CD3^+4^-$) T cell populations are determined by flow cytometry. No decrease is observed in the lymphocyte populations for any of the VSVΔG/EboBunGP vaccinated NHPs. In contrast, control animals who are not protected from EboBun show lymphocyte numbers decreased by 28-57%.

Macrophage numbers are slightly increased in control animals. However, the number of $CD14^+$ cells is greater in the VSVΔG/EboBunGP vaccinated groups with the IM route showing the most significant increases.

In order to determine the long term immune response after challenge, EboBunGP-specific $CD4^+$ and $CD8^+$ memory T-lymphocytes are examined for their ability to proliferate ($CFSE^-$) or produce IFN-γ in response to EboBunGP peptides at 6 months post-vaccination. EboBunGP-specific memory responses are observed as a result of vaccination followed by a ZEBOV challenge. These responses persist for at least 6 months. The memory populations in OR and IN inoculation routes demonstrate the greatest potential for proliferation and IFN-γ production post-challenge.

Any patents or publications mentioned in this specification are incorporated herein by reference to the same extent as if each individual publication is specifically and individually indicated to be incorporated by reference. The sequence listing submitted with this application is hereby incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims. All numerical ranges are inclusive of the whole integers and decimals between the endpoints, and inclusive of the endpoints.

REFERENCES

1. Suzuki, Y., and Gojobori, T., (1997) The origin and evolution of Ebola and Marburg viruses. Mol Bio Evol, 14(8): 800-806.
2. Sanchez, A., Geisbert, T. W., Feldmann, H. in Fields Virology (ed. Knipe, D. M., Howley, P. M.) 1409-1448 (Lippincott Williams and Wilkins, Philadelphia, 2007).
3. Leroy, E. M. et al., (2005) Fruit bats as reservoirs of Ebola virus. Nature, 438, 575-6.
4. Towner, J. S. et al., (2007) Marburg virus infection detected in a common African bat. PLoS ONE, 2(8), e764.
5. Swanepoel, R. et al., (2007) Studies of reservoir hosts for Marburg virus. Emerg Infect Dis, 13(12), 1847-51.

6. Le Guenno, B. et al., (1995) Isolation and partial characterization of a new species of Ebola virus. Lancet, 345(8960), 1271-4.
7. Ksiazek, T. G. et al. (1999) Clinical virology of Ebola hemorrhagic fever (EHF): virus, virus antigen, IgG and IgM antibody findings among EHF patients in Kikwit, 1995. J. Infect Dis 179 (suppl 1), S177-S187.
8. Cox-Foster, D. L. et al. (2007) A metagenomic survey of microbes in honey bee colony collapse disorder. Science 318, 283-7.
9. World Health Organization (2008) Ebola outbreak contained in Uganda. Features, 22 February, www.who.int/features/2008/ebola_outbreak/en/.
10. Sullivan, N. J., Sanchez, A., Rollin, P. E., Yang, Z.-Y. & Nabel, G. J. (2000) Development of a preventive vaccine for Ebola virus infection in primates. Nature 408, 605-609.
11. Ksiazek, T. G., West, C. P., Rollin, P. E., Jahrling, P. B. & Peters, C. J. (1999) ELISA for the detection of antibodies to Ebola viruses. J. Infect Dis 179 (suppl 1), S191-S198.
12. Rodriguez, L. et al. (1999) Persistence and genetic stability of Ebola virus during the outbreak in Kikwit, Zaire 1995. J. Infect Dis 179 (suppl 1), S170-S176.
13. Sanchez, A. et al. Detection and molecular characterization of Ebola viruses causing disease in human and nonhuman primates. J. Infect Dis 179 (suppl 1), S164-S169 (1999).
14. Jones, S. M. et al. (2005) Live attenuated recombinant vaccine protects nonhuman primates against Ebola and Marburg viruses. Nat Med 11, 786-90.
15. Geisbert, T. W. et al. (2008) Recombinant vesicular stomatitis virus vector mediates postexposure protection against Sudan Ebola hemorrhagic fever in nonhuman primates. J Virol 82, 5664-8.
16. Towner, J. S., Sealy, T. K., Ksiazek, T. & Nichol, S. T. (2007) High-throughput molecular detection of hemorrhagic fever virus threats with applications for outbreak settings. J. Inf Dis 196 (suppl 2), S205-212.
17. Towner, J. S. et al. (2006) *Marburgvirus* genomics and association with a large hemorrhagic fever outbreak in Angola. J Virol 80, 6497-516.
18. Posada, D. & Crandall, K. A. (1998) MODELTEST: testing the model of DNA substitution. Bioinformatics 14, 817-818.
19. Swofford, D. L. (2002) PAUP*: phylogenetic analysis using parsimony (*and other methods) version 4.0b 10. Sinauer Assoc., Sunderland, Mass.
20. Felsenstein, J. (1985) Confidence limits on phylogenies: an approach using the bootstrap. Evolution 39, 783-791.
21. Ronquist, F. & Huelsenbeck, J. P. (2003) MRBAYES 3: Bayesian phylogenetic inference under mixed models. Bioinformatics 19, 1572-1574.
22. Nylander, J. A. A., Wilgenbusch, J. C., Warren, D. L. & Swofford, D. L. (2008) AWTY (are we there yet?): a system for graphical exploration of MCMC convergence in Bayesian phylogenetics. Bioinformatics 24, 581-583.

The invention claimed:
1. An immunogenic composition comprising:
a protein consisting of an amino acid sequence of:
at least 70 contiguous residues of the amino acid sequence of SEQ ID NO: 9(GP); and
an immunostimulatory adjuvant present in an amount that increases an immune response to the immunogenic composition in a subject.

2. The immunogenic composition of claim 1, wherein the protein consists of at least 80 contiguous residues of the amino acid sequence of SEQ ID NO: 9.

3. The immunogenic composition of claim 1, wherein the protein consists of at least 100 contiguous residues of the amino acid sequence of SEQ ID NO: 9.

4. The immunogenic composition of claim 1, wherein the protein consists of at least 150 contiguous residues of the amino acid sequence of SEQ ID NO: 9.

5. The immunogenic composition of claim 1, wherein the protein consists of at least 200 contiguous residues of the amino acid sequence of SEQ ID NO: 9.

6. The immunogenic composition of claim 1, wherein the protein consists of at least 300 contiguous residues of the amino acid sequence of SEQ ID NO: 9.

7. The immunogenic composition of claim 1, wherein the protein consists of at least 400 contiguous residues of the amino acid sequence of SEQ ID NO: 9.

8. The immunogenic composition of claim 1, wherein the protein consists of at least 500 contiguous residues of the amino acid sequence of SEQ ID NO: 9.

9. The immunogenic composition of claim 1, wherein the protein consists of at least 600 contiguous residues of the amino acid sequence of SEQ ID NO: 9.

10. The immunogenic composition of claim 1, wherein the protein consists of the amino acid sequence of SEQ ID NO: 9.

11. An immunogenic composition comprising:
a protein comprising an amino acid sequence at least 75% identical to SEQ ID NO: 9; and
an immunostimulatory adjuvant present in an amount that increases an immune response to the immunogenic composition in a subject.

12. The immunogenic composition of claim 11, wherein the protein consists of an amino acid sequence at least 80% identical to SEQ ID NO: 9.

13. The immunogenic composition of claim 11, wherein the protein consists of an amino acid sequence at least 85% identical to SEQ ID NO: 9.

14. The immunogenic composition of claim 11, wherein the protein consists of an amino acid sequence at least 90% identical to SEQ ID NO: 9.

15. The immunogenic composition of claim 11, wherein the protein consists of an amino acid sequence at least 95% identical to SEQ ID NO: 9.

* * * * *